United States Patent
Hosoda et al.

(10) Patent No.: US 6,464,633 B1
(45) Date of Patent: Oct. 15, 2002

(54) LIGHT SOURCE DEVICE FOR ENDOSCOPE USING DMD

(75) Inventors: Seiichi Hosoda, Hino; Masahide Yamaki; Yutaka Koshikawa, both of Hachioji, all of (JP)

(73) Assignee: Olympus Optical Co., Ltd. (JP)

( * ) Notice: Subject to any disclaimer, the term of this patent is extended or adjusted under 35 U.S.C. 154(b) by 92 days.

(21) Appl. No.: 09/641,058

(22) Filed: Aug. 17, 2000

(30) Foreign Application Priority Data

| Aug. 23, 1999 | (JP) | 11-235710 |
| Jan. 25, 2000 | (JP) | 2000-016312 |
| Jan. 27, 2000 | (JP) | 2000-018951 |
| Jan. 27, 2000 | (JP) | 2000-018952 |
| Feb. 7, 2000 | (JP) | 2000-029516 |
| Feb. 8, 2000 | (JP) | 2000-030828 |
| Feb. 8, 2000 | (JP) | 2000-030829 |
| Feb. 22, 2000 | (JP) | 2000-044900 |
| Jun. 12, 2000 | (JP) | 2000-175796 |

(51) Int. Cl.$^7$ .................................................. A61B 1/66
(52) U.S. Cl. ................... 600/178; 600/180; 600/181; 302/574; 348/68; 348/69; 348/70
(58) Field of Search ................... 600/160, 178, 600/180, 181; 362/574; 348/68–70

(56) References Cited

U.S. PATENT DOCUMENTS

| 5,006,965 A | 4/1991 | Jones |
| 5,452,024 A | * 9/1995 | Sampsell ............ 345/84 |
| 5,642,456 A | 6/1997 | Baker et al. |

FOREIGN PATENT DOCUMENTS

| DE | 19741616 | 4/1999 |
| JP | 61-51119 | 3/1986 |

* cited by examiner

*Primary Examiner*—John Mulcahy
(74) *Attorney, Agent, or Firm*—Ostrolenk, Faber, Gerb & Soffen, LLP

(57) ABSTRACT

A larger number of micromirrors arranged on an illumination optical path of a lamp in a light source device for supplying an illumination light to an endoscope and by using a silicon chip as a base are arranged the micromirrors in a two-dimensional are set at two angles. When the micromirrors are set at one of the two angles, a reflected light is supplied to the light guide. When the micromirrors are set at the other angle, the micromirrors are driven such that the reflected light is not supplied to the light guide. An intensity of illumination light supplied to the light guide or the like is adjusted at a high speed by using a brightness level by selected the micromirrors at the two angles respectively, so that an endoscope image which can be easily observed is obtained.

8 Claims, 74 Drawing Sheets

■ SHIELD REFLECTION
☐ ALL LEVEL REFLECTION

■ SHIELD REFLECTION
□ ALL LEVEL REFLECTION

■ SHIELD REFLECTION
☐ ALL LEVEL REFLECTION

■ SHIELD REFLECTION
☐ ALL LEVEL REFLECTION

■ SHIELD REFLECTION
☐ ALL LEVEL REFLECTION
▨ INTERMEDIATE LEVEL REFLECTION

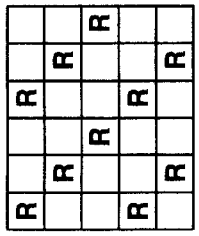
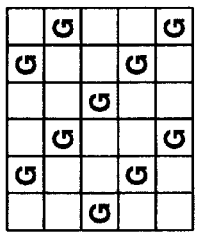
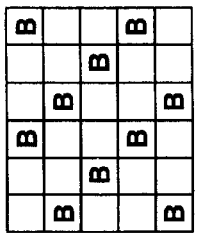
FIG.42A  DMD DRIVE STATE
FIG.42B  CCD DRIVE PULSE
FIG.42C  DMD EMISSION LIGHT PWM
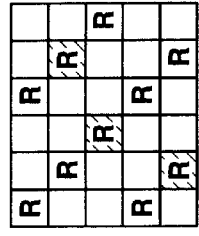
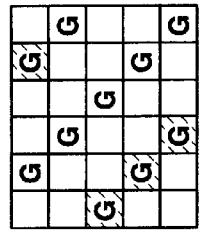
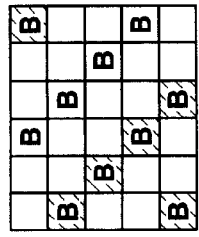
FIG.42D  DMD DRIVE STATE

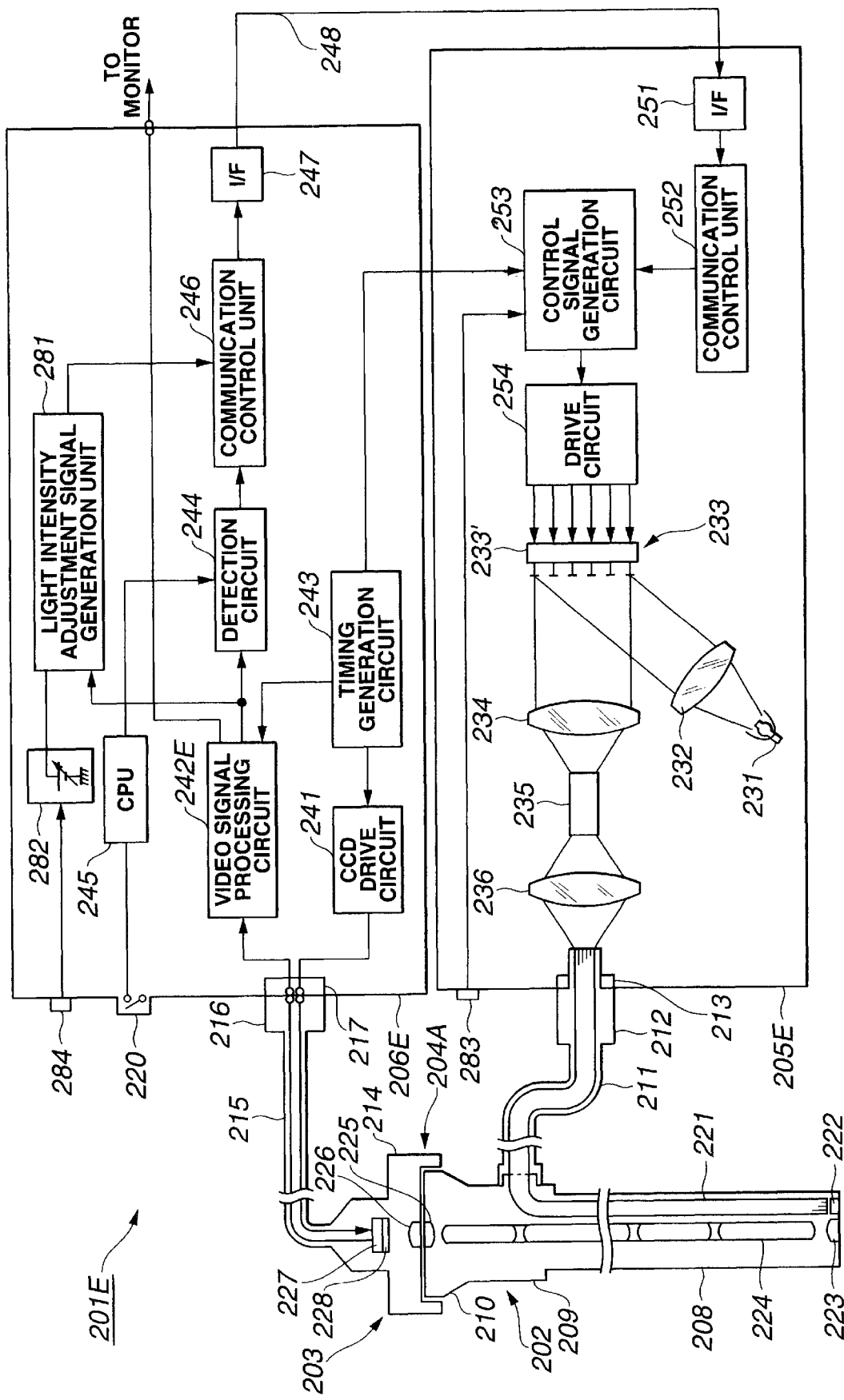

FIELD SEQUENTIAL METHOD

SYNCHRONOUS METHOD

FIG.58A BEFORE CONTROL
FIG.58B QUICK MOVEMENT
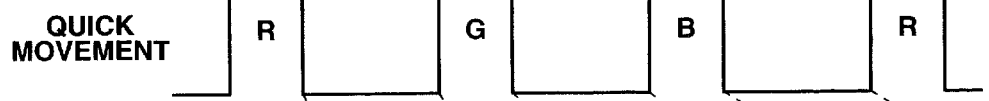
FIG.58C SLOW MOVEMENT
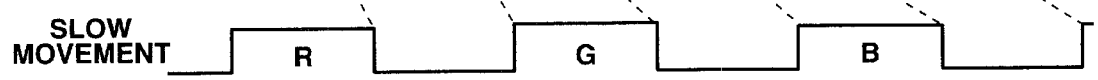
FIG.59A
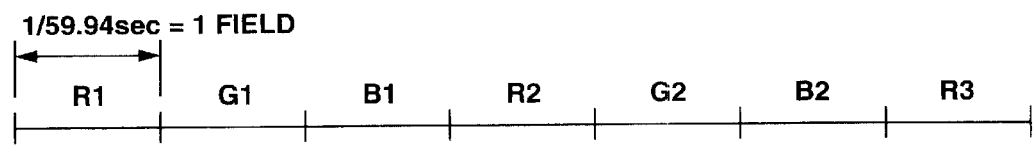
FIG.59B
FIG.59C
FIG.59D
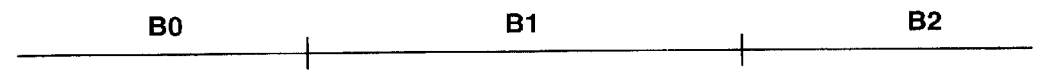
FIG.59E

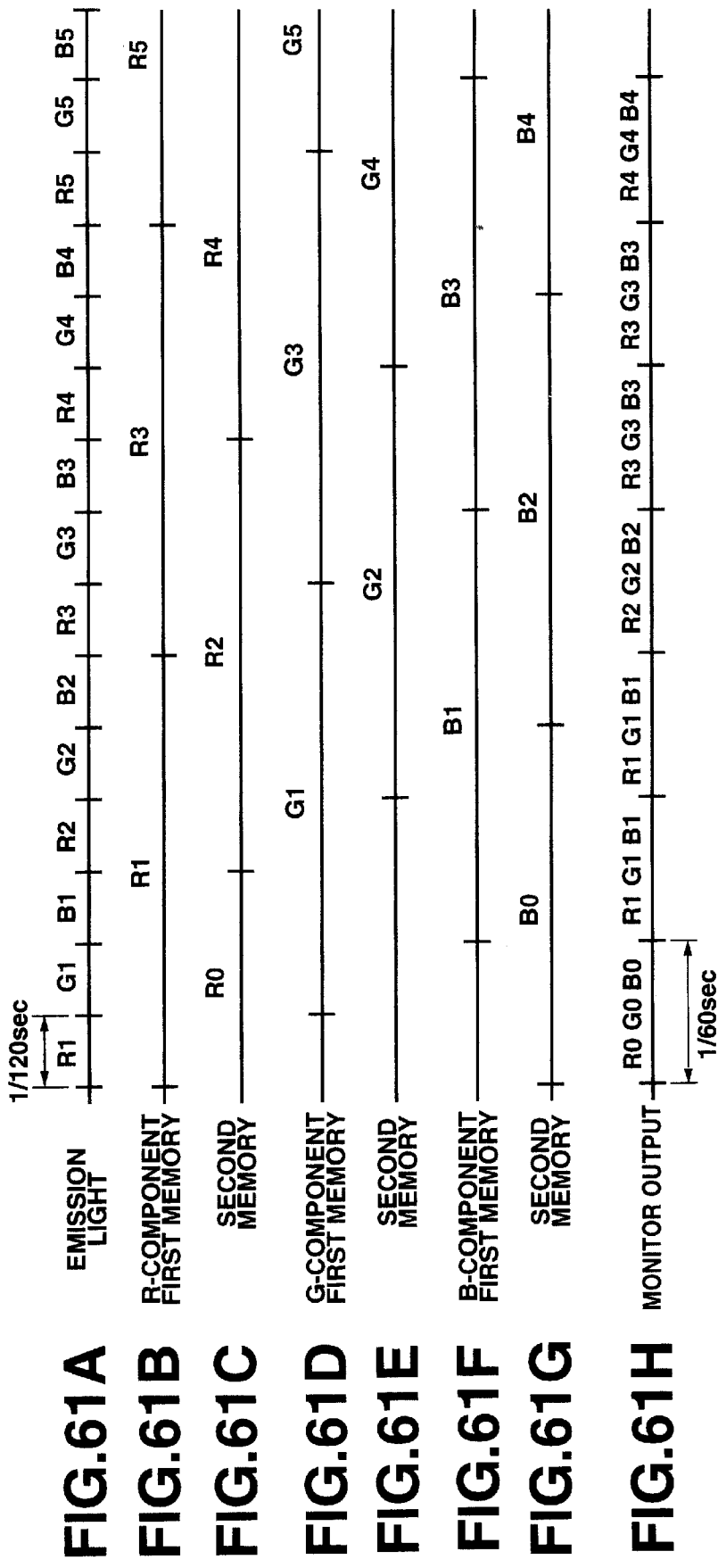

DECREASE IN LIGHT INTENSITY

INCREASE IN LIGHT INTENSITY

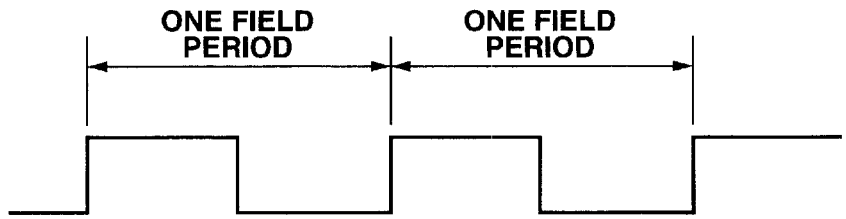
FIG.77A
FIG.77B
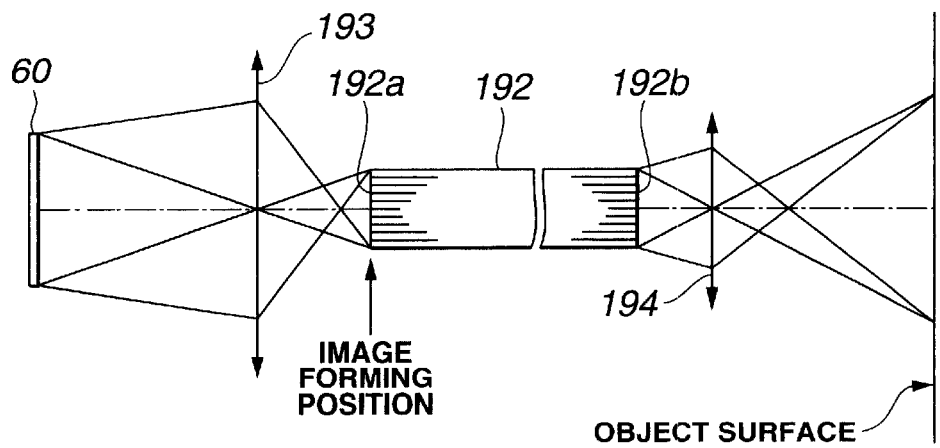
FIG.78

FIG. 79A FIG. 79B
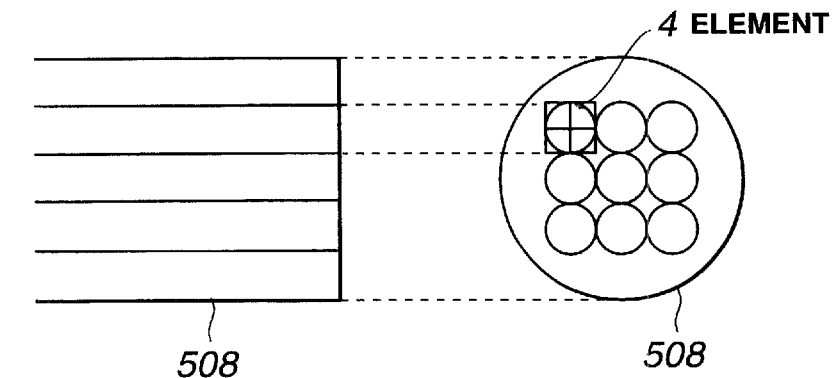
FIG. 82A
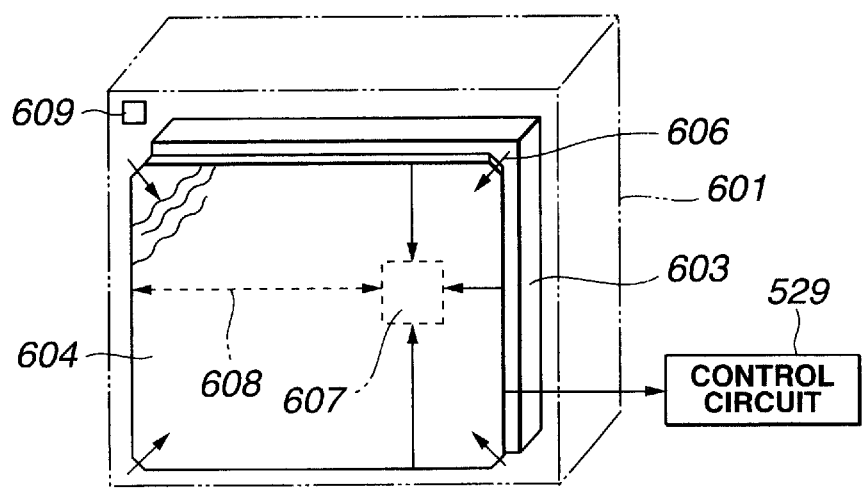
FIG. 82B
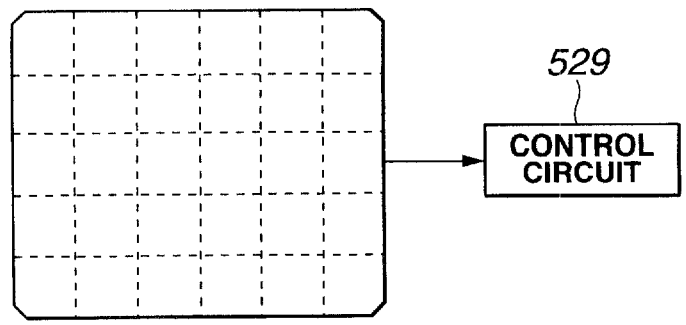

LIGHT SOURCE DEVICE FOR ENDOSCOPE USING DMD

This application claims benefit of Japanese application No. Hei 11-235710 filed in Japan on Aug. 23, 1999, 2000-016312 filed in Japan on Jan. 25, 2000, 2000-018951 filed in Japan on Jan. 27, 2000, 2000-018952 filed in Japan on Jan. 27, 2000, 2000-029516 filed in Japan on Feb. 7, 2000, 2000-030828 filed in Japan on Feb. 8, 2000, 2000-030829 filed in Japan on Feb. 8, 2000, 2000-044900 filed in Japan on Feb. 22, 2000, 2000-175796 filed in Japan on Jun. 12, 2000, the contents of which are incorporated by this reference.

BACKGROUND OF THE INVENTION

1. Field of the Invention

The present invention relates to a light source device for an endoscope for controlling an intensity of an illumination light delivered to a light guide of an endoscope by using a DMD.

2. Description of the Related Art

An endoscope device for performing endoscbpe inspection by using an endoscope has popularly been used in medical fields and industrial fields.

The endoscope inspection is performed to various objects to be observed (object to be inspected) such as a tubular object or a recessed surface, e.g., the inner wall of a stomach. For example, observation is performed such that a planar portion is magnified and closely observed.

For this reason, illumination is desirably performed such that an endoscope image in which an object to be observed can be easily diagnosed or inspected is objected.

Therefore, for example, DE19741616 discloses a method of eliminating dotted reflective luminescent spots generated on the surface of a mucosa by using one matrix field constituted by a optical elements capable of reflection and/or absorption as an illumination device.

However, the detailed configuration of the method is not disclosed.

OBJECTS AND SUMMARY OF THE INVENTION

It is an object to provide a light source device for an endoscope device which can easily perform such illumination that an endoscope image which can be easily diagnosed or inspected a depending on an object to be observed.

It is another object of the present invention to provide an endoscope device which can perform brightness control at a high response speed.

It is still another object of the present invention to provide a light source device and an endoscope device which can be easily set in a white balance state.

According to the present invention, there is provided an endoscope device for observing the inside of an object to be inspected,-comprising:

- a light source lamp for generating an illumination light supplied to an endoscope;
- the mirror device constituted by a silicon chip, arranged on an optical path of the illumination light generated from the light source lamp, and having a reflective surface formed by a plurality of micromirrors on a light-exposing side of the illumination light,
- the micromirrors on the reflective surface being designed such that the micromirror can be moved within a predetermined angle range;
- a receptacle to which a light guide of the endoscope is connected;
- the receptacle being arranged on an optical path of a reflected light obtained by reflecting the illumination light generated from the light source lamp when the angles of the micromirrors formed in the mirror device are fixed to a predetermined position;
- an image pickup element for picking up the image of an object to be photographed illuminated with the illumination light;
- a video signal processing circuit for performing video signal processing of an output signal from the image pickup element;
- an illumination light intensity setting circuit for setting an intensity of illumination light illuminating the object;
- an illumination light intensity adjustment circuit for outputting an adjustment signal for adjusting the illumination light being incident on the light guide of the endoscope in the form of a pattern on the basis of the illumination light intensity set by the illumination light intensity setting circuit and the video signal processed by the video signal processing circuit; and
- a mirror element drive circuit for outputting a drive signal for changing each micromirror formed in the mirror device to arbitrary angle positions on the basis of the adjustment signal output from the illumination light adjustment circuit,
- the mirror element drive circuit operating each micromirror between a first angle position at which at least a part of a reflected light obtained such that the illumination light generated by the light source lamp is reflected on the reflective surfaces of the mirror device is incident on the light guide and a second angle position at which the part of the reflected light is not incident on the light guide.

The mirror device is driven by the video signal obtained by picking up the image of the object through the mirror element drive circuit, so that an image having such brightness that the object can be easily diagnosed or inspected at a high response speed.

BRIEF DESCRIPTION OF DRAWINGS

FIG. 1 is a diagram showing the appearance of an endoscope device;

FIG. 2 is a diagram showing the configuration of an operation panel arranged on a light source device in FIG. 1;

FIG. 3 is a block diagram showing the configuration of the light source device in FIG. 1;

FIGS. 4 to 11 are diagrams conceptually showing first to eighth patterns of the reflective surface pattern of a DMD in FIG. 3;

FIG. 12 is a graph for explaining an operation of the light source device in FIG. 3 when the shape of an object to be observed is a convex shape;

FIG. 13 is a graph for explaining an operation of the light source device in FIG. 3 when the shape of an object to be observed is a tubular shape;

FIG. 14 is a block diagram showing the configuration of a light source device;

FIG. 15 is a first graph for explaining an operation of the light source device in FIG. 14;

FIG. 16 is a second graph for explaining an operation of the light source device in FIG. 14;

FIGS. 17 to 22 are related to the third embodiment of the present invention, and FIG. 17 is a block diagram showing the configuration of an endoscope device;

FIGS. 18A to 22D are diagrams for explaining operations of the endoscope device in FIG. 17;

FIG. 24 is a block diagram showing the configuration of the endoscope device;

FIG. 25 is a graph showing the configuration of an RGB rotating filter in FIG. 24;

FIG. 26 is a chart for explaining an operation of the endoscope device in FIG. 24;

FIGS. 27 to 36 are related to the sixth embodiment of the present invention, and FIG. 27 is a block diagram showing the configuration of an endoscope device;

FIG. 28 is an enlarged view of an optical system in the light source device in FIG. 27;

FIG. 29 is a view for explaining an operation performed by a light modulation device;

FIG. 30 is a view showing an optical system in which a light reflected by the light modulation device is irradiated on an object to be photographed;

FIG. 31 is a view showing an optical system near an integrator;

FIG. 33 is a view for explaining an operation performed when light distribution control is performed by a light distribution pattern;

FIG. 35 is a view showing the optical system of a light source device according to the first modification of the sixth embodiment;

FIG. 36 is a view showing the optical system of a light source device according to the second modification of the sixth embodiment;

FIGS. 37 to 40D are related to the seventh embodiment of the present invention, and FIG. 37 is a perspective view showing the appearance of an endoscope device according to the seventh embodiment;

FIG. 38 is a block diagram showing the detailed configuration of FIG. 37;

FIG. 39 is a perspective view showing the configuration of a light modulation device;

FIGS. 40A to 40D are views showing typical examples of light distribution patterns of the RGB filter of the light modulation device;

FIGS. 41 to 42D are related to the eighth embodiment of the present invention, and FIG. 41 is a block diagram showing the configuration of an endoscope device according to the eighth embodiment;

FIGS. 42A to 42D are views for explaining an operation;

FIG. 43 is a block diagram showing the configuration of an endoscope device according to the ninth embodiment;

FIG. 44 is an explanatory view showing the structure and the operation of a light modulation device;

FIGS. 45 to 46B are related to the tenth embodiment of the present invention, and FIG. 45 is a block diagram showing the configuration of an endoscope device according to the tenth embodiment;

FIGS. 46A and 46B are views for explaining an operation;

FIG. 47 is block diagram showing the configuration of an endoscope device;

FIG. 48 is a chart for explaining R, G, and B field sequential illumination;

FIG. 49 is a diagram for explaining a light intensity control pattern;

FIG. 50 is a diagram showing a drive pattern of a light modulation device when colors are balanced;

FIG. 51 is a block diagram of an endoscope device;

FIG. 52 is a chart for explaining a drive manner of a light modulation device in case of a field sequential method;

FIG. 53 is a chart for explaining a drive manner of the light modulation device in case of a simultaneous method;

FIGS. 54 to 59E are related to the thirteenth embodiment of the present invention, and FIG. 54 is a perspective view showing the appearance of an endoscope device according to the thirteenth embodiment;

FIG. 55 is a block diagram showing the internal configuration of a light source device or the like;

FIG. 56 is a block diagram showing the configuration of a video signal processing circuit;

FIG. 57 is a block diagram showing the configuration of a decision circuit;

FIGS. 58A to 58C are charts showing manners in which an image pickup period is changed depending on movement of an object to be photographed;

FIGS. 59A to 59E are charts showing read and write operations of a chromatic signal in/from a memory;

FIGS. 60A to 61H are related to the fourteenth embodiment of the present invention, and FIGS. 60A and 60B are charts for explaining an operation of the fourteenth embodiment;

FIGS. 61A to 61H are timing charts for explaining operations;

FIGS. 62 to 66 are related to the fifteenth embodiment of the present invention, and FIG. 62 is a block diagram showing the configuration of an endoscope device according to the fifteenth embodiment;

FIG. 63 is a block diagram showing the configuration of a video signal processing circuit;

FIG. 65 is a graph showing the relationships between brightnesses (distances) and accumulation times when a light of a primary color system and a light of a complementary color system are emitted;

FIG. 66 is a timing chart of read and write operations for a signal obtained by image pickup from/into a memory when a light of a complementary color system is emitted;

FIGS. 67 to 75 are related to the sixteenth embodiment of the present invention, and FIG. 67 is a perspective view showing the appearance of an endoscope device according to the sixteenth embodiment;

FIG. 68 is a block diagram showing the configuration of a light source device or the like;

FIG. 69 is a block diagram for explaining an operation for causing a main part of FIG. 68 to correspond to a light modulation device and a CCD pixel;

FIG. 70 is a circuit diagram showing the configuration of a peak point detection circuit;

FIG. 72 is a flow chart showing the contents of a corresponding process between the light modulation device and a CCD pixel in an initial setting:

FIG. 73 is a flow chart showing the contents of a process of correcting a brightness to an appropriate brightness when bright spots/dark spots in an endoscope observation;

FIG. 75 is a circuit diagram showing the internal configuration of a decision circuit;

FIGS. 76 to 78 are related to the seventeenth embodiment of the present invention, and FIG. 76 is a block diagram showing the configuration of an endoscope device according to the seventeenth embodiment;

FIGS. 77A and 77B are waveform charts showing a brightness pattern signal and a synthesis pattern signal;

FIG. 78 is a view showing the basic configuration of an optical system subsequent to a light modulation device;

FIGS. 79A and 79B are related to the eighteenth embodiment, and FIG. 79A is a diagram showing a portion near an end face of a light guide on an incident side;

FIG. 79B is a diagram showing the relationship between an element of the light modulation device and a fiber diameter of the light guide;

FIGS. 81 to 82B are related to the twentieth embodiment of the present invention, and FIG. 81 is a block diagram showing the configuration of an endoscope device according to the twentieth embodiment;

FIGS. 82A and 82B are diagrams for explaining the structure of a new operation panel;

FIG. 83 is a block diagram showing the configuration of an endoscope device according to the twenty-first embodiment;

FIG. 84 is a diagram showing gamanner in which an illumination light is supplied to a light guide constituted by a group of microlenses;

FIGS. 85 to 87C are related to the twenty-second embodiment of the present invention, and FIG. 85 is a block diagram showing the configuration of an endoscope device according to the twenty-second embodiment;

FIGS. 86A to 86C are charts for explaining the operation of performing field sequential illumination and image pickup by a visual light;

FIGS. 87A to 87C are charts for explaining the operation of performing field sequential illumination and image pickup by a special light;

FIG. 88 is a block diagram showing the configuration an endoscope device according to the twenty-third embodiment, FIG. 89 is a diagram showing regulative patterns of supply reflection/non-supply reflection performed when a light modulation device is driven;

FIGS. 90A to 90C are charts for explaining a drive timing of the light modulation device, a timing of infrared detection, and the like;

FIG. 91 is a flow chart showing the contents of the process of infrared level detection;

FIG. 92 is a block diagram showing the configuration of an endoscope device;

FIG. 93 is a flow chart for explaining the operation of an infrared level detection circuit in FIG. 92;

FIG. 94 is a view showing a configuration in which a cooling fan is arranged in a light source device in FIG. 92;

FIG. 95 is a view showing a modified configuration in which a cooling fan is arranged in a light source device in FIG. 88;

FIGS. 96 to 97B are related to the twenty-fifth embodiment of the present invention, and FIG. 96 is a block diagram showing the configuration of an endoscope device; and FIGS. 97A and 97B are chart for explaining operations.

DETAILED DESCRIPTION OF PREFERRED EMBODIMENTS

The first embodiment of the present invention will be described below with reference to FIGS. 1 to 13.

Figure 1:
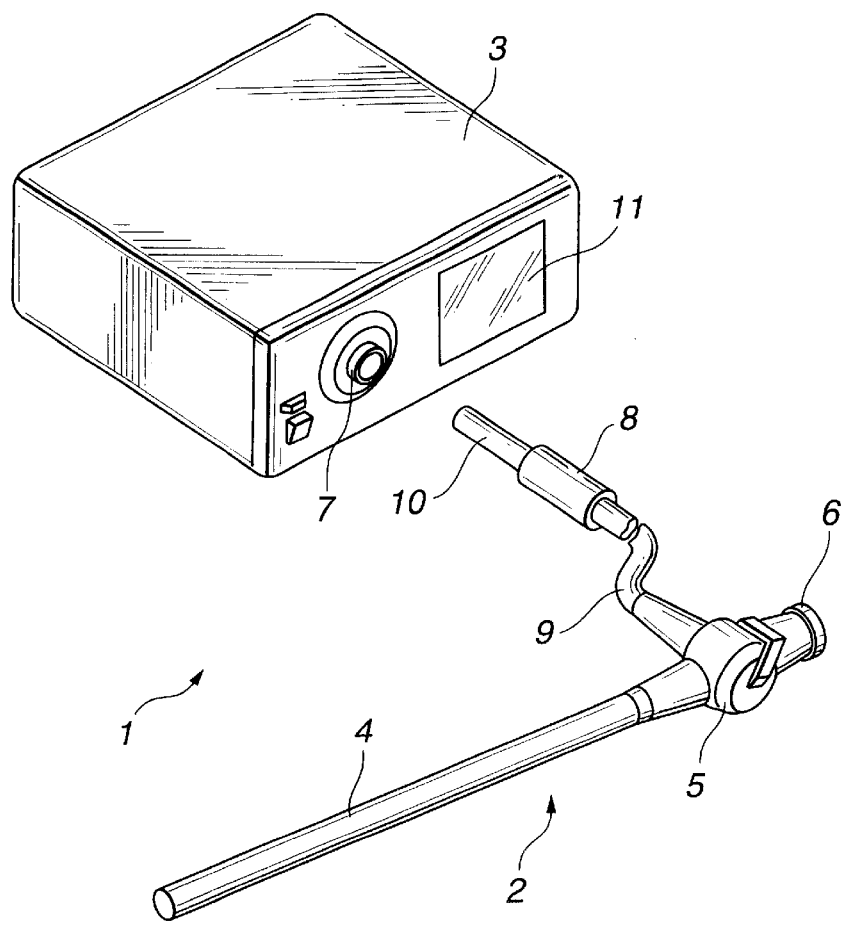
FIGS. 1 to 13 are related to the first embodiment of the present invention.

As shown in FIG. 1, an endoscope device 1 according to this embodiment is constituted by an endoscope 2 consisting of a rigid endoscope used to observe a meniscal of a joint, and a light source device 3 for supplying an illumination light to the endoscope 2.

The endoscope 2 is constituted by an insertion portion 4 inserted into a body cavity; a grasping portion 5 arranged to be connected to the proximal end of the insertion portion 4; an eyepiece portion 6, arranged on the grasping portion 5, for observing the image of an observed portion in a body by an image transmission means (e.g., an image guide fiber or a relay lens) (not shown) arranged in the insertion portion 4; and a light guide cable 9 extending from the grasping portion 5 and having a light guide connector 8 to be connected to a receptacle 7 of the light source device 3 at the proximal end of the light guide cable 9. When the light guide connector 8 is connected to the receptacle 7 of the light source device 3, an illumination light is supplied to the light guide cable 9 and an incident end (on the light source device 3 side) of a light guide 10 equiped in the insertion portion 4, and the illumination light is transmitted through the light guide 10 to illuminate an observed portion from the distal end of the insertion portion 4.

Figure 2:
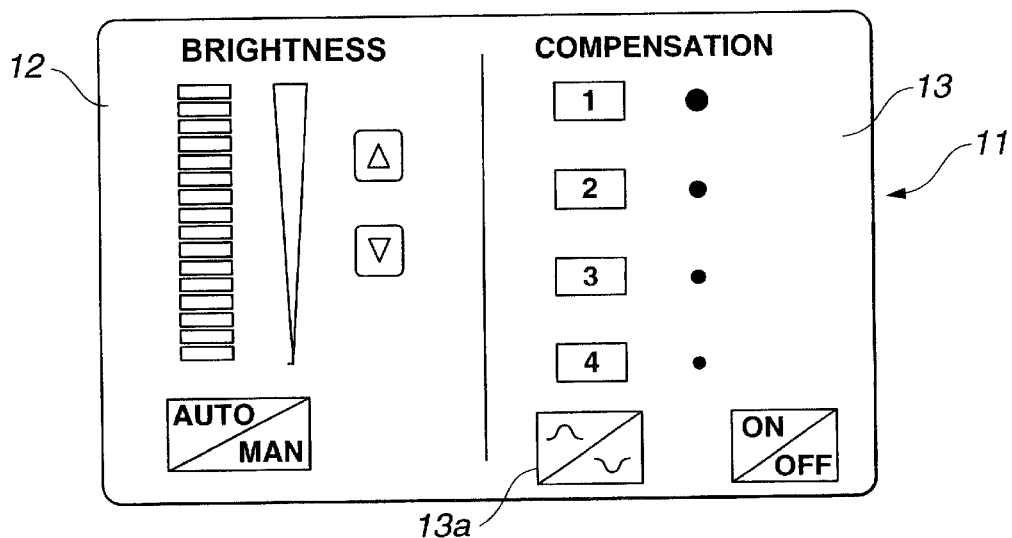

In addition to the recptacle 7, an operation panel 11 as shown in FIG. 2 is arranged in the light source device 3. The operation panel 11 is constituted by a brightness level operation portion (BRIGHTNESS) 12 and a correction level operation portion (COMPENSATION) 13 having a pattern setting switch 13a for performing pattern selection (to be described later). Various settings are performed by the two operation portions, so that a desired illumination light (to be described later) is supplied to the endoscope 2.

Figure 3:
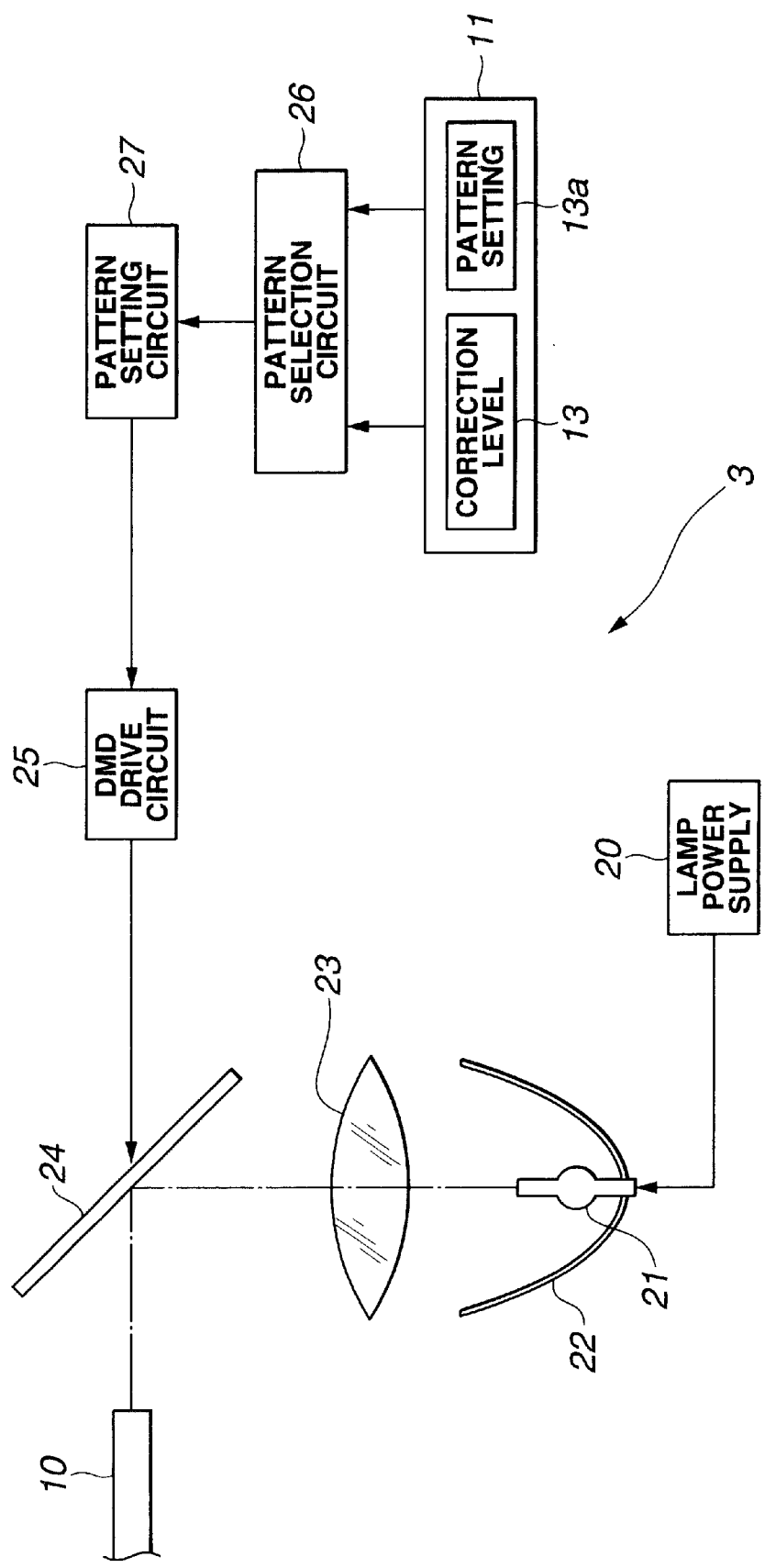

The light source device 3, as shown in FIG. 3, comprises a light source lamp 21 for emitting an illumination light, a lamp power supply 20 for supplying a power to the light source lamp 21, a parabolic mirror 22 on which a film having infrared transmission characteristics for outgoing the illumination light emitted from the light source lamp 21 as a parallel light is coated, and a DMD (Digital Micromirror Device) 24 for reflecting the parallel light from the parabolic mirror 22 through a lens 23 to condense the parallel light to the incident end of the light guide 10.

Figure 29:
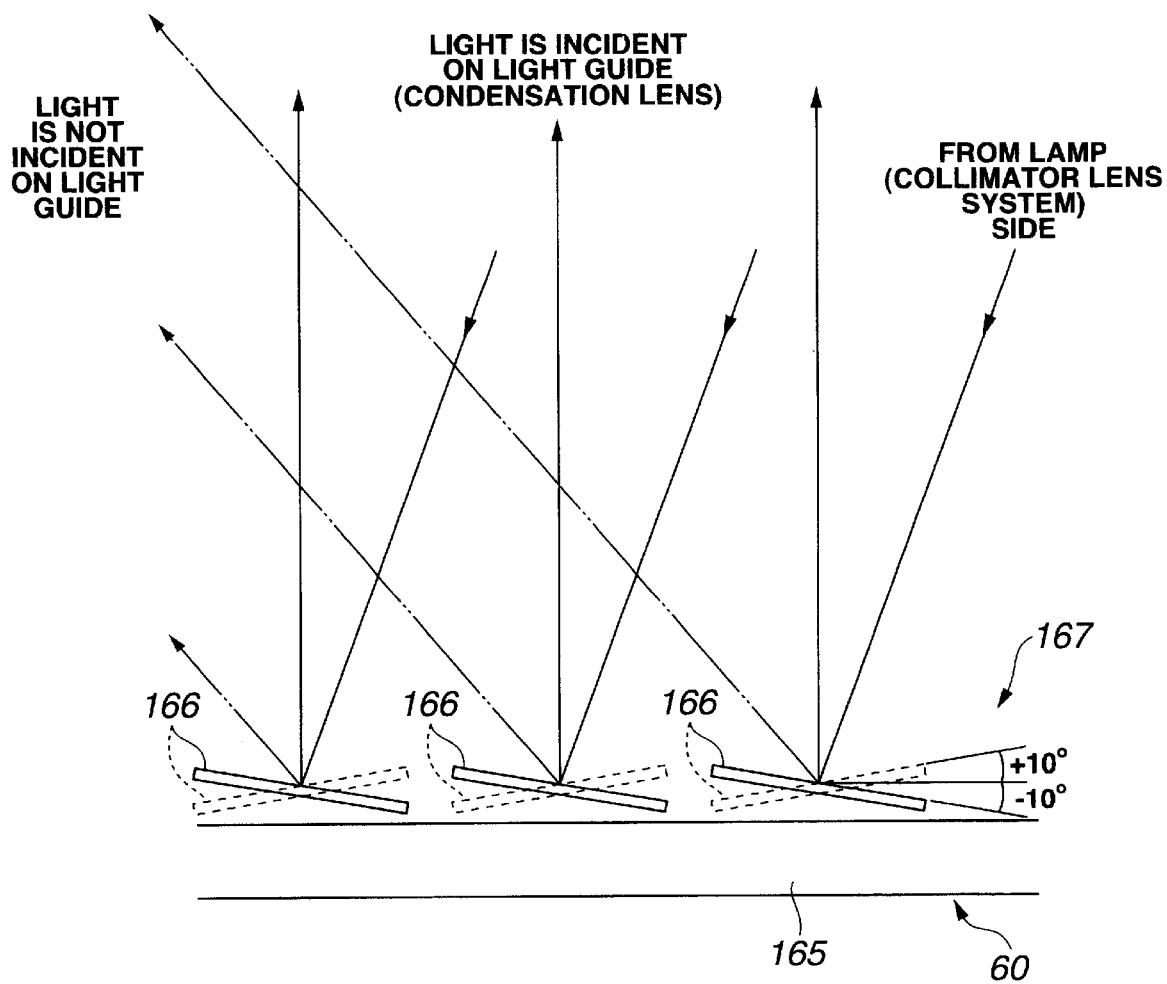

The DMD 24 is available from, e.g., Texas Instruments. The DMD 24 is an element in which a micromirror having a size of 640×480 is arranged on a silicon chip and which is held by a holding member on a yoke rotated about diagonals between two stable states and rotated in a horizontal direction within a range of ±10°. The DMD 24 is designed such that the parallel light from the parabolic mirror 22 through a lens 23 is reflected from the reflective surface of the 640×480 mirror of the DMD 24 through the lens 23 to be condensed and incident on the light guide 10 (another embodiment (to be described later), see, e.g., FIG. 29. In FIG. 29, the DMD is indicated by 60).

As the lamp power supply 20, a lamp such as a xenon lamp or a metal halide lamp having a short arc is appropriately used.

The light source device 3 comprises a DMD drive circuit 25 for rotationally control the mirrors of the DMD 24, a pattern selection circuit 26 for receiving a pattern selection in a pattern selection portion 13a of the operation panel 11 to select reflective surface patterns of the mirrors of the DMD 24, and a pattern setting circuit 27 for controlling the DMD drive circuit 25 on the basis of the reflective mirror pattern selected by the pattern selection circuit 26 to set each mirror of the DMD 24 in a desired reflective mirror pattern.

Figure 4:
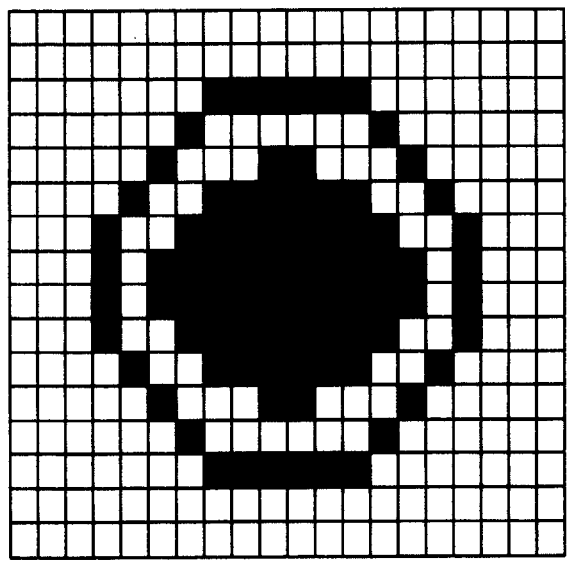
Figure 5:
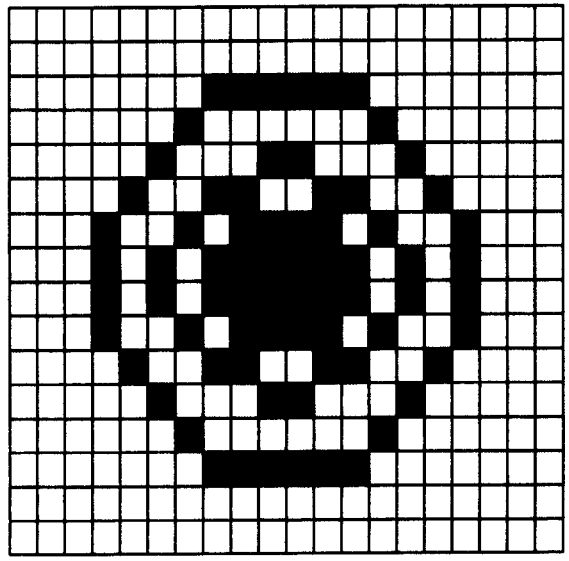

When the mirrors of the DMD 24 are inclined at 0° to +10° in one direction by the pattern selection portion 13a, a reflected light is not incident on the light guide 10. In the mirrors, reflection is indicated by white, and non-reflection is indicated by black. In this case, in the DMD mirror arrangements, as conceptual reflective mirror patterns, various reflective mirror patterns as shown in FIG. 4 (first pattern) to FIG. 11 (eighth pattern) are obtained.

More specifically, when a convex object to be observed is used, a light being incident on the light guide 10 and reflected from the mirrors of the DMD 24 arranged at the central portion is not converged. In this case, an excessive light is not output from the central portion. Forth is reason, the reflective mirror pattern of the DMD 24 is changed as shown in FIG. 4 (first pattern) to FIG. 7 (fourth pattern), and an optimum pattern appropriate to the condition is selected, so that the light can be incident on the light guide 10. Similarly, when the object to be observed is tubular, by using the reflective mirror patterns shown in FIG. 8 (fifth pattern) to FIG. 11 (eighth pattern), the light can be converged to the light guide while the intensity of a around light such as peripheral.

These reflective mirror patterns are generated by the pattern setting circuit 27. The generated reflective mirror patterns are output to the DMD drive circuit 25, the positions of the respective mirrors of the DMD 24 are controlled by the DMD drive circuit 25. The pattern selection circuit 26 is connected to the pattern setting circuit 27, and a pattern is selected by the pattern setting switch 13a for each input object image so as to set whether the object to be observed is convex or tubular.

Unless the conditions for converging a light to the. light guide 10 are not changed depending on the object to be observed, even though the object is tubular, the patterns cannot cope with the thick tube. Therefore, a setting of a correction level matched by changing the reflective patterns of the DMD 24 can be performed by the correction level operation portion 13 of the operation panel 11.

Figure 12:
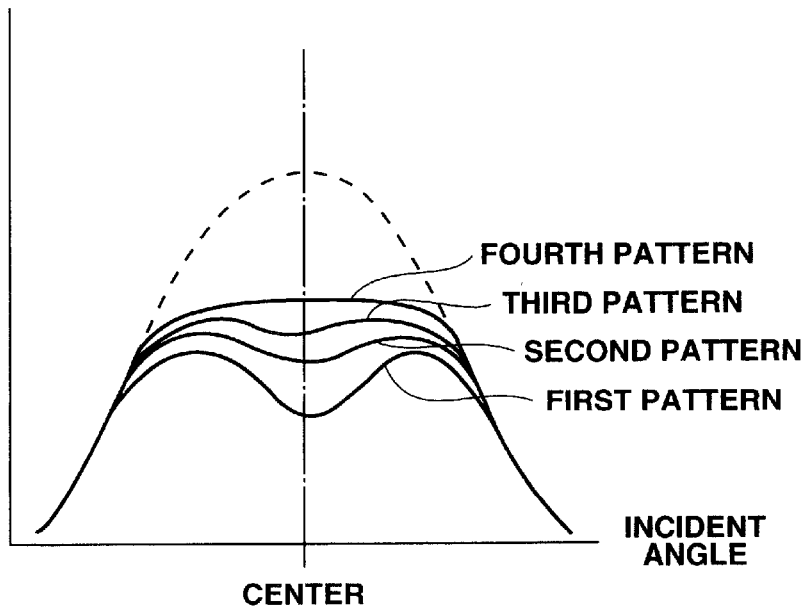
Figure 13:
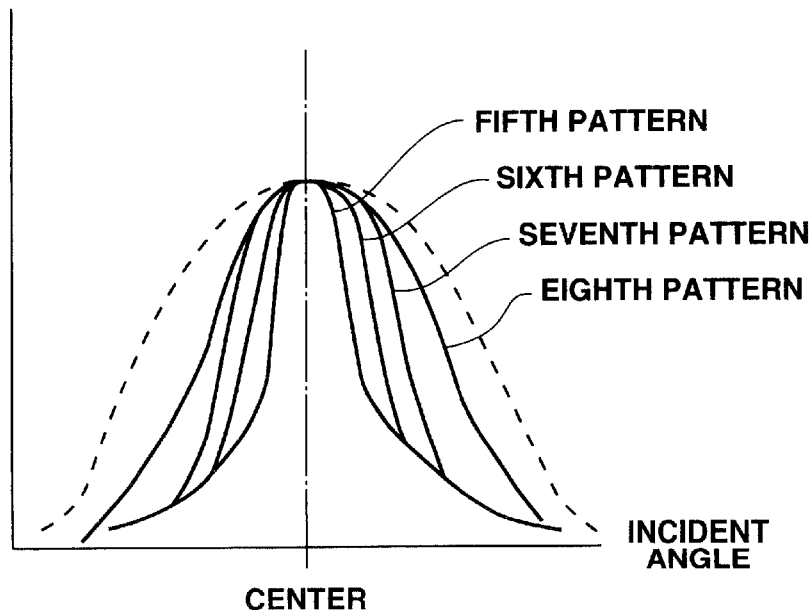

The parallel light emitted from the light source lamp 21 through the lens 23 is reflected by the mirrors of the DMD 24. However, a reflection distribution is dependent on the reflective mirror pattern of the DMD 24 at this time. More specifically, since a light being incident on the light guide 10 decreases, a part which is not reflected by the mirrors is reflected such that the distribution of a non-reflective mirror is shaped into a mosaic by setting in the brightness level operation portion 12 and the correction level operation portion 13, so that the intensity of an intermediate light is obtained. In this manner, the distribution of the light being incident on the light guide 10 is corrected as shown in FIG. 12 depending on FIG. 4 (first pattern) to FIG. 7 (fourth pattern) when the object to be observed has a convex shape, and the distribution is corrected as shown in FIG. 13 depending on FIG. 8 (fifth pattern) to FIG. 11 (eighth pattern) when the object to be observed is has a tubular shape.

Although the fiber position of an incident end and the fiber position of an outgoing end do not have a one-to-one correspondence in general, in this embodiment as described above, since pattern setting and correction are performed to a radial distribution of a parallel light transmitted through the light guide, the fiber position of the incident end and the fiber position of the outgoing end need not have a one-to-one correspondence. However, as the light guide, a fiber bundle such as an image guide in which the fiber position of the incident end and the fiber position of the outgoing end have a one-to-one correspondence can also be used, as a matter of course.

The operation of this embodiment will be described below.

In the endoscope device 1 of this embodiment, when a knee joint is observed by the endoscope 2, the endoscope 2 is inserted into the lumen of the joint in a state in which reflux liquid flows to perform observation.

Although the meniscal of the knee joint can be observed in this state, since the patella consisting of a bone component, the patella has a reflectance higher than that of an ordinary tissue, and the patella is located at the center. For this reason, when an external TV camera is connected to the eyepiece portion 6 to perform observation using the TV device, a so-called white out state occurs disadvantageously.

Therefore, the operation panel 11 is operated to make it possible to perform correction, and a reflective surface pattern of each mirror state of the DMD 24 corresponding to a convex shape is selected. Therefore, when a correction level is selected by the degree of a white out state, the white out state of the central portion can be avoided, and the around tissue state can be observed at an appropriate level.

This embodiment has the following effect.

Conventionally, when an output from the light source device is controlled to be decreased, a total of light intensity decreases, and the peripheral tissue to be observed becomes dark. As a result, observation cannot be properly performed. However, the method according to the present invention can be performed without any problem. The object is tubular. For this reason, by changing only the setting of a convex shape, the light source device can be effectively used.

The second embodiment of the present invention will be described below with reference to FIGS. 14 to 16.

The second embodiment is almost the same as the first embodiment. For this reason, only different points will be described, the same reference numerals as in the first embodiment denote the same parts, and a description thereof will be omitted.

Figure 14:
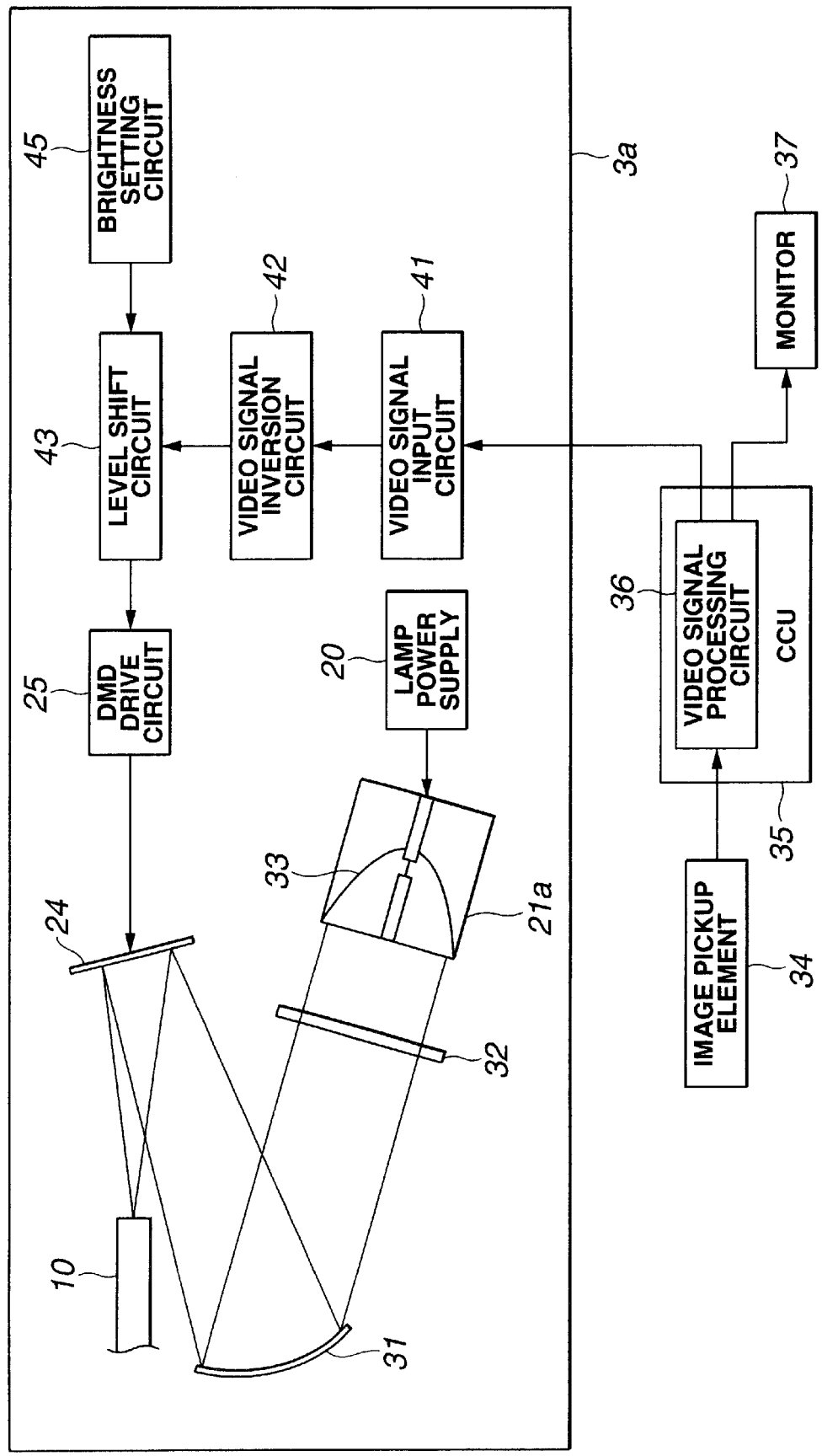
FIGS. 14 to 16 are related to the second embodiment of the present invention.

In a light source device 3a according to this embodiment, as shown in FIG. 14, in order to reflecting a light being incident on the light guide 10 by the plurality of mirrors of the DMD 24, an optical system constituted by a mirror 31 for converting an optical path to converge a light to the light guide and a filter 32 for cutting an infrared ray is arranged between the DMD 24 and a light source lamp 21a.

The light source lamp 21a according to this embodiment is a lamp obtained such that a xenon gas is filled in a short arc discharge tube in which a reflective mirror 33 having a parabolic surface is formed on a ceramics.

In this embodiment, a TV camera (not shown) is detachably connected to the eyepiece portion 6, and an image pickup element 34 arranged on the TV camera is designed to photograph an endoscope image. An electronic endoscope in which the image pickup element 34 is arranged inside the distal end of the insertion portion 4 may be used.

An image pickup signal from the image pickup element 34 is converted into a video signal which can be observed with a monitor 37 by means of a video signal processing circuit 36 in a camera control unit (to be referred to as a CCU hereinafter) 35.

The video signal from the video signal processing circuit 36 is also output to the light source device 3a of this embodiment. In the light source device 3a, the video signal is output to a video signal inversion circuit 42 through a video signal input circuit (buffer circuit) 41. In the video signal inversion circuit 42, the video signal is inverted to generate a base signal of a correction signal to the DMD 24. Thereafter, the level of the inverted signal from the video signal inversion circuit 42 is shifted by a level shift circuit 43 to a level set by a brightness setting circuit 45.

The set level in the brightness setting circuit 45 can be set by the brightness level operation portion 12 of the operation panel 11. In this manner, the correction level is made variable by the level shift in the level shift circuit 43, so that the level is adjusted to obtain an appropriate observed image.

An output from the level shift circuit 43 is output to the DMD drive circuit 25, and an inverted image of an endoscope image obtained by image pickup is input to the DMD 24 as a correction signal.

The operation of this embodiment will be described below.

Figure 15:
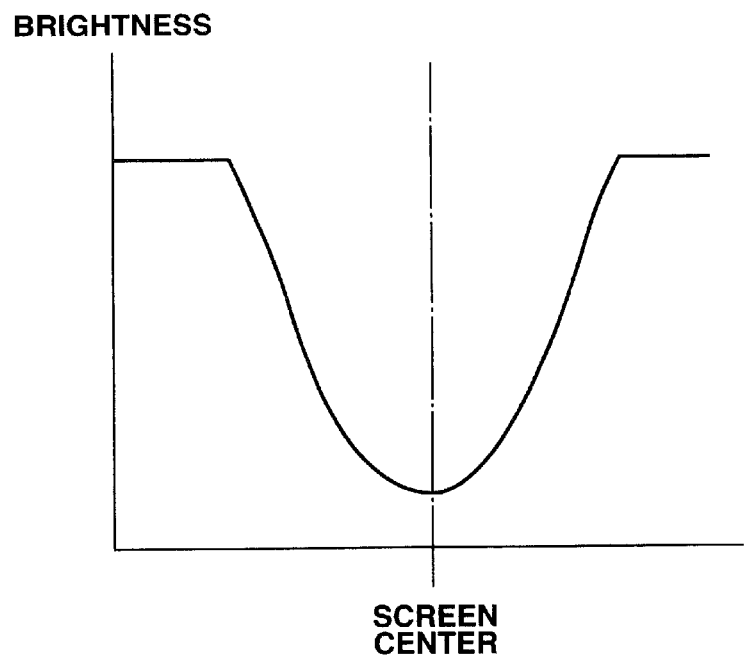
Figure 16:
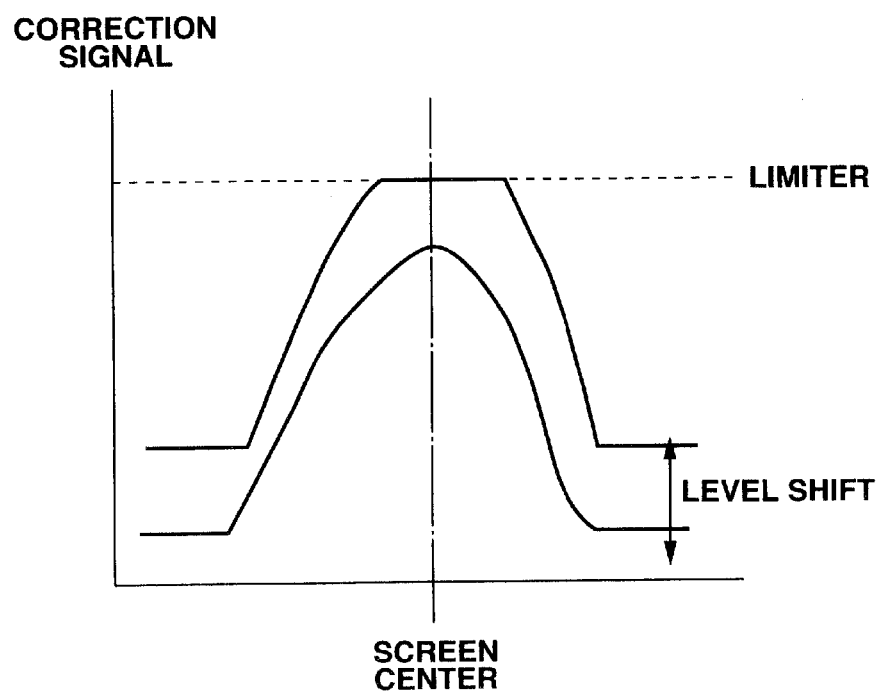

The level of a video signal serving as a tubular object to be observed is shown in FIG. 15, and a correction signal obtained at this time is shown in FIG. 16. In case of the tubular object, as shown in FIG. 15, the peripheral portion reaches the maximum amplitude of the video signal to be clipped, a "white out" state is set. Therefore, as a correction method, when an object has a screen center as a center, the DMD drive circuit 25 is controlled by using a correction signal obtained such that an inverted signal from the video signal inversion circuit 42 as shown in FIG. 16 is shifted by a level set by the brightness setting circuit 45, and an illumination light is supplied to the light guide 10 through the DMD 24 to illuminate an observed portion, so that the video signal is not set in the "white out" state clipped at the periphery. When the object is observed by using the screen center as the center, the optimum state can be obtained, and the signal level falls within the range in which observation can be performed.

When the object is not observed by using the screen center as the center, and the inverted image is input to the DMD 24, an incident light to the light guide 10 is being incident at a level obtained by integrating the image by coaxial circles. For this reason, the brightness of the center is enhanced, an outgoing light from the light source is controlled to decrease the peripheral brightness. When the convex object is used, a phenomenon which is contrast to the phenomenon of the convex object occurs. The brightness at the center decreases, and an outgoing light from the light source which does not darken the periphery is obtained.

When an object to be observed is not tubular and convex, an incident light to the light guide is incident at a level at which the image is integrated by coaxial circles. For this reason, when one half of the screen is bright, and the other half is dark, lights having averaged levels (light distribution is not changed) are incident on the light guide. Therefore, when an object which is axially symmetrical with respect to the screen center, correction is made. Otherwise, correction is not made as a result, a light distribution can be used without being changed.

This embodiment has the following effect.

The first embodiment describes a method of making correction by selecting a panel operation. However, the panel operation must be performed, and the operation is cumbersome. However, in this embodiment, the correction can be automatically made. More specifically, since distribution of an incident light to the light guide is automatically controlled on the basis of a video signal, an operator can continue appropriate observation without operating the operation panel.

In the embodiments described above, as a portion to which the endoscope is applied, a thin tubular object, e.g., a bronchus or a urinary duct may be used. In addition, the present invention can also be effectively used in pipe inspection with an industry endoscope. In addition, as the endoscope, not only a rigid endoscope but also a flexible endoscope can be used.

The third embodiment of the present invention will be described below with reference to FIGS. 17 to 22.

Figure 17:
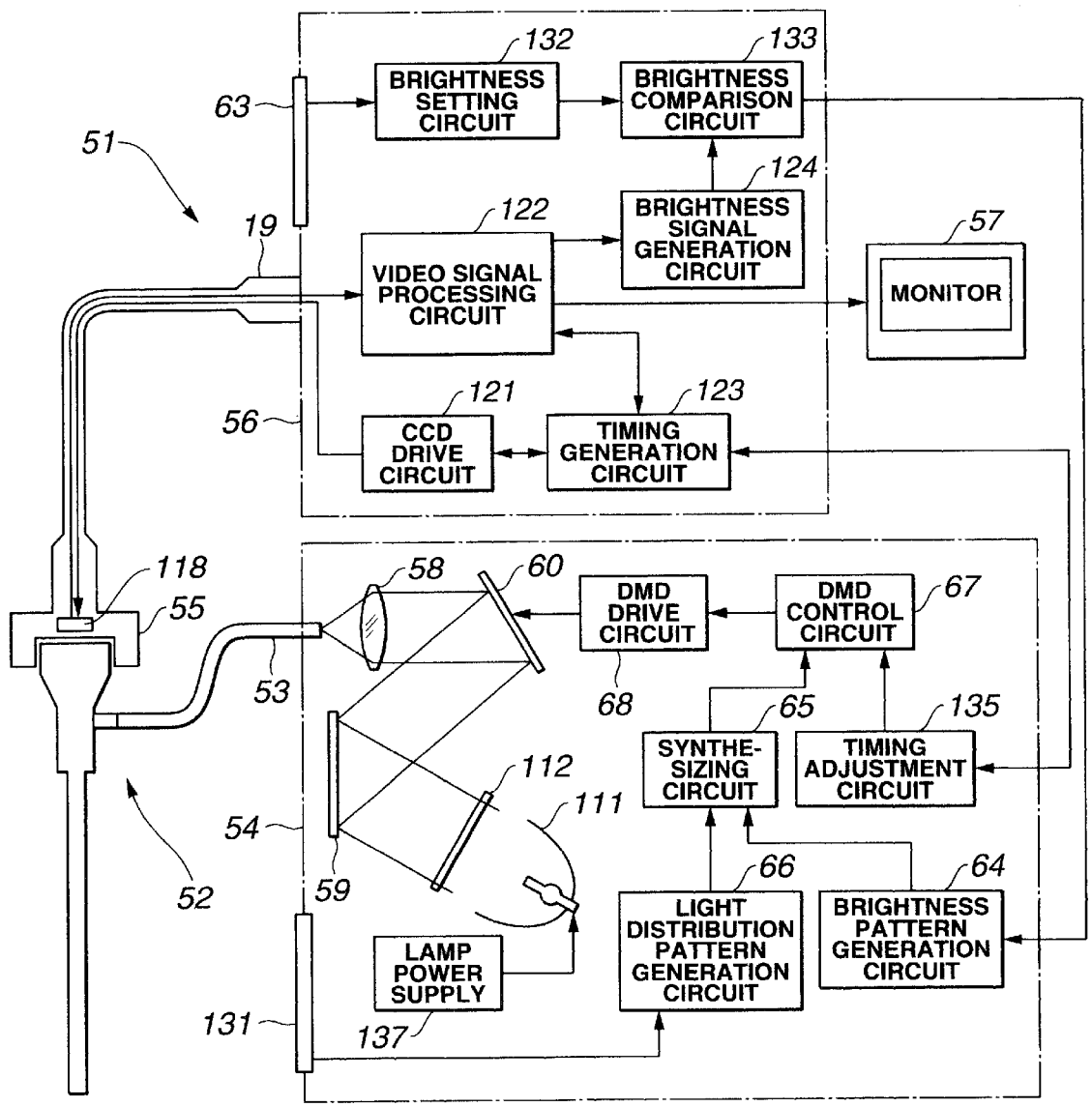

As shown in FIG. 17, an endoscope device 51 according to this embodiment comprises a rigid endoscope 52 for obtaining a tissue image in a living body through, e.g., a trocar or the like, a light source device 54 for supplying an illumination light to the rigid endoscope 52 through a light guide 53, a TV camera head 55, which is detachably connected to an eyepiece portion arranged on the rigid endoscope 52 on the hand side, for picking an image obtained by the rigid endoscope 52, and a camera control unit (to be referred to as a CCU hereinafter) 56 for processing an image pickup signal obtained by image pickup by the TV camera head 55 to display an observed image on a monitor 57.

A light source lamp 111 turned on by a lamp power supply 137 is arranged on the light source device 54, and a light from the light source lamp 111 is incident on a planar mirror 59 through an infrared cut filter 112. The reflected light from the planar mirror 59 is incident on a light modulation device 60, and the reflected light from the light modulation device 60 is converged by a convergent lens 58 to be incident on the light guide 52 by the optical lens system 58 for converging a light to the light guide 52. The optical system 58 is constituted by a single lens and a group of lenses.

Here, the light source lamp 111 has a parabolic surface, is designed to emit a parallel light, and is constituted by a high-pressure discharge tube such as a xenon lamp or a metal halide lamp having a high luminance.

The light modulation device 60 is an element in which a micromirror having a size of 640×480 is arranged on a silicon chip and which is held by a holding member on a yoke rotated about diagonals between two stable states and changed in a horizontal direction within a range of ±10°. This element is called a DMD (Digital Micromirror Device).

On the other hand, a CCD 118 is arranged in the TV camera head 55, and the TV camera head 55 is connected to the CCU 56 with a connector 119.

The camera control unit 56 comprises a CCD drive circuit 121 for driving the CCD 118, a video signal processing circuit 122 for processing an image pickup signal from the CCD 118 to output a video signal (e.g., an NTSC TV signal) to the monitor 57, a timing generation circuit 123 for generating a timing signal for synchronizing an image pickup timing of the CCD 116 and signal processing in the video signal processing circuit 122, and a bright signal generation circuit 124 for detecting the brightness of an image from the video signal from the CCD drive circuit 121 to generate a brightness signal.

The CCU 56 has an operation panel 63 having a brightness switch, and an operation signal of the bright switch is input to a brightness setting circuit 132 to set a brightness level serving as a reference. An output from the brightness setting circuit 132 is input to a brightness comparison circuit 133, and the brightness comparison circuit 133 compares the level of the output with the brightness level generated by the bright signal generation circuit 124 from an output from the video signal processing circuit 122 to generate a brightness control signal (comparison result).

The control signal (comparison result) generated by the brightness comparison circuit 133 is input to a brightness pattern generation circuit 64 of the light source device 54. An output from the brightness pattern generation circuit 64 outputs a brightness pattern (to be described later) in the light modulation device 60 to a pattern synthesizing circuit (to be referred to as a synthesizing circuit hereinafter) 65.

An operation switch which makes an instruction to uniformly illuminate a convex or concave object to be observed is arranged on the operation panel 131 of the light source device 54, and the operation switch inputs a selection signal to a light distribution pattern generation circuit 66. The light distribution pattern generation circuit 66 generates a pattern shown in FIG. 9 to input the pattern to the pattern synthesizing circuit 65.

Figure 18A:
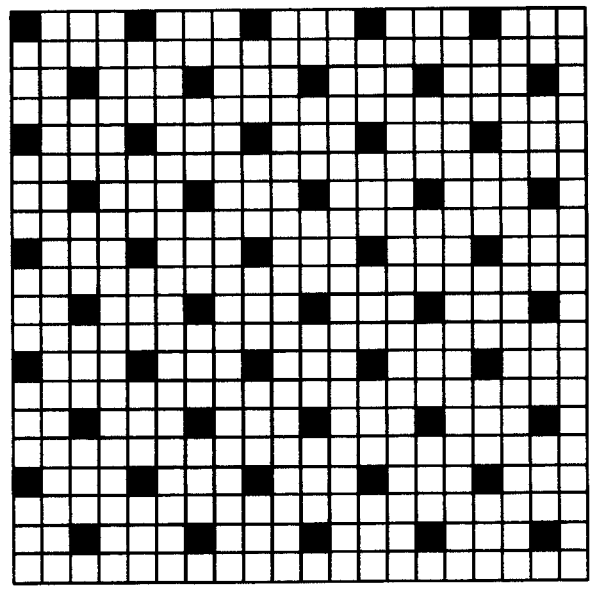
Figure 18B:
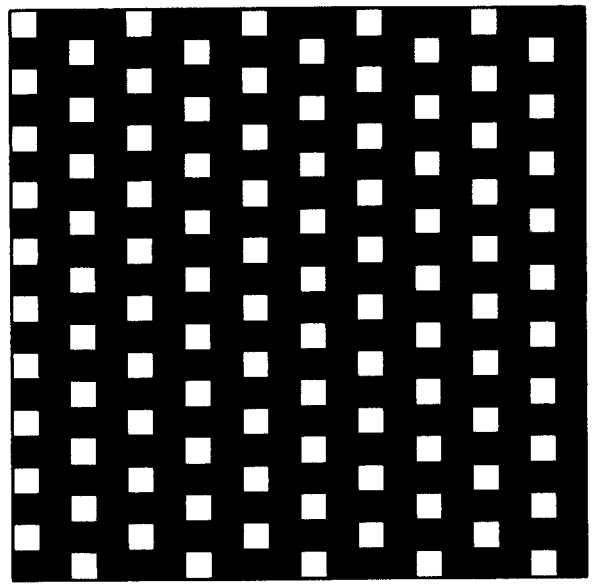
Figure 19A:
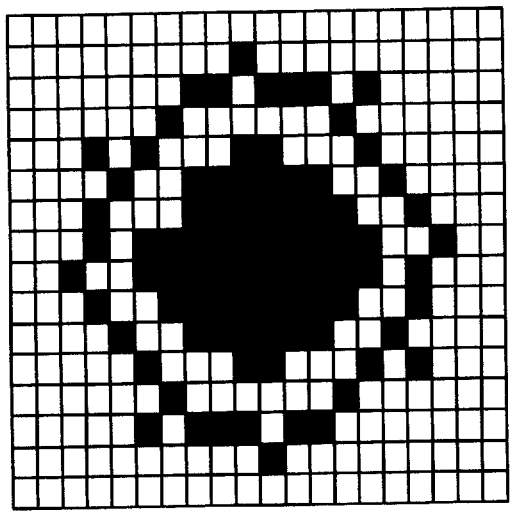
Figure 19B:
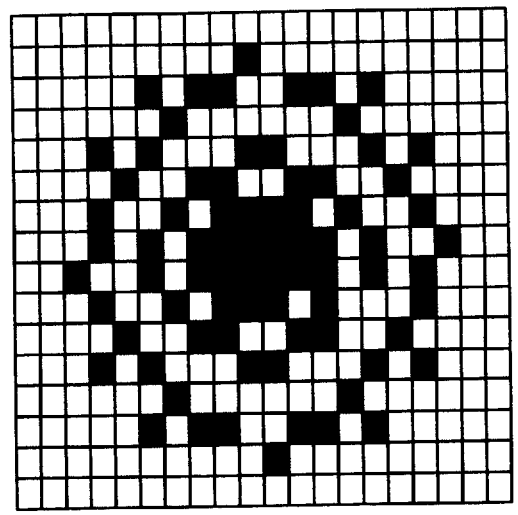
Figure 19C:
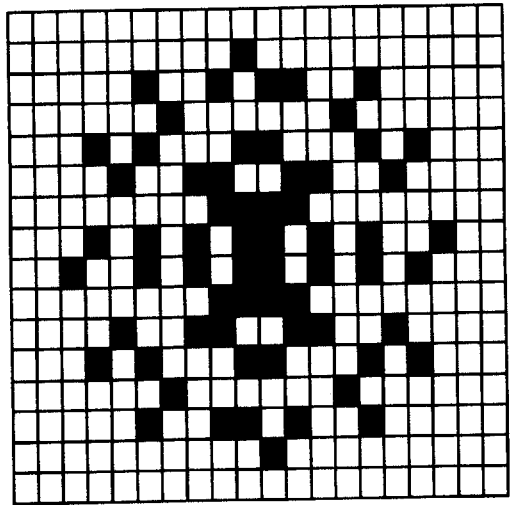
Figure 19D:
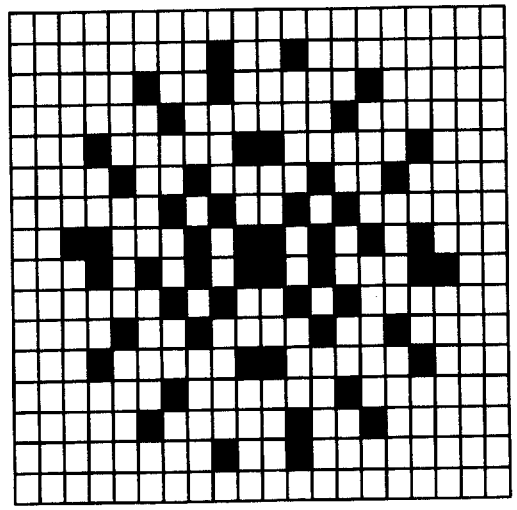

The pattern synthesizing circuit 65 synthesizes patterns as shown in FIGS. 18A and 18B with light distribution patterns as shown in FIGS. 19A to 19D to obtain patterns as shown in FIGS. 20A to 20D. The patterns in FIGS. 20A to 20D are input to a DMD control circuit 67 as control signals, and the DMD control circuit 67 controls a DMD drive circuit 68 to cause the DMD drive circuit 68 to drive a two-dimensional arranged element of the light modulation device 60.

Here, FIG. 18A shows a brightness pattern obtained when the pattern is determined as a dark pattern by the brightness comparison circuit 133, and FIG. 18B shows a brightness pattern obtained when the pattern is determined as a bright pattern by the brightness comparison circuit 133. FIGS. 19A to 19D show light distribution pattern for an concave object to be observed. FIGS. 20A to 20D show synthesis patterns obtained by synthesizing brightness patterns with the light distribution patterns for the concave object to be observed.

Figure 20A:
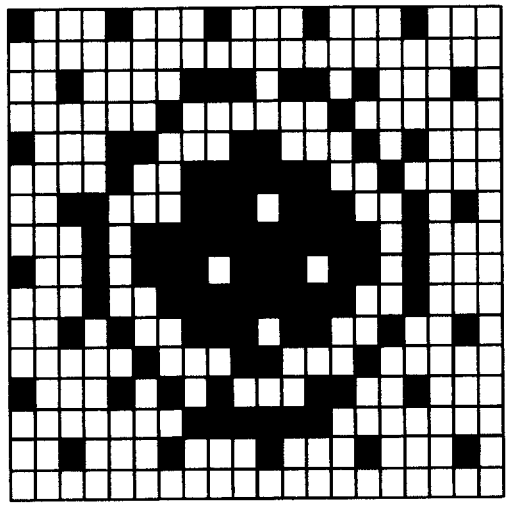
Figure 20B:
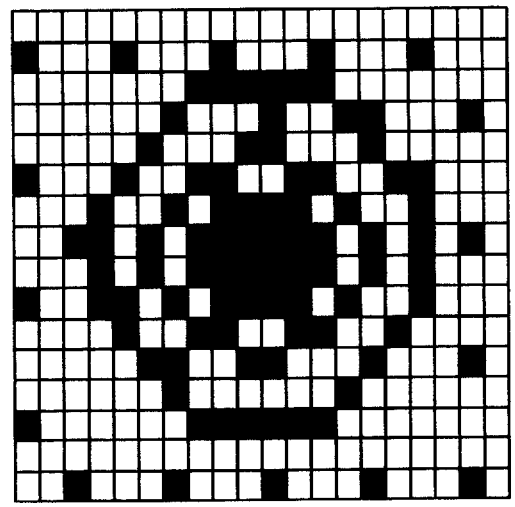
Figure 20C:
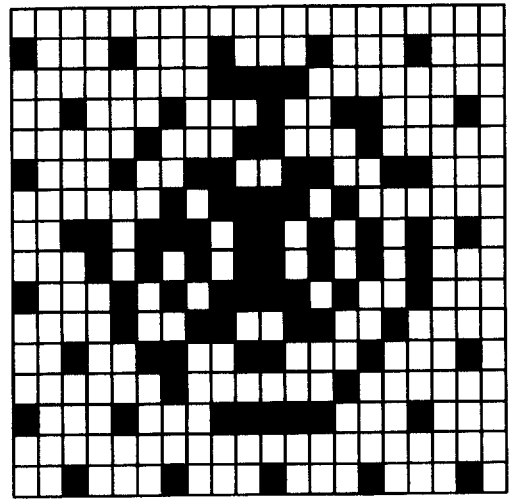
Figure 20D:
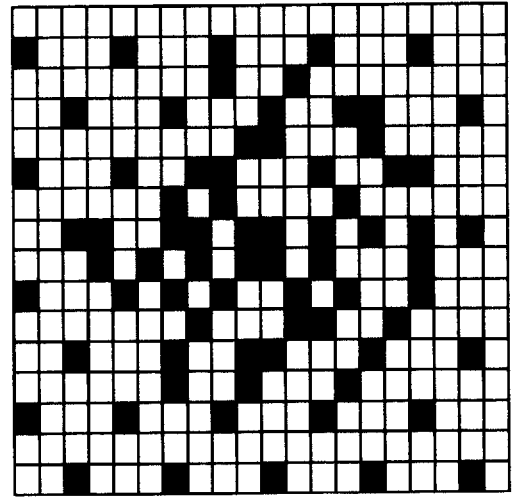
Figure 21A:
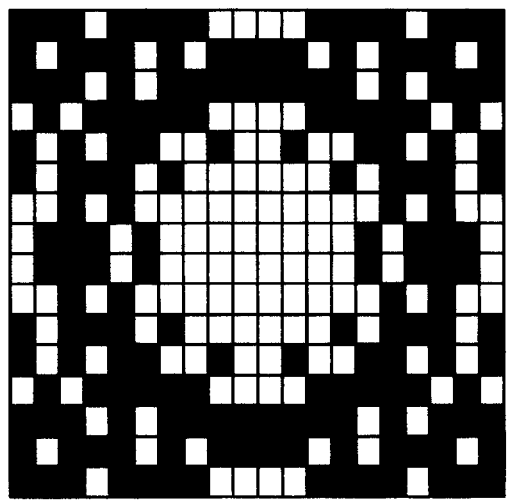
Figure 21B:
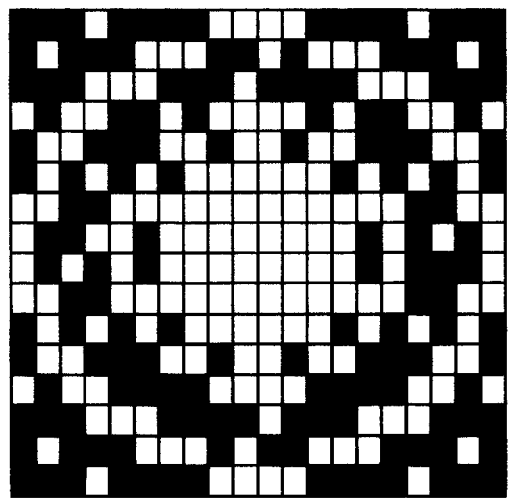
Figure 21C:
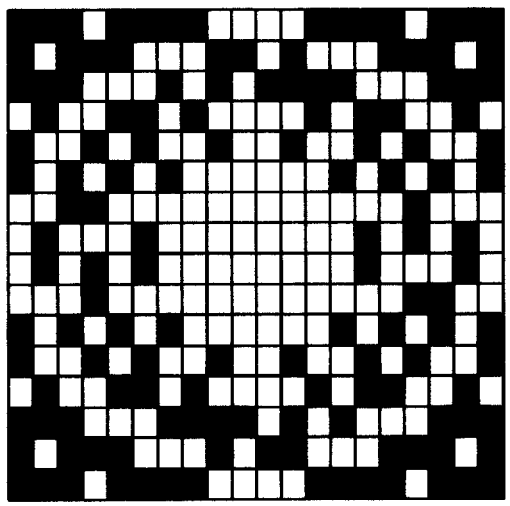
Figure 21D:
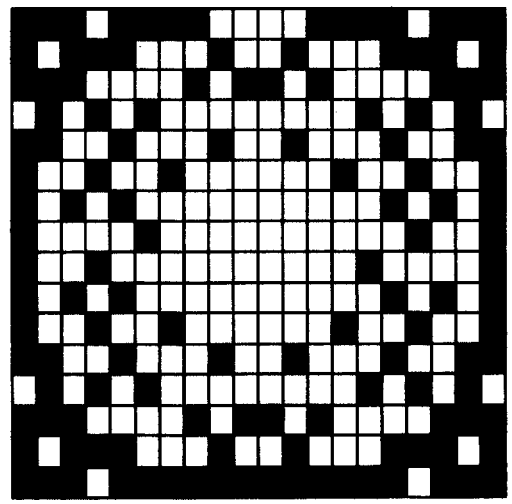

FIGS. 20C and 20D show the patterns whose brightnesses are controlled to be slightly darkened. In the pattern synthesizing circuit 65, to keep uniformity, simple addition is not performed to a concentrated dark portion, but an exclusive OR operation is performed to the portion. In addition, FIGS. 21A to 21D show light distribution patterns for a convex object to be observed or an intraluminalorgan. On the basis of patterns obtained by synthesizing the brightness patterns shown in FIGS. 18A to 18B with the light distribution patterns, the light modulation device 60 is driven.

When the micromirror serving as the two-dimensional arranged element of the light modulation device 60 is positioned at +10°, a light is incident on the light guide 53. When the micromirror is positioned at −10°, a light is not incident on the light guide 53. A portion to be brightened controls the pattern signal at +10°.

Figure 22A:
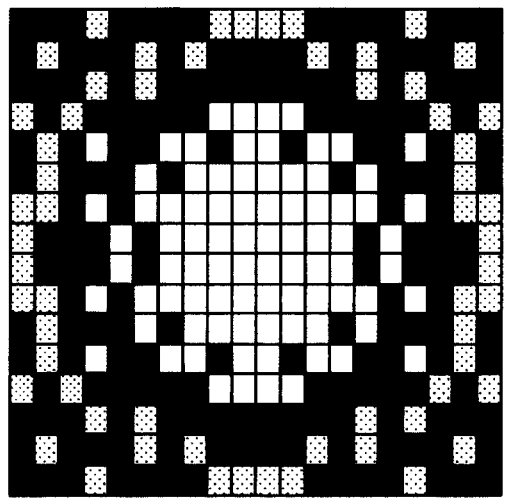
Figure 22B:
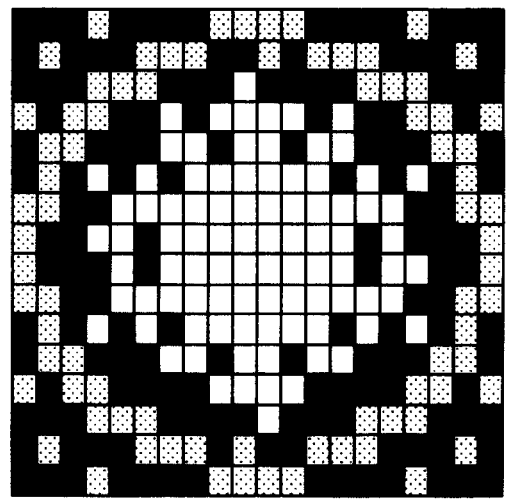
Figure 22C:
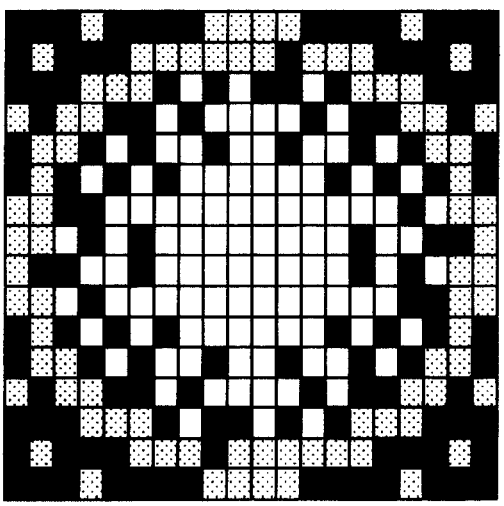
Figure 22D:
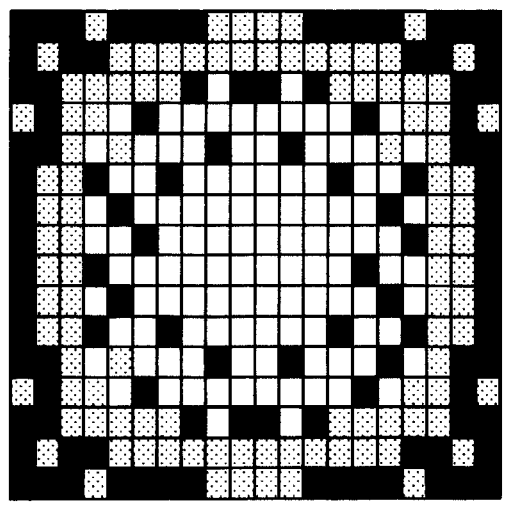

Changes of patterns added to the light modulation device 60 are shown in FIGS. 22A and 22D. In FIGS. 22A and 22D, the intensity of an incident light to the light guide 53 obtained by brightness control is the intensity of an intermediate passing light by performing, e.g., pulse drive to the micromirror serving as the two-dimensional arranged element of the light modulation device 60. FIGS. 22A to 22D show patterns obtained when the central portion is more bright. In FIGS. 22A and 22D, the patterns having intermediate levels are added. In this manner, gradual patterns can be performed as control including a smaller change.

The synthesizing circuit 65 switches a brightness pattern from the brightness pattern generation circuit 64 and a synthesized pattern from the light distribution pattern generation circuit 66 in a time series manner on the basis of a brightness signal input from the brightness comparison circuit 133.

The operation of this embodiment will be described below.

The TV camera head 55 is connected to the rigid endoscope 52, and the rigid endoscope 52 is inserted into the trocar inserted into a abdominal subjected to insufflation to perform endoscope observation. An endoscope image is picked by the CCD 116, and signal processing is performed by the CCU 56 to make it possible to perform observation with the monitor 57.

At this time, the timing generation circuit 123 outputs a signal corresponding to the brightness of the endoscope image. It is detected by comparison in the brightness comparison circuit 133 that the signal is darker than a reference set signal from the brightness setting circuit 132 or brighter than the reference set signal. The comparison result is input to the pattern generation circuit 64.

In the pattern generation circuit 64, mosaic patterns (shown in FIGS. 18A and 18B) which are gradually changed depending on a brightness are generated. In addition, when the operation switch of the operation panel 31 is selected depending on an object to be observed, the light distribution patterns in FIGS. 19A to 19D or in FIGS. 21A to 21D are output from the light distribution pattern generation circuit 66, and both the patterns are synthesized by the synthesizing circuit 65 to generate patterns shown in FIGS. 20A to 20D or the like. The two-dimensional arranged element of the light modulation device 60 is driven through the DMD control circuit 67 and the DMD drive circuit 68 in an all level reflection or shielding reflection state (in addition, an intermediate level reflection state).

For example, as a comparison result, it is determined that the endoscope image is dark with respect to the reference set signal. In this case, a pattern in which an illumination light is brighter than that of the previous state is generated, and the pattern generation circuit 64 is operated such that the number of all level reflections of the two-dimensional arranged element of the light modulation device 60 is increased. In this manner, an emission light (illumination light) from the light source device 54 becomes bright, and the endoscope image can be observed at appropriate brightness.

In contrast to this, if it is determined the emission light is too bright, such a pattern that the number of two-dimensional arranged elements in a shielding reflection state in the light modulation device 60 increases is set, and an operation is performed to decrease the intensity of an illumination light from the light source device 54.

According to this embodiment, the light modulation device 60 can control the intensity of the illumination light in a state in which a rate of usage of the light for a reflection method.

This embodiment has the following effect. Drive patterns the number of which is equal to the number of two-dimensional arranged elements of the light modulation device 60 constituted by a DMD are used in maximum usage or at an intermediate level, brightness control can be performed in a very wide dynamic range. In addition, since the response speed of the micromirror of the light modulation device 60 is very high, i.e., about 2 μm, high-speed brightness control can be performed.

The DMD can make the rate of usage of the light higher than the transmittance of a liquid crystal due to the reflection method.

Although the intermediate level of the intensity of an incident light to the light guide 53 can be obtained by pulse control by a pattern (see FIGS. 22A to 22D), an intermediate level obtained by continuously changing the level of the intensity of the incident light to the light guide 53 by PWM (pulse width control) or PFM (pulse frequency modulation) can also be obtained.

The fourth embodiment of the present invention will be described below with reference to an endoscope device according to the fourth embodiment in FIG. 23.

In this embodiment is almost the same as the third embodiment. For this reason, only different points will be described, the same reference numerals as in the third embodiment denote the same parts, and a description thereof will be omitted.

Figure 23:
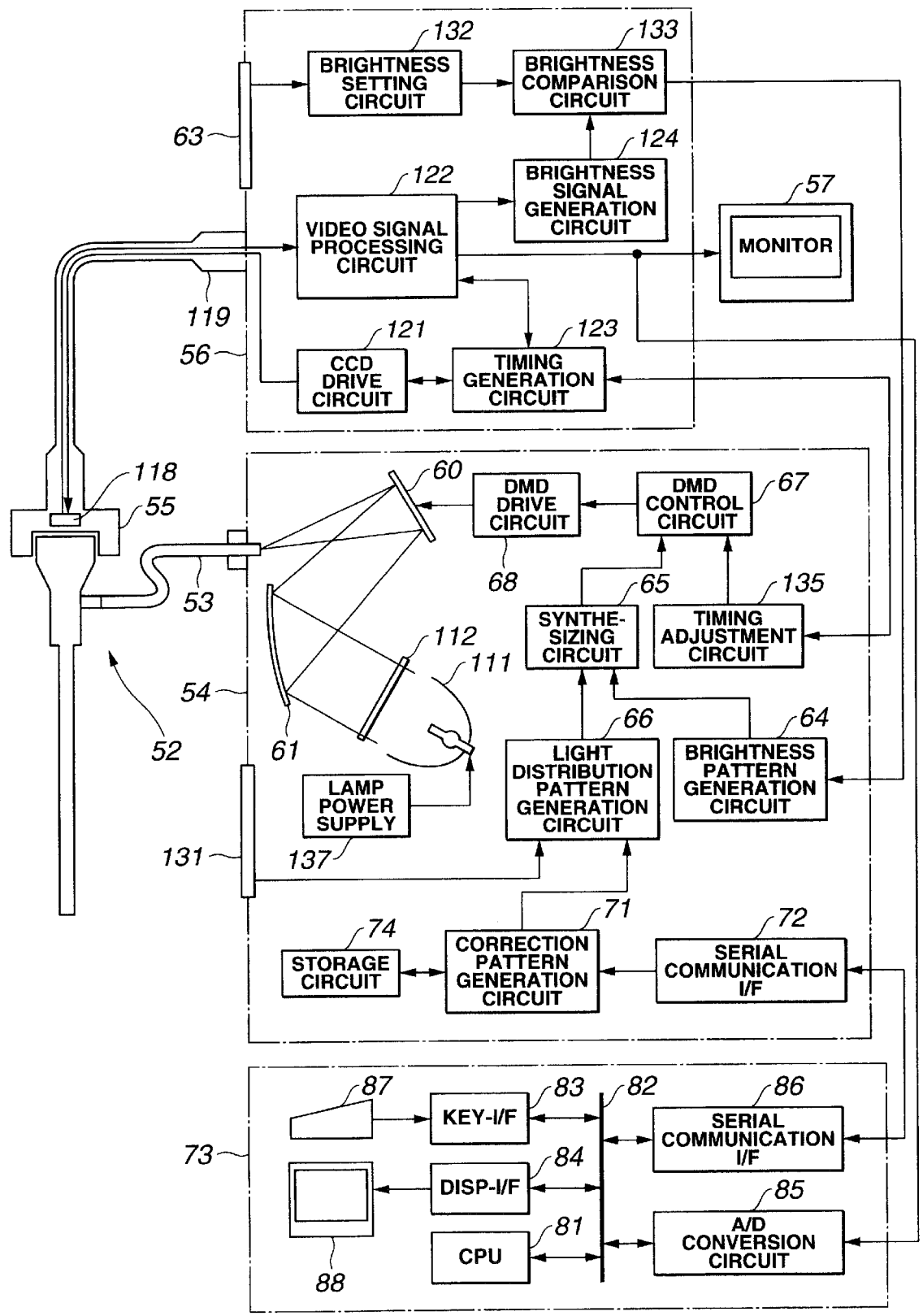
FIG. 23 is a block diagram showing the configuration of an endoscope device according to the fourth embodiment of the present invention.

In this embodiment, as shown in FIG. 23, a correction pattern generation circuit 71 is connected to the pattern generation circuit 66, and a serial communication I/F 72 is arranged in the correction pattern generation circuit 71 as an interface to an external device 73 (personal computer or the like). A storage circuit 74 in which a correction pattern from the external device 73 is stored is connected to the correction pattern generation circuit 71.

In the external device 73, a CPU 81 is connected to a BUS 82, an A/D conversion circuit 85, having an input/output interface of a DISSP-I/F 84, for A/D-converting a video signal from the video signal processing circuit 122 and a serial communication I/F 86 for performing communication with the serial communication I/F 72 of the insertion portion 4. A keyboard 87 is connected to the KEY-I/F 83, and a display 88 is connected to the DISSP-I/F 84, so that the external device 73 can be operated.

In the light source device 54, the illumination light of the light source lamp 111 is incident on a concave mirror 61 through an infrared cut filter 112. The concave mirror 61 has a reflective surface for converging a light. The reflected light from the concave mirror 61 is incident on the light modulation device 60, and the reflected light from the light modulation device 60 is incident on the light guide 53. The other configuration is the same as that of the third embodiment.

The operation of this embodiment will be described below.

In the external device 73, a control pattern in which an appropriate brightness and light distribution can be performed on the basis of a video signal is formed, and the pattern is loaded on the light source device 54, so that optimum control can be performed.

A correction pattern is stored in the storage circuit 74, and the correction pattern is selected by operating an operation panel 131 of the light source device 54. In this case, an external correction pattern stored in the storage circuit 74 is output to the synthesizing circuit 65 by the correction pattern generation circuit 71. In the synthesizing circuit 65, correction patterns and the brightness patterns shown in FIGS. 20A to 20D are alternately selected in a time series manner. Selection time is controlled such that a ratio of a light distribution to a brightness is determined by a brightness level, and a brightness and a light distribution (correction) which are appropriate to observation are obtained. The other operation is the same as that in the third embodiment.

This embodiment has the following effect.

In this manner, in this embodiment, in addition to the effect of the third embodiment, a brightness pattern can be set from the outside. For this reason, in particular, an industrial endoscope can applied in a wide range and used in a non-destructive testing or the like. The endoscope cannot be completely controlled by only a predetermined control pattern. The range in which the endoscope is applied can be increased.

Figure 25:
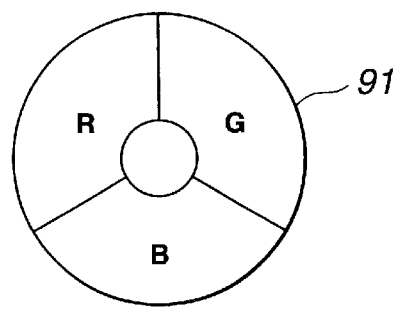
Figure 26:
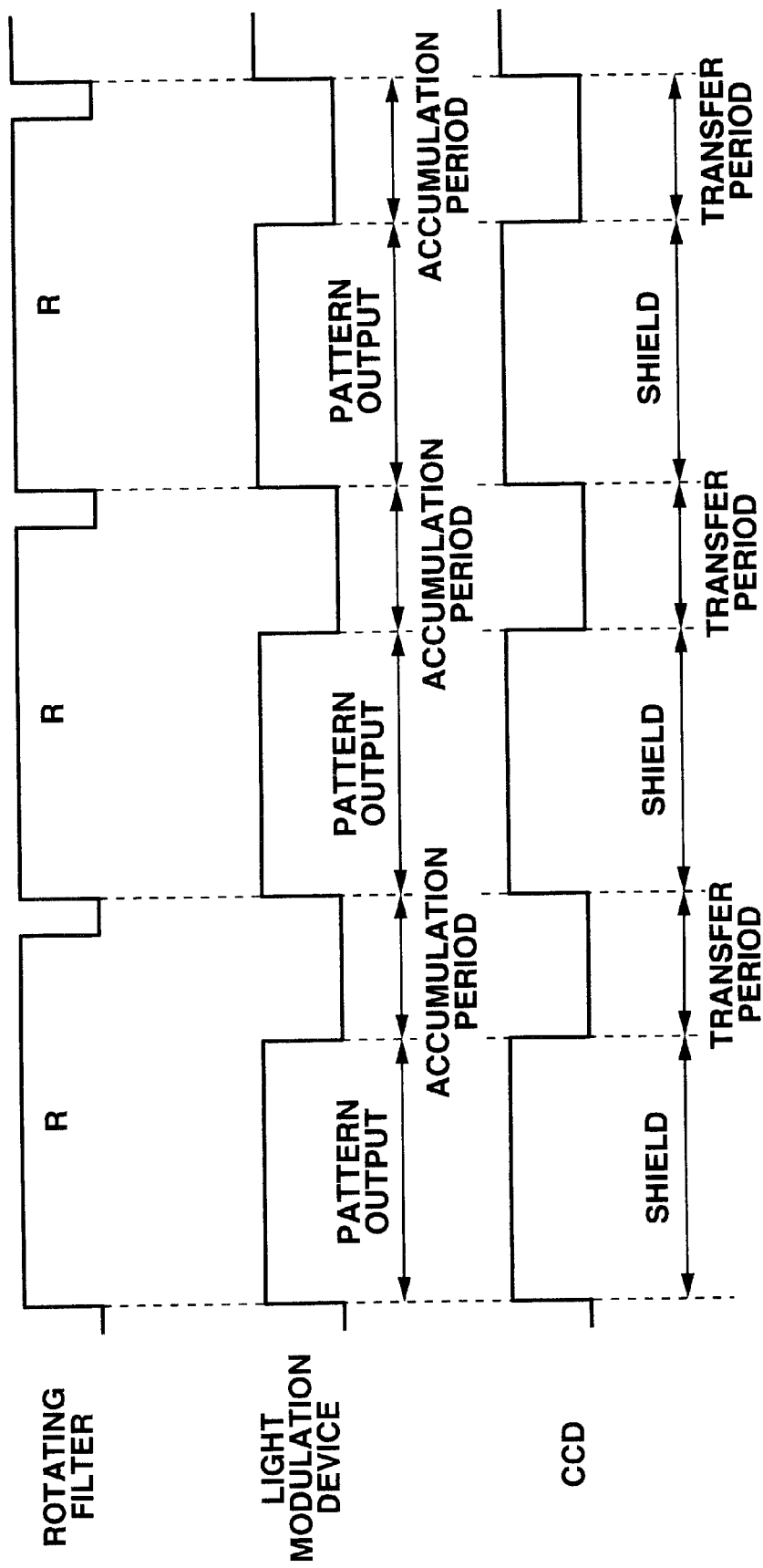

The fifth embodiment of the present invention will be described below with reference to FIGS. 24 to 26.

Since the fifth embodiment is almost the same as the third embodiment, only different points will be described. The same reference numerals as in the third embodiment denote the same parts in the fifth embodiment, and a description thereof will be omitted.

Figure 24:
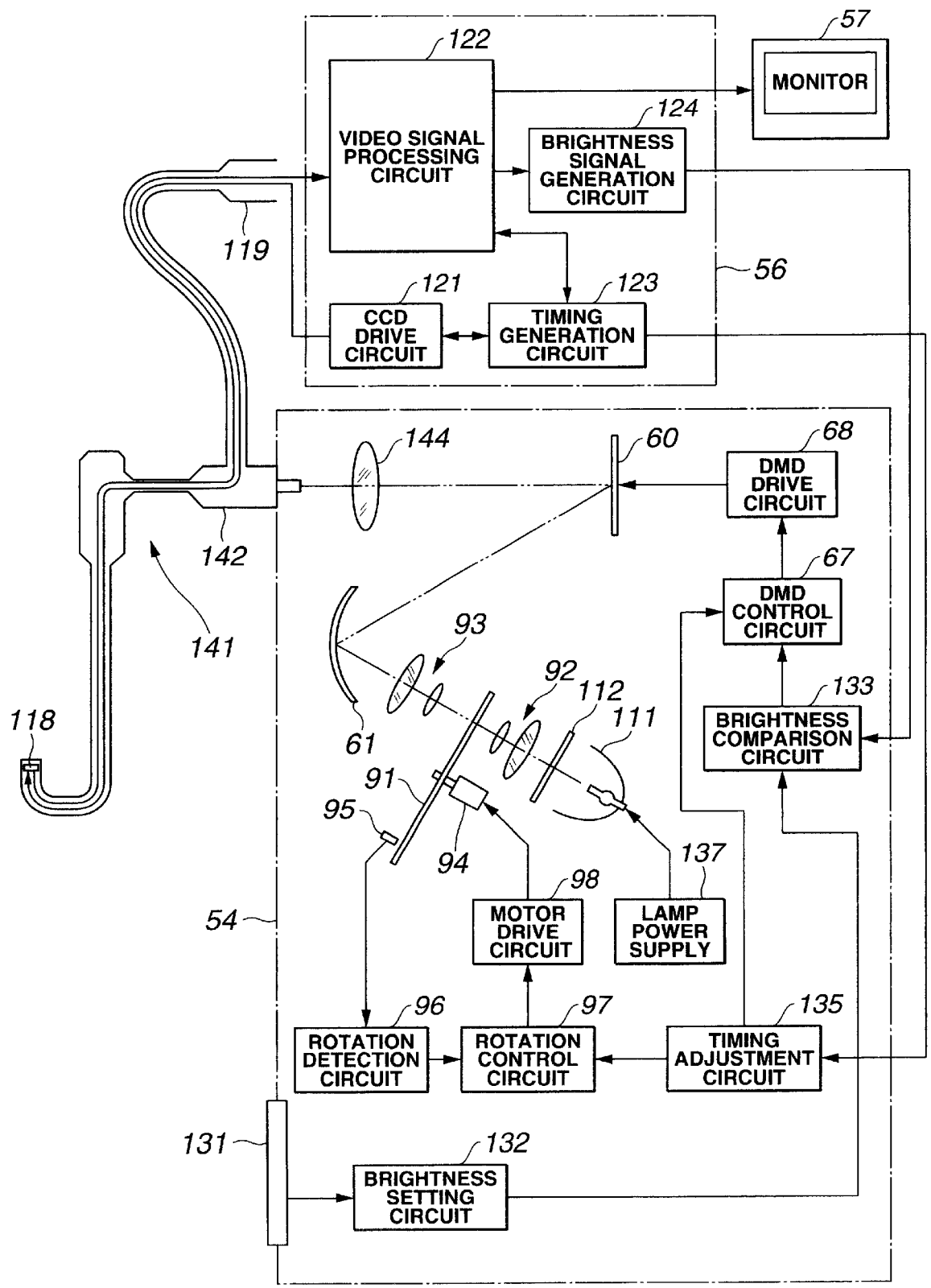
FIGS. 24 to 26 are related to the fifth embodiment of the present invention.

In this embodiment, as shown in FIG. 24, an electronic endoscope 141 is used in place of the rigid endoscope 52. As a signal line connected to the CCD 116 arranged on the distal end of the insertion portion of the electronic endoscope 141, the connector 119 arranged at the distal end of the cable extending from a connector 142 connected to the light source device 54 is detachably connected to the CCU 56.

In the light source device 54, an illumination light from the light source lamp 111 through a infrared cut filter is incident from an optical system lens 92 for decreasing the diameter of a flux of light passing through the filter of an RGB rotation filter 91 onto the mirror 61 through an optical system lens 93 for returning the diameter of the flux of light passing through the RGB rotation filter 91. Here, the RGB rotation filter 91 is designed R, G, and B filters shown in FIG. 25 are rotated to emit field sequential lights of R, G, and B.

The light reflected from the concave mirror 61 is incident on the light modulation device 60, and the light reflected by the two-dimensional array pattern of the micromirror of the light modulation device 60 is incident on the incident end face of the light guide 2 by a convergent lens 44.

The RGB rotation filter 91 is rotated by a motor 94, and the rotation is detected by a rotation sensor 95, so that the rotation is controlled to be synthesized with an image pickup timing from the CCU 56. An output from the rotation sensor 95 is input to a rotation detection circuit 96, a rotation detection signal is input to a rotation control circuit 97, and a drive signal is generated by the rotation control circuit 97 to establish synchronization with a timing output from the timing adjustment circuit 135. The drive signal is input to a motor drive circuit 98

A CCD 18 has no monochromatic transfer region, and is of a type in which an image is picked up by field sequence of RGB. A light shield period (read period of CCD signal) of a field sequential method is set at an image pickup timing on the basis of a signal from the timing adjustment circuit of the light modulation device. This relationship is shown in FIG. 16. Light distribution and brightness control are performed in the same manner as that of the third embodiment, the light distribution control and the brightness control are performed when a field sequential light is output. The other configuration is the same as the configuration in the third embodiment.

The operation of this embodiment will be described below.

Even in field sequence, the light modulation device 60 is driven by a pattern for controlling light distribution and brightness in field sequential emission, and control is performed to establish a state appropriate to observation. The other operation is the same as that of the third embodiment.

This embodiment has the following effect.

In this manner, in this embodiment, in addition to the effect of the third embodiment, control of light distribution and control of brightness can be performed by the field sequential method, and a high response speed and a wide dynamic range can be obtained.

A method by outputting a pattern matched to an observation station is applied to brightness control. However, brightness control performed by pulse width modulation such as PWM or PFM can also be realized. The target object can be achieved by combining a pattern control method and a pulse width control method.

The sixth embodiment of the present invention will be described below with reference to FIGS. 27 to 36.

Since the sixth embodiment is similar to the third embodiment, only different points will be described. The same reference numerals as in the third embodiment denote the same parts in the sixth embodiment.

Figure 27:
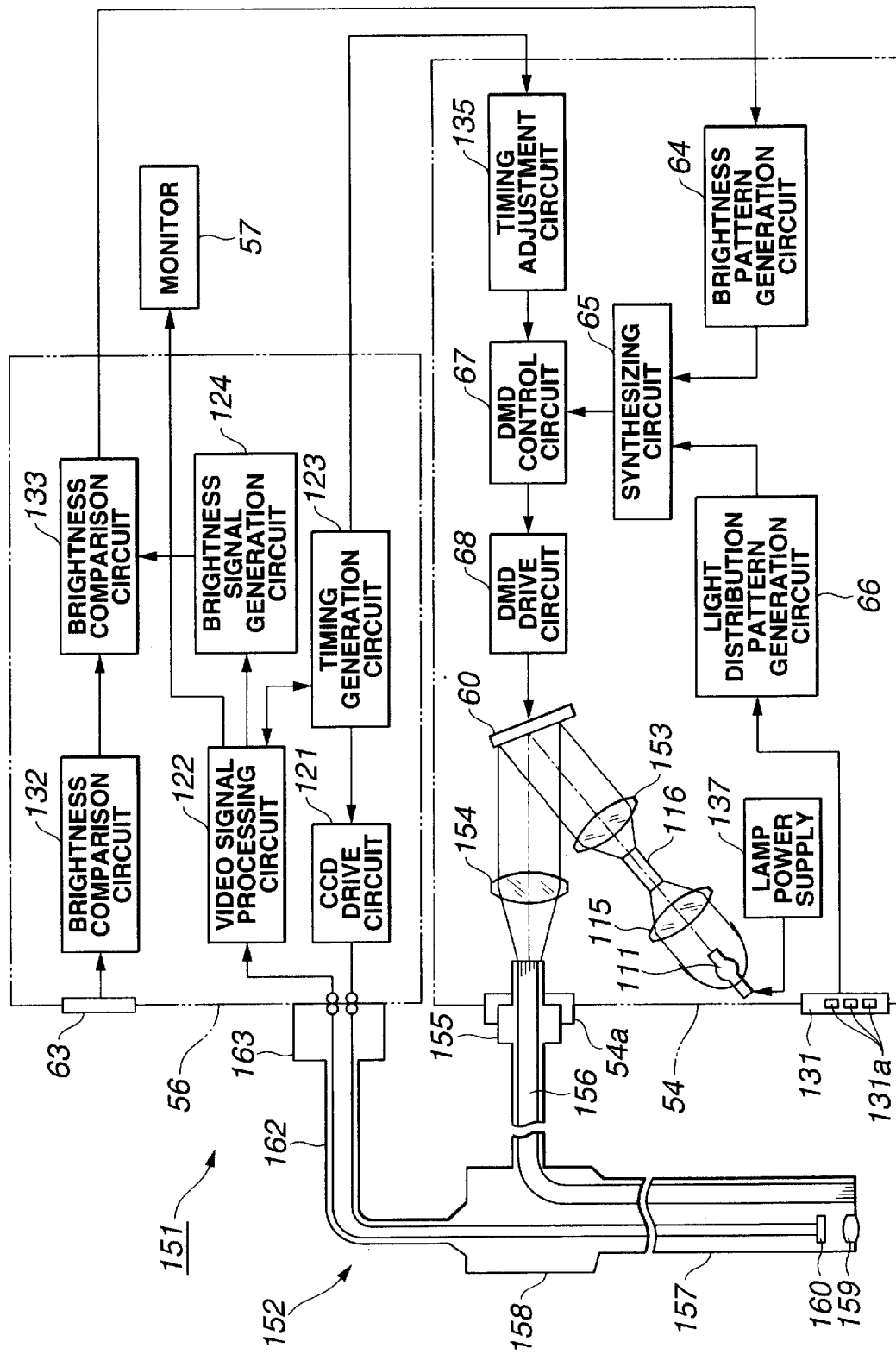

An endoscope device 151 according to this embodiment shown in FIG. 27 is constituted by an electronic endoscope 152, the light source device 54, the CCU 56, and the monitor 57.

Figure 28:
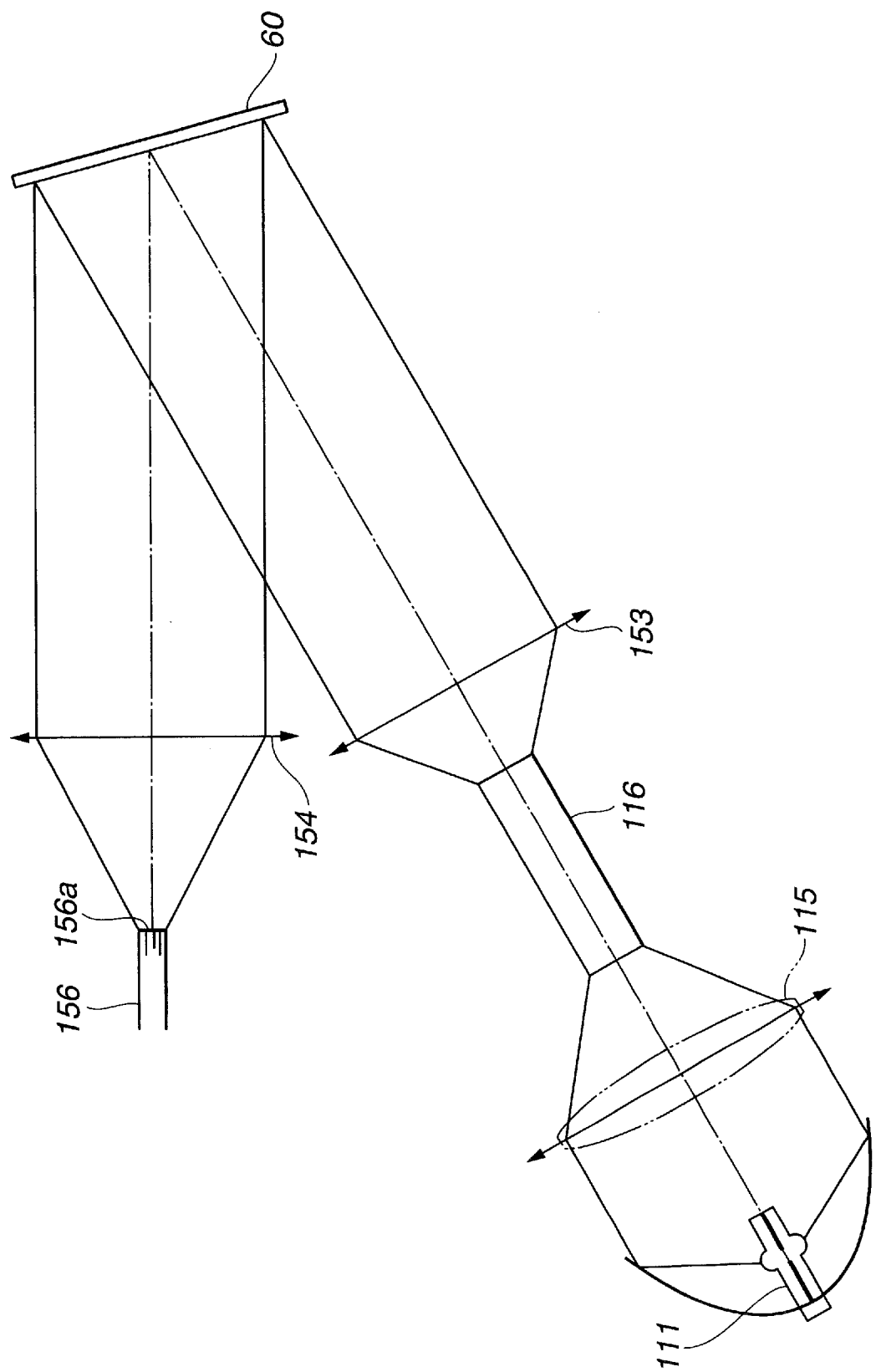

In the light source device 54, as shown in FIG. 28, a light of the light source lamp 111 is incident on an integrator (rod lens) 116 by a convergent lens system 115 arranged on the optical path of the light. A light uniformed by the integrator 116 is converted into a parallel flux of light by a collimator lens system 153 to be incident on the light modulation device 60 arranged on the illumination optical path. The light reflected by the light modulation device 60 is incident from the end face of a light guide connector 155 of the electronic endoscope 152 arranged on the light guide connector support 54a of the light source device 54 onto a light guide 156 serving as a light transmission means (light guide means) by a condensation optical system constituted by, e.g., a single lens or a group of lenses.

(As will be described below in FIG. 30), in this case, if the light modulation device 60 is set as an object point, arrangement is performed such that a pupil is projected on the end face of the light guide 156, thereby making it possible to perform light distribution control of coaxial circles.

The electronic endoscope 152 shown in FIG. 27 has. an insertion portion 157 inserted into a body cavity, and an operation unit 158 is arranged at the rear end of the electronic endoscope 152. A light incident on the light guide 156 is transmitted to the distal end portion of the insertion portion 157, and the light is delivered from the distal end face of the insertion portion 157 to illuminate an object to be photographed such as an affected part in the body cavity.

The image of the illuminated object is formed at a focusing position of an objective lens 159 by the objective lens 159. A CCD 110 is arranged at the focusing position to perform photoelectric conversion.

The CCD 110 is connected to a signal line, and the signal line is inserted through the cable 112 extending from the rear end of the electronic endoscope 152 to be connected to the CCU 56 through a signal connector.

In the light modulation device 60, as shown in FIG. 29, a large number of micromirrors 166 are arranged at grating points on a silicon substrate 165 such that the micromirrors 166 can be freely pivote dat, e.g., ±10°, so that a light receiving surface 167 is formed. With respect to an incident light from the (light source lamp 111) collimator lens system 153, when the micromirrors 166 is set at, e.g., −10°, as indicated by solid lines, the micromirrors 166 are set such that a reflected light is incident on the light guide 156 through the condensation optical system 154. As indicated by a dotted line, when the micromirrors 166 are set at +10°, the reflected lights are reflected in different directions, and the reflected lights are not incident on the light guide 156.

Figure 30:
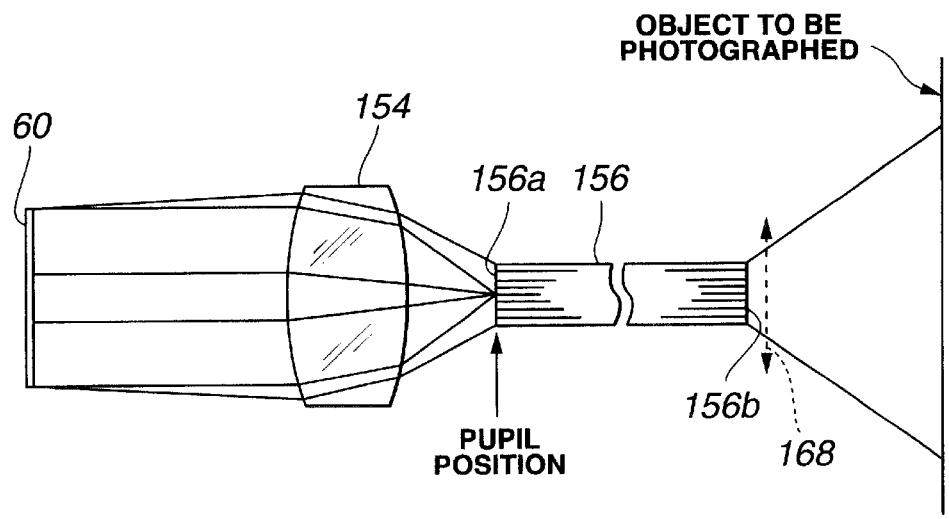

FIG. 30 shows a manner in which a light reflected by the light modulation device 60 is projected on an object to be photographed. If the light guide 156 is regarded as an object point, the light modulation device must be arranged at an approximate pupil position or near the pupil position, and the condensation optical system 154 must be arranged to condense the light to an end face 156a of the light guide 156 on the incident side.

If the light modulation device 60 is regarded as an object point, it can be said that a light is condensed by the condensation optical system 154 to the end face 156a on the incident side of the light guide 156 arranged at the approximate pupil position or near the pupil position. The light incident on the end face of proximal 156a is transmitted to a distal end face (end face on delivery side) 156b by the light guide 156, and a light delivered from the distal end face 156b is projected on the object to be photographed. As indicated by a dotted line, an illumination lens system 168 may be arranged opposite to the distal end face 156b (FIG. 30).

Figure 31:
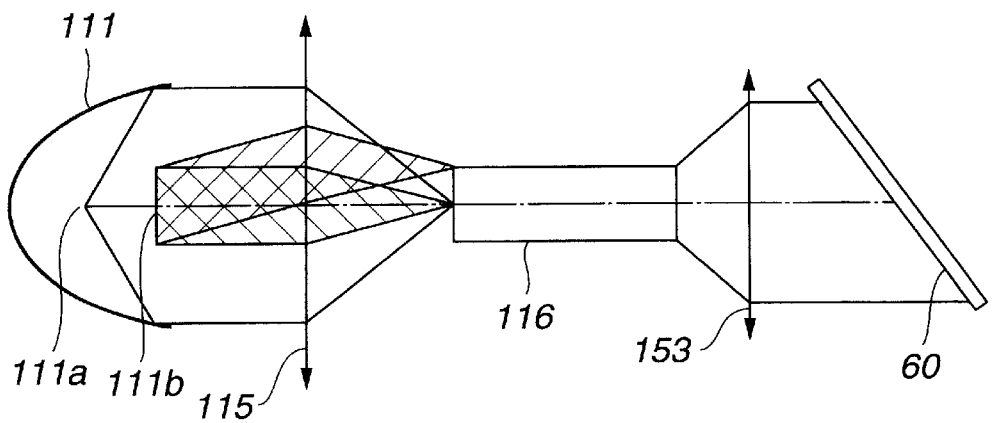

FIG. 31 shows an optical system near the integrator 116.

As shown in FIG.28 since the light source lamp 111 causes a luminescent spot of the ends of two electrodes to emit light, the emitted light is shielded at a portion near the optical axis by the electrodes arranged in the direction of the optical axis. Therefore, when the light is guided to the light modulation device 60, the light modulation device 60 may set an uneven illumination state.

In this embodiment, in order to eliminate the uneven illumination, as shown in FIG. 31, a light from the luminescent spot of the lamp 111 is incident on the integrator 116 having the incident end face arranged at the approximate pupil position by the convergent lens 115.

When the integrator 116 is arranged at the approximate pupil position, the illuminance distribution of the incident end face of the integrator 116 is high at the center and is low at the around. However, when total reflection is repeated in transmission by the integrator 116, the illuminance distribution on the emission end face is made uniform.

When the integrator 116 is arranged such that the emission end face and the front focal point position approximately coincide with each other, and when the light modulation device 60 is arranged at a position spaced apart from the rear focal point position of the collimator lens 153, the distribution of a shielded portion (hatched portion shown in FIG. 31 is a shielded portion 111b obtained by the electrodes) indicated by a hatched portion in FIG. 31 is made uniform, and a uniform parallel light can be supplied to the light modulation device 60.

In this embodiment, depending on the bright/dark characteristics of an object to be photographed (object to be observed), when the object is tubular, a plurality of selection switches 131a for selecting an object which is convex at the center or the like are arranged on the operation panel 131. By the selection operation of the selection switches 131a, the light distribution pattern generation circuit 66 generates a corresponding light distribution pattern. The other configuration in this embodiment is the same as that in FIG. 17.

The operation of this embodiment will be described below.

In this embodiment, a light reflected by the light modulation device 60 is guided to the end face 156a on the incident side of the light guide 156 of the electronic endoscope 152 arranged at the approximate pupil position by the condensation lens system 154, and a light transmitted from the distal end face 156b of the light guide 156 is delivered to illuminate an object to be photographed such as an affected part.

Figure 32A:
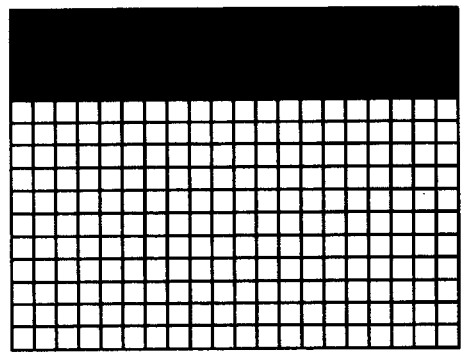
FIGS. 32A to 32C are diagrams showing light distribution patterns.
Figure 32B:
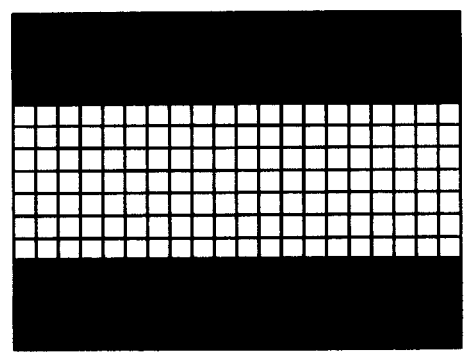
Figure 32C:
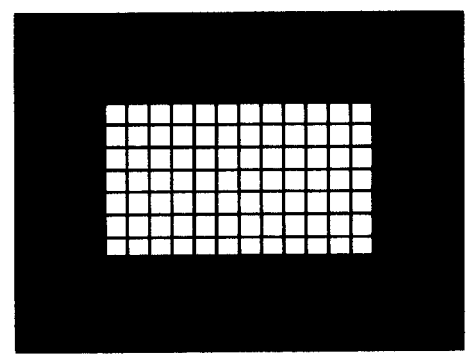

When a tubular object to be photographed has a dark central portion and a bright periphery is used, the selection switch 131a for the tubular object is operated, light distribution patterns shown in FIGS. 32A, 32B, and 32C are generated. In this case, when the difference of the brightnesses of the central portion and the around portion is on a low level, the pattern in FIG. 32A is obtained; when the difference is on an intermediate level, the pattern shown in FIG. 32B is obtained; and when the difference is on a high level, the pattern shown in FIG. 32C is obtained.

The light distribution pattern generated by the light distribution pattern generation circuit 66 and a brightness pattern from the pattern generation circuit 64 are synthesized with each other by the synthesizing circuit 65 to output the synthesized pattern to the DMD drive circuit 68 through the DMD control circuit 67, and the light modulation device 60 is driven by an output signal from the DMD drive circuit 68.

Figure 33:
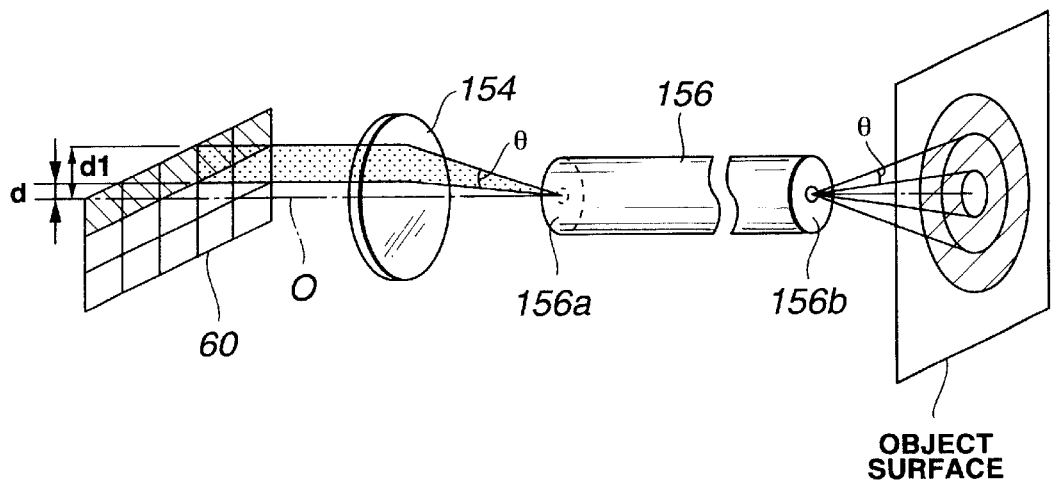

FIG. 33 shows a manner in which an object to be photographed is illuminated with a light reflected by the light modulation device 60 having a micromirror having the light distribution pattern in FIG. 32A. In FIG. 33, a micromirror portion in which a light is not incident on the light guide is indicated by a hatched portion.

In this case, a micromirror (hatched portion) having a distance d from an optical axis O is in a state in which a light is not incident on an end face 106a on the incident side of a light guide 106. When the light is incident at the angle, a coaxial angle distribution is obtained on the emission side due to the characteristics of the light guide. When a light is irradiated from a distal end face 106b of the light guide 106 onto the object, the peripheral portion is darker than the central portion.

More specifically, in FIG. 33, for example, in a state which an angle-θ portion indicated by a halftone portion is shielded by a shield reflection portion having the distances d to d1, when a light is incident on the end faces 106a on the incident side of the fibers of the light guide 106, the light is transmitted through the fibers and emitted from the distal end face 106b, the light is emitted to the object in a state in which the angle-θ portion is darker than the central portion in the form of coaxial circles.

Therefore, on the light modulation device 60 side, for example, when all ring portions each having the distances d to d1 are set in the state of the shield reflection state, the angle-θ portion of the object on the object side is entirely dark. In general, on the light modulation device 60 side, in the ring portion having a distance from the optical axis O, when a ratio of the area of the shielded portion in the ring portion to the area of the ring portion is high, the coaxial angle portion corresponding to the distance becomes dark.

FIG. 33 shows a manner in which a light is incident or emitted by one fiber. However, the same operation is performed by a bundle of fibers.

For this reason, when a tubular object to be photographed is illuminated by employing the light distribution pattern, the dark portion on the center side can be illuminated with a light having a higher intensity. In comparison with a case in which an object is uniformly illuminated, the brightness distribution of an object image is flattened and easily diagnosed. Therefore, with simple brightness correction, an image having a brightness at which the image can be diagnosed can be obtained.

According to the embodiment, when the simple light distribution pattern is used as described above, an illumination state in which a tubular object can be easily diagnosed can be set.

Figure 34A:
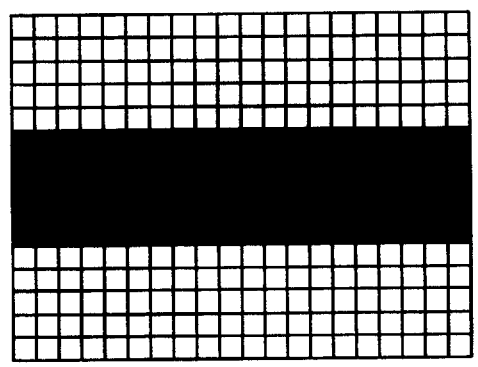
FIGS. 34A to 34C are diagrams of other light distribution patterns.
Figure 34B:
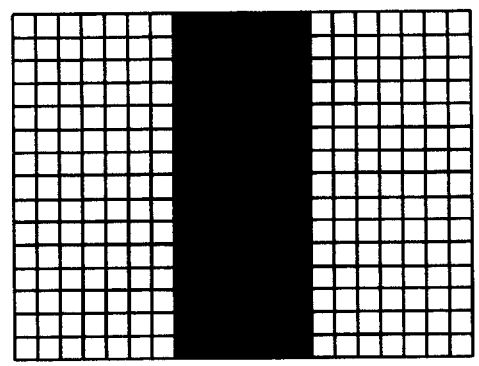
Figure 34C:
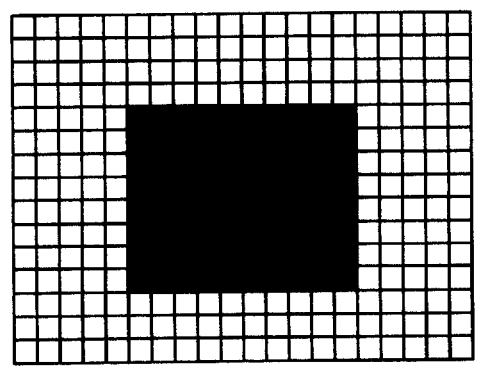

In addition, when an object to be photographed having a central portion which is projected as a projection is uniformly illuminated, the projected portion is too bright. For this reason, when the selection switches 131a, arranged on the operation panel 131, for an object having a central portion which is projected is selectively operated, light distribution patterns shown in FIGS. 34A, 34B, and 34C are generated. In this case, the difference between the brightness of the central projected portion and the brightness of the peripheral portion is on a low level, the light distribution pattern shown in FIG. 34A is obtained; when the difference is on an intermediate level, the pattern shown in FIG. 34B is obtained; when the difference is on a high level, the pattern shown in FIG. 34C is obtained.

Also in this case, by a simple light distribution, an illumination state in which diagnosis can be easily performed can be set even though an object to be photographed which is projected at the central portion is used.

In the embodiment, when the light modulation device 60 is arranged at the pupil position, coaxial light distribution control is performed. The other operation is performed as in the third embodiment.

The embodiment has an advantage that such illustration that an image which can be easily diagnosed by a light distribution pattern depending on the brightness/darkness distribution of an object to be photographed is performed.

As shown in FIG. 30, an optical system in which the convergent lens 154 is arranged to locate the light modulation device 60 at an approximate pupil position can be applied to a light source device having a configuration different from the optical system shown in FIG. 27.

Figure 35:
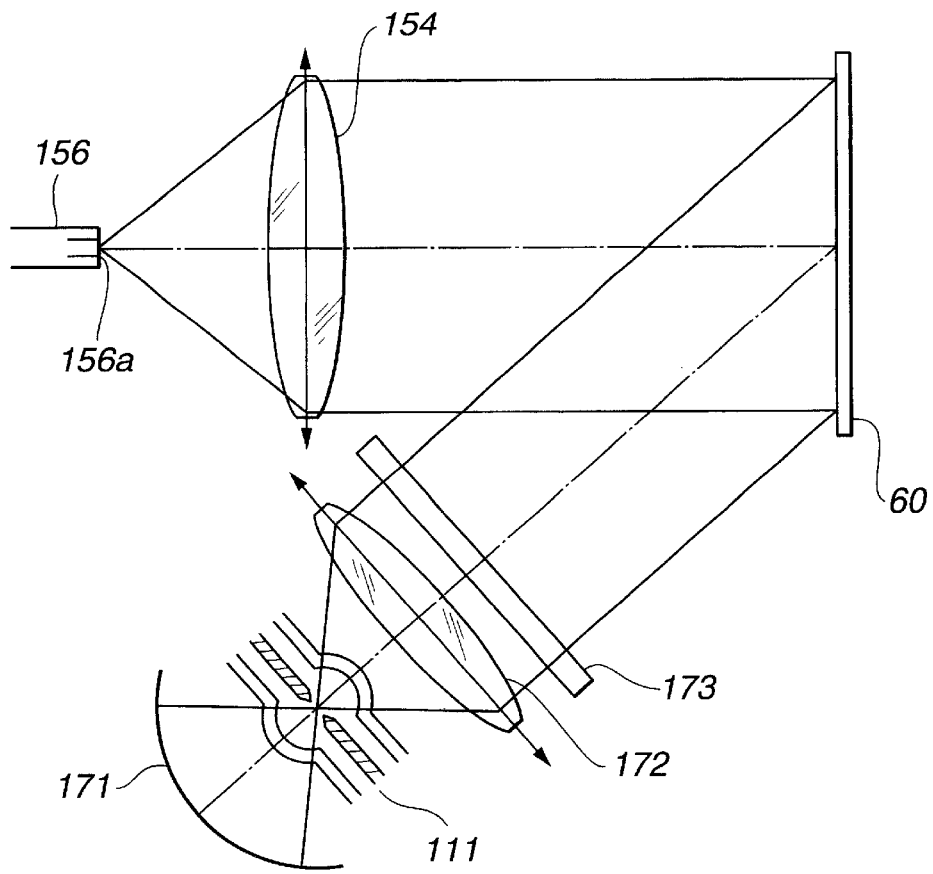

FIG. 35 shows an optical system in a modification in which uneven illumination is prevented from being performed. In this modification, a vertical light source lamp 111 perpendicular to an optical axis is employed.

As described above, for example, the light source lamp 111 shown in FIG. 28 is of a horizontal type in which both the electrodes are arranged in the direction of an optical axis. However, in FIG. 35, both the electrodes are vertical to the optical axis.

A light forwardly emitted from a portion between both the electrodes and a light backwardly emitted and reflected by a spherical mirror 171 are incident on a convergent lens system 172 for converging a parallel flux of light to be converted into a parallel flux of light. The flux of light passes through an IR/UV cut filter 173 for cutting infrared rays and ultraviolet rays, and only a white light component is transmitted through the IR/U cut filter 173. The white light component is incident on the light modulation device 60.

The reflected light reflected by the light modulation device 60 arranged at an approximate pupil position is converged by the convergent lens system 154 to be incident on the light guide 156 in which the end face 156a on the incident side is arranged. In this case, the shield by both the electrodes does not affected to the light being incident on the light modulation device 60, uneven illumination is reduced.

Figure 36:
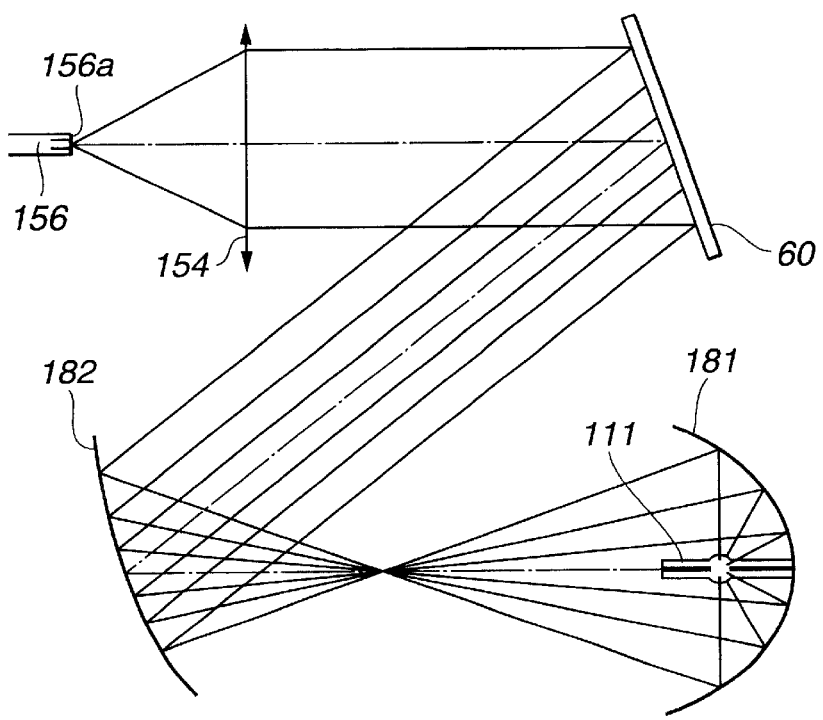

FIG. 36 shows a modification in which a light reflected by the mirror 61 in FIG. 17 is incident on the light modulation. device 60, for example.

The light from the lamp 111 is reflected by a concave mirror 181 having a converging function to be converged on one point. Thereafter, the converged light is enlarged and reflected by the concave surface of a spherical mirror 182 to obtain a parallel flux of light. The resultant light is incident on the light modulation device 60 arranged at an approximate pupil position, and the reflected light is incident on the end face 156a on the incident side of the light guide 156 by the convergent lens 154.

In the embodiments described above, even though the light guide is a bundle of optical fibers which are not arrayed, an intensity distribution obtained by an incident angle of the incident light is stored, and the intensity distribution is used as the intensity distribution of an emitted light. For this reason, light distribution control is effectively operated. As the light guide, not only a light guide constituted by a bundle of optical fibers, but also a liquid type light guide may be used.

In the third to sixth embodiments, as the light source lamp 111, a lamp having a high luminance is preferably used, and a high-pressure arc discharge lamp such as a xenon lamp or a metal halide lamp is preferably used. As the lamp 111, a tungsten lamp or a halogen lamp may also be used.

In addition, in each of the embodiments described above, a rigid endoscope, an electronic endoscope, or the like is used as an endoscope. However, another endoscope (rigid endoscope, optical flexible endoscope, electronic endoscope, side-viewing endoscope, and a stereoscopic endoscope, or the like), e.g., any endoscope in which an illumination light is supplied from a light source device to be irradiated from the distal end onto a portion to be observed may be used.

The seventh embodiment of the present invention will be described below with reference to FIGS. 37 to 40.

An endoscope device 201A according to the seven them bodiment of the present invention shown in FIG. 37 comprises a TV-camera-connected endoscope 204A obtained by connecting a TV camera 203 to an optical endoscope device 202, a light source device 205 for supplying an illumination light to the optical endoscope device 202, a camera control unit (to be referred to as a CCU hereinafter) 206 for performing signal processing to an image pickup element incorporated in the TV camera 203, and a monitor 207 for displaying a video signal from the camera control unit 206.

The optical endoscope device 202 is constituted by, e.g., a rigid endoscope. The rigid endoscope has a rigid and narrow and long insertion portion 208, a grasping portion (operation portion) 209 arranged at the rear end of the insertion portion 208 and having a large diameter, and an eyepiece portion 210 arranged at the rear end of the grasping portion 209. A light guide connector 212 at the other end of a light guide cable 211 having a proximal end connected to the grasping portion 209 is detachably connected to a light guide connector support 213 of the light source device 205.

A camera head 214 of the TV camera 203 is connected to the eyepiece portion 210, and a signal connector 216 at the end of a camera cable 215 extending from the camera head 214 is detachably connected to a signal connector support 217 of the CCU 206.

In addition to the light guide connector support 213, a power supply switch and an operation panel 218 are arranged on the front surface of the light source device 205, and a light intensity setting switch 219 is arranged on the operation panel 218.

The signal receptacle 217 and a color balance setting switch 220 are arranged on the front surface of the CCU 206.

Figure 37:
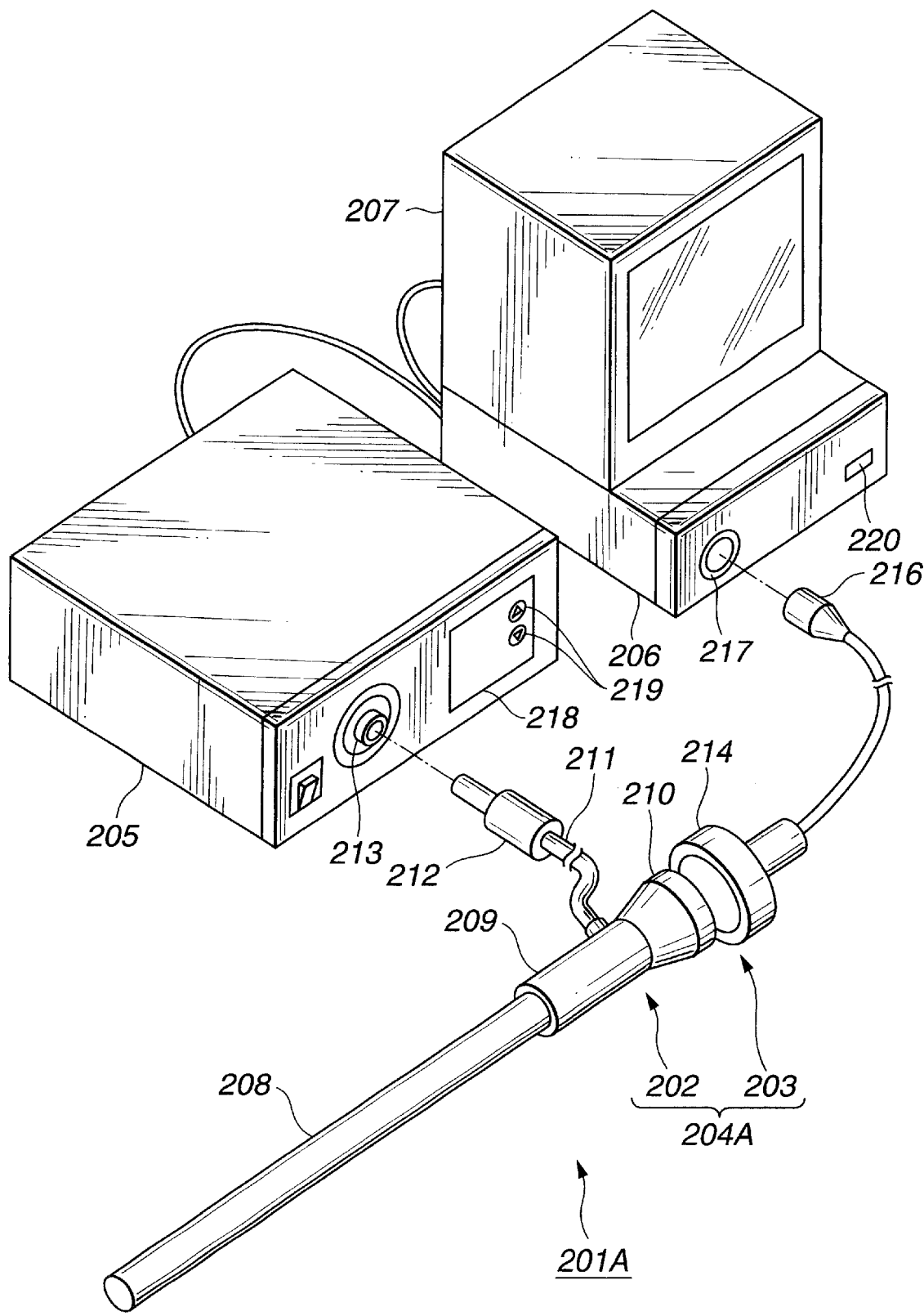
Figure 38:
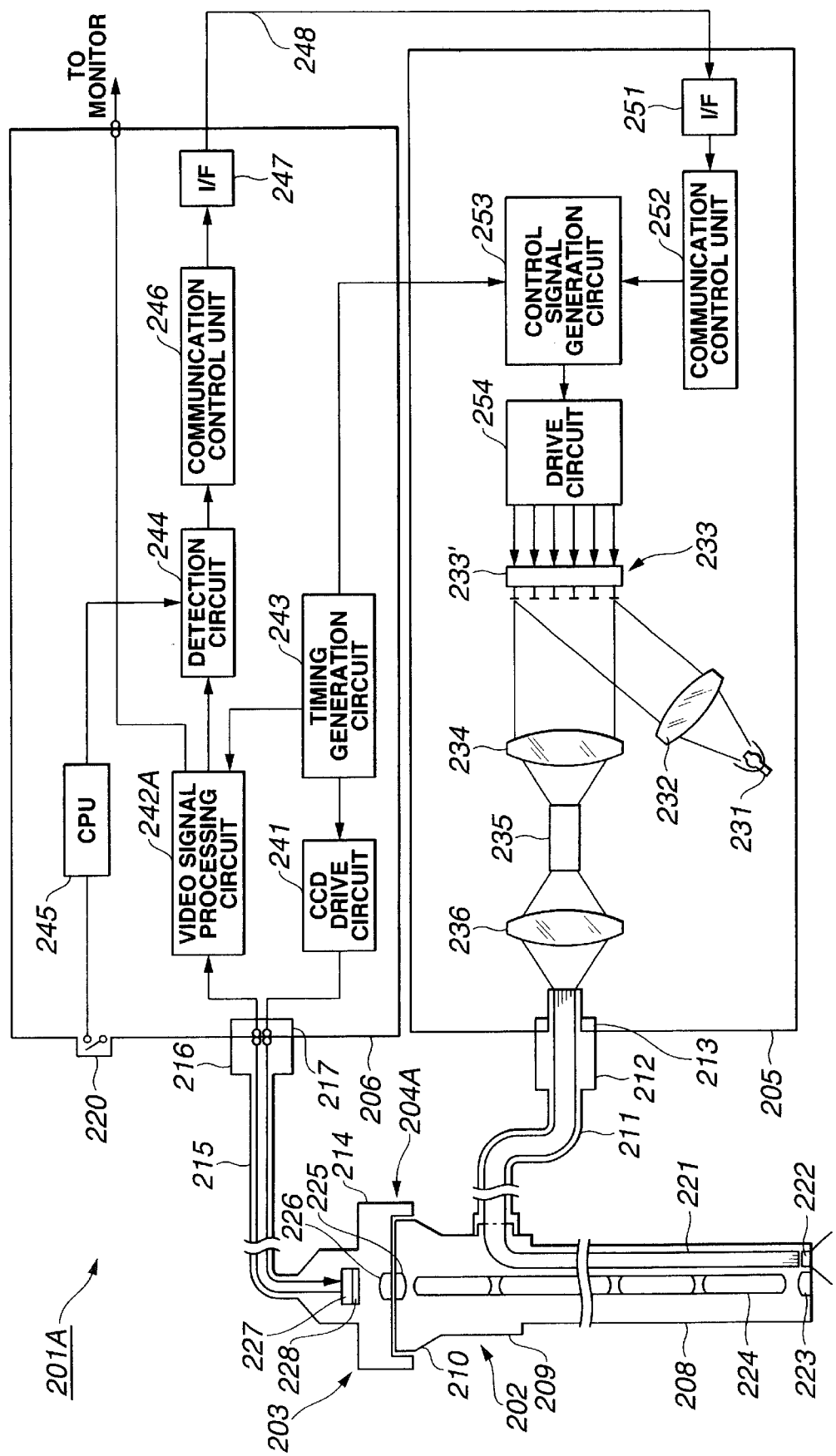

FIG. 38 shows the detailed configuration of FIG. 37.

A light guide 221 for transmitting an illumination light is equipped in the insertion portion 208 of the optical endoscope 202, and an illumination light from the light source device 205 is supplied to the light guide cable 221 through a light guide cable 211 (of light guide). This illumination light is transmitted to the distal end face, and forwardly delivered through a projection lens system 222 attached to an illumination window to illuminate a portion to be observed such as an affected part in a peritoneal cavity.

An objective lens system 223 is attached to an observation window adjacent to the illumination window to form an optical image of the illuminated object to be photographed. This image is transmitted to the eyepiece portion 210 by a relay lens system 224. Magnifying observation can be performed from the eyepiece portion 210 through an eyepiece lens 225. At the same time, when the camera head 214 is connected to the eyepiece portion 210, an image is formed through an image forming lens 226, e.g., a charge coupling element (to be abbreviated as a CCD) is arranged at the image forming position as an image pickup element, and photoelectric conversion is performed by the CCD 227.

A color separation filter 228 such as a mosaic filter or the like for separating wavelength components of R, G, and B is arranged on the image pickup surface of the CCD 227 to separate colors to the pixels.

A light source lamp 231 for generating an illumination light is arranged in the light source device 205. The light from the light source lamp 231 is converted by, e.g., a parallel lens (collimator lens) 232 into a parallel flux of light, and the parallel flux of light is incident on a light modulation device 233 of a reflective type.

The light reflected by the light modulation device 233 and being incident on a convergent lens system 234 is condensed by the condensation lens system 234 to be incident on one end face of an integrator 235. The incident light is made uniform and transmitted from the other end face. The light is condensed by a condensation lens 236 to be incident on the end face on proximal side of the light guide connector 212.

The light passes from the distal end face of the light guide 221 through the projection lens system 222 to illuminate a portion to be observed, and the optical image of a portion to be observed is formed by the objective lens system 223. The image is transmitted through the relay lens system 224 to form an image on the CCD 227.

A CCD drive signal is applied from a CCD drive circuit 241 in the CCU 206 into the CCD 227. The signal is subjected to photo electric convers iontoreadan accumulated signal charge, and is input to a video signal processing circuit 242 in the CCU 206.

The video signal processing circuit 242 separates the input CCD output signal into a luminance signal and a color-difference signal by a color separation circuit, and the luminance signal and the color-difference signal are converted into RGB chrominance signals by a matrix circuit. The RGB chrominance signals are output to the monitor 207 as standard video signals (together with not shown a synchronous signal).

Timing signals are input from a timing generation circuit 243 to the CCD drive circuit 241 and the video signal processing circuit 242. The CCD drive circuit 241 and the video signal processing circuit 242 perform generation of a CCD drive signal and video processing in synchronism with the timing signals.

In the video signal processing circuit 242, RGB chrominance signals from the video signal processing circuit 242 are input to a detection circuit (correction signal generation circuit) 244. When the color balance setting switch 220 is operated, by controlling a CPU 245, the respective RGB chrominance signals in one frame period are integrated with each other to detect a shift value (or a relative ratio of the respective chrominance signals) from, e.g., a reference value (to achieve a color balance), thereby generating a correction signal.

The correction signal is converted into a transmission signal by a communication control unit 246 for performing communication control, and the resultant signal is transmitted to an I/F 251 on the light source device 205 located outside the CCU 206 by a transmission cable 248 through an interface (to be abbreviated as an I/F)247.

In the light source device 205, a signal transmitted to the I/F 251 is converted (modulated) into a signal before transmission by a communication control unit 252. There sultant signal is input to a control signal generation circuit 253.

A timing signal from the timing generation circuit 243 is also input to the control signal generation circuit 253. The control signal generation circuit 253,controls the (light modulation device) drive circuit 254 in synchronism with the timing signal, so that the light modulation device 233 can be driven by a drive circuit 254.

Figure 39:
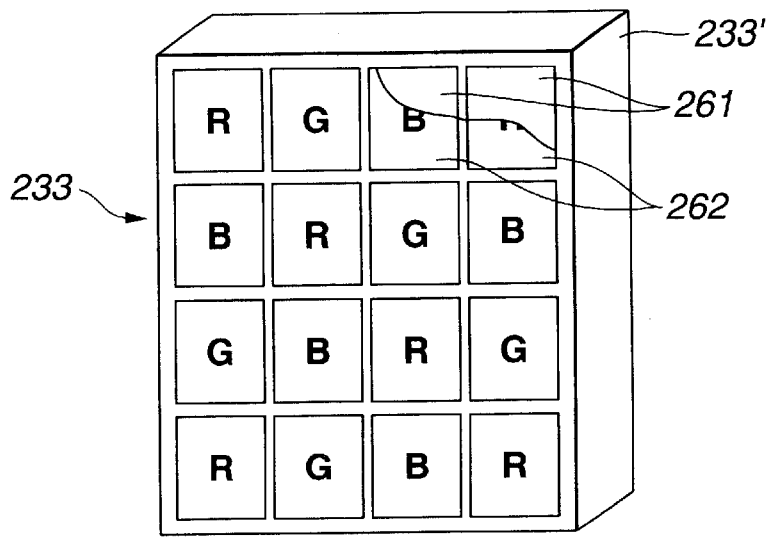

FIG. 39 shows the light modulation device 233. In the light modulation device 233, micromirrors (to be simply abbreviated as mirrors) 261 which are operated by an electrostatic field effect and constituted by, e.g., 15-micron-square aluminum materials are regularly and two-dimensionally arranged.

The respective mirrors 261 are supported by mirror holding posts on a yoke which can be stably set in two states about diagonals, and can be rotated in the horizontal direction to be kept at, e.g., about ±10°. This is called a DMD.

In this embodiment, R, G, and B color filters 262 are formed on the reflective surfaces of the micromirrors 261 by, e.g., screen printing or the like in the form of a checkered pattern to form a two-dimensional array element. More specifically, the light modulation device 233 is obtained such that the R, G, and B color filters 262 are formed on the reflective surfaces of the micromirrors 261 in a light modulation device body 233' serving as the DMD.

In this embodiment, by applying a drive signal from the drive circuit 254, the mirrors are set at +10° or −10°. When the mirror is set at, e.g., −10°, the mirror reflects a light from the light source lamp 231 such that the light is incident on the convergent lens system 234. However, when the mirror is set at +10°, the mirror reflects the light from the light source lamp 231 in a direction in which the light is not incident on the convergent lens system 234. For this reason, in this specification, it is called shield or OFF that the mirror 261 of the light modulation device 233 is set at +10° by the drive circuit 254, and it is called non-shield or ON that the mirror 261 is set at −10°.

In this embodiment, when the image of a white object to be photographed is picked up, a shift value representing that the level of the chrominance signal is shifted from the reference value is detected, and a correction signal corresponding to the shift value. A drive signal pattern for turning on/off all the mirrors of the light modulation device 233 of the drive circuit 254 is controlled, so that a setting to a white balance state in which the levels of the respective chrominance signals are equal to each other (uniform) can be easily performed by the light source device 205 side.

FIGS. 40A to 40D show array patterns of the R, G, and color filters 262 arranged in the two-dimensional array element constituting the light modulation device 233.

Figure 40A:
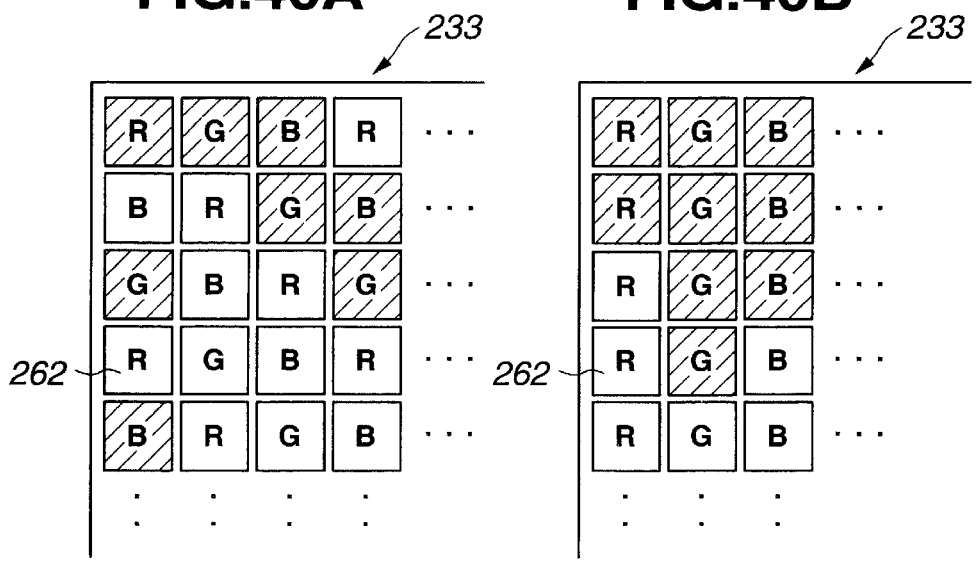
Figure 40B:
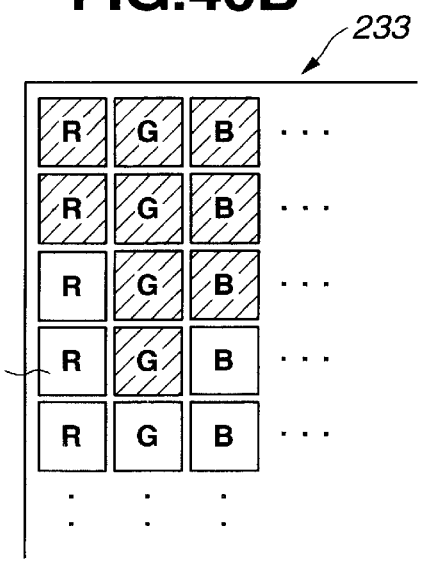
Figure 40C:
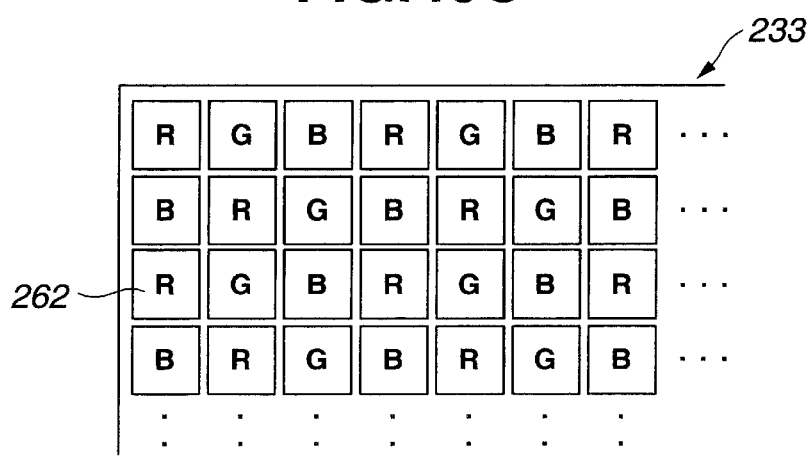
Figure 40D:
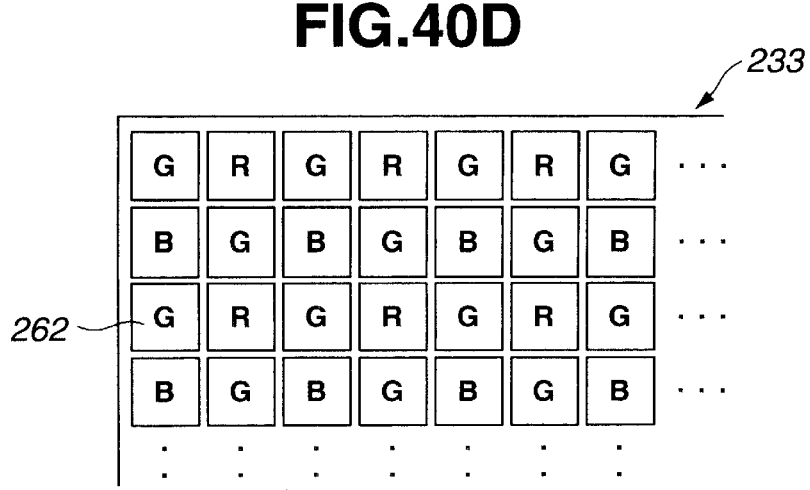

FIG. 40A shows a mosaic array pattern, and FIG. 40B shows a case in which the R (Red), G (Green), and B (Blue) filters are arrayed in a (longitudinal) line. FIGS. 40D and 40C show the same case in which the filters are arrayed at random such that the filters are not arrayed in a line (veered array). The control signal generation circuit 253 can know the information of an array pattern of the R, G. and B color filters 262 arranged in the two-dimensional array element constituting the light modulation device 233 with an internal memory or the like.

The embodiment has the following characteristic feature. That is, the color balance setting switch 220 is operated, so that an illumination light which keeps a white balance state can be easily supplied by the light source device 205.

The operation of the embodiment will be described below.

The TV camera 203 is attached to the optical endoscope device 202, and the light guide connector 212 of the optical endoscope device 202 is connected to the light source device 205. The signal connector 216 of the TV camera 203 is connected to the CCU 206, the endoscope device 201A is set such that the monitor 207 is connected to the CCU 206. Before a surgery is performed, an object to be photographed such as a sheet of white paper or a white gauze is placed in front of the distal end of the endoscope 202 to obtain a white observation image, and the color balance setting switch 220 is pressed to perform a color balance setting operation.

At this time, a color correction signal is transmitted from the CCU 206 to the light source device 205, and a control signal for generating a drive signal for driving the light modulation device 233 of the light source device 205 by the control signal generation circuit 253 on the basis of the correction signal. The ratio of the intensities of R, G, and B lights supplied to the light guide 221 when the light modulation device 233 is driven are controlled to achieve a color balance.

For example, when a correction signal which can achieve a color balance when the ratio of the intensities of the R, G, and B lights is set to be 6:2:4 is input to the control signal generation circuit 253, a drive signal which turns off an RGB array pattern indicated by a hatched portion in FIG. 40A when the array pattern shown in FIG. 40A is employed is generated.

In FIG. 40A, of 20 R, G. and B color filters 262 which constitute one unit, the 6 R color filters 262 are turned on, the 2 G color filters 262 are turned on, and the 4 B color filters 262 are turned on, so that a color balance is maintained. More specifically, control is performed such that R:G: B=6:2:4 is established, and the colors are mixed by the integrator 235 to achieve a uniform color. The colors are mixed at a ratio of R:G:B=6:2:4, and the light from the distal end of the endoscope 202 illuminates the white object to be photographed.

Even in the array pattern shown in FIG. 40B, when the correction signal is input to the control signal generation circuit 253, of 15 color filters constituting one unit shown in FIG. 40B, 3 R color filters 262 are turned on, one G color filter is turned on, and 2 B color filters 262 are turned on, so that a color balance is maintained. More specifically, control is performed such that a ratio of R:G:B=6:2:4 (=3:1:2), and the colors are mixed by the integrator 235 to achieve a uniform color. The colors are mixed at a ratio of R:G:B= 6:2:4, and the light from the distal end of the endoscope 202 illuminates the white object to be photographed.

In this case, since the color filters 262 are set for lines, respectively, a uniforming function obtained by integrator 235 is sufficiently achieved. Even though control is performed such that a ratio of R:G:B=6:2:4 (3:1:2) is established for each of the RGB lines, the same effect as described above can be obtained.

As in the RGB pattern in FIG.40C, the color filters are arranged at random such that the color filters are not arranged in a stripe, or control is performed by using the RGB array pattern shown in FIG.40D, so that an illumination light of the light source device 205 can be uniformly irradiated on the object without causing the integrator 235 to uniformly synthesize a color balance.

In this manner, a setting is performed by control on the light source device 205 side to achieve a color balance, and a white object to be photographed is displayed in white on the monitor 207. Preparation for actually performing (endoscope inspection) is completed.

For example, pneumoperitoneum is performed to a peritoneal cavity by a pneumoperitoneum device (not shown), and a surgery is observed by the endoscope device 201A under the endoscope. Since an appropriate color balance is set, observation having good color reproduction can be performed.

When, e.g., a metal halide lamp is used in the embodiment, the metal halide lamp has a characteristic feature that a color balance of emission lights is changed by aging of the metal halide lamp. The aging deteriorates the color reproduction of an endoscope image.

However, as in the embodiment, a color balance is achieved before use, and the color balance is corrected every aging. For this reason, preferable color reproduction can be achieved.

When a light source device changed into a xenon lamp is used for the light source lamp 231 in the embodiment, by setting the ratio of RGB emission lights according to the xenon lamp, preferable color reproduction can be similarly achieved. As the light source lamp 231, not only a metal halide lamp or a xenon lamp, but also a discharge tube or a tungsten lamp may be used. Even though these lamps are used, the same effect as described above can be obtained.

According to the embodiment, a state in which emission lights have a preferable white balance or the like can be simply obtained by the light source device 205 having the simple configuration. A complex setting operation for a gain to R, G, and B signals in a color balance setting circuit is not required on a video processing means in a prior art.

In the embodiment, when a white object to be photographed is set, and the color balance setting switch 220 is operated, a correction signal for driving the light modulation device 233 is input from the detection circuit 244 on the CCU 206 side to the control signal generation circuit 253 of the light source device 205 through the communication control unit 246. The light modulation device 233 is controlled such that the control signal generation circuit 253 emits an illumination light whose color balance is automatically achieved by the correction signal.

Not only this configuration, but also the following configuration may be used. A signal for a manual operation is input to the control signal generation circuit 253, so that an illumination light whose a color balance (white balance) is achieved is emitted.

For example, in a state in which the image of a white object to be photographed is picked up, the light intensity setting switches 219 for R, G, and B arranged in the light source device 205 are operated such that the image is displayed in white on the monitor 207, and the control signal generation circuit 253 operates the intensity setting switches for R, G, and B to increase/decrease a ratio of ON/OFF states of the micromirrors 261 having the color filters 262 formed thereon. When the object is displayed in white on the monitor 207, a completion switch is pressed to store the data of the state in the internal memory of the control signal generation circuit 253. There after, a drive pattern of the light modulation device 233 may be determined by the data.

The eighth embodiment of the present invention will be described below with reference to FIG. 41 and FIGS. 42A to 42D. The same reference numerals as in the seventh embodiment denote the same parts in the eighth embodiment, and a description thereof will be omitted.

Figure 41:
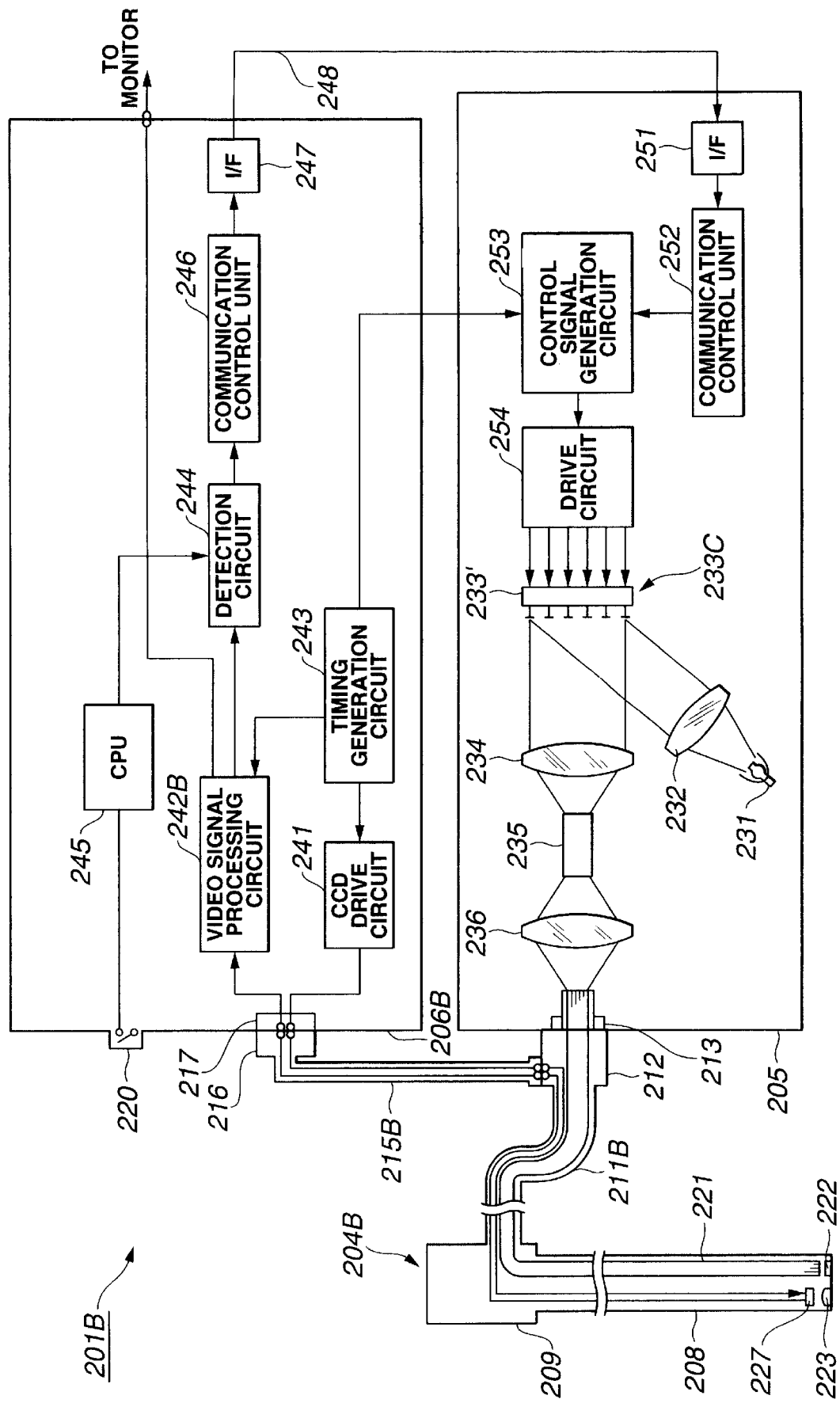

A field sequential endoscope device 201B shown in FIG. 41 is constituted by an electric endoscope 204B, a light source device 205, a CCU 206B, and a monitor (see FIG. 37) 207.

The electric endoscope 204B has a narrow and long insertion portion 208 having flexibility, an operation portion 209 arranged on the rear end of the insertion portion 208, and a universal cable 211B extending from the operation portion 209.

A light guide 221 for transmitting an illumination light is inserted into the insertion portion 208 of the electric endoscope 204B, the light guide 221 is inserted into the universal cable 211B, and a light guide connector 212 on the end portion of the universal cable 211B is detachably connected to the light source device 205. An illumination light supplied from the light source device 205 is transmitted through the light guide 221, and the illumination light is emitted from the distal end face to a portion to be observed through an illumination lens 222 attached to an illumination window.

A CCD 227 is arranged at the image forming position of an objective lens system 223 attached to an observation window adjacent to the illumination window to perform photoelectric conversion of a formed optical image. The electric endoscope 204B is an electronic endoscope, for field sequential image pickup, which employs a monochromatic CCD 227 having no color separation filter 228 arranged on an image pickup surface of the CCD 227.

A signal line connected to the CCD 227 is inserted into a scope cable 215B extending from the light guide connector 212, and a signal connector 216 arranged on the end portion of the signal line is detachably connected to the CCU 206B.

The CCU 206B employs a field sequential video signal processing circuit 242B in place of the synchronous video signal processing circuit 242A in the CCU 206 in FIG. 38. A CCD drive circuit 241 has the same configuration as that in FIG. 38. However, since the control signal generation circuit 253 selectively sequentially controls the regions of respective colors on the basis of the timing generation circuit 243 to irradiate a field sequential light on the object to be photographed, luminance components corresponding to the colors can be obtained by image pickup for each frame.

In the field sequential video signal processing circuit 242B, a CCD output signal input from the CCD 227 is converted into a digital signal by an A/D conversion circuit (not shown) in the video signal processing circuit 242B. The digital signals are sequentially stored in three frame memories and are simultaneously read in a read operation. RGB chrominance signals are D/A-converted to be output to the monitor 207.

The RGB chrominance signal is also input to the detection circuit 244. When the color balance setting switch 220 is operated, the detection circuit 244 detects a shift value from a reference value as described in the seventh embodiment, and transmits a correction signal to the light source device 205.

In the seventh embodiment, the correction signal is a signal for driving and controlling the R, G, and B color filters (mirrors having these filters) of the light modulation device 233 (or DMD 233') at once. However, in the eighth embodiment, correction signals are sequentially output to the light source device 205 in synchronism with the R, G, and B field sequential illumination lights.

In this embodiment, although the light source device 205 has the same configuration as that of the seventh embodiment, the light source device 205 operates to perform field sequential illumination. The level or time of an emission light from the light source device 205 is made variable according to an image pickup timing of a color field sequential method to achieve a color balance.

The operation of the embodiment will be described below.

As shown in FIG. 41, the endoscope device 201B is set to turn on the power supply, as shown in a DMD drive state in FIG. 42A, drive signals for sequentially setting a mirror having an R color filter 262 arranged thereon, a mirror having a G color filter 262 arranged thereon, and a mirror having a B color filter 262 arranged thereon in ON states (more specifically, as shown in FIG. 42C, in ON/OFF states by PWM control including an OFF period) are output to cause the R, G, and B illumination light stoper form R, G, and B field sequential illumination. In this case, as shown in FIG. 42B, the DMD 233' is set in a shield state (OFF) of +10° such that a shield period is formed after R, G, and B illumination periods.

In an R illumination period in which an R emission light is output, the image of an object to be photographed is picked up to perform charge by the CCD 227 accumulation. After the R illumination, all the mirrors of the DMD 233' are turned off in a read period in which signals accumulated by the CCD 227 are read to set a shield state. Signals read from the CCD 227 are temporarily stored in an R signal memory in a video signal processing circuit 242B.

A G emission light is output, and charge accumulation is performed by the CCD 227 in the G illumination period. After the G illumination period, all the mirrors of the DMD 233' are turned off in a read period in which signals accumulated by the CCD 227 to set a shield state. The signals read from the CCD 227 are temporarily stored in the G signal memory in the video signal processing circuit 242B.

A B emission light is output, and charge accumulation is performed by the CCD 227 in the B illumination period. After the B illumination period, all the mirrors of the DMD 233' are turned off in a read period in which signals accumulated by the CCD 227 to set a shield state. The signals read from the CCD 227 are temporarily stored in the B signal memory in the video signal processing circuit 242B.

The RGB chrominance signals temporarily stored in the R, G, and B signal memories in the video signal processing circuit 242B are simultaneously read and output to the monitor 207 to display an object image as a color image.

In this case, when a white object to be photographed is set as an object to be photographed, and the color balance setting switch 220 is operated, RGB chrominance signals in one color frame period are input to the detection circuit 244. A correction signal for achieving a color balance is generated by the detection circuit 244 to be input to the control signal generation circuit 253 of the light source device 205.

Before correction (i.e., in a state in which no correction state is input), the control signal generation circuit 253 controls the drive circuit 254 such that R, G, and B emission lights are PWM-controlled by data from an internal memory 253a in which the correction signal obtained in a previous setting. However, when the correction signal is input, the internal memory 253a is updated by a newly input correction signal, and a control signal for performing PWM control by the correction signal is output to the drive circuit 254.

For example, when a correction signal for achieving a balance at a ratio of the intensities of R, G, and B lights= 7:6:4 is generated, the control signal generation circuit 253 controls the drive circuit 254 such that the DMD emission light of PWM control as shown in FIG. 42C is output.

The ratio of the R, G, and B emission lights is 7:6:4 in the R, G, and B illumination periods, and field sequential illumination lights achieving a white balance are output.

In endoscope inspection performed thereafter, the drive circuit 254 is controlled by using data stored in the memory 253a, the ratio of the intensities of R, G, and B emission lights obtained by the DMD 233' is kept at 7:6:4.

In this manner, in endoscope inspection for an ordinary body cavity, a state in which field sequential illumination is performed in a white balance state is maintained.

According to the embodiment, as in the seventh embodiment, the color balance setting switch 220 is pressed before endoscope inspection is performed, so that a setting can be performed such that field sequential illumination lights in a color balance state can be easily emitted from the light source device 205.

In the description of the embodiment, the matrix pattern shown in FIG. 42A is employed to control emission lights by PWM control shown in FIG. 42C, thereby achieving a color balance. However, the emission lights are controlled by the matrix pattern shown in FIG. 42D, so that a color balance can be achieved.

FIG. 42D is obtained such that, in FIG. 42A, in place of PWM control of mirrors having R, G, and B color filters in R, G. and B illumination periods, of 10 mirrors having R, G, and B color filters arranged thereon, the mirrors are turned on at a ratio of 7:6:4, so that a field sequential light having a color balance can be emitted.

More specifically, in accordance with the R, G, and B illumination periods, the emission intensities of respective colors can be controlled by a number controlled by the emission side of the two-dimensional array element.

More specifically, the patterns of different two-dimensional array elements are used for R, G, and B as shown in FIG. 42D, ON/OFF control is performed such that the numbers of two-dimensional array elements for R, G, and B are kept at a ratio of R:G:B=7:6:4, so that an illumination light having a color balance can be emitted.

In addition, according to the embodiment, without arranging a new shield means, the effect of shield can be obtained by using the light modulation device 233.

The ninth embodiment of the present invention will be described below with reference to FIGS. 43 and 44. The same reference numerals as in the seventh embodiment denote the same parts in the ninth embodiment, and a description thereof will be omitted.

Figure 43:
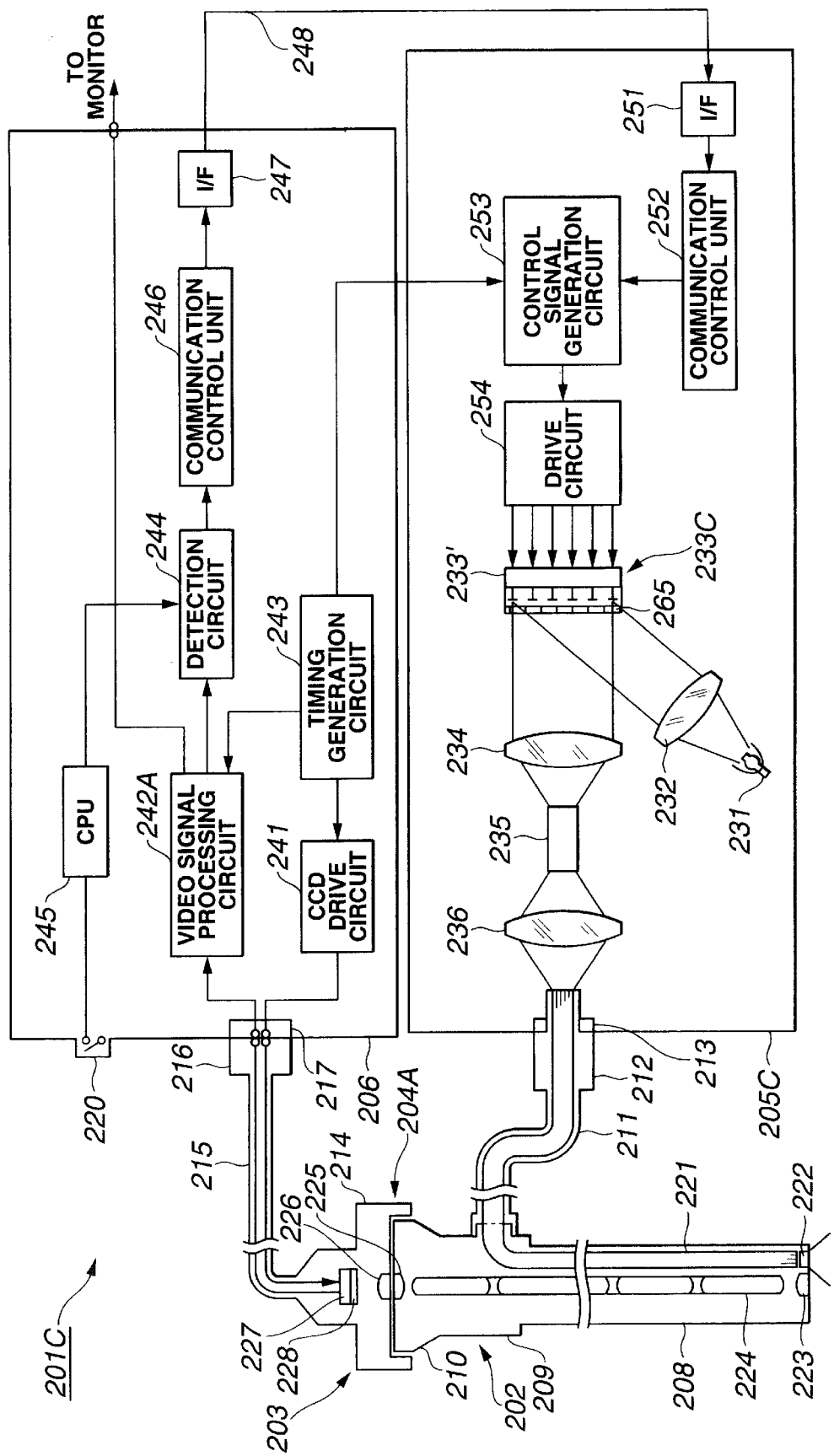

As shown in FIG. 43 an endoscope device 201C according to the ninth embodiment of the present invention employs a light source device 205C which employs a light modulation device 233C which is partially different from the light modulation device of the seventh embodiment.

In the seventh embodiment, the R, G, and B color filters 62 are formed on the micromirrors 261 by screen printing or the like. In the ninth embodiment, the light modulation device 233C in which R, G, and B filters 265 arranged in a checked pattern are formed immediately before the micromirrors 261 is employed.

FIG. 43 is a block diagram for explaining the schematic configuration and the operation of the light modulation device 233C. As shown in FIG. 44, the light modulation device 233C comprises a light modulation device body 233' having the micromirrors 261 and the R, G, and B filters 265 arranged in a checked pattern before the light modulation device body 233' (note that the light modulation device 233 according to the seventh embodiment has a configuration in which the R, G, and B filters 262 are directly formed on the micromirrors 261 in the light modulation device body 233').

Figure 44:
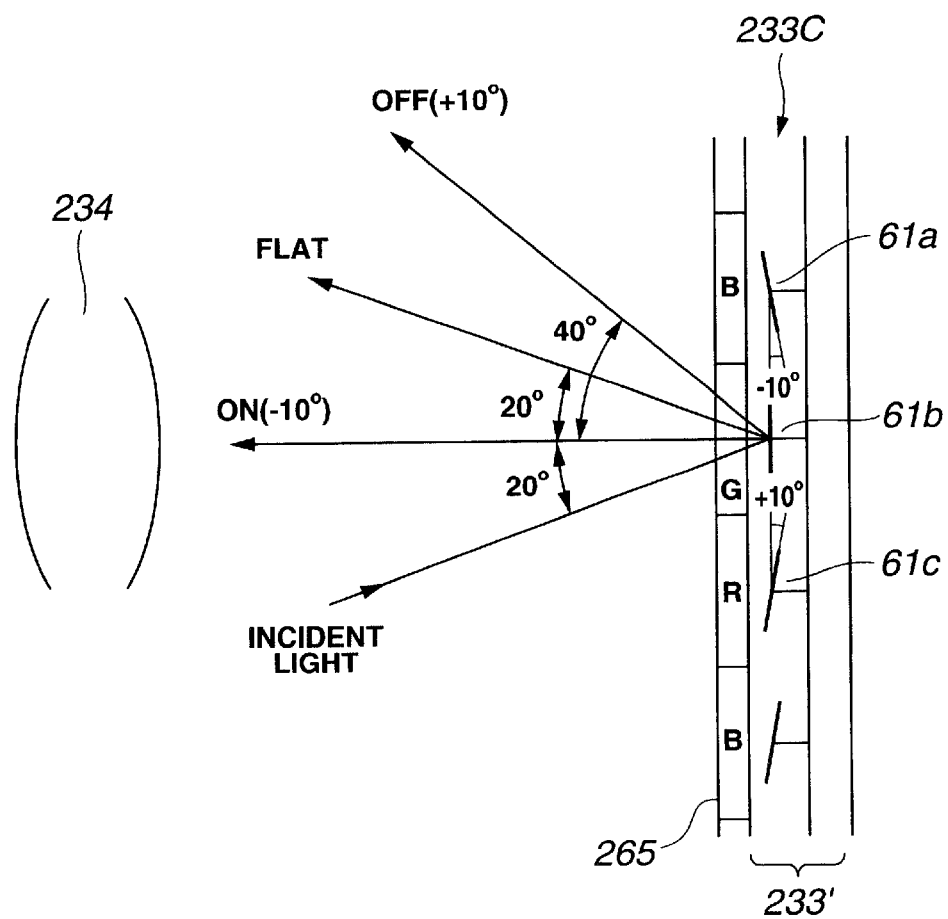
FIGS. 43 and 44 are related to the ninth embodiment of the present invention.

As shown in FIG. 44, the micromirrors 261 set at −10° and +10° are defined as micromirrors 261a, 261b, and 261c, a light is incident on the light modulation device 233C through the parallel lens 232, the reflected light is incident on the condensation lens system 234 when the micromirror is set at −10°, and is set in a state similar to a shield state in which the light is completely deviated from the incident direction of the condensation lens system 234 when the micromirror is set at +10°.

The micromirrors 261 are set at −10° or +10° by a drive signal from a drive circuit 254, and an illumination light from the light source lamp 231 is reflected. The light is set in a shield state in which the light is used or not used in illumination, so that an operational effect which is substantially the same as that of the seventh embodiment can be obtained.

The tenth embodiment of the present invention will be described below with reference to FIGS. 45 to 46B. The same reference numerals as in the seventh embodiment denote the same parts in the seventh embodiment, and a description thereof will be omitted.

An endoscope device 201E according to the tenth embodiment of the present invention shown in FIG. 45, for example, in the seventh embodiment, the CCU 206 further comprises a brightness light intensity adjustment signal generation unit 281 to obtain a CCU 206E having the following configuration. The brightness light intensity adjustment signal generation unit 281 integrates a chrominance signal output from a video signal processing circuit 242E in an appropriate frame period to generate an average brightness signal. A shift signal from a signal from a reference value setting unit 282 for outputting a reference level signal corresponding to a reference brightness is output to a communication control unit 246 as a light intensity adjustment signal. The communication control unit 246 transmits the light intensity adjustment signal to an I/F 251 through I/F 247, modulated by a communication control unit 252, and output to a control signal generation circuit 253.

The control signal generation circuit 253 controls a drive circuit 254 depending on the light intensity adjustment signal when an automatic light intensity adjustment switch 283 is turned on and keeps a white balance state to increase or decrease an illumination light intensity. The control signal generation circuit 253 performs control such that an average brightness signal is equal to a reference level.

The value of the reference level of the reference value setting unit 282 can be variably set by a setting switch 284. The other configuration is the same as that in the seventh embodiment.

The operation of the this embodiment will be described below.

An operation performed when a power supply is turned on and when a color balance setting switch 220 is operated is the same as that in the seventh embodiment. A state in which an illumination light is emitted in a white balance state is set.

In this case, the white balance state is kept as described in the operation in the seventh embodiment, a ratio of R, G, and B color filters used in illumination is set to be a:b:c. In this case, when a portion to be observed is observed, when a brightness signal in an illumination state at this time, e.g., a brightness light intensity adjustment signal for increasing an illumination light intensity by d% is generated, on the basis of the number of R, G, and B color filters which are turned on at this time, the R, G, and B filters are turned on at rates of a/(a+b+c)×d/100, b/(a+b+c)×d/100, and c/(a+b+C)×d/100.

In this case, the ratio of a:b:c is set to be 3:2:1. When a brightness light intensity adjustment signal for increasing an illumination light intensity by 50% is generated in the state shown in FIG. 46A, the state shown in FIG. 46B is obtained.

Figure 46A:
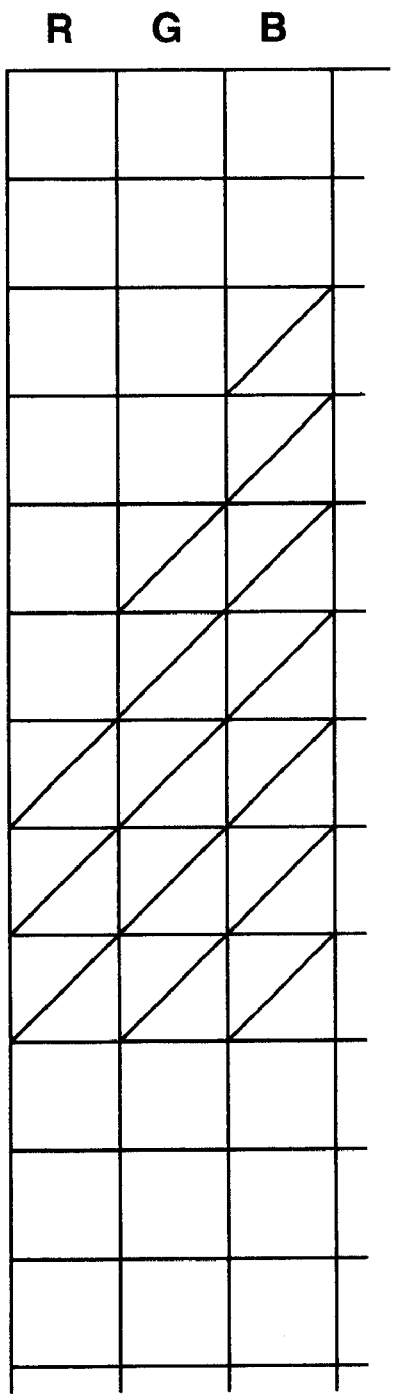
Figure 46B:
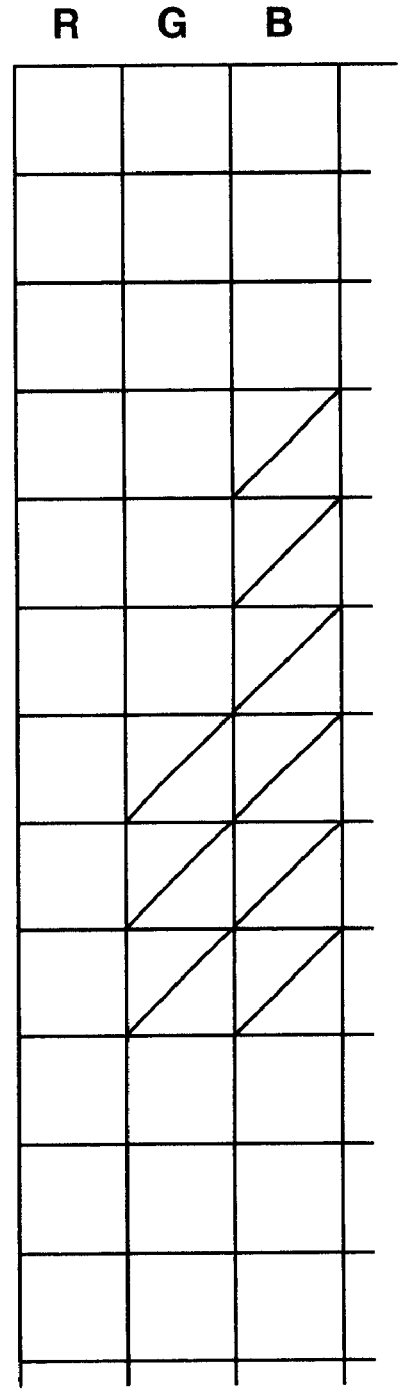

More specifically, in the state in FIG. 46A (R, G, and B color filters are arrayed in a vertical line, six of the nine R color filters are turned on, four of the nine G color filters are turned on, and two of the nine B color filters are turned on), when a brightness light intensity adjustment signal for increasing the illumination light intensity by 50%, as shown in FIG. 46B, a state in which nine of the nine R color filters are turned on, six of the nine G color filters are turned on, three of the nine B color filters are turned on is set.

With this change, a ratio of the ON R, G, and B color filters is equal to a ratio before the change (i.e., 6:4:2→9:6:3), and a white balance state is maintained. The illumination light intensity increases from 12/27 to 18/27, i.e., by 50%.

In this manner, according to this embodiment, automatic brightness control can be easily performed in a state in which a white balance is maintained.

In this embodiment, the present invention is applied to a synchronous method. However, the present invention can also be applied to field sequential illumination.

As is apparent from the FIGS. 38 and FIG. 41, the light source device 205 can be used as a light source device for a synchronous method and a field sequential method.

The light source device can be realized by a simple structure, i.e., such that the light modulation device 233 or the like can be used on a single chip. Even though a single plate is used, the light source device can be used as a light source device of an endoscope device in both the field sequential method and the synchronous method.

An embodiment or the like obtained by partially combining the embodiments described above to each other also belongs to the present invention.

The eleventh embodiment of the present invention will be described below with reference to FIGS. 47 to 50.

Figure 47:
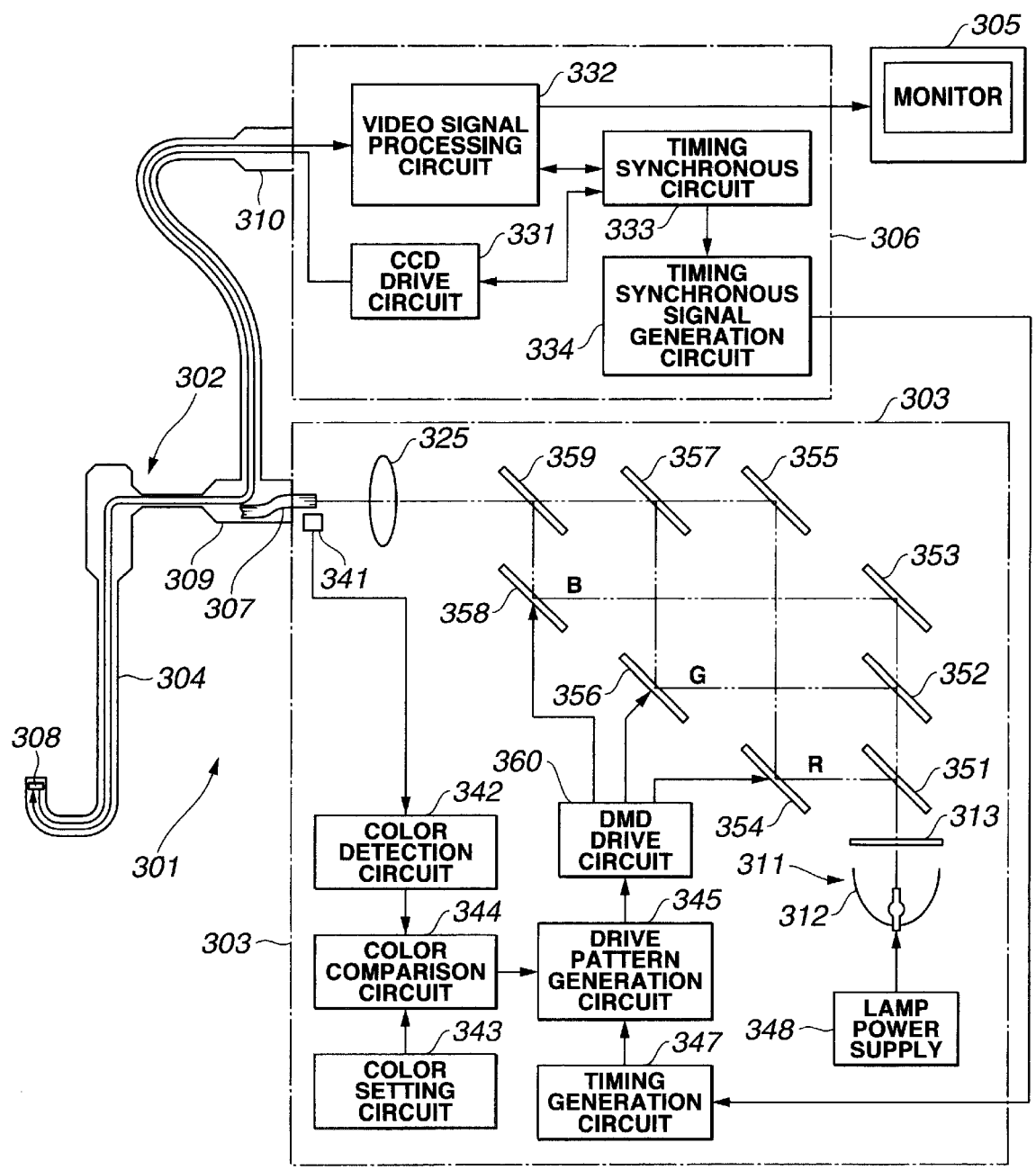
FIGS. 47 to 50 are related to the eleventh embodiment of the present invention.

As shown in FIG. 47, an endoscope device 301 according to the embodiment comprises an electric endoscope 302 which is inserted into a tubular cavity in, e.g., a body cavity to pick up a tissue image in vivo, a light source device 303 for supplying an illumination light to the electric endoscope 302, and a video signal processing device 306 for processing the image pickup signal picked by the electric endoscope 302. A light guide 307 serving as an optical transmission means for transmitting an illumination light supplied from the light source device 303 to the distal end of an insertion portion 304 is equipped in the electric endoscope 302, and a CCD 308 for picking up the image of a portion to be observed is arranged in the distal end of the insertion portion 304.

The electric endoscope 302 is connected to the light source device 303 through a light guide connector 309 and connected to the video signal processing device 306 by a connector 310 through the light guide connector 309. In this manner, an image pickup signal from the CCD 308 is output to the video signal processing device 306 through the light guide connector 309.

The optical system of the light source device 303 is described. When an illumination light is generated from an illumination lamp 311, the illumination light is emitted as a parallel light by a parabolic mirror 312 arranged on the illumination lamp 311. An infrared ray of the parallel light emitted from the illumination lamp 31.1 is cut infrared rays by a infrared cut filter 313, and the parallel light is incident on dichroic mirrors 351 and 352. A transmission light of the dichroic mirror 352 is incident on a total reflection mirror 353.

Here, the dichroic mirror 351 reflects an R light component and transmits the other light components. The dichroic mirror 352 reflects a G light component and transmits the other light components.

The reflected light of the dichroic mirror 351 is incident on a light modulation device 354, and the reflected light from the light modulation device 354 is incident on a total reflection mirror 355. Similarly, the reflected light from the dichroic mirror 352 is incident on a light modulation device 356, and the reflected light from the light modulation device 356 is incident on a dichroic mirror 357. The reflected light from the total reflection mirror 353 is incident on a light modulation device 358 as a B-component, and the reflected light from the light modulation device 358 is incident on the dichroic mirror 359.

The reflected light (R) from the total reflection mirror 355 is transmitted through the dichroic mirror 357, and a light transmitted through the dichroic mirror 357 is incident on the dichroic mirror 359 and condensed on the incident end face of the light guide 307 by a condensation lens system 325.

The light (B) reflected by the dichroic mirror 357 is incident on the dichroic mirror 359, transmitted through the dichroic-mirror 359, and condensed on the incident end face of the light guide 307 by the condensation lens system 325. The light (G) reflected by the dichroic mirror 359 is condensed on the incident end face of the light guide 307 by the condensation lens system 325.

Figure 48:
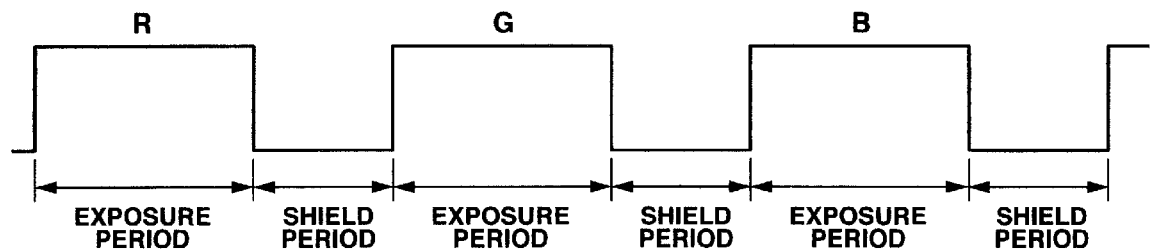

The lights controlled by the light modulation devices 354, 356, and 358 are emitted from the light source device 303 as field sequential lights as shown in FIG. 48.

The light modulation devices 354, 356, and 358 are elements each having the following configuration. A small micromirror having a size of 640×480 is arranged on a silicon chip, and the mirror is held by a holding member on a yoke rotated about diagonals between two stable states and can be changed at +10° in the horizontal direction. The element is called a DMD (digital micromirror device), is driven by a DMD control circuit 360 on the basis of a drive pattern from a drive pattern generation circuit 345, and is arranged such that a reflected light is output from the light source when the micromirror (two-dimensional array element) is set at −10°. In addition, the timing of the shield period of the CCD 308 can be obtained such that shield is performed when the micromirrors (two-dimensional array elements) of the light modulation devices 354, 356, and 358 are controlled at +10°.

As the illumination lamp 311, a high-luminance lamp such as a short work xenon discharge tube or a metal halide lamp is preferably used.

The video signal processing device 306 comprises a CCD drive circuit 331 for driving the CCD 308, a video signal processing circuit 332 for processing an image pickup signal from the CCD 308 and outputting a video signal (e.g., an NTSC television signal) to a monitor 305, a timing generation circuit 333 for generating a timing signal for synchronizing the image pickup timing of the CCD 308 with signal processing in the video signal processing circuit 332, and a timing synchronous signal generation circuit 334 for outputting a timing synchronous signal synchronized with the timing signal of the timing generation circuit 333.

A light source device 303 comprises a sensor 341 for detecting an emission light from the condensation lens system 325, a color detection circuit 342 for detecting a color component of the emission light detected by the sensor 341, a color comparison circuit 344 for comparing a color preset by the color setting circuit 343 with the color component, a drive pattern generation circuit 345 for generating a drive pattern for controlling the light modulation devices 354, 356, and 358 on the basis of a comparison result of the color comparison circuit 344, a DMD control circuit 360 for driving the light modulation devices 354, 356, and 358 on the basis of the drive pattern, a timing synchronous circuit 347 for controlling a generation timing of the drive pattern in the drive pattern generation circuit 345 on the basis of the timing synchronous signal from the timing synchronous signal generation circuit 334, and a lamp power supply 348 for turning on the illumination lamp 311 to constitute a field sequential output light control unit.

The operation of the embodiment will be described below.

In the light source device 303, an emission light is detected by the sensor 341, and the color component of the detected emission light is detected by the color detection circuit 342. The color component of the emission light detected by the color comparison circuit 344 is compared with an output from the preset color setting circuit 343, and a color control signal is output to the drive pattern generation circuit 345 for generating a drive pattern for controlling the light modulation devices 354, 356, and 358 on the basis of a comparison result.

In the drive pattern generation circuit 345, a drive pattern for determining an output level when field sequential colors is output to the DMD control circuit 360. The DMD control circuit 360 drives the light modulation devices 354, 356, and 358 such that the two-dimensional array elements are arranged in the determined drive pattern.

The field sequential output light control unit of the light source device 303 sets a reflection state (−10° state) in which the light modulation devices 354, 356, and 358 guide lights to the light guide 307 at field sequential light emission timings by a timing of the timing synchronous circuit 347 which is synchronous with an image pickup timing of the CCD 308 and a reflection state (+10° state) in which the light modulation devices 354, 356, and 358 do not guide lights.

Field sequential output timings, as shown in FIG. 48, are timings at which RGB lights are sequentially irradiated. As shown in FIG. 48, the light modulation devices 354, 356, and 358 are set in the −10° reflection state and the +10° reflection state in which lights are not guided by the drive pattern at the field sequential light emission timings, so that the levels of the emission lights of the R, G, and B colors are changed. In the shield period in FIG. 48, all the light modulation devices 354, 356, and 358 are set in the +10° state.

Figure 49:
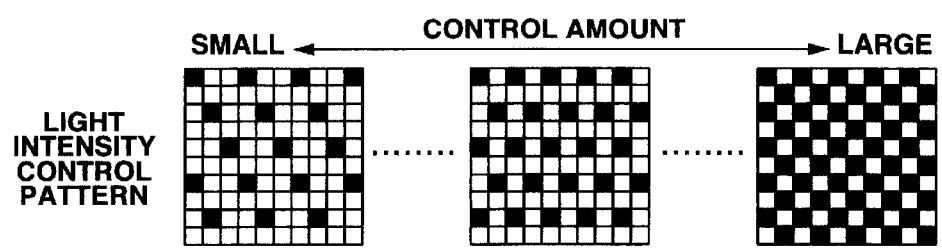
Figure 50:
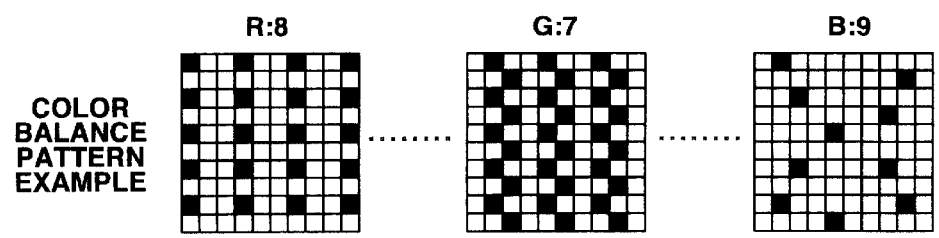

In this manner, a color balance can be set at a ratio of R:G:B=8:7:9 as shown in FIG. 50. More specifically, in the drive pattern generation circuit 345, in order to control of output lights of respective colors, the levels of the emission lights are changed by using a light intensity control pattern of the two-dimensional array element as shown in FIG. 49.

The embodiment has the following effect.

In this manner, in the embodiment, even though the video signal processing device 306 is not set, when the color balance of an illumination light automatic supplied by a light source 303 is made appropriate, an endoscope image can be observed with appropriate color reproduction. In addition, when the light modulation devices are used for respective colors, control can be performed without using a field sequential rotation filter, and light intensity levels of the respective colors can also be adjusted at the same time.

Figure 51:
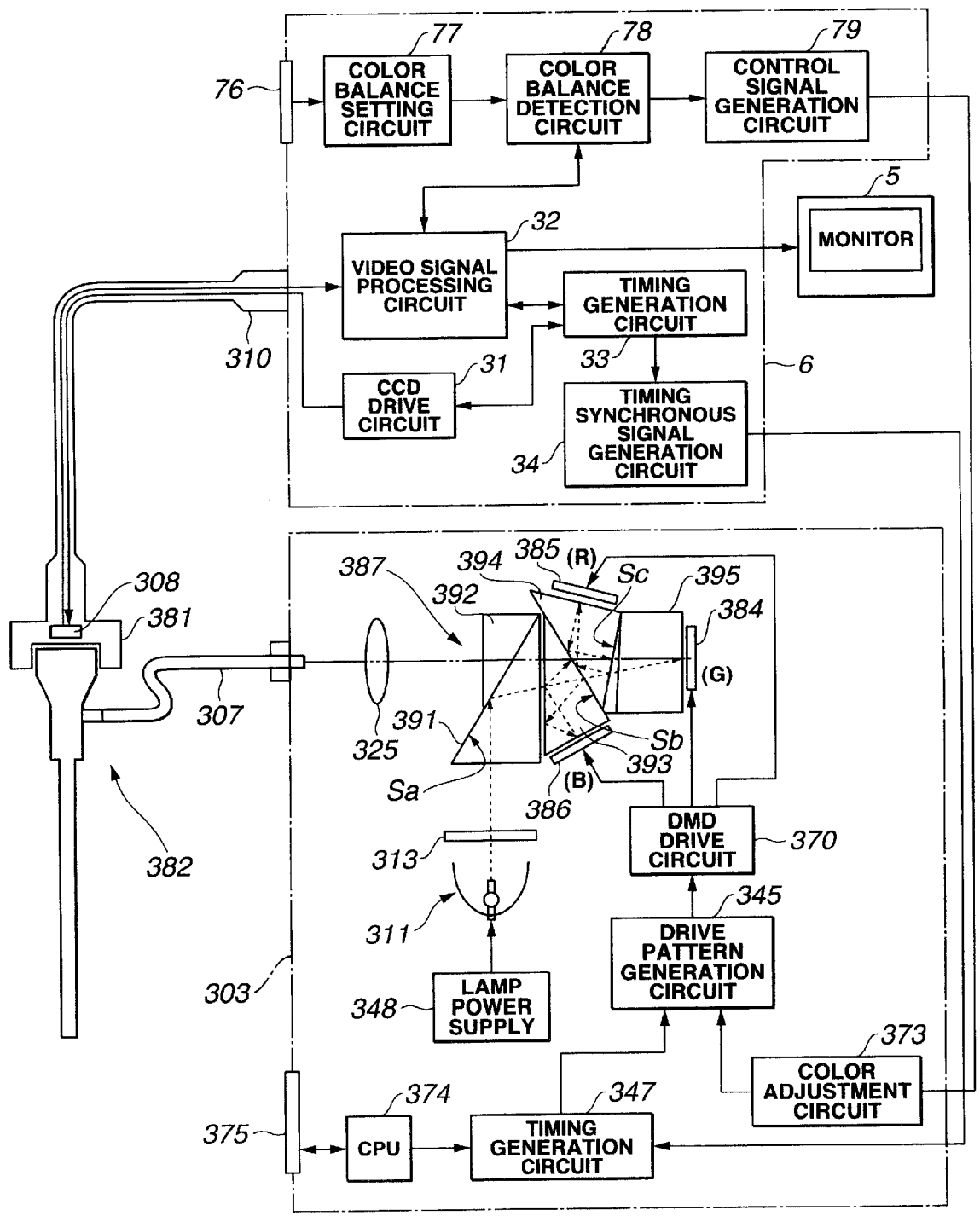
FIGS. 51 to 53 are related to the twelfth embodiment of the present invention.
Figure 52:
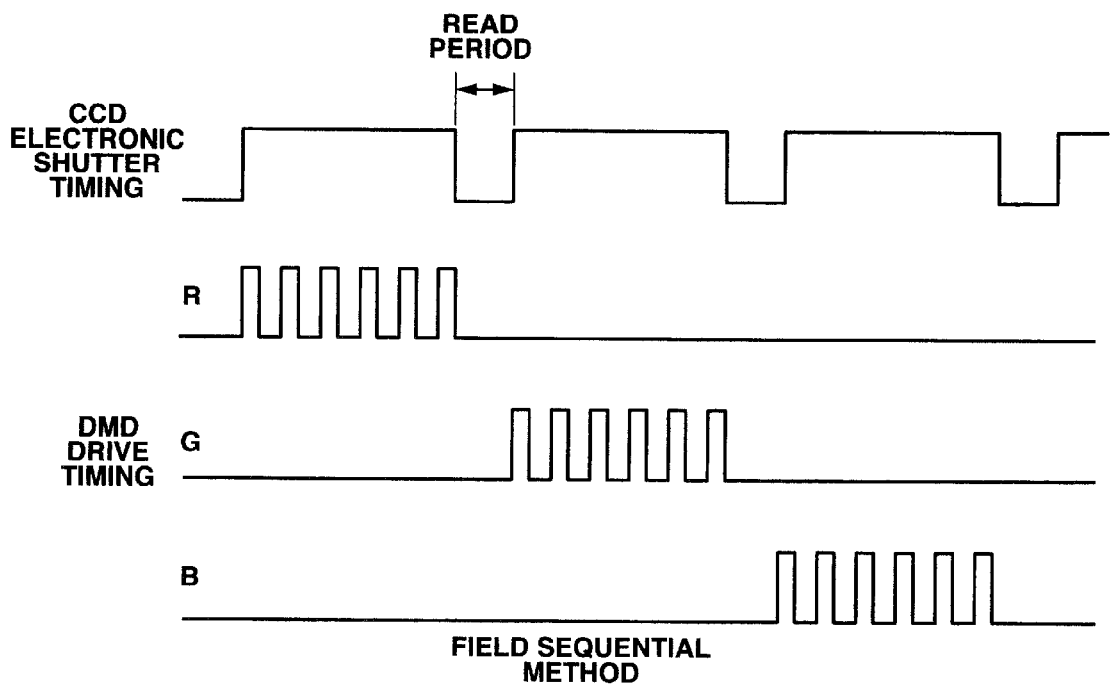
Figure 53:
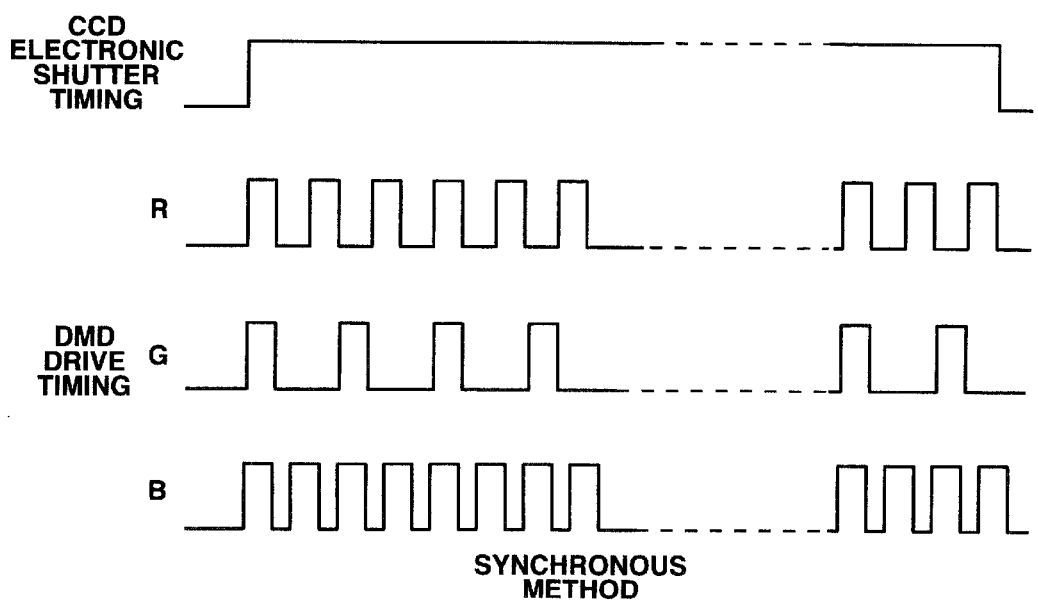

The twelfth embodiment of the present invention will be described below with reference to FIGS. 51 to 53.

In this embodiment, a light source device has the following structure. That is, as shown in FIG. 51, in place of the electric endoscope 302, a rigid endoscope 382 in which a TV camera head 381 is detachably connected to the eyepiece portion is used. Lights from the illumination lamp 311 are incident on light modulation devices 384, 385, and 386 constituted by DMDs at an angle of +10°, and the reflected lights from the light modulation devices 384, 385, and 386 are directed at +10° to be condensed on the light guide 307 by the condensation lens system 325. The light source device comprises an optical prism system 387 for dividing the lights being incident on the light modulation devices 384, 385, and 386 into R, G, and B lights.

The configuration of the optical prism system 387 is constituted by five prisms 391, 392, 393, 394, and 395 based on the thought opposite to that of a three-color separation prism. The optical prism system 387 may be called a three-color dividing/synthesizing prism. The optical prism system 387 efficiently transmits the light from the illumination lamp 311, and, at the same time, the positional relationships of the pixels (two-dimensional array elements) of the mirrors of the RGB DMDs are equal to each other, so that effective control can be performed. This configuration is known as the configuration of a projector using DMDS. The embodiment has a characteristic feature in which the DMDs are operated in synchronism with image pickup of a CCD as an illumination light source to be applied to the endoscope device.

More specifically, the light from the illumination lamp 311 is incident on the prism 391, and other rays than an infrared ray is reflected by a reflective surface Sa of the prism 391. The light transmitted through the prism 391 is emitted to the opposite surface of the prism 392. It is desirable that an absorbing member for the light transmitted from the prism 392 is arranged.

The light reflected by the reflective surface Sa is incident on the prism 393, and a B region is reflected by a reflective surface Sb. The light transmitted through the reflective surface Sb is incident on the prism 394, and an R region is reflected by a reflective surface Sc. The light transmitted through the reflective surface Sc serves as a G region, and the G region is incident on the prism 395. The light transmitted through the prism 395 is incident on the light modulation device 384.

Here, in the light modulation devices 384, 385, and 386, micromirrors each having a size of about 15 $\mu$m are arranged in the form of a lattice having a size of 1024×768, and the angles of the respective micromirrors are controlled to be −10° and +10°. A control signal therefor is generated by a DMD control circuit 370.

The micromirrors of the light modulation device 384 are driven by the DMD control circuit 370, and a light reflected by a micromirror controlled at +10° linearly propagates through the prism 395 toward the condensation lens system 325 at an incident angle of 0° set with respect to the light guide.

The light of the R region reflected by the reflective surface Sc is incident on the light modulation device 385. Similarly, the positional relationships of the micromirrors of the light modulation device 385 and the light modulation device 384 are equal to each other. Since the mirrors having equal positional relationships are driven at +10°, in the same manner as described above, the light reflected by the light modulation device 385 is synthesized with the light of the G region from the light modulation device 384 by the prism 394. The resultant light propagates at a light (G+R) toward the condensation lens system 325.

The relationship between the prism 393 and the light modulation device 386 is the same as described above. The lights (G+R+B) are synthesized with each other by the prism 393. The resultant light propagates through the prism 391, is transmitted through the prism 392, is incident on the condensation lens system 325, and is incident on the light guide 307.

The light modulation devices 384, 385, and 386 are driven by the DMD control circuit 370 on the basis of a drive pattern from a drive pattern generation circuit 345. When the field sequential method is used, as a drive signal, a PFM signal shown in FIG. 52 is input. A control signal may be obtained by PWM control. More specifically, as control of the light modulation devices 384, 385, and 386, as shown in FIG. 52, PFM control is performed to control an RGB color balance is controlled when field sequential lights are emitted. When the reflection time of a micromirror is elongated to increase the pulse width of the PFM control, the intensity of the wavelength region increases. For this reason, the intensities of the respective wavelengths can be adjusted. When the pulse width decreases, the control is reversely performed, and a target color balance can be controlled. In a shield period, control for preventing emission is performed by setting all the DMDs at −10°.

In addition, the embodiment can cope with a synchronous image pickup method. However, as shown in FIG. 53, the emission lights of R, G, and B components from the light source device 303 are PFM-controlled at a timing equal to a synchronous image pickup timing to achieve a color balance.

The embodiment has the following effect.

In this manner, in the embodiment, the same effect as that in the eleventh embodiment can be obtained. Even though constants of the color matrix of a video signal processing circuit 332 are not prepared for respective lamps to solve the problem of color balance, a color balance of lights from the light source device 303 can be achieved. For this reason, the endoscope device can be used without any complex setting.

In the embodiment, a light is divided in R, G, and B optical axes when the light is separated into wavelength components, light modulation devices are inserted into the divided optical axes to obtain fluxes of spectral light whose wavelength components are controlled. For this reason, control in the wavelengths which are reliably separated can be performed. In addition, since a light can be selectively separated into light components having wavelengths by using optical filters, the wavelengths of spectral regions can be reliably obtained by sharp filter characteristics. In the embodiment, light components having typical RGB wavelengths are described. However, the shield wavelengths of the filters are arbitrarily set, a spectral distribution which can be changed can be obtained.

The present invention has been described by using the eleventh and twelfth embodiments. However, as described above, a cumbersome setting of a video signal processing circuit performed by control of a light source device at high efficiency need not be changed to obtain a desired color balance. In addition, the color balance can be controlled by a simple structure under the control of the light source device.

More specifically, it means that illumination can be performed by an optical spectral distribution appropriate to color image pickup can be performed.

For example, when a color balance is achieved by processing a video signal, a B component has a low intensity, and a color balance is achieved by amplifying a signal to compensate for the B component. In this case, an S/N ratio becomes low, and noise is conspicuous in a dark portion of a screen. However, when a color balance is achieved by the light source, a video signal need not be operated, and an image having a high S/N ratio can be obtained.

In addition, when a method using. pattern control and a method using PWM are used as a color balance. control method, the same effect as described above can be obtained in not only a field sequential method but also a synchronous method.

The thirteenth embodiment of the present invention will be described below with reference to FIGS. 54 to 59E.

Figure 54:
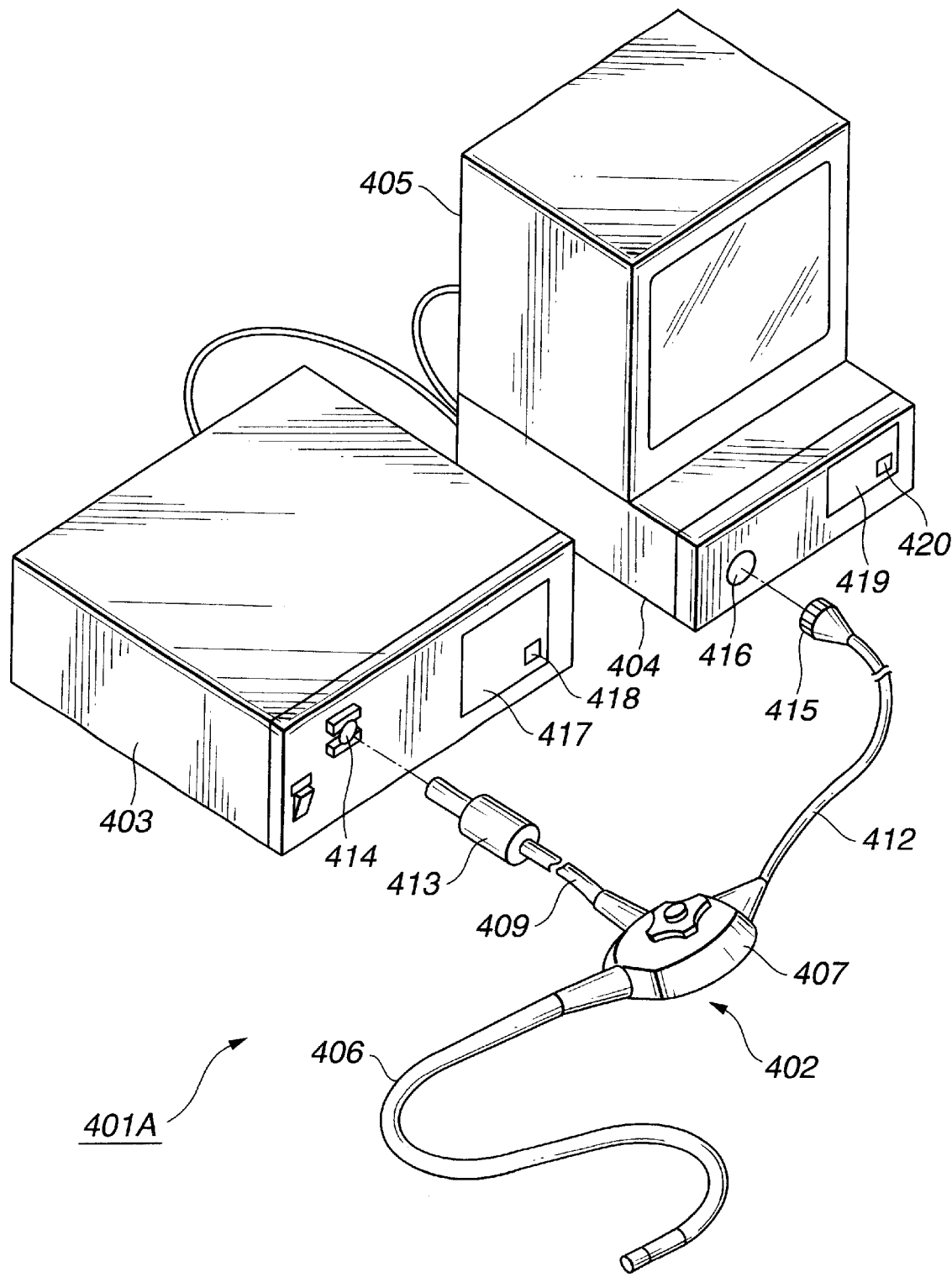

As shown in FIG. 54, an endoscope device 401A according to the thirteenth embodiment of the present invention is constituted by an electric endoscope 402, a light source device 403 for supplying an illumination light to the electric endoscope 402, a camera control unit (to be abbreviated as a CCU hereinafter) 404 for performing signal processing to an image pickup element incorporated in the electric endoscope 402, and a monitor 405 for displaying a video signal from the CCU 404.

The electric endoscope 402 includes a narrow and long insertion portion 406 having flexibility, an operation portion 407 which is a thick grip arranged on the rear end of the insertion portion 406, a light guide cable 409, extending from a side of the operation portion 407, in which a light guide 408 (see FIG. 55) serving as an optical transmission means for transmitting an illumination light is inserted, and a signal cable 412 in which a signal line 411 (see FIG. 55) extending from the rear end of the operation portion 407 is inserted. A light guide connector 413 connected to the end portion of the light guide cable 409 is detachably connected to a light guide connector support 414 of the light source device 403, and a signal connector 415 connected to the end portion of the signal cable 412 is detachably connected to a signal connector support 416 of the CCU 404.

Not only the light guide connector support 414, but also a power supply switch and an operation panel 417 are arranged on the front surface of the light source device 403, and a white balance setting switch 418 is arranged on the operation panel 417.

The signal connector support 416 and an operation panel 419 are arranged on the front surface of the CCU 404, and an image pickup variable switch 420 for changing an image pickup operation depending on the movement of an object to be photographed is arranged on the operation panel 419.

Figure 55:
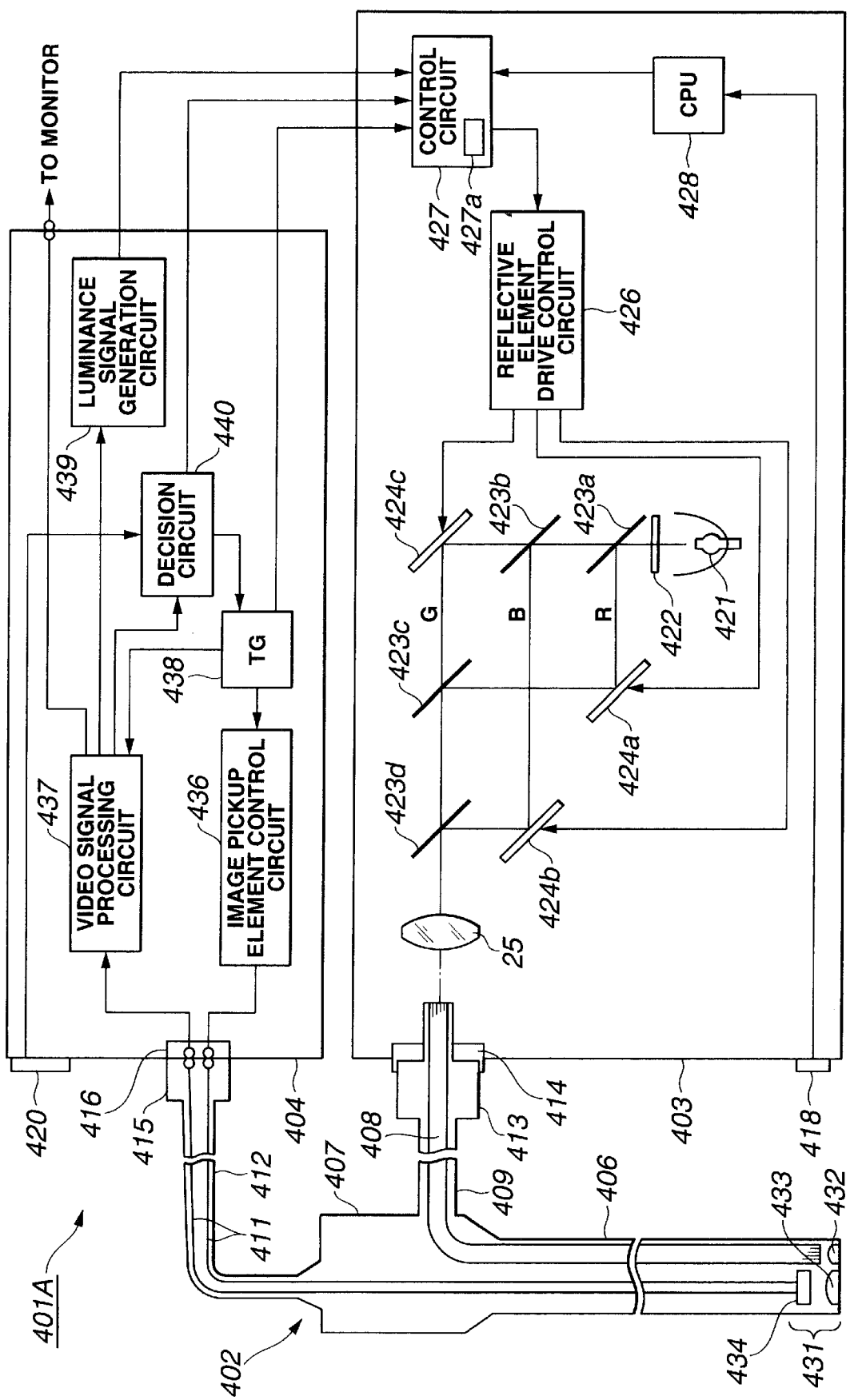

FIG. 55 shows a further detailed configuration of FIG. 54.

The light source device 403 comprises a light source lamp 421 for generating an illumination light and an optical system having the following configuration. That is, an illumination light generated by the light source lamp 421 is converted into a white light component whose infrared component is removed by a infrared cut filter 422 arranged on the optical path (optical axis) of the illumination light, and the white light component is separated into lights having three wavelengths used in field sequential illumination, i.e., R, G, and B lights by a wavelength dividing means (wavelength separation) arranged on the optical axis. Field sequential lights are input to the light guide 408 through a means for optically modulating the separated lights into a light which is incident on the light guide 408 and a light which is not incident on the light guide 408 such that small reflective elements are two-dimensionally arranged. The light modulation intends to turn on/off an emission light from the light source device 403 by a time interval as in the embodiment or to make the emission lights in an array pattern and to modulate the emission lights by a combination of the time interval and the array pattern.

More specifically, of the illumination light whose infrared component is removed by the infrared cut filter 422, R and B wavelength components are reflected by a dichroic mirror 423a serving as a color separation means for reflecting a light of an R (red) wavelength component arranged on the optical axis in front of the infrared cut filter 422 and a dichroic mirror 423b arranged in front of the dichroic mirror 423a, for reflecting a light of a B (blue) wavelength component. The remaining G (green) wavelength component is transmitted through the dichroic mirror 423a and the dichroic mirror 423b.

The light of the R wavelength component (R component) reflected by the dichroic mirror 423a is incident on a light modulation device 424a, and the light of the B component reflected by the dichroic mirror 423b is incident on a light modulation device 424b, so that these lights are optically modulated.

The light of the G component transmitted through the dichroic mirrors 423a and 423b is incident on a reflective type light modulation device 424c to be optically modulated. The modulated light is guided to the front of the reflection optical path, and is transmitted through dichroic mirrors 423c and 423d arranged on the reflection optical path.

The light of the R component optically modulated and reflected by the light modulation device 424a is incident on the dichroic mirror 423c for reflecting the light of the R component, and is transmitted through the dichroic mirror 423d, arranged in front of the dichroic mirror 423c, for reflecting the light of the B component as in the case of the light of the G component reflected by the dichroic mirror 423c and transmitted through the dichroic mirror 423c.

The modulated light of the B component is incident on the dichroic mirror 423d to be reflected, is incident on a condensation lens 425 arranged in front of the dichroic mirror 423d as in the case of the lights of the R and G components transmitted through the dichroic mirror 423d, is converged by the convergent lens 425, and is incident from the end face of the light guide connector 413 onto the light guide 408.

In the light source device 403, when the reference of the light intensity is set by a reflective element drive control circuit 426 for driving the light modulation devices 424a, 424b, and 424c, a control circuit 427 for generating a signal for controlling drive states of the light modulation devices by the DMD drive circuit 426, and a first indication means 418, a CPU 428 compares the reference of the light intensity with aluminance signal transmitted from a CCU 404 (to be described later) in the control circuit 427 to generate a light intensity control signal.

Here, the light modulation devices 424a, 424b, and 424c are reflective type elements. The light modulation devices 424a, 424b, and 424c are elements each having the following configuration. A micromirror serving as a two-dimensional array element is arranged on a silicon chip, and the mirror is held by a holding member on a yoke rotated about diagonals between two stable states and can be angularly changed at ±10° with respect to the plane direction of the silicon chip. The element is called a DMD (digital micromirror device). When the element is driven to −10°, the element is set in an ON state in which the light is incident on the light guide connector 8. When the element is driven to +10°, the element is. set in an OFF state (shield state) in which the light is incident on the light guide 408.

In the embodiment, for example, a two-dimensional array element having a size of 800×600 is used. The light modulation devices 424a, 424b, and 424c are designed such that ON/OFF (shield) states obtained by reflection of a light can be set by a drive signal from the drive circuit 426.

In the embodiment, in a period in which the light modulation device 424a arranged on an optical path on which the light of the R component is incident as will be described later, the other light modulation devices 424b and 424c are set in an OFF state, and only the light of the R component is supplied to the light guide 408. Thereafter, after all the light modulation devices 424a, 424b, and 424c are turned off, in the period in which the light modulation device arranged on the optical path on which the light of the G component is incident is turned on, the other optical modulation devices 424a and 424c are set in an OFF state, only the light of the G component is supplied to the light guide 408. Thereafter, after all the light modulation devices 424a, 424b, and 424c are turned off, in the light modulation device 424b arranged on an optical path on which the light of the B component is incident is turned on, the other light modulation devices 424a and 424b are turned off, only the light of the B component is supplied to the light guide 408. Thereafter, after all the light modulation devices 424a, 424b, and 424c are turned off, the light modulation device 424a is driven to be turned on again, and field sequential illumination lights are supplied to the light guide 408.

When a state in which the image of a white object to be photographed is picked up is set in an initial setting, and when the white balance setting switch 418 is operated, a luminance signal generation circuit 439 supplies signals corresponding to shifts of R, G, and B color signals from a reference brightness or a luminance level to the control circuit 427. The control circuit 427 adjusts the number of ON light modulation devices of the light modulation devices 424a, 424b, and 424c such that the shifts from the transmitted signals are canceled.

In this manner, the light source device 403 sets a ratio of light intensities of the R, G, and B emission lights to achieve a white balance. Thereafter, the control circuit 427 holds the data in an internal memory 427a. In a normal usage state in which an endoscope inspection is performed, the R, G, and B emission lights are directed at the ratio of light intensities.

When the image pickup cycle variable switch 420 is operated to make it possible to change an image pickup cycle and an illumination cycle, the intensities of the emission lights are changed by an output signal from the luminance signal generation circuit 439 while the ratio of light intensities is kept (when the image pickup period is shortened with respect to objects having equal brightnesses, the intensities of the emission lights are increased).

The electric endoscope 402 transmits field sequential illumination lights from the light source device 403 to a distal end portion 431 of the insertion portion 406 through the light guide 408, and R, G, and B field sequential illumination lights are irradiated from the distal end face of the light guide of the distal end portion 431 onto an object to be photographed such as an affected part in a body cavity through an irradiation lens 432 attached to an illumination window.

By an objective lens 433 attached to an observation window adjacent to the illumination window, an optical image is formed at the image forming position of the distal end portion 431. At the image forming position, an image pickup element 434 such as a charge coupling element (to be abbreviated as a CCD) is arranged to convert an optical image into an electric image pickup signal. The image pickup element 434 is a monochromatic image pickup element having no optical color separation filter, and can perform color image pickup by field sequential image pickup. The image pickup element 434 is used in a CCD camera or the like, and is an image pickup element in which optical sensors are two-dimensionally arrayed to constitute a large number of pixels.

The image pickup element 434 is connected to the CCU 404 through the signal line 411. An image pickup element drive signal is applied from an image pickup element control circuit 436 in the CCU 404 to the image pickup element 434, so that an image pickup signal obtained by converting an optical image into an electric image pickup signal is input to a video signal processing circuit 437 in the CCU 404. A standard video signal is generated from the image pickup signal by the video signal processing circuit 437 and output to the monitor 405, and an object image picked by the image pickup element 434 is displayed.

Timing signals are input from a timing generator (to be abbreviated as a TG hereinafter) 438 to the image pickup element control circuit 436 and the video signal processing circuit 437. An image pickup element drive signal is generated or video signal processing is performed in synchronism with the timing signals.

The CCU 404 includes the luminance signal generation circuit 439 for generating a brightness signal or a luminance signal in one cycle from an output signal from the video signal processing circuit 437, and a decision circuit 440 for deciding the movement of an object to be photographed (with respect to the distal end portion 431) on the basis of input R, G, and B signals. The decision result of the decision circuit 440 is input to the TG 438. The decision circuit 440 is connected such that a timing signal from the TG 438 and a control signal from the control circuit 427 of the light source device 403 can be made variable.

An output signal from the luminance signal generation circuit 439 is also input to the control circuit 427. The control circuit 427 controls the modulation states of the light modulation devices 424a, 424b, and 424c through the drive circuit 426 when the image pickup cycle and the illumination cycle are changed such that the level of the output signal from the luminance signal generation circuit 439 does not change even though the image pickup cycle and the illumination cycle are changed.

Figure 56:
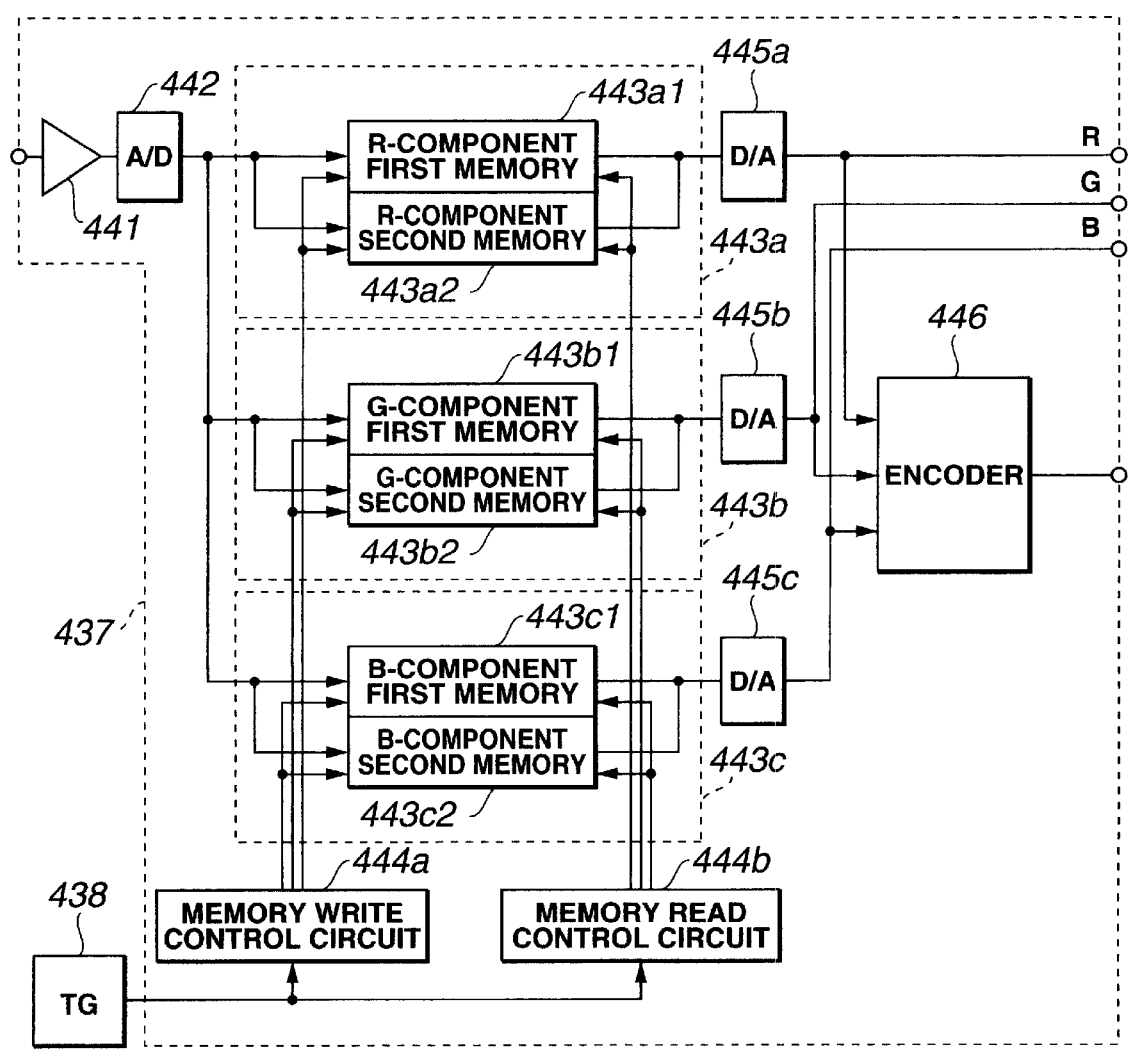

FIG. 56 shows the configuration of the video signal processing circuit 437.

An output signal from the image pickup element 434 is amplified by an amplifier 441 and then converted into a digital signal by an A/D conversion circuit 442. The digital signal is sequentially stored (written) in an R-component memory 443a (an R-component first memory 443a1 and an R-component second memory 443a2), a G-component memory 443b (a G-component first memory 443b1 and a G-component second memory 443b2), and a B-component memory 443c (a B-component first memory 443c1 and a B-component second memory 443c2).

More specifically, an R-component signal (from the image pickup element 434) obtained by image pickup performed under an R-component illumination light is stored in the R-component memory 443a, a G-component signal (from the image pickup element 434) obtained by image pickup performed under a G-component illumination light is stored in the G-component memory 443b, and a B-component signal (from the image pickup element 434) obtained by performing image picked up under a B-component illumination light is stored in the B-component memory 443c.

Write control to the R-component memory 443a, the G-component memory 443b, and the B-component memory 443c is performed by a memory write control circuit 444a, and read control from the R-component memory 443a, the G-component memory 443b, and the B-component memory 443c is performed by a memory read control circuit 444b. The memory write control circuit 444a and the memory read control circuit 444b receive write and read timing signals from the TG 438, and writes and reads data in synchronism with the timing signals.

The memory write control circuit 444a performs write control to the R-component memory 443a, the G-component memory 443b, and the B-component memory 443c in synchronism with the input R, G, and B signals. The memory read control circuit 444b performs control for simultaneously reading the R, G, and B signals from the R-component memory 443a, the G-component memory 443b, and the B-component memory 443c in synchronism with the timing of a standard video signal.

Each of the R-component memory 443a, the G-component memory 443b, and the B-component memory 443c is constituted by two memories, so that signals can be independently written and read at different timings.

The signals simultaneously read from the R-component memory 443a, the G-component memory 443b, and the B-component memory 443c are converted into analog R, G, and B chrominance signals by D/A conversion circuits 445a, 445b, and 445c, and these signals are output from R, G, and B output terminals to the monitor 405 or the like.

The R, G, and B chrominance signals are input to an encoder 446 for converting a signal into an NTSC composite video signal, and a video signal can also be output from an NTSC video output terminal.

Figure 57:
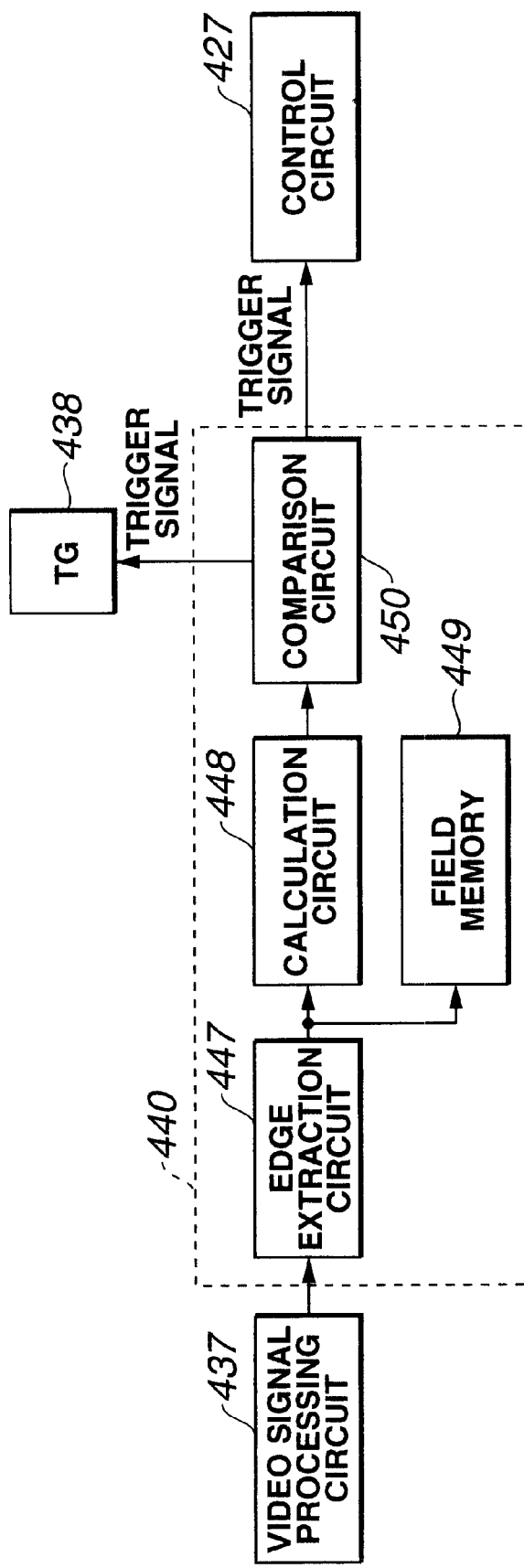

FIG. 57 shows the detailed configuration of the decision circuit 440.

The convergent lens 44 is constituted by an edge extraction circuit 447 for extracting edges by interpolation for performing subtraction of field sequential R, G, and B signals of the pixels, a calculation circuit 448 for calculating the edges of the R, G, and B signals to calculate differences there between, a field memory 449 for adjusting the timings of the field sequential R, G, and B signals in calculation, and a comparison circuit 450 for comparing the calculated differences with a reference value to decide movement, selectively determining a trigger signal to the TG 438, and selectively determining a trigger signal output to the control circuit 427 to make amounts of exposure before and after the change of the TG 438 constant.

In the embodiment, an image pickup period and an illumination period are changed depending on the movement of an object to be photographed (object to be observed). When the movement is detected, a short image pickup period and a short illumination period are set, so that an endoscope image having high image quality and small color breakup (or blur) can be obtained.

The operation of the embodiment will be described below.

The electric endoscope 402 is inserted into a body cavity to perform observation. When the electric endoscope 402 is operated near a heart in observation or when a bending operation of the electric endoscope 402 is performed, observation may be performed in a state in which an object to be observed quickly moves (with respect to the image pickup element 434 of the distal end portion 431 of the electric endoscope 402). In this case, the image pickup cycle variable switch 420 is operated to make an image pickup cycle and an illumination cycle changeable. Even though the image pickup cycle variable switch 420 is not arranged, the image pickup cycle and the illumination cycle may be made changeable.

The signal obtained by performing image pickup by the image pickup element 434 is input to the video signal processing circuit 437, and a standard video signal is generated by the video signal processing circuit 437. The standard video signal is output to the monitor 405 (not as shown), so that the image of an object to be observed displayed on the display surface of the monitor 405 can be observed. The R, G, and B chrominance signals obtained by the video signal processing circuit 437 are input to the decision circuit 440 to decide whether blur or color breakup occurs or not.

In the decision circuit 440, the edges of the R, G, and B chrominance signals from the video signal processing circuit 437 are extracted by the edge extraction circuit 447, the timings are adjusted by the field memory 449, and the differences between the R, G, and B signals are calculated by the calculation circuit 448. The calculation results are compared with a reference value which is set in the comparison circuit 450 in advance. If it is determined that color breakup (or blur) occurs, trigger signals are output to the TG 438 and the control circuit 427.

If it is determined by the decision circuit 440 that the R, G, and B chrominance signals to be observed has color breakup, a trigger signal is input to the TG 438. The TG 438 changes an accumulation time of the image pickup element control circuit 436 to shorten an accumulation period (image pickup period).

An image pickup timing signal shortened by the TG 438 is also input to the control circuit 427, and the control circuit 427 controls the timings of the direction lights from the light modulation devices 424a to 424c to synchronize an image pickup timing and R, G, and B field sequential direction lights of the light source device 403 (the illumination period of the field sequential illumination lights is also shortened to be synchronized with the image pickup period).

On the basis of the control signal, the reflective element drive control circuit 426 drives the light modulation devices 424a to 424c. However, in accordance with shortening of a drive cycle (increase in speed) of the light modulation devices 424a to 424c, the decision circuit 440 inputs a trigger signal to the control circuit 427 to make the amounts of exposure of the R, G, and B signals of the image pickup element 434 before and after the shortening of the drive cycle constant. A control signal for controlling the light modulation devices 424a to 424c to increase the intensities of reflected lights is generated, and the reflective element drive control circuit 426 performs modulation for elongating the ON times (within illumination periods or image pickup periods) of the light modulation devices 424a to 424c or for increasing the number of ON mirror elements, so that the amounts of exposure of the image pickup elements are kept constant.

The detailed operation is shown FIGS. 58A to 58C. FIG. 58A shows an exposure period (illumination period) and a shield period before control, FIG. 58B shows a case in which an exposure period is shortened to cancel color breakup when an object quickly moves, and FIG. 58C shows a case in which an exposure period is elongated when an object slowly moves.

In this manner, if it is determined by the decision circuit 440 that color breakup occurs, the exposure period of the image pickup element 434 as shown in FIG. 58B to short (exposure period in which image pickup of one color frame is performed by a field sequential method). In accordance with the exposure period, the direction timings of the light modulation devices 424a to 424c are synchronized with each other. Similarly, when an object to be observed which slowly moves is used, the result shown in FIG. 58C is obtained.

The amounts of exposure of the image pickup element before and after the change of timing by the control signal of the control circuit 427 is made constant by the trigger signal from the decision circuit 440. For this reason, the intensities of reflected R, G, and B lights from the light modulation devices 424a to 424c are increased to keep the brightness of the monitor 405 constant, and a total of image pickup times(total exposure times) of the R, G, and B lights are shortened. Even though an object to be observed which quickly moves is used, color breakup does not occur.

Image pickup signals which are free from color breakup are sequentially input to the video signal processing circuit 437. The R, G, and B image pickup signals are temporarily stored in first memories 443i1 (i=a, b, and c) by the memory write control circuit 444a.

The R, G, and B signals written in a memory 443i are simultaneously read by the memory read control circuit 444b, and the simultaneously read R, G, and B signals are converted into analog R, G, and B signals by D/A conversion circuits 445i to be output to the monitor 405 or the like.

More specifically, as shown in FIG. 59A, of signals sequentially obtained by performing image pickup as R1, G1, and B1, for example, the signal R1 is stored in the (R component) first memory 443a1, and, as shown in FIG. 59B, the signal R1 is held until a signal R2 of the next R component is input.

FIGS. 59C and 59D, the G and B components are processed by the same manner as described above. As shown in FIG. 59E, signals R1, G0, and B0 are simultaneously read at field frequencies in an interlace of about 1/60 sec from the memories, and signals R1, G1, and B0 are simultaneously read, so that the image of an object to be observed is displayed in color on the monitor 405.

FIGS. 59A to 59E show a case in which an image pickup timing of 1/59.94 sec and a monitor output are used. The image pickup timing is set to be an image pickup timing of an electronic endoscope to match the format of present television broadcast such as NTSC. The frame frequency of an interline transfer method based on interlace is 29.97 Hz, and the field frequency is 59.94 Hz.

In this manner, according to the embodiment, an image pickup time and an illumination period are changed to be interlocked with each other depending on the movement of an object to be photographed. When the object quickly moves, the image pickup time and the illumination period are shortened to be interlocked with each other, and an endoscope image having slight color breakup and high image quality can be obtained. An endoscope device which can easily perform an endoscope diagnosis or an endoscope inspection can be realized.

The twelfth embodiment of the present invention will be described below with reference to FIGS. 60A to 61H. The configuration of the embodiment is the same as that in FIG. 55. When the decision circuit 440 quickly moves, the frequency of an image pickup element drive signal obtained by the image pickup element control circuit 436 is doubled, and an image pickup cycle is shortened. An image having high image quality and small color breakup or blur is obtained.

For this reason, when it is determined by the decision circuit 440 that the object quickly moves, the signal is transmitted to the TG 438, and the TG 438 outputs a timing signal by a clock signal having a double frequency and a cycle which is ½ the cycle of the clock signal serving as a reference used when the timing signal is generated.

Figure 60A:
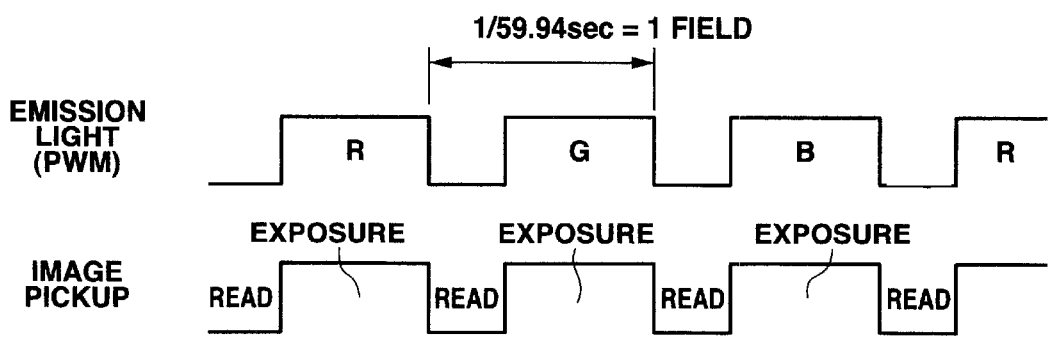
Figure 60B:
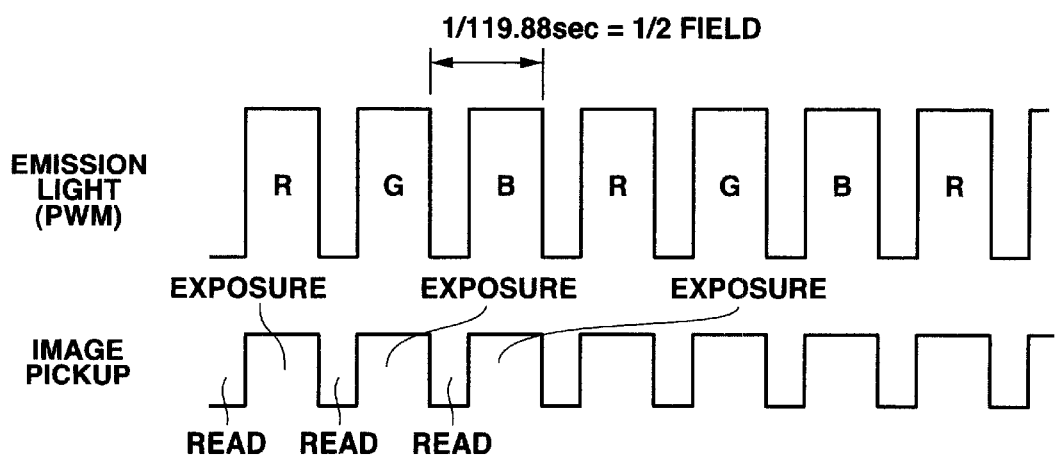

FIG. 60A shows the timing of an emission light emitted through a light modulation device and the timing of image pickup when an object is normal or slowly moves, and FIG. 60B shows a case in which it is determined that the object quickly moves, and image pickup is performed in a cycle which is ½ the cycle in FIG. 60A.

As described in thirteenth embodiment, the embodiment also has a configuration in which the timings of the shifts of the cycles of output signals to the monitor 405 obtained by changing the image pickup period are adjusted by using R-, G-, and B-component memories and first and second memories by the RGB memory control circuits 444a and 444B.

The operation of the embodiment will be described below.

As in the thirteenth embodiment, it is determined by the decision circuit 440 that an image pickup signal obtained by endoscope observation has color breakup, the TG 438 outputs a timing signal for making an image pickup time ½.

Being interlocked with the timing signal, the emission timings of the light modulation devices 424a to 424c are synchronized with each other to control the intensities of emission lights. When the image pickup time is shortened, color breakup or the like is canceled. At this time, an endoscope image is output to the monitor 405, the timing of interlace must be adjusted.

For example, as shown in FIG. 60A, when observation is performed at the timing of 1/59.94 sec in a normal image pickup cycle, and when it is determined by the decision circuit 440 that color breakup occurs, as shown in FIG. 60B, the cycle of the timing signal from the TG 438 is switched to 1/119.88 sec and making an image pickup time ½ by the trigger signal of the decision circuit 440.

Depending on the change of the timing, the trigger signals is also input from the decision circuit 440 to the control circuit 427, and control for doubling the intensities of the reflected lights from the light modulation devices 424a to 424c is performed not to change the brightness of the display on the monitor 405 before and after the switching. The image pickup cycle is shortened, and the intensities of the reflected lights from the light modulation devices 424a to 424c are controlled to be interlocked with the image pickup cycle. The intensities of the reflected lights are held not to change an amount of exposure, and an image having high image quality and small color breakup can be obtained.

A monitor output obtained when the image pickup cycle is changed will be described below. As shown in FIG. 61A, the emission light (and image pickup cycle) is changed to 1/120 sec (exactly, 1/119.88), R, G, and B image pickup signals are transmitted. As in the thirteenth embodiment, for example, when a signal R1 is transmitted, the signal R1 is stored in an R-component first memory by the control means on the input side as shown in FIG. 61B.

When the next signal R2 is transmitted, the signal R2 is stored in an R-component second memory as shown in FIG. 61C. When the signal R3 is transmitted, the signal R3 is stored in a first memory as shown in FIG. 61B. Subsequently, then the signal R4 is transmitted, the signal R4,is stored in a second memory. These memories continuously hold the previously stored signals until the next signals are input to the memories. The G component and the B component are similarly stored as shown in FIGS. 61D to 61G.

Here, when a monitor output is output, the operation shown in FIG. 61H is performed. More specifically, outputs from the first and second memories are selected by a control means on the output side to output R, G, and B signals at once. For example, the signal R0 is selected as the R component from the second memory, the signal G0 is selected as the G component from the second memory, and the signal B0 is selected as the B component from the second memory. These signals are simultaneously output. In the next output operation, the R-component second memory must store the signal R2 during the monitor output. For this reason, the signal R1 of the first memory is selected. Therefore, the signal G1 is selectively output as the G component, and the B1 is selectively output as the B component.

However, the input/output selection control is only an example. An optimum monitor output can be obtained by adjusting the input/output of the first and second memories.

In this case, the cycle of the emission light (image pickup) is set to be 1/59.94 sec which is one field period in a normal state. When the object moves, the cycle is set to be 1/119.88 sec which is ½ field period. However, the time of the image pickup cycle is variably controlled by a timing signal, so that the number of memories is increased depending on the speed of the image pickup cycle or so that the memory capacity is adjusted. For this reason, the embodiment can cope with any image pickup cycle.

Even though the image pickup cycle is made variable to prevent color breakup from occurring, a monitor output can cope with a known interline transfer method, and an endoscope image having small color breakup can be obtained.

In this manner, interlocking control of an image pickup cycle and an illumination period is performed depending on the movement of an object to be photographed even in the embodiment. For this reason, observation can be performed without color breakup at various portions in a body cavity or the like.

The fifteenth embodiment of the present invention will be described below with reference to FIGS. 62 to 66. An endoscope device 401C according to the fifteenth embodiment of the present invention shown in FIG. 62, in the endoscope device 401A of the thirteenth embodiment, a light source device 403C having a function of emitting R, G, and B field sequential illumination lights and a function of emitting field sequential lights of complementary colors, i.e., Mg (magenta), Cy (cyan), and Ye (yellow) is employed in place of the light source device 403 for emitting R, G, and B field sequential illumination lights, and a CCU 404C having a function of performing signal processing to signals obtained by performing image pickup under the R, G, and B field sequential illumination lights and a function of performing signal processing to signals obtained by performing image pickup under the Mg, Cy, and Ye field sequential illumination lights is employed in place of the CCU 404 for performing signal processing to signals obtained by performing image pickup under the R, G, and B field sequential illumination lights.

In the light source device 403C according to this embodiment, a light from the light source lamp 421 is transmitted through an infrared cut filter 422 to reflect an R light component, and is incident on a dichroic mirror 461a for transmitting the other light components. The R light component reflected by the dichroic mirror 461a is reflected by a total reflection mirror 463 through a relay lens 462a, and is incident on a reflective type light modulation device 424a through a relay lens 462b to be optically modulated. The modulated light component is incident on a prism 453.

The light transmitted through the dichroic mirror 461a is reflected with respect to a G light component, and is incident on a dichroic mirror 461b for transmitting the other light components. The G light component reflected by the dichroic mirror 461b is incident on a reflective light modulation device 424b to be optically modulated. The modulated light component is incident on the prism 453.

The B light component transmitted through the dichroic mirror 461b is incident on a reflective light modulation device 424c to be optically modulated. The modulated light component is incident on the prism 453.

The reflective type light modulation devices 424a to 424c are driven by a reflective element drive control circuit (DMD drive circuit) 426.

The prism 453 synthesizes an incident light to a condensation lens system 425, and the light condensed by the condensation lens 425 is incident on a light guide 408.

As an electronic endoscope 402b in the embodiment, an electronic endoscope in which a signal line 411 is also inserted in a light guide cable 409, and the signal cable 411 extends from a connector 413.

The CCU 404C has the following configuration. That is, in the CCU 404 in FIG. 55, a CPU 465 is employed in place of the decision circuit 440. A priority switch 466 for giving priority to one of an S/N ratio and color reproduction is arranged in the switch 420, and a video signal processing circuit having the configuration shown in FIG. 63 is employed as a video signal processing circuit 437b.

Figure 63:
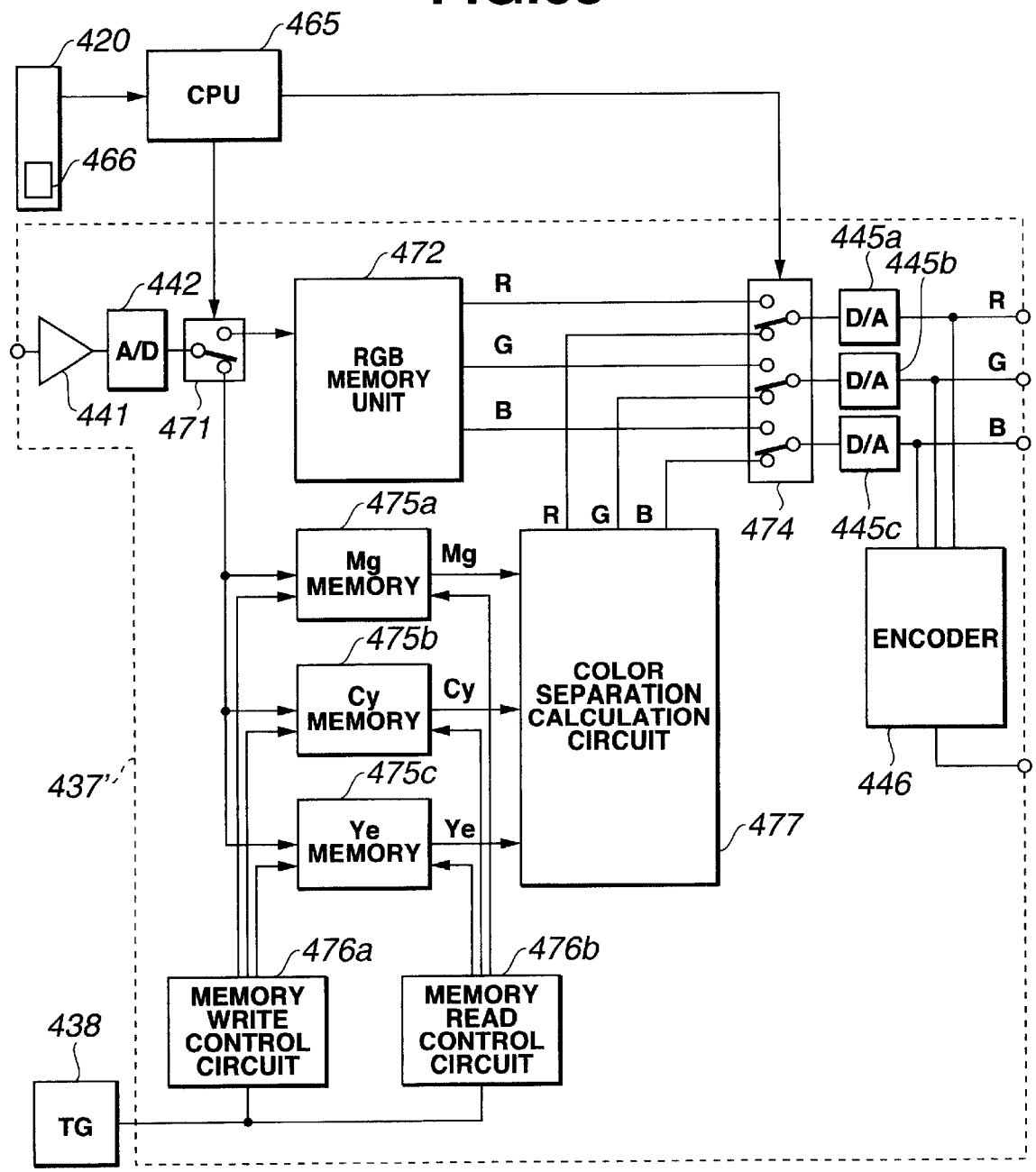

The video signal processing circuit 437b shown in FIG. 63 has the following configuration. That is, in the video signal processing circuit 437 shown in FIG. 56, an output from the A/D conversion circuit 442 is input to an RGB memory unit 472 or an MgCyYe memory unit 473 which is selected through a switch 471 whose switching operation is controlled through the CPU 465.

R, G, and B signals from the RGB memory unit 472 are output to the D/A conversion circuits 445a to 445c through a switch 474 whose switching operation is controlled through the CPU 465.

The MgCyYe memory unit 473 has an Mg memory 475a, a Cy memory 475b, and a Ye memory 475c. These Mg, Cy, and Ye memories 475a to 475c are controlled by a memory write control circuit 476a and a memory read control circuit 476b with respect to write and read operations.

Mg, Cy, and Ye signals read from the Mg, Cy, and Ye memories 475a to 475c are input to a color separation calculation circuit 477 to be converted in to R, G, and B color signals. The converted signal are output to the D/A conversion circuits 445a to 445c through the switch 474.

In the color separation calculation circuit 477, the following calculation to generate R, G, and B chrominance signals:

(Mg+Ye)−Cy=2R (Mg+Cy)−Ye=2B (Cy+Ye)−Mg=2G

The RGB memory unit 472 in FIG. 63 represents the R- to B-component memories 443a to 443c, the memory write control circuit 444a, and the memory read control circuit 444b which are shown in FIG. 56.

Figure 64A:
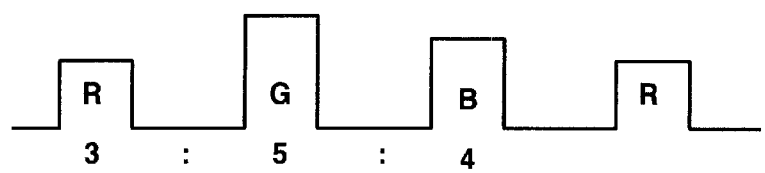
FIGS. 64A to 64C are explanatory diagrams of a change from a primary color system to a complementary color system depending on the brightness of an object to be photographed.
Figure 64B:
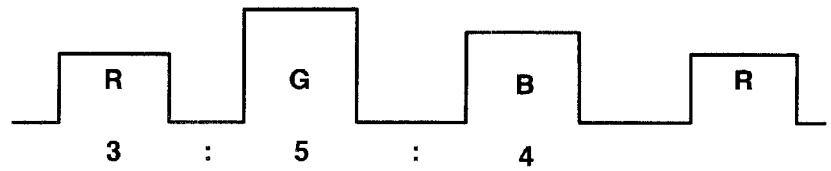

In the embodiment, when the priority switch 466 gives priority to an S/N ratio, and the switch 420 is turned on, an image pickup cycle is changed depending on the brightness of an object to be photographed under the R, G, and B field sequential illumination lights as shown in FIGS. 64A and 64B.

The state shown in FIG. 64A represents a bright state, and the state shown in FIG. 64B represents a dark state. However, R, G, and B emission lights are emitted such that a ratio of R, G, and B emission lights is kept at 3:4:5.

Even in the state in FIG. 64B, when the intensity of an emission light is short, the emission light is changed into an emission light and image pickup of a complementary color system. In this case, Mg (=G+B), Cy (=B+R), and Ye (=R+G) emission lights are emitted such that the ratio of the emission lights is kept at 9:7:8.

More specifically, in general, an output signal corresponding to the brightness of the luminance signal generation circuit 439 is input to the control circuit 427 under R, G, and B field sequential illumination lights, and light intensity control is performed such that a brightness appropriate to observation is obtained by the output signal.

The output signal is also input to the CPU 465 to monitor the level. Even though an image pickup cycle is elongated to a predetermined cycle serving as a reference under the R, G, and B field sequential illumination lights, when the brightness does not reach an appropriate brightness, the CPU 465 transmits a control signal for switching the R, G, and B field sequential illumination lights to Mg, Cy, and Ye field sequential illumination lights.

Figure 64C:
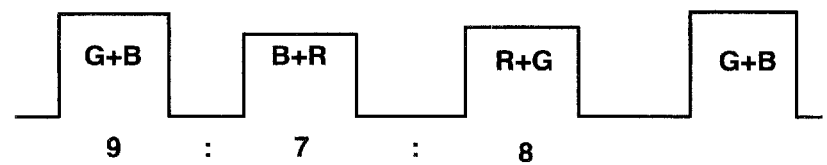
Figure 62:
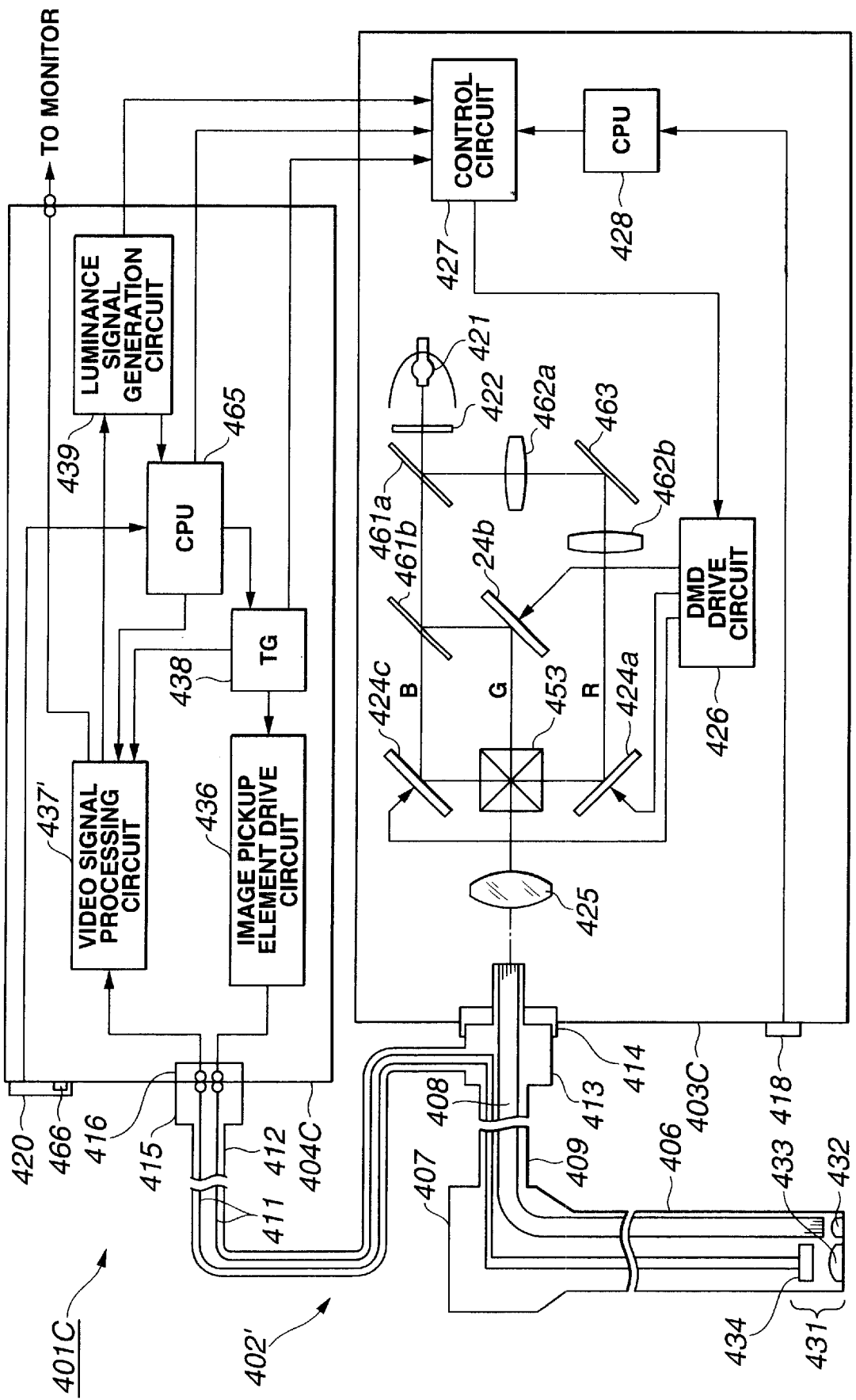

The control circuit 427 controls the reflective type light modulation devices 424a to 424c through the DMD drive circuit 426 so that Mg (=G+B), Cy(=B+R), and Ye (=R+G) field sequential illumination lights are output as shown in FIG. 64C The CPU 465 controls a video signal processing circuit 437'. More specifically, the switches 471 and 474 are switched, and the MgCyYe memory unit 473 side is used to generate R, G, and B signals.

Figure 66:
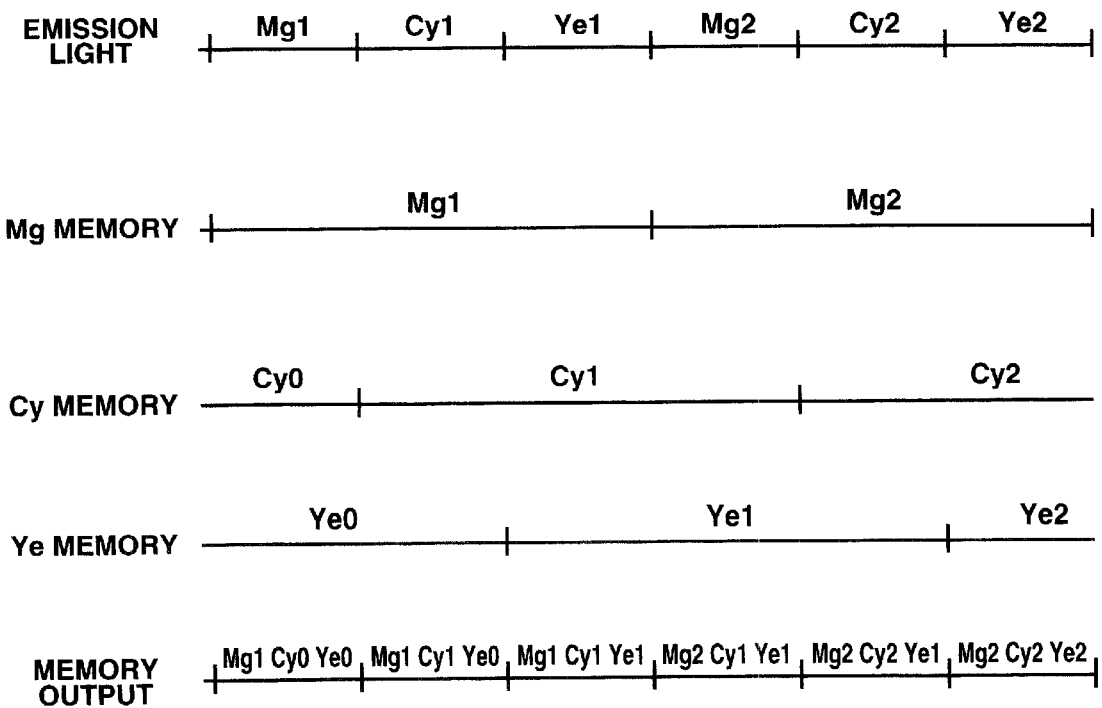

FIG. 66 shows read/write the timing of a signal in the MgCyYe memory unit 473 and the timing of a memory output when the Mg, Cy, and Ye emission lights are used.

More specifically, the signals obtained by performing image pickup under the Mg, Cy, and Ye emission lights are written in the Mg memory 475a, the Cy memory 475b, and the Ye memory to 475c. These signals are simultaneously read, converted into R, G, and B chrominance signals by the color separation calculation circuit 477, and converted into analog signals by the D/A conversion circuits 445a to 445c to output the analog signal to the monitor.

In this manner, in the embodiment, when image pickup performed under the RGB field sequential illumination is switched to image pickup performed under the MgCyYe field sequential illumination to prevent the image pickup cycle from being longer than the predetermined cycle, so that color breakup or blur is suppressed from occurring.

Figure 65:
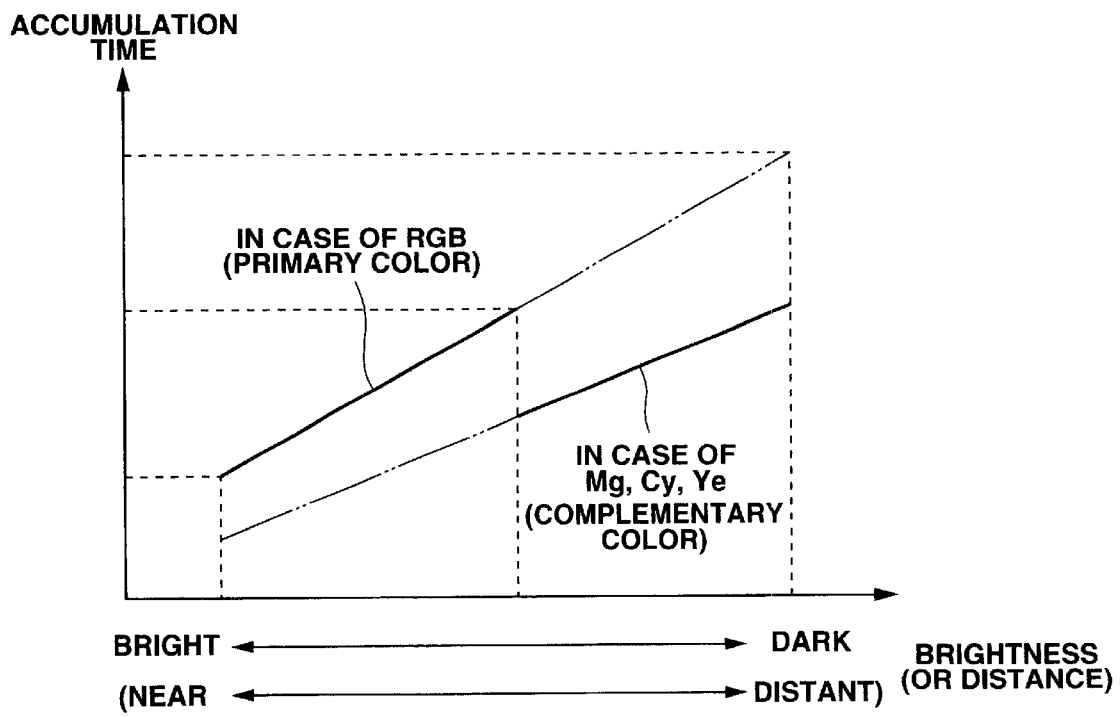

More specifically, as shown in FIG. 65, when brightness is higher than the brightness (or distance) of an object to be observed (in case of short distance), illumination and image pickup are performed by the RGB color system, i.e., the primary color system. When the brightness is lower than the brightness of the object (in case of long distance), illumination and image pickup are performed by the MgCyYe color system, i.e., the complementary color system. Therefore, an image pickup cycle is made shorter than that used when illumination and image pickup are performed by the primary color system, and color breakup or blur can be suppressed from occurring.

In addition, in case of short distance, when the object to be observed quickly moves, the mode is switched to a complementary mode, and an accumulation time is shortened to obtain an optimum intensity of light, so that color breakup can be canceled.

The operation of the embodiment will be described below.

When the priority switch 466 is set to give priority to color reproduction, and when the switch 420 is turned on, image pick up is performed while an RGB illumination state is maintained. In this case, the embodiment is the same as the thirteenth embodiment.

On the other hand, when the priority switch 466 is set to give priority to an S/N ratio, and when the switch 420 is turned on, illumination and image pick up are performed by the primary color system up to a predetermined image pickup cycle and a predetermined illumination period. When brightness is short even though the cycle is elongated to the predetermined cycle, a switching operation is performed such that illumination and image pickup are performed by the complementary color system.

In the video signal processing circuit 437b, when image pickup is performed by illumination lights of complementary colors, chrominance signals of the primary color are generated by the above configuration from chrominance signals of the complementary colors included in an image pickup signal. In this manner, a total image pickup time can be shortened, and observation can be performed with small color breakup.

More specifically, by the switching operation, intensities of illumination lights can be higher than those of the illumination lights of the primary color system. For this reason, in comparison with the primary color system, a predetermined brightness can be maintained in short illumination and short image pickup periods. Since the illumination and image pickup periods can be shortened, an endoscope image having small color breakup is obtained.

In the embodiment, the optical light modulation devices 461a to 461c and the prism 453 can be arranged such that the optical distances from the optical light modulation devices 461a to 461c to the prism 453 can be almost equal to each other, balances obtained when complementary colors are synthesized with each other are equal to each other, advantageously.

By using the complementary color system, illumination lights can be made brighter than those obtained when field sequential lights of the primary color system. Accordingly, an exposure time can be shortened, and color breakup can be more effectively canceled.

However, when color breakup is canceled by the complementary colors in the operation, color reproduction is deteriorated depending on cases. For this reason, in observation in which color reproduction is regarded as an important condition, the priority switch 466 is set such that priority is given to color reproduction, so that observation can be performed while holding the RGB mode.

According to the embodiment, the timing is controlled to an image pickup timing depending on the condition of an object to be photographed, and the light modulation device is controlled to be interlocked with the image pickup timing, so that field sequential lights can be emitted by the RGB primary color system or the complementary color system. Forth is reason, when a moving object to be photographed is used, an endoscope image having high image quality and small color breakup can be obtained.

The sixteenth embodiment of the present invention will be described below with reference to FIGS. 67 to 75.

Figure 67:
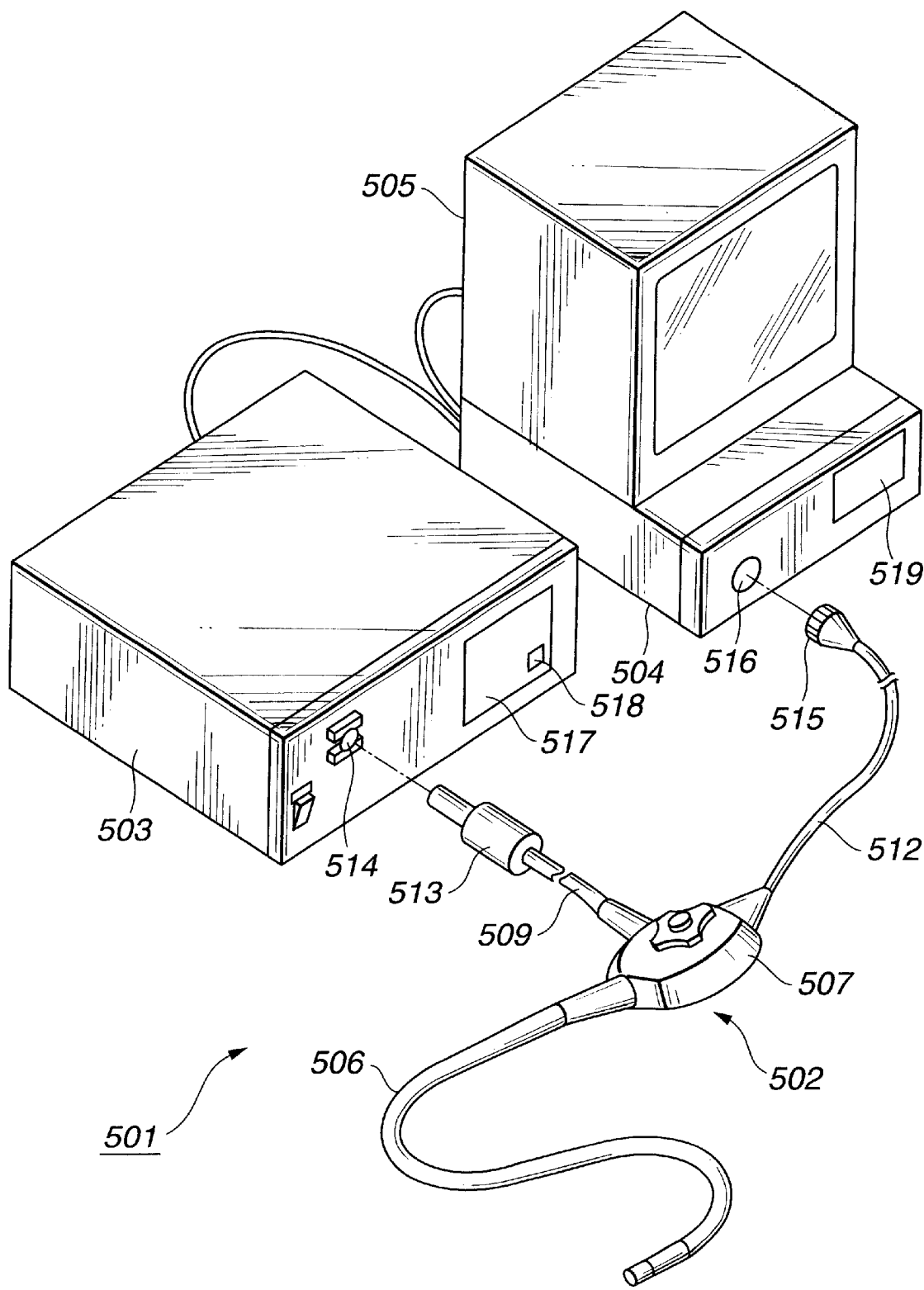

An endoscope device 501 according to the sixteenth embodiment of the present invention shown in FIG. 67 is constituted by an electronic endoscope 502, a light source device 503 for supplying an illumination light to the electronic endoscope 502, a camera control unit (to be abbreviated as a CCU hereinafter) 504 for performing signal processing to an image pickup element incorporated in the electronic endoscope 502, and a monitor 505 for displaying a video signal from the CCU 504.

The electronic endoscope 502 has a narrow and long insertion portion 506, an operation portion 507 having a large width and arranged at the rear end of the insertion portion 506, a light guide cable 509 which extends from a side portion of the operation portion 507 and in which a light guide 508 (see FIG. 68) serving as a light transmission means for transmitting an illumination light is equipped, and a signal cable 512 in which a signal line 511 (see FIG. 68) extending from the rear end of the operation portion 507 is equipped. A light guide connector 513 on the end of proximal side of the light guide cable 509 is detachably connected to a light guide connector support 514 of the light source device 503, and a signal connector 515 on the end portion of the signal cable 512 is detachably connected to a signal receptacle 516 of the CCU 504.

On the front surface of the light source device 503, not only the light guide receptacle 514, but also a power supply switch and an operation panel 517 are arranged. An initial setting switch 518 is arranged on the operation panel 517.

The signal receptacle 516 and an operation panel 519 are arranged on the front surface of the CCU 504.

Figure 68:
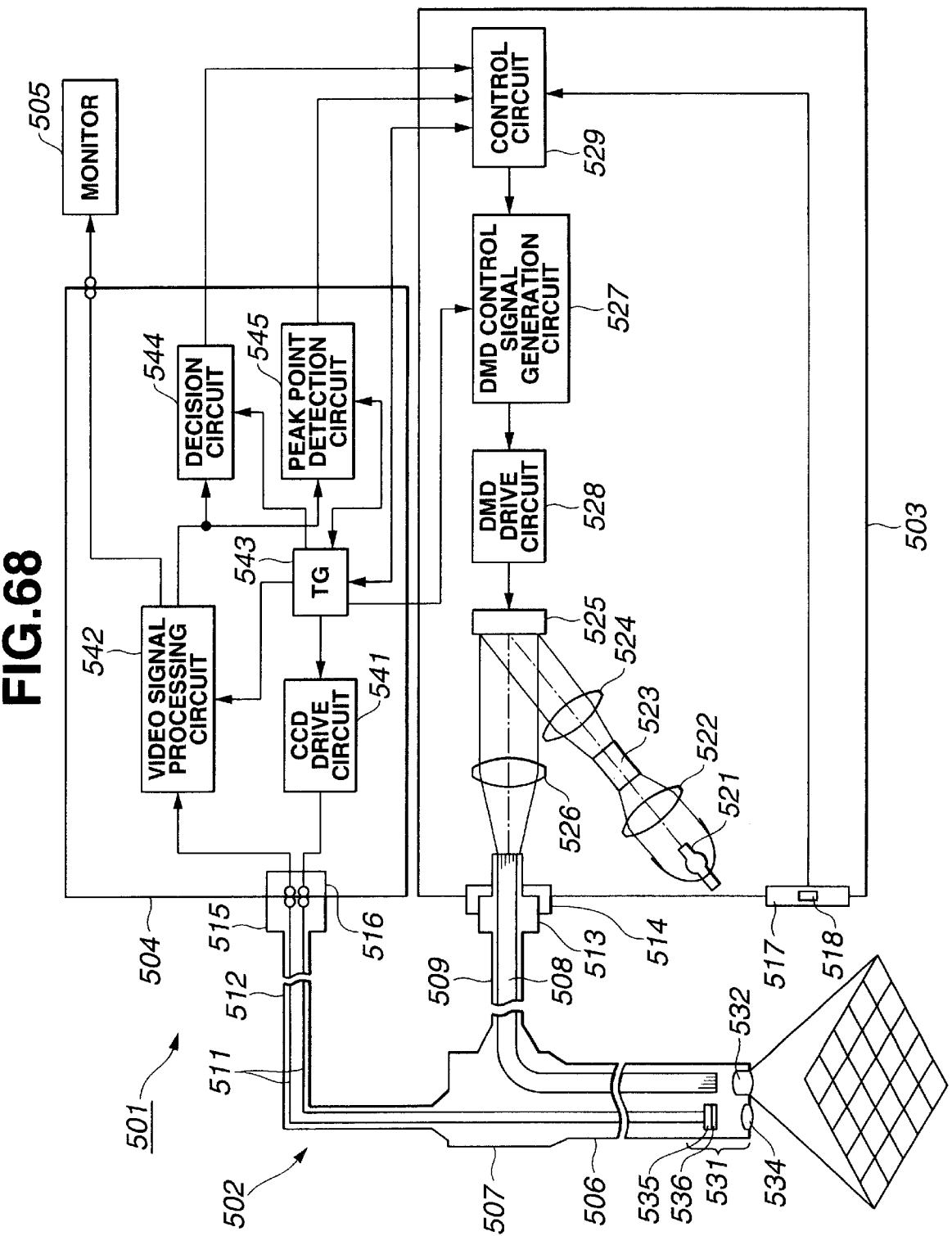

FIG. 68 shows the detailed configuration of FIG. 67.

The light source device 503 incorporates a discharge tube type light source lamp 521 for generating an illumination light, e.g., for performing light emission at a high luminance. The illumination light generated by the light source lamp 521 is incident on an integrator 523, for uniforming the light distribution of the lamp 521, by a condensation lens 522 arranged on the optical path of the illumination light, and the light uniformed by the integrator 523 is condensed by a collimator lens 524 into parallel fluxes of light. The parallel fluxes of light are incident on a reflective type light modulation device 525 arranged on the illumination optical path, and the light reflected by the light modulation device 525 is incident to the end face of the light guide connector 513 attached to the light guide receptacle 514 onto the light guide 508 having an image transmission function and serving as a light transmission means (light guide means) by an image forming lens system 526 for forming an image. The light is irradiated to an object to be photographed to be two-dimensionally spread.

In the embodiment, the light guide 508 is a bundle of array type optical fibers. More specifically, in the light guide 508, a fiber array on one end face is equal to a fiber array on the other end face, and, therefore, the fiber array is similar to the fiber array of a so-called image guide having a function of transmitting an optical image, so that the illumination light can be transmitted.

The light modulation device 525 is a device having the following configuration. That is, a large number of micromirror elements which are two-dimensionally arrayed in, e.g., a square lattice are arranged on a silicon chip such that part of parallel fluxes of light which are two-dimensionally spread, and each mirror (element) is held by a holding member on a yoke rotated about the diagonals of the element between two stable states and can be changed at ±10° in the horizontal direction. The light modulation device 525 is called a DMD (digital micromirror device). In the embodiment, as the light modulation device 525, a two-dimensional array element having a size of, e.g., 800×600 is used.

The light modulation device 525 is driven such that a DMD drive signal from the DMD drive circuit 528 is applied by a DMD control signal generated by a DMD control signal generation circuit 527.

A light reflected by a mirror driven at, e.g., +10° is out of an optical path which is incident on the image forming lens system 526 and is not incident on the light guide 508 to be set in a shield state (may be abbreviated as an OFF state). The light reflected by a mirror driven at −10° is incident on the image forming lens system 526 to be set in a state (may be abbreviated as an ON state) in which the light contributes to illumination being correctly incident on the light guide 508. When the mirror is set at an intermediate value between these values, the following operation or the like is performed. That is, a light which is limited depending on the intermediate state is incident on the light guide 508.

More specifically, the reflective characteristics of the mirrors are controlled by the DMD drive signal applied to the light modulation device 525 to be set at −10°. The light reflected by the mirror contributes to illumination, and the light reflected by the mirror set at +10° distributes to illumination.

The DMD control signal generation circuit 527 is controlled by a control circuit 529. A control signal is input from the CCU 504 to the control circuit 529.

When the light guide connector 513 is connected to the light source device 503, the relationship between the light guide 508 and the light modulation device 525 is always kept (locked) in the same state. For this reason, the light guide connector 513 is attached to the light guide connector support 514 through a positioning mechanism such as a positioning pin in the peripheral direction.

The light transmitted to the light guide 508 is further projected from the distal end face fixed to a distal end portion 531 of the insertion portion 506 onto the object side by an optical lens system (projection lens) 532 for performing projection, and two-dimensionally illuminates the object side.

On the distal end portion 531, an objective lens system 534 is attached to an observation window arranged adjacent to an illumination window to which the optical lens system 532 is attached, and the optical image of the object is formed. At the image forming position, as a solid state image pickup element, a charge coupling element (to be abbreviated as a CCD) 535 is arranged, and the optical image is converted into an electric image pickup signal by the charge coupling element 535. Note that a color separation filter 536 for optically performing color separation is arranged on an image pickup surface of the CCD 535 to separate colors into R, G, B, and the like for pixels.

The CCD 535 is connected to the CCU 504 by the signal line 511. A CCD drive signal is applied from a CCD drive circuit 541 in the CCU 504 to the CCD 535 to read an image pickup signal which is photoelectrically converted by the CCD 535. The image pickup signal is input to a video signal processing circuit 542 in the CCU 504 to generate a standard video signal. The video signal is output to the monitor 505 to display an object image in color.

A timing signal is input from a timing generator (to be abbreviated as a TG) 543 to the CCD drive circuit 541 and the video signal processing circuit 542. In synchronism with the timing signals, a CCD drive signal is generated.

A luminance signal generated by the video signal processing circuit 542 is input to a decision circuit 544 for deciding whether a point is a luminescent spot or not from the luminance signal and a peak point detection circuit 545 for causing the CCD pixels to correspond to the positions of the micromirror elements of the light modulation device 525.

In this case, when initial setting is performed, a luminance signal is input to the peak point detection circuit 545. As will be described later, one of the micromirror elements of the light modulation device 525 is set in an ON state to illuminate an object side. In this case, only an illumination area obtained by one ON micromirror element is brightly illuminated. The peak point of the luminance signal detected in the image pickup performed in this state is detected, and address data at this peak point is held and output to the control circuit 527. When these operations are performed, the data of positional information obtained by making a one-to-one correspondence between the micromirror elements contributing to the illumination positions (illumination areas) obtained by the light modulation device 525 and the CCD pixels which perform image pickup of the illumination positions in this case can be obtained by the control circuit 527.

More specifically, in the initial setting, a luminance signal from the video signal processing circuit 542 is input to the peak point detection circuit 545. In synchronism with the luminance signal, the address of the luminance signal is input to the peak point detection circuit 545 by the TG 543. The input luminance signal and the input address are designed to be stored in memories which make a one-to-one correspondence to the light modulation device 525 such that the luminances of pixels in one frame are compared with each other by the peak point detection circuit 545 and the addresses of the pixels of the CCD 535 are input to the control circuit 529.

After the initial setting, in use of a normal endoscope, the luminance signal is input to the decision circuit 544.

An output signal from the decision circuit 544 is input to the control circuit 529 to perform an operation for controlling the light modulation device 525. For example, (may occur before control) the intensity of a light irradiated on a luminescence spot portion is reduced, and the light modulation device 525 is controlled without generating a luminescence spot to obtain a reflection intensity at which observation can be easily performed. With respect to a dark spot portion, the intensity of a light irradiated on the portion is increased, and the light modulation device 525 is controlled without generating a dark spot to obtain a reflection intensity at which observation can be easily performed.

In the control circuit 529, the internal CPU 547 (see FIG. 69) switches the TG 543 to an initial setting mode according to an instruction from the initial setting switch 518 in initial setting, and a luminance signal from the video signal processing circuit 542 is input to the peak point detection circuit 545. A positional correspondence between the pixels of the CCD 535 and the elements of the light modulation device 525 is made, and the CPU 547 switches the TG 543 to a normal mode. A luminance signal of the video signal processing circuit 542 is input to the decision circuit 544 to generate a correction signal for correcting a luminescence spot or a dark spot, and the CPU 547 controls the intensities of two-dimensional array elements of the light modulation device 525 for performing illumination of a portion where a luminescence spot or a dark spot is generated.

A timing signal is input from the TG 543 to the decision circuit 544, the peak point detection circuit 545, and the control circuit 529, and an operation synchronized with the timing signal is performed. A timing signal is also input from the TG 543 into the DMD control signal generation circuit 527, and an operation synchronized with the timing signal is performed.

Figure 69:
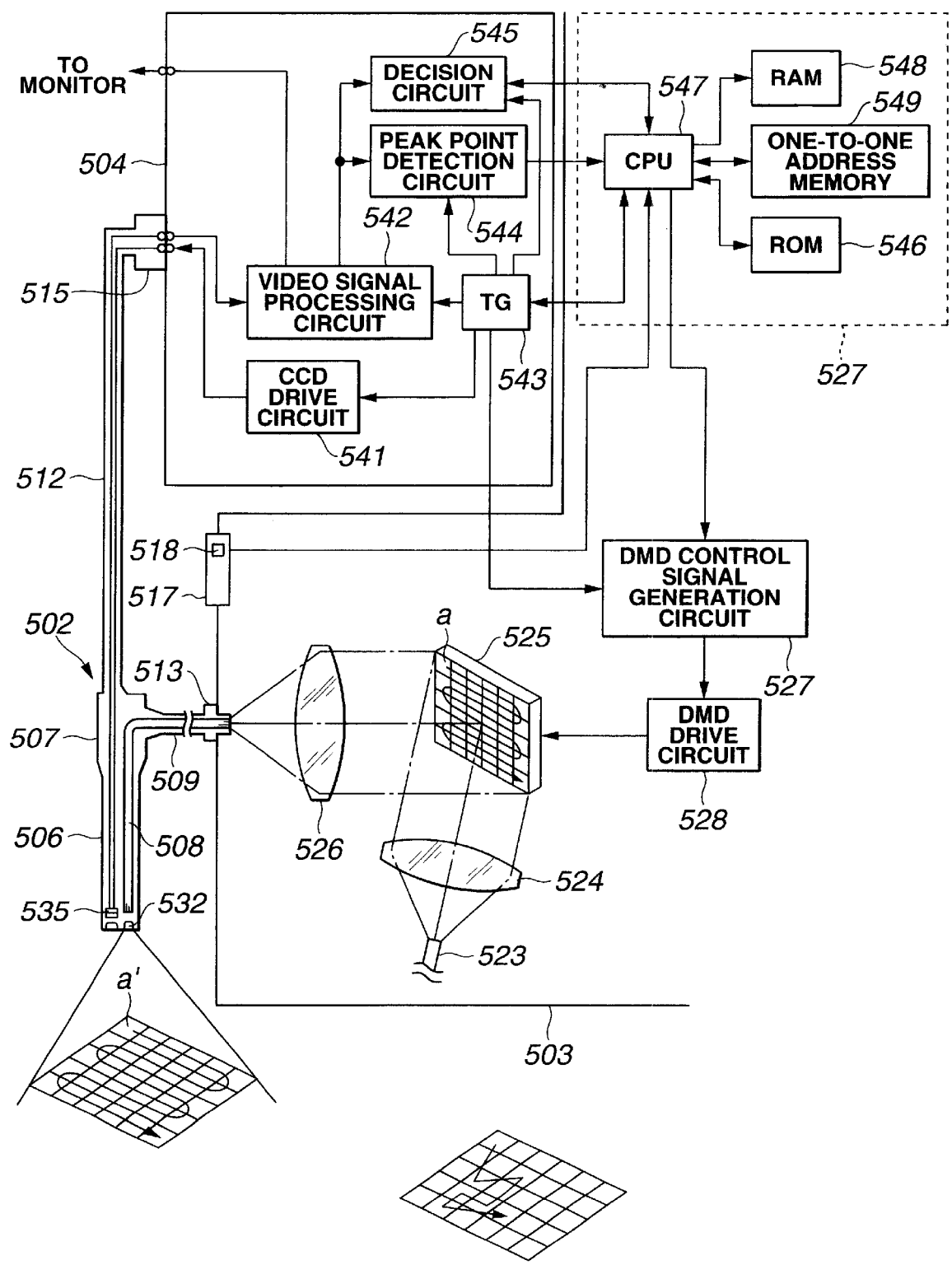

The control circuit 529 is constituted by a ROM 546 in which an operation program is stored as shown in FIG. 69, a CPU 547 for reading the program from the ROM 546 to execute a corresponding control operation, and a one-to-one address memory 549 in which one-to-one corresponding address data are stored by the CPU 547 and in which address signals (corresponding to the pixels of the CCD 535) are read and used when the light modulation device 525 is controlled.

Figure 70:
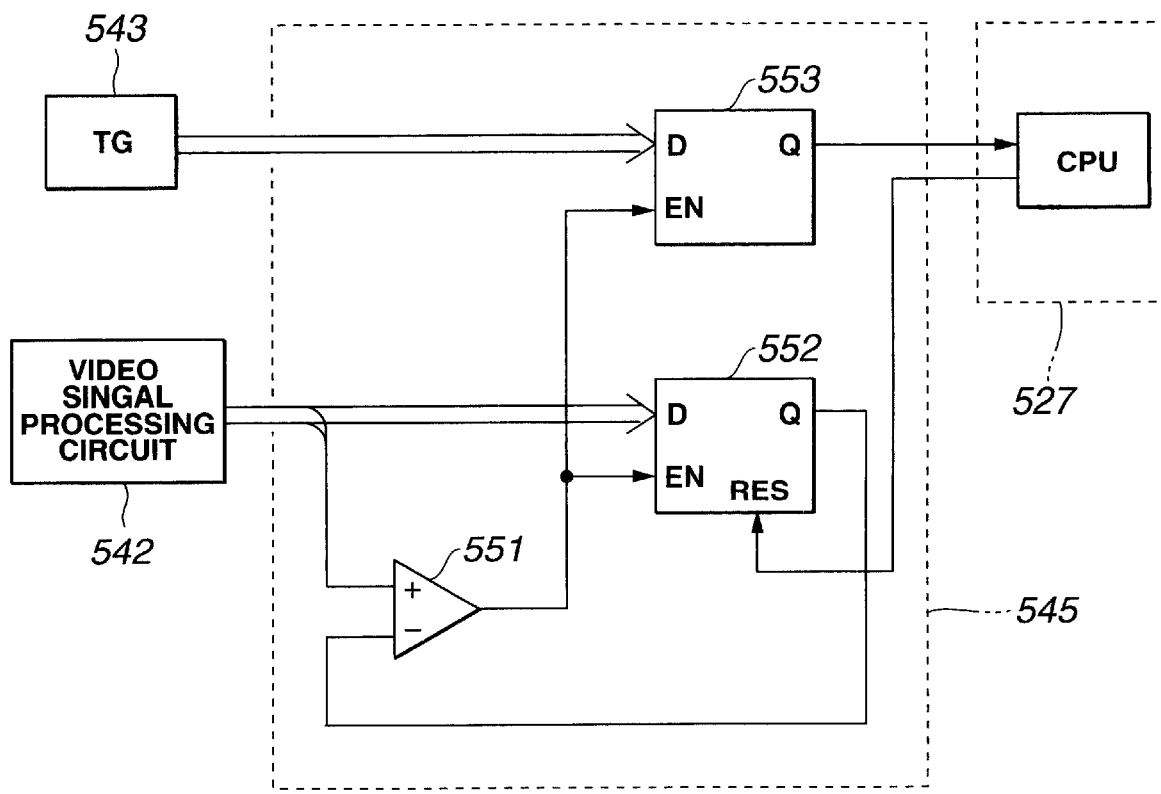

The configuration of the peak point detection circuit 545 is shown FIG. 70. A luminance signal Y from the video signal processing circuit 542 is input to (non-inversion input terminal of) a comparison circuit 551 and applied to a data input terminal D of a first latch circuit 552. A timing signal (more specifically, address signals corresponding to the horizontal and vertical positions of the luminance signal of a video signal read and generated from the CCD 535) from the TG 543 is applied to an data input terminal D of a second latch circuit 553.

An output signal from the comparison circuit 551 is applied to latch enable terminals EN of the first latch circuit 552 and the second latch circuit 553. A signal from an output terminal Q of the first latch circuit 552 is input to the (inversion) input terminal of the reference side of the comparison circuit 551, and a signal from an output terminal Q of the second latch circuit 553 is input to the CPU 547 of the control circuit 529.

The first latch circuit 552 is designed to be reset by the CPU 547. As will be described later, the address data for making a one-to-one correspondence between the CCD pixels and the micromirror elements of the light modulation device 525 is held in the second latch circuit 553, and the address data is transmitted to the CPU 547 and stored in the one-to-one address memory 549 by the CPU 547.

Figures 71A, 71B:
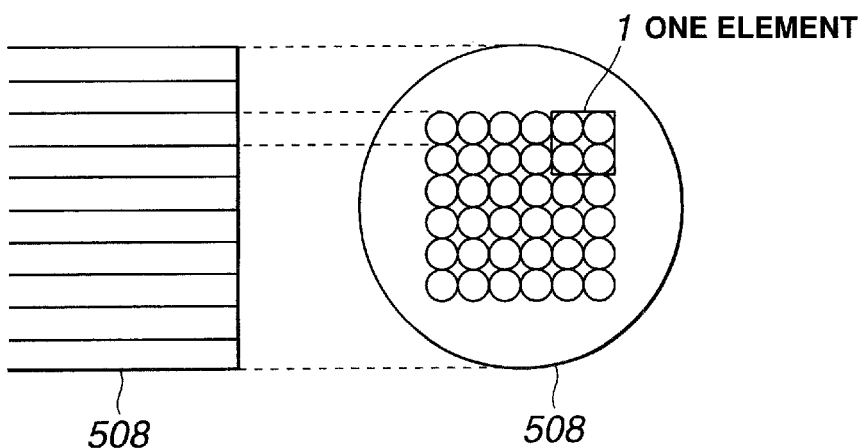
FIG. 71A is a diagram showing a portion near an end face of a light guide on an incident side.
FIG. 71B is a diagram showing the relationship between an element of the light modulation device and a fiber diameter of the light guide.

FIG. 71B shows the relationship between the size of each element of the light modulation device 525 and a fiber diameter obtained when an image is formed on the end face of the light guide 508 in the embodiment. FIG. 71A shows the light guide 508.

Any problem is not posed when a fiber diameter obtained when a light controlled by the light modulation device.525 is focused on the end face of the light guide 508 by the image forming lens system 526 is equal to the size of each element of the light modulation device 525. In addition, FIG. 71B shows the following case. That is, when the size of each element of the light modulation device 525 and the fiber diameter of the light guide 508 satisfy a relationship, i.e., (the size of each element)>(fiber diameter), the light of one element of the light. modulation device 525 is transmitted to a portion to be observed, and the light can be stored in a one-to-one correspondence with respect to each pixel of the CCD 535. For this reason, any problem is not posed.

The operation of the embodiment having the above. configuration will be described below.

When the initial setting switch 518 is turned on, an output signal of the luminance signal of the video signal processing circuit 542 is input to the peak point detection circuit 545, and the luminance signal is input to the decision circuit 544 in the sequential normal operation.

A signal for controlling the two-dimensional array elements of the micromirrors in a matrix consisting of rows and columns by luminance signals corresponding to the two-dimensional array elements of the light modulation device 525 is input to the DMD control signal generation circuit 527.

The address correspondence of the pixels will be described first with reference to the flowchart in FIG. 72, the explanatory diagram in FIG. 69, and the peak point detection circuit 545 in FIG. 70.

Before an endoscope inspection is performed in a state in which the electronic endoscope 502 is connected to the light source device 503 and the CCU 504, a correspondence between the light modulation device 525 and the CCD pixels is made.

Figure 72:
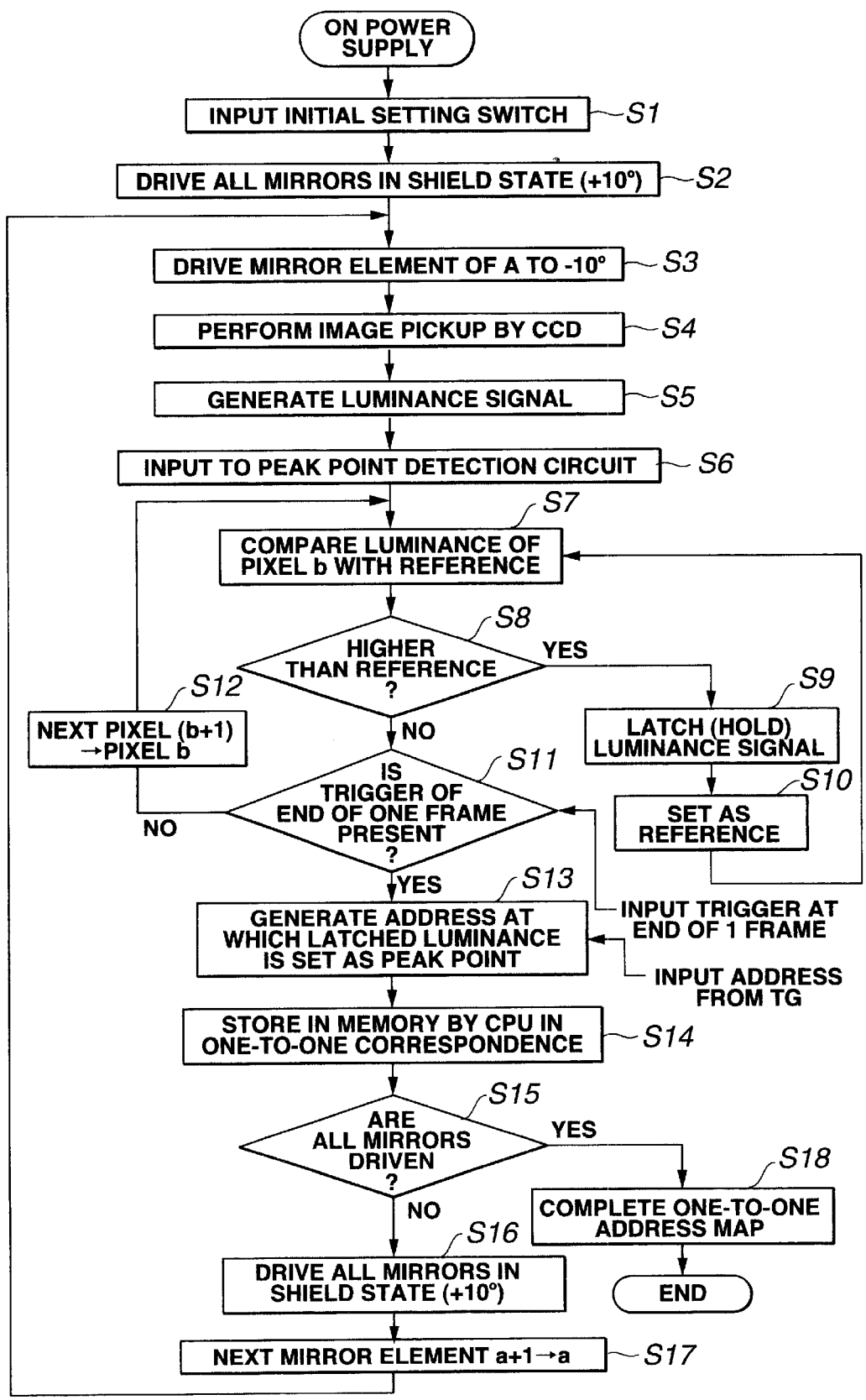

When the power supply for the light source device 503 and the CCU 504 is turned on, as indicated in step S1 in FIG. 72, the CPU 547 of the control circuit 527 can accept an input of the initial setting switch 518 arranged on the front panel 517.

When the initial setting switch 518 is turned on, as indicated in step S2, the CPU 547 controls a drive signal from the DMD drive circuit 528 through the DMD control signal generation circuit 527, and temporarily drives all the DMD mirrors of the light modulation device 525 at +10° such that a shield state in which an illumination light from the light source device 503 is not output is set.

As indicated in step S3, an element drives one mirror of a (initial value is 1) at −10°, so that a light reflected by only the mirror of a is output. A light component reflected by the mirror of a is focused on the end face of the light guide 508, transmitted to the distal end face by fibers located at the focused position, and projected on an object surface by the optical lens system 532. In FIG. 69, a projection component reflected by the mirror of a, transmitted by the fibers, and projected on the object surface is indicated by a'. Only the portion of the projection component a' is brightly illuminated (therefore, the luminance of a signal of a portion where image pickup of the projection component a' is maximum (peak)). An object image obtained at this time is picked up (step S4), the image is input to the video signal processing circuit 542 to generate a luminance signal (step S5), and input to the peak point detection circuit 545 (step S6). The luminance signal of each pixel b (b=1 in the first pixel) is compared with a reference by the comparison circuit 551 incorporated in the peak point detection circuit 545 shown in FIG. 70 (step S7).

It is checked by the comparison whether the luminance signal is higher than the reference (Ref) or not (step S8). If the luminance signal is higher than the reference, an output from the comparison circuit 551 becomes Hi, the first latch circuit 552 is made enable, and the input luminance signal is held (step S9). Being interlocked with this, the second latch circuit 553 is made enable, and the address data of the timing (obtained by the TG 543) of the luminance signal held in the first latch circuit 552 is held in the second latch circuit 553.

The luminance signal held by the first latch circuit 552 is input to the reference input terminal comparison circuit 551, and the luminance signal serves as a reference which will be compared with the next (step S10).

On the other hand, if the input luminance signal is lower than the reference in the determination instep S8, it is checked in step S11 whether a trigger input at the end of one frame is present or not. If the trigger input at the end of one frame is not present, the next pixel (b+1) in step S12 is defined as a pixel b (in this case, b=2), the flow returns to step S7.

Similarly, the luminance of the pixel b is compared with the reference, and the process of checking whether the luminance is higher than the reference or another process is repeated.

As described above, when the luminance level is higher than the reference in the comparison circuit 551, an output from the comparison circuit 551 becomes Hi, the holding data (reference signal data) of the first latch circuit 552 is updated. At the same time, the address data in the second latch circuit 553 is updated.

In this manner, when sequential comparing operations are performed to the pixels of one frame, a trigger at the end of one frame is input in step S11, and it is determined by the CPU 547 that the trigger at the end of one frame is present. The flow shifts to step S13 to perform the process of generating (holding) an address having a latched luminance as a peak point.

The address held in the second latch circuit 553 is the address of a peak point pixel, and the address is output to the CPU 547. As indicated in step S14, address data in which a one-to-one correspondence between the two-dimensional array elements of the light modulation device 525 and the pixel addresses of the peak points of the CCD 535 is made in the one-to-one address memory 549 (e.g., at an address corresponding to a). However, the CPU 547 determines the end of the comparison of one frame, the CPU 547 resets the first latch circuit 552. An address signal and a luminance signal in FIG. 70 are signals each having a predetermined bit width, and synchronized with each other by the TG 543.

As indicated in step S15, it is checked whether all the mirrors are driven or not. Since the condition is not satisfied, all the mirrors are driven in a shield state as indicated in step S16 to drive the next mirror. The mirror (a+1) of the next mirror is defined as the mirror a, and the flow returns to step S3. The mirror a is driven at −10°, and the address of peak point pixel in this case is held. The address data is stored (at an address corresponding to, e.g., (a+1)) in the one-to-one address memory 549.

In addition, the peak point of the brightness of the CCD pixel is detected in the peak point detection circuit 545 by the same method as the comparison method, and, as described above, the positional relationships are stored in the one-to-one address memory 549. Peak point detection, comparison, and storage of all the elements of the DMD are sequentially performed until these operations are completed. When all the addresses are sequentially stored, the flow shifts from step S15 to step S18, a one-to-one address map is completed, and the process is ended. In this manner, the relationship between the positions of the mirrors of the DMD and the pixels of the CCD 535 corresponding to the mirrors is determined.

For example, when the DMD mirrors are sequentially set in a drive state as indicated by an arrow in FIG. 69, the projection components of light points are formed on the object side as indicated by an arrow. The addresses of the light points of the projection component obtained by image pickup performed in the CCD 535 are detected. Address data obtained in this case are stored in the one-to-one address memory 549.

When the number of two-dimensional array elements of the DMD mirrors is different from the number of pixels of the CCD 535, the plurality of two-dimensional array elements are grouped and sequentially driven, so that a correspondence between the mirrors of the DMD and the pixels of the CCD can be similarly made by using the means described above.

The one-to-one address memory 549 is constituted by a plurality of memories. Addresses in the initial setting are loaded such that the addresses are sequentially stored in the plurality of memories by setting performed from the operation panel 517 having the initial setting switch 518 arranged thereon. In normal setting, of the one-to-one corresponding addresses of the light modulation device 525 and the CCD 535, an address signal corresponding to a luminance signal address is read at random.

Figure 73:
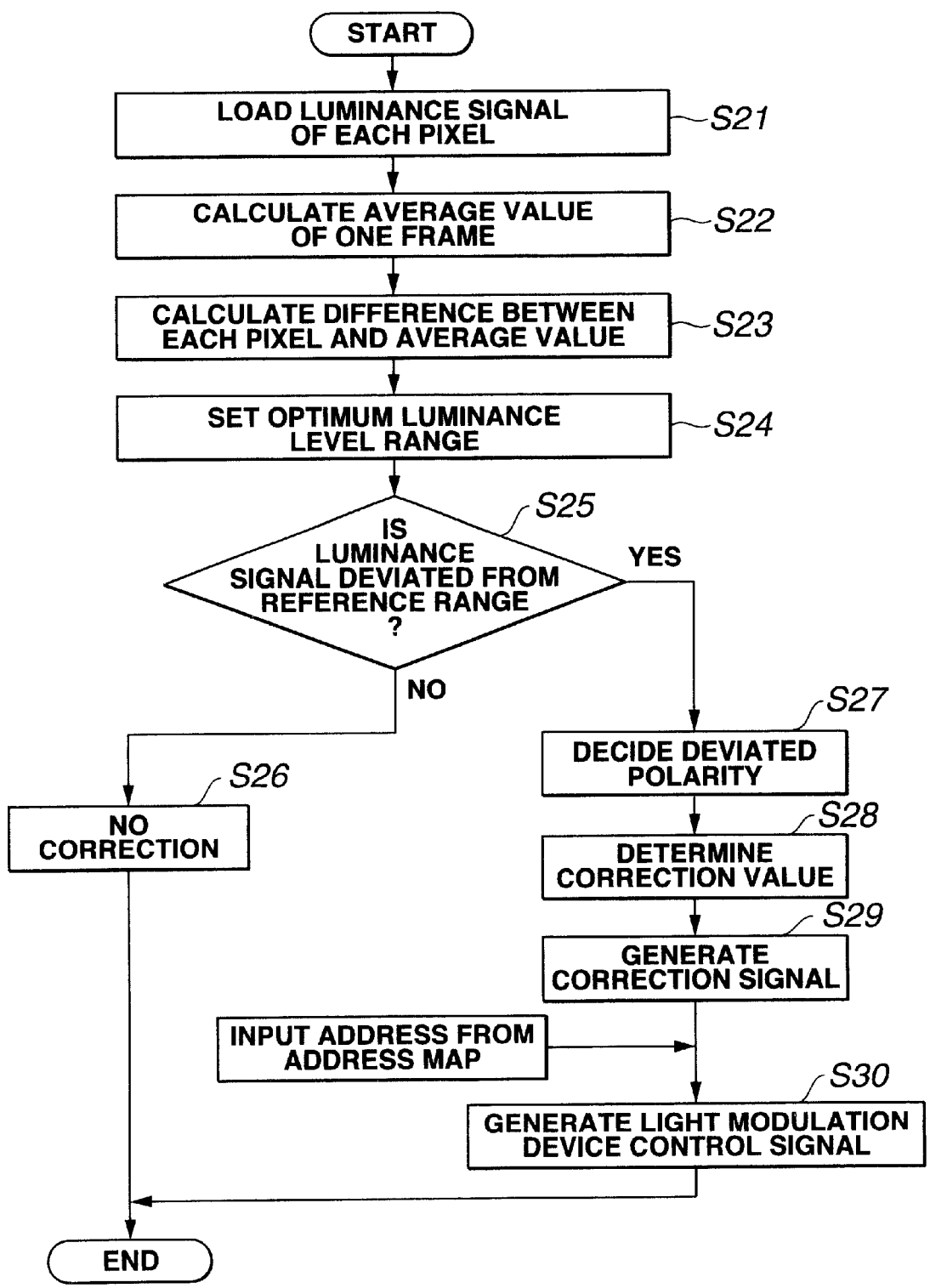

The operation of the decision circuit 544 shown in FIG. 68 in a normal usage state will be described below with reference to the flow chart in FIG. 73 and the graphs for explaining operations in FIGS. 74A to 74F.

When the power supply is turned on to set the CCU 504 and the like in an operation state, the CCD 535 is driven by the CCD drive circuit 541, and a signal obtained by image pickup performed by the CCD 535 is input to the video signal processing circuit 542 to be processed. As indicated in step S21 in FIG. 73, luminance signals of the pixels of the CCD 535 output from the video signal processing circuit 542 are input to the decision circuit 544 (loaded).

Figure 74A:
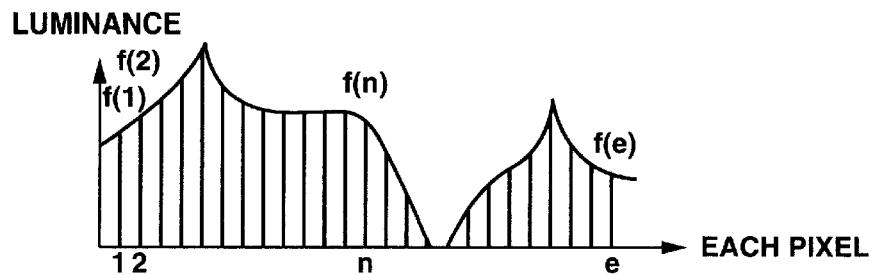
FIGS. 74A to 74F are graphs for explaining operations in FIG. 73.
Figure 74B:
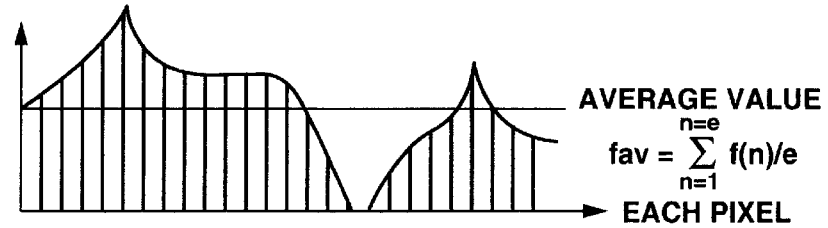

An example of the luminance signals obtained in this case is shown in FIG. 74A. In FIG. 74A, the luminance signal of a pixel n is represented by f(n). In the decision circuit 444, as indicated in step S22, an average value of one frame is calculated. When the average value is represented by fav, and when the number of pixels is represented by e, the average value is expressed as shown in FIG. 74B.

Figure 74C:
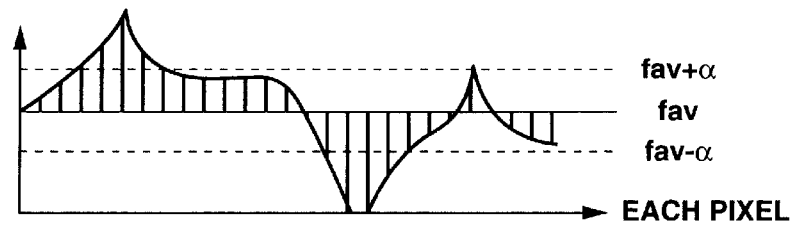

The decision circuit 544 calculates the difference between the luminance of each pixel and the average value as indicated in step S23. As shown in step S24, with respect to the luminance signal, addition and subtraction of the average value fav and positive and negative reference value a are performed to set an optimum luminance level range (also called a reference range) of the CCD 535. The luminance level range is shown in FIG. 74C (the reference range is a range of a level (fav−α) to level (fav+α)).

Figure 74D:
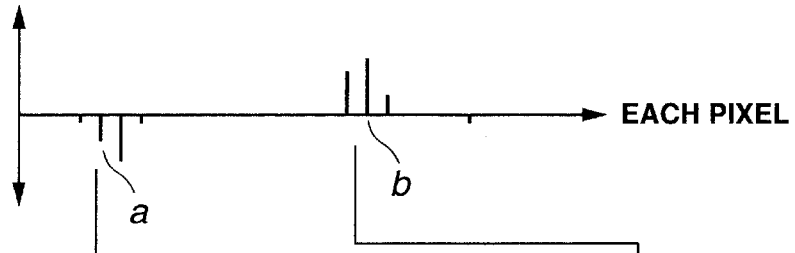

As shown in step S25, it is checked whether a luminescence/dark spot departs from the optimum luminance level range, so that correction is not performed to a portion which does not depart from the range (step S26). In contrast to this, if the luminescence/dark spot departs from the optimum luminance level range, a polarity (luminescence or dark spot) which departs from the luminance level range is decided (step S27). The decided manner is shown in FIG. 74D.

A correction value is determined depending on the departing polarity and the departing value (step S28).

After the correction value is determined, a correction signal for setting the departing portion in the optimum luminance level range is generated (step S29). The correction signal is output from the decision circuit 544 to the control circuit 529.

Correction signals corresponding to the two-dimensional array elements of the light modulation device 525 and the address signals of the correction signals are output to the DMD control signal generation circuit 527, and a control signal for controlling pulse width modulation (to be referred to as PWM hereinafter) is generated such that the two-dimensional array elements of the light modulation device 525 can supply optimum intensities of light to a portion to be observed (step S30).

Figure 74E:
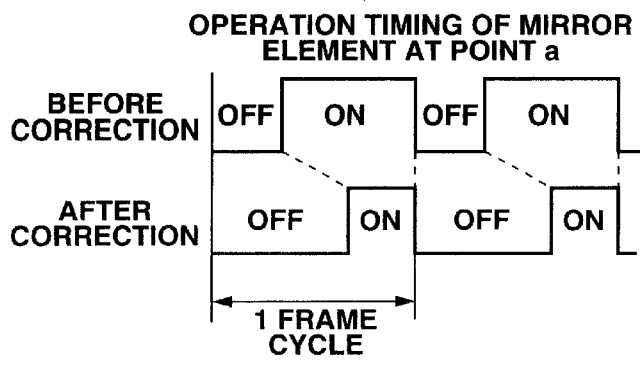
Figure 74F:
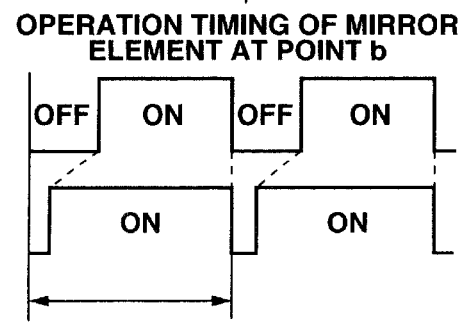

FIG. 74E is a block diagram showing a case in which an OFF time of one element of the light modulation device 525 is elongated to perform correction for reducing an intensity of irradiation light, and FIG. 74F is a block diagram showing a case in which an ON time is elongated to perform correction for increasing an intensity of illumination light. In each of FIGS. 74E and 74F, the upper side indicates a control signal for PWM when an element is not corrected, and the lower side indicates a control signal for PWM when an element is corrected. The two-dimensional array elements are driven by the DMD drive circuit 528.

Figure 75:
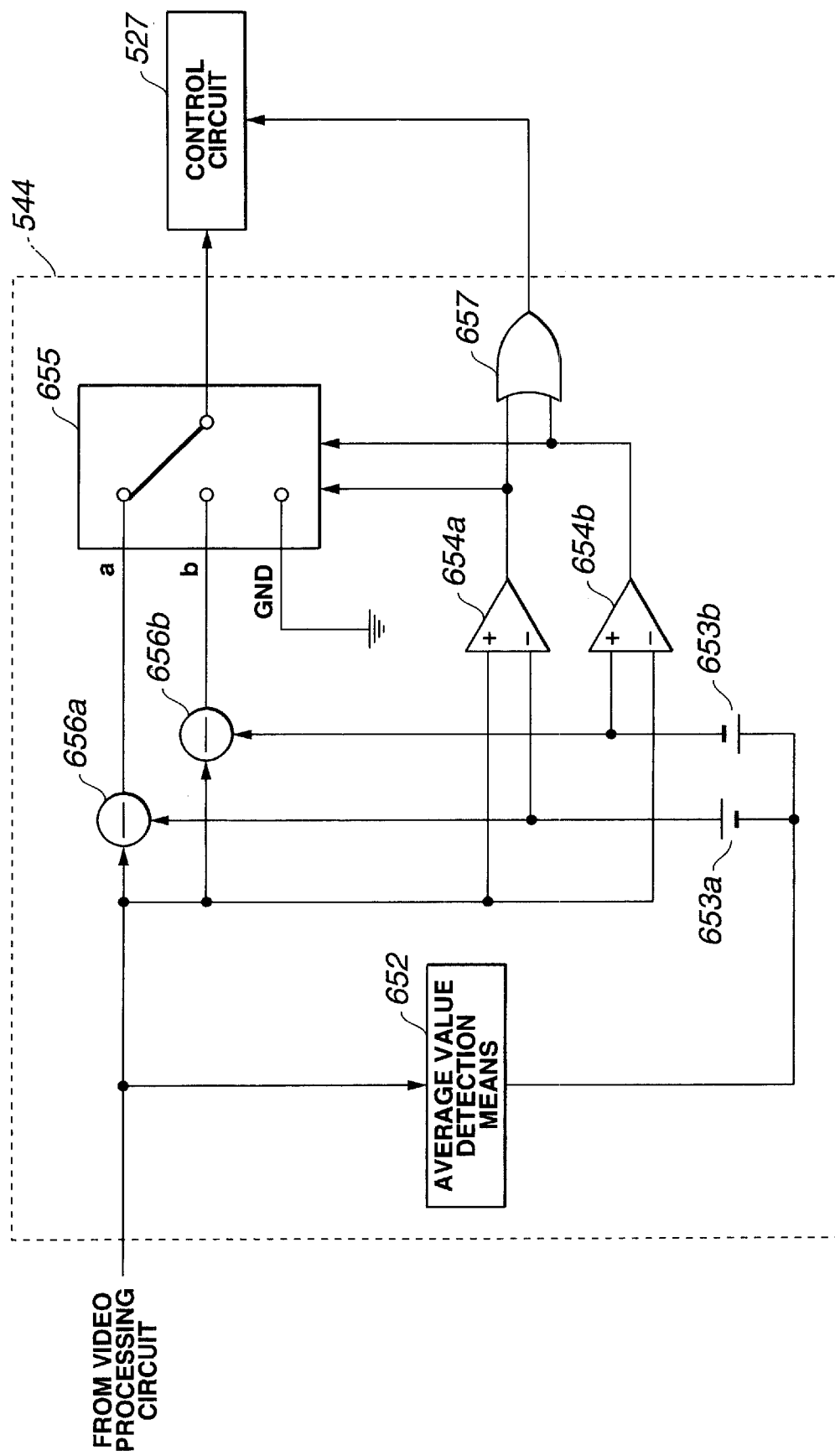

FIG. 75 shows the internal configuration of the decision circuit 544.

The decision circuit 544 is constituted by an average value detection means 652 for averagely detecting luminance signals input to the video signal processing circuit 542, decision level setting means 653a and 653b for adding predetermined offset levels to an output from the average value detection means 652 to set decision-levels of a bright portion and a dark portion, comparators 654a and 654b for comparing the input luminance signals with the decision levels set by the decision level setting means 653a and 653b, subtraction units 656a and 656b for subtracting the decision levels from the input luminance signals to output the results as correction signals for the bright portion and the dark portion, and a selection unit 655 for selecting the correction signals of the subtraction units 656a and 656b on the basis of the comparison result obtained in the comparators 654a and 654b.

The luminance signals input from the video signal processing circuit 542 are averagely detected by the average value detection means 652. Addition and subtraction of the average result and the predetermined offset levels are performed by the decision level setting means 653a and 653b to generate decision levels. The bright portion decision level to which the offset level is added is input to the inversion input terminal of the comparator 654a, and the dark portion decision level from which the offset level is subtracted is input to the non-inversion input terminal of the comparator 654b.

The luminance signals input from the video signal processing circuit 542 are input to the comparators 654a and 654b. When the input luminance signal indicates a bright portion, if the level of the bright portion is higher than the bright portion decision level input to the comparator 654a, an output from the comparator 654a becomes High. When the input luminance signal indicates a dark portion, if the level of the dark portion is lower than the dark portion decision level input to the comparator 654b, an output from the comparator 654b becomes High.

In addition, the decision levels are subtracted from the luminance signals input from the video signal processing circuit 542 by the subtraction units 656a and 656b to generate a bright portion correction signal and a dark portion correction signal. The generated bright portion correction signal and the generated dark portion correction signal are input to a selection unit 655. If an output from the comparator 654a is High, the selection unit 655 selects the bright portion correction signal. If an output from the comparator 654b is High, the selection unit 655 selects the dark portion correction signal. When the luminance signal is lower than the bright portion decision level and higher than the dark portion decision level, both the comparators 654a and 654b output Low each. For this reason, the selection unit 655 selects a GND level, and the correction signal shown in FIG. 74D is output to the control circuit 527. An OR gate of the outputs from the comparators 654a and 654b is calculated, so that the OR gate is output to the control circuit 527 as a dark/bright portion position pulse signal.

The above operations are summarized, so that the following results are obtained.

Before the endoscope is used, the corresponding operation is performed by the operation panel 517. When the initial setting switch 518 of the operation panel 517 is turned on, data for making a one-to-one correspondence between the elements of the light modulation device 525 and the pixels of the CCD 535 for performing image pickup is generated in the light guide 508 connected to the initial setting switch 518.

In the initial setting operation, the elements of the light modulation device 525 are lit one by one, and the lights from the elements are picked up by CCD 535, and peak point detection is performed by the peak point detection circuit 545. The obtained peak points are written in a memory as pixels corresponding to the elements of the light modulation device 525 in a one-to-one relationship. The elements of the light modulation device 525 are sequentially lit, a one-to-one correspondence is made, and writing operations are sequentially performed. Upon completion of all the elements, a one-to-one address map is completed.

Thereafter, the endoscope is inserted into a body cavity to perform observation.

In endoscope observation, a signal obtained by image pickup performed by the CCD 535 is input to the video signal processing circuit 542. A luminance signal from the video signal processing circuit 542 decides a luminescence/dark spot by the above calculation method in the decision circuit 544, and is output to the control circuit 529 as a correction signal.

The positional relationship between the CCD pixels whose correction signal is detected from the control circuit 529 and the light modulation device 525 is read from the one-to-one address memory 549 by the CPU 547, and the positional relationship is output from the one-to-one address memory 549 to the control circuit 527 as a read address signal.

By the input correction signal and the input address signal, a control signal is generated by the PWM such that an intensity of light supplied to an object to be photographed has an appropriate brightness level. The DMD drive circuit 528 controls a pixel of the light modulation device 525 corresponding to an address at which a light is irradiated to a portion whose correction signal is detected.

In this case, the PWM control modulates a pulse width by a correction signal which is a difference between the intensity of light and the appropriate intensity of light. By the operation, a light supplied to the object is controlled such that the pixels of the CCD 535 correspond to the pixels of the light modulation device 525 in a one-to-one relationship, and in a luminescence spot portion of a mucosal tissue whose image is not picked up with an appropriate intensity of light, intensities of reflected lights of the two-dimensional array elements of the light modulation device 525 corresponding to the pixels of the CCD 535 corresponding to the luminescence spots in a one-to-one relationship, so that an intensity of light supplied to only the luminescence spot portion which is too bright to be seen is reduced. The brightness is set to be a brightness which can be easily observed, and an endoscope image which can be observed can be obtained.

Since the dark spot portion is dark even though an intensity of light irradiated on the dark spot portion is increased, the image of a portion which is not easily observed can be observed can be observed as a bright image.

As described above, according to the embodiment, the following effect can be obtained.

One-to-one correspondence between the pixels of the light modulation device 525 and the pixels of the CCD 535 serving as an image pickup element is performed to control light supplied depending on the shape of the object, so that an endoscope image can be obtained.

According to the embodiment, an endoscope image which can be always easily observed can be obtained in almost real time. More specifically, when an object to be photographed such as a mucosal portion which is so bright that the portion has white out or which is so dark that the portion is not easily recognized is subjected to endoscope inspection, according to the embodiment, an intensity of light on the mirror for immediately illuminating a portion which is too bright is suppressed. In contrast to this, an intensity of light on a mirror for immediately illuminating a portion which is too dark is controlled to be increased, and is controlled such that an endoscope image having an appropriate brightness can be always obtained.

In endoscope inspection, the one-to-one address memory 549 is a programmable memory which is designed to cope with respective transmission patterns. A RAM 548 may be changed into an SRAM to perform a high-speed operation for address correspondence of correction signals obtained by the CPU 547.

Only some region in which a surgeon is interested in an observation field in which image pickup is performed by the CCD 535 is illuminated with a spot light to darken the other regions, the interested region may be observed in a state in which the region is easily observed.

In this case, a region which is illuminated with a spot light may be designated by an illumination region designation means such as a joystick.

The seventeenth embodiment of the present invention will be described below with reference to FIGS. 76 to 78.

Figure 76:
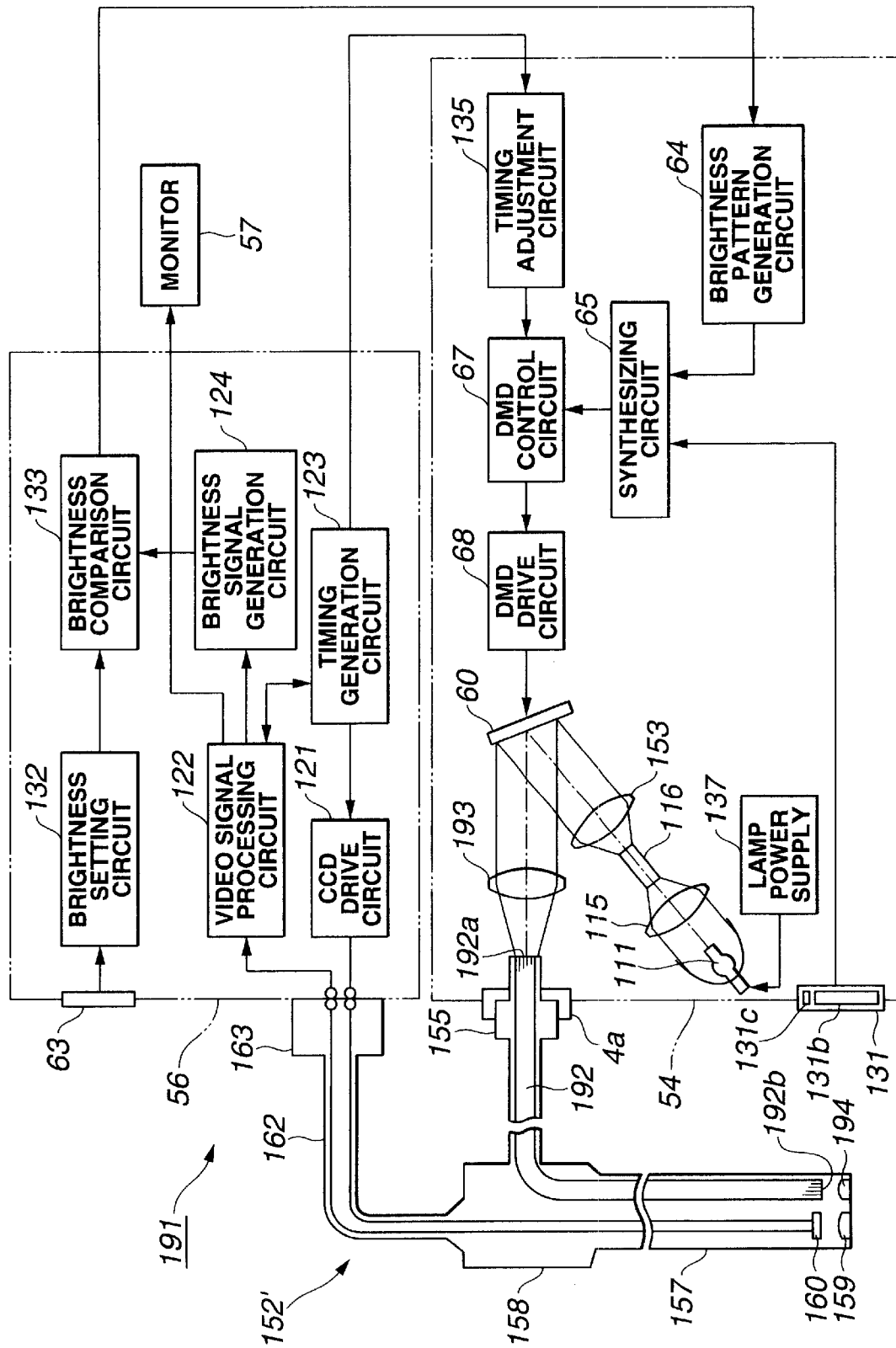

An endoscope device 191 shown in FIG. 76 employs an electronic endoscope 152' using an image guide 192 having an image transmission function in place of a light guide 156 of an electronic endoscope 152 in the endoscope device 151 in FIG. 27. An end face 192a on the incident side of the image guide 192 is arranged at the image forming position of an image forming lens 193 arranged instead of a condensation lens system 154.

A projection lens 194 is arranged opposite to an end face 192b on the emission side of the image guide of distal end 192 to project a light emitted from the end face 192b on an object side.

A position designation panel 131b for designating an arbitrary position of an endoscope image displayed on a monitor 57 and an up/down switch 131c for increasing/decreasing the luminance of a designated portion are arranged on an operation panel 131 of a light source device 54.

In FIG. 27 or the like, a pattern generation circuit 64 generates a pattern shown in FIG. 18A. However, in the embodiment, the pattern generation circuit 64 outputs a signal of a brightness pattern for controlling a ratio of an all level reflection time and a shield reflection time within the time of one field.

For example, by a brightness comparison circuit 133, when illumination control is performed to a portion from which an average brightness is detected, the pattern generation circuit 64 outputs a brightness pattern signal such that a ratio of an "H" level at which all level reflection is performed to an "L" level at which shield reflection is performed depending on the degree of brightness detected in one field period as shown in FIG. 77A.

When the position designation panel 131b of the operation panel 131 is operated, e.g., when the up switch of the up/down switch 131c is operated, a designation signal for increasing a luminance at a designated position is input to a synthesizing circuit 65.

For example, an instruction for increasing the luminance of the portion in which a brightness is detected in FIG. 77 is made, a synthesizing circuit 65 generates a synthesized pattern signal shown in FIG. 77B and synthesized such that a ratio of the "H" level in a brightness pattern corresponding to the designated position is increased by a predetermined amount in the next and subsequent fields. The synthesized pattern signal is output to the DMD control circuit 67 to control an illumination luminance.

When the down switch is operated, a ratio of the "H" level in a brightness pattern signal corresponding to a designated position is decreased by a predetermined amount in the next and subsequent fields to control an illumination luminance.

The positions (micromirror positions) of the light modulation device 60 form an image on the end face 192a on the incident side of the image guide 192 arranged at the image forming position by the image forming lens 193, and the information of the image is transmitted to the end face 192b on the distal end side through the fibers of the image guide 192.

A light delivered from the end face 192b on the distal end side is projected on the object image by the projection lens 194. In this case, on the object side, a luminance distribution on the end face 192a on the incident side of the image guide 192 is transmitted to the end face 192b to project the luminance distribution on the object surface.

Therefore, it is desired that the projection lens 194 is arranged such that the position of the object surface is equal to an image forming position. However, the position of the object surface may be slightly offset from the image forming position not to project a mesh pattern obtained by the image guide 192.

The other configuration is the same as that in FIG. 17. Even in the endoscope device 191 according to the embodiment, the brightness pattern of the light modulation device 60 is set such that a set brightness is obtained by the brightness switch of an operation panel 63. However, it can be performed by the operation of the position designation panel 131b that a user performs observation such that the user more brightly illuminates a desired portion or darkens the portion.

Therefore, according to the endoscope device 191, the illumination intensity of the portion at an arbitrary position of the object is increased, so that an observation image having a high S/N ratio can be obtained.

In the configuration in FIG. 76, the drive pattern of the light modulation device 60 is controlled with respect to time by the signal of a comparison signal obtained by comparing a brightness set by the operation of the operation panel 63 with the brightness of a video signal. However, the present invention can be applied to a configuration in which the control is not performed.

In this configuration, if an excessively bright portion or an excessively dark portion exists, the intensity of illumination on the portion is decreased or increased by the operation of the operation panel 131 of the light source device 54, so that an endoscope image which can be diagnosed can be obtained.

The optical system in FIG. 78 can be also applied to the case of the sixteenth embodiment.

The eighteenth embodiment of the present invention will be described below with reference to FIGS. 79A and 79B.

FIG. 79B is different from FIG. 71B, when a relationship (the size of an element of the light modulation device 525)<(the fiber diameter of the light guide 508) is satisfied, even though one element of the light modulation device 525 is lit, lights emitted to an object to be photographed by the light guide 508 do not correspond to the elements in a one-to-one correspondence.

When the fiber diameter is larger than the size of the element of the light modulation device 525, for example, as shown in FIG. 79B, the plurality of elements (four elements in FIG. 79B) of the light modulation device 525 are grouped to correspond to one fiber. FIG. 79A shows the light guide 508.

The elements of the light modulation device 525 are grouped, and the elements in a group are controlled to be simultaneously driven, so that the same effect as described above can be obtained.

As indicated by the lower side in FIG. 69, the grouping, the one-to-one corresponding of the CCD 535 and the light modulation device 525, and the peak point detection performed by the control circuit 529 are performed, so that the light guide 508 serving as a light transmission means is not arrayed. In this case, one pixel of a peak point whose image is picked up by the CCD 535 corresponds to the position of the light modulation device 525, so that the same effect as that obtained by luminescence spot control performed when the light transmission means are arrayed can be obtained.

In the lower side in FIG. 69, when a light is incident on the incident end as indicated by an arrow on the side of the incident end to the light guide 508, a non-array type light guide which transmits light at random is shown on the delivery end side.

The nineteenth embodiment of the present invention will be described below with reference to FIG. 80. The embodiment shows a case in which a corresponding operation between the optical modulation device and the CCD and illumination can be simultaneously performed by the same optical system.

Figure 80:
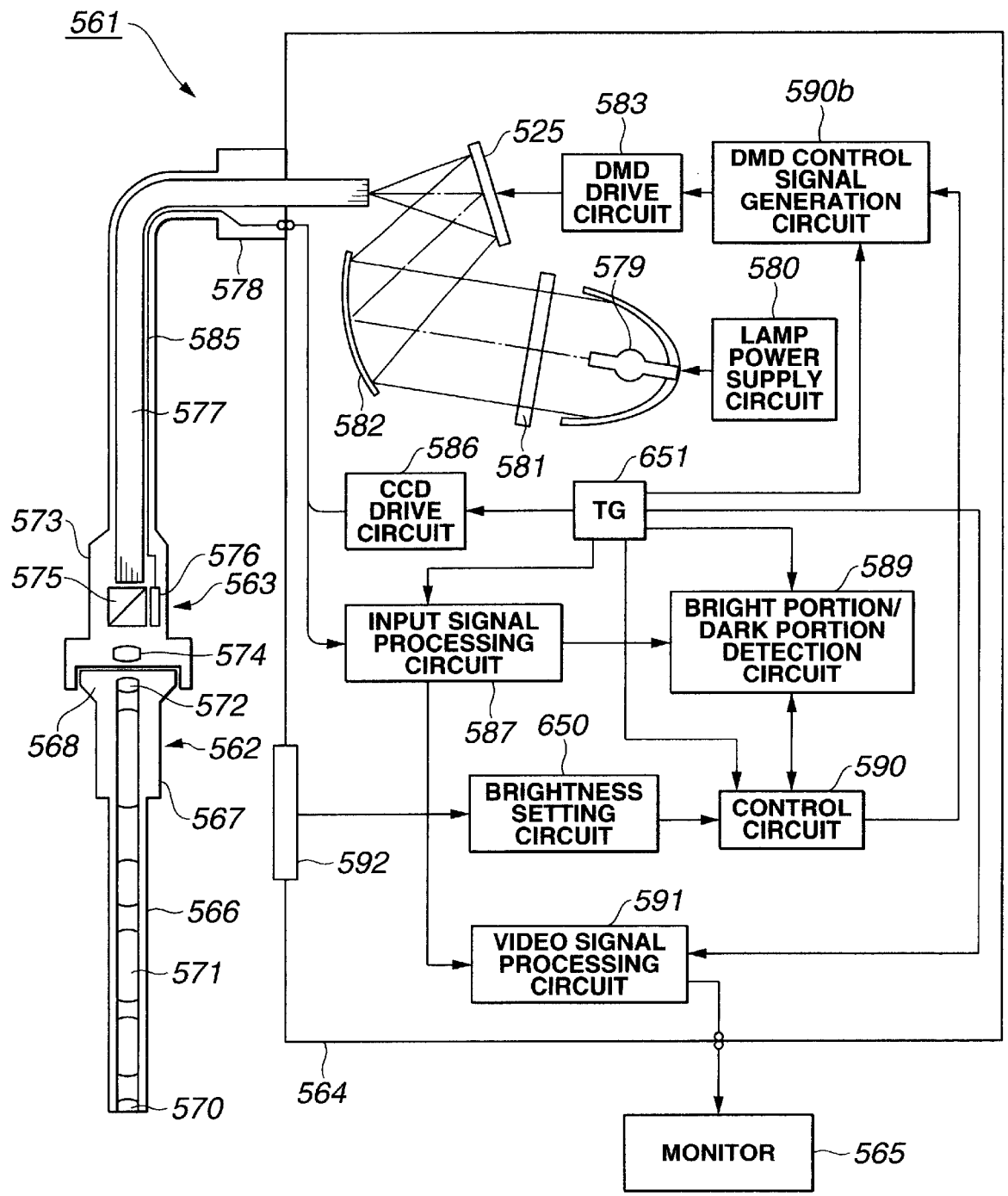
FIG. 80 is a block diagram showing the configuration of an endoscope device according to the nineteenth embodiment of the present invention.

A endoscope device 561 shown in FIG. 80 is constituted by a rigid endoscope 562, a TV camera 563 serving as an adaptor attached to the rigid endoscope 562, a light source CCU device 564 for supplying an illumination light to the rigid endoscope 562 and performing video processing, and a monitor 565 for displaying an endoscope image.

The rigid endoscope 562 has a narrow and long insertion portion 566 having rigidity, a grasping portion 567 formed at the rear end of the insertion portion 566, and an eyepiece portion 568 arranged at the rear end of the grasping portion 567.

An objective lens 570 is arranged on an observation window (having the function of an illumination window) at the distal end of the insertion portion 566, and an optical image obtained by the objective lens 570 is transmitted to a relay lens system 571 serving as an image transmission optical system.

The optical image transmitted by the relay lens system 571 is focused on a CCD 576 by an eyepiece lens 572 of the eyepiece portion 568 and an image forming lens 574 arranged on a camera head portion 573 of the TV camera 563 through a beam splitter 575. The CCD 576 is a color image pickup element having a color separation filter.

An array type light guide 577 constituted by an image guide serving as a light transmission means and having an image transmission function is equipped in a cable extending from the camera head portion 573. An end face on the delivery side of the light guide 577 is arranged opposite to the beam splitter 575, and an end face on the proximal side of the light guide 577 is extended from a connector 578 to be connected to the light source CCU device 564.

A lamp 579 is arranged in the light source CCU device 564, the lamp 579 is lit by a lamp lighting power supply from a lamp power supply circuit 580. A light is reflected by a reflection mirror 582 through an infrared cut filter 581 to be incident on the light modulation device 525, and is optically modulated by the light modulation device 525 driven by a DMD drive circuit 583. The modulated light is incident on the end face on the proximal side of the light guide 577.

The light is transmitted from the light guide 577, transmitted through the beam splitter 575, transmitted to the distal end side of the insertion portion 566 by the lenses 574 and 572 and the relay lens system 571, and projected on the object side through the objective lens 570.

The light reflected by the object side is incident on the beam splitter 575 through an opposite optical path, is reflected by the beam splitter 575, and forms an image on the CCD 576 to be photoelectrically converted. The signal from the CCD 576 is input to a eyepiece portion 568 and an input signal processing circuit 587 through the connector 578.

In the input signal processing circuit 587, the signal from the CCD 576 is amplified, and CDS (correlative double sampling) is performed to output a brightness signal component for a CCD pixel.

An output from the input signal processing circuit 587 is input to a video signal processing circuit 591, and a video signal is generated by the video signal processing circuit 591, so that an endoscope image can be observed with the monitor 565.

A luminance signal from the input signal processing circuit 587 is input to a bright portion/dark portion detection circuit 589 to detect the level of the luminance signal, and an address corresponding to a signal obtained by detecting a bright portion/dark portion is input from a TG 651, and an intensity of reflected light corresponding to the bright portion/dark portion of a two-dimensional array element of the DMD can be controlled through a control circuit 590. In this case, the TG 651 outputs predetermined synchronized signals to respective circuits to synchronize the operation timings of the circuits with each other.

A panel 592 is connected to the control circuit 590 through a brightness setting circuit 650 for setting a brightness. The panel 592 can perform setting of the level of brightness detection and brightness setting or the like for suppressing and setting a brightness when the luminance detection is performed.

The control circuit 590 outputs a signal to the DMD drive circuit 583 for driving the light modulation device 525 through a DMD control signal generation circuit 590b, and the light modulation device 525 is driven by the DMD drive circuit 583.

The relationship between the CCD 576 and the light modulation device 525 is set such that the position of a two-dimensional image of the light modulation device 525 transmitted by the light guide 577 serving as a light transmission means and the position of the CCD 576 are equal to each other by a half prism (or beam splitter) 575. In this case, the number of pixels of the CCD 576 is preferably equal to the number of micromirrors of the light modulation device 525. However, these numbers are not equal to each other, the same effect as described above can be obtained.

In the embodiment when luminescence spots are generated by mucus such that the endoscope is adopted to a body cavity, the mirror of the light modulation device 525 is driven at −10° depending on the position of the luminescence spot detected by the bright portion/dark portion detection circuit 589, and an intensity of illumination light to the position is decreased to darken the portion and to suppress luminescence spots from being generated. For this reason, a level appropriate to observation can be set.

As a matter of course, an intensity of light irradiated on a dark sport portion is increased to obtain a brightness at which the portion can be easily observed.

In the embodiment, unlike the sixteenth embodiment, the same effect as that obtained in the sixteenth embodiment without a corresponding operation between the light modulation device 525 and the pixels of the CCD 576.

More specifically, when the half prism 575 is arranged to make the illumination light and the image pickup system coaxial, an intensity of light supplied to an object to be photographed can be controlled by the light modulation device 525 without the one-to-one corresponding operation.

The twentieth embodiment will be described below with reference to FIGS. 81 to 82B. The same reference numerals as in the sixteenth embodiment denote the same parts in the twentieth embodiment, and a description thereof will be omitted.

In this embodiment, an optical part called a taper is used, a light is efficiently supplied to an object to be photographed in an array type light transmission means, and a new operation panel is further arranged. An intensity of light of a light modulation device can be partially and arbitrarily controlled by an observer.

Figure 81:
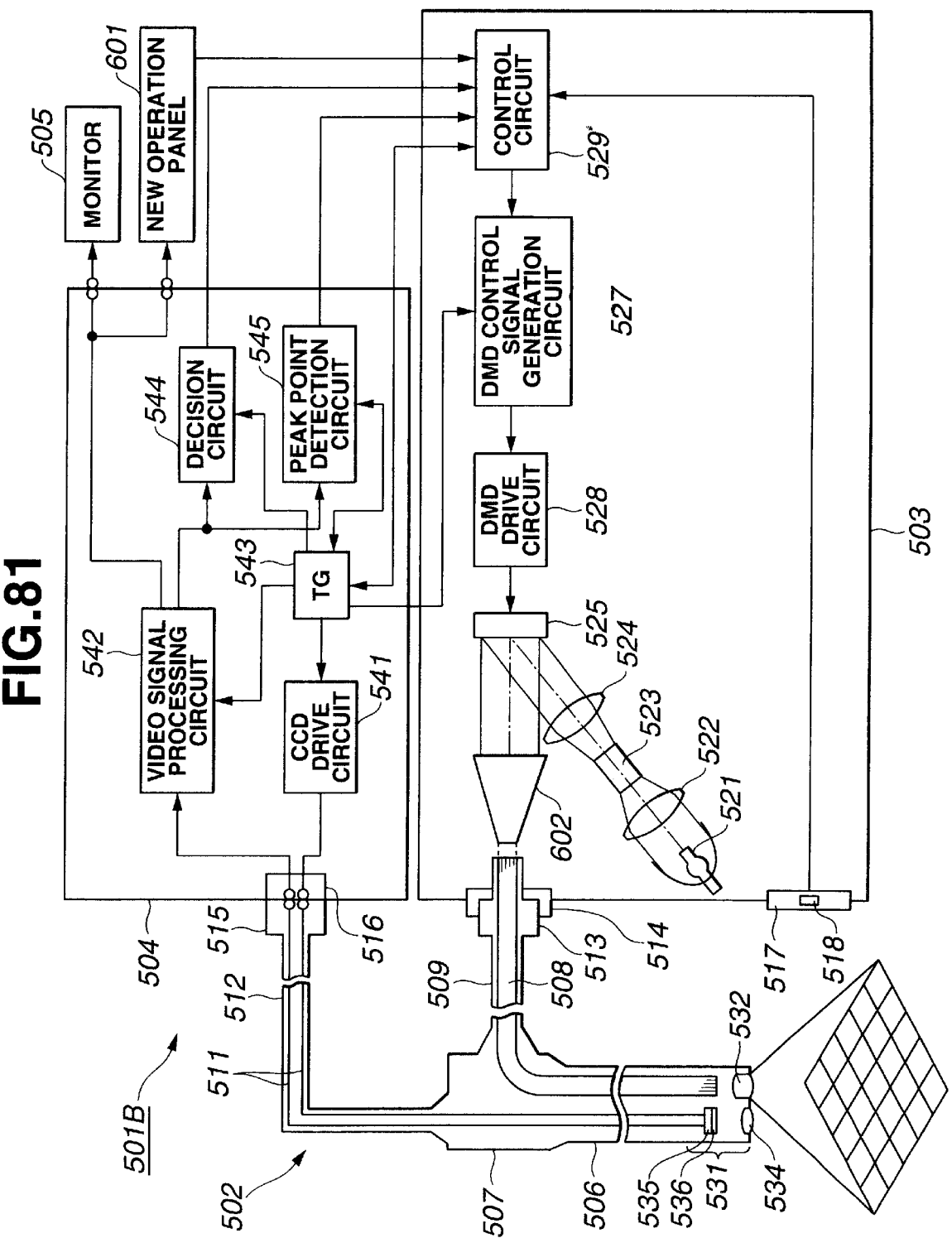

As shown in FIG. 81, an endoscope device 501B according to the twentieth embodiment comprises a new operation panel 601 for controlling an illumination light generated by the light modulation device 525 in the endoscope device 501 in FIG. 68. The endoscope device 501B employs a light source device 503B in which a taper 602 is arranged in place of the image forming lens system 526 in the light source device 503 in FIG. 68.

In the light source device 503B, an illumination light from the light modulation device 525 is efficiently incident on the light guide 508 serving as an array type light transmission means by using a known optical part called a taper 602.

A video signal from the video signal processing circuit 542 is input to the new operation panel 601 and display an endoscope image on a display surface of a liquid crystal monitor 603 or the like constituting the new operation panel 601 as shown in FIG. 82A. A position detection sensor such as a touch panel 604 consisting of a transparent material is attached to the front surface of the display surface of the liquid crystal monitor 603. When the touch panel 604 is touched with a finger, the signal of the touched position is input to the control circuit 529, so that an illumination light supplied to the object can be controlled More specifically, an endoscope image obtained by image pickup is transmitted from the video signal processing circuit 542, and the image can be monitored by the liquid crystal monitor 603. When an observer touches the touch panel 604 on the front surface of the liquid crystal monitor 603, a plurality of two-dimensional array elements of the light modulation device 525 corresponding to a zone of the endoscope image displayed on the liquid crystal monitor 603 are controlled. A signal from the touch panel 604 is connected to the control circuit 529 to control an intensity of light.

Here, a theoretical configuration of the touch panel 604 called a known analog capacity coupling method is shown in FIGS. 82A and 82B.

As indicated by an arrow 606 in FIG. 82A, a voltage is applied from electrodes arranged at the four corners of the touch panel 604.

An electric field spreads from the electrodes, so that an electric field having a uniform voltage can be formed on the screen.

When a finger touches the touch panel 604 which is a part represented by 607, currents which are proportional to distances from the sides of the touch panel 604 to the finger flow.

On the basis of the respective current values, a controller (not shown) calculates the coordinates of the position of the finger.

As shown in FIG. 82B, the touch panel 604 is divided into zones. The signal of a zone corresponding to the coordinates of the position obtained by the configuration causes the control circuit 529 to selectively control an intensity of reflected light of a zone constituted by a plurality of pixels of the light modulation device 525.

A selection switch 609 is arranged on the new operation panel 601, so that modes for brightening and darkening a selected portion can be switched by a touch panel operation.

In order to brighten a portion by the touch panel operation, a zone is selected and operated, so that the zone can be brightened. In order to darken a portion, a switching operation is performed by the selection switch 609, and the portion can be darkened by the same operation as described above.

As the touch panel 604, a touch panel using the analog capacity coupling method is described. However, any touch panel sensor which is a touch panel sensor for performing the same operation as in an ultrasonic method or the like may be used.

The operation of the embodiment will be described below.

In endoscope observation, the luminance of an endoscope image obtained by image pickup performed by the CCD 535 changes depending on the state of an object to be photographed, the shape of the object, and the like. The same video image as the endoscope image displayed on the monitor 505 is displayed on the liquid crystal monitor 603 of the new operation panel 601. For example, in observation in a body cavity which is considerably uneven, an excessive dark portion or an excessive bright portion is generated. Although the brightness is changed into a brightness which is in a reference range serving as a reference in the sixteenth embodiment, some observer may feel that the portion be excessively bright or excessively dark.

In such a case, when the observer wants to brighten the dark portion, the observer selects a zone to be brightened, and can increase the intensity of light by the touch operation of the touch panel 604. Furthermore, when the observer wants to darken an excessively bright portion, the observer presses the selection switch 609 to perform a mode switching operation, and the observer selects a zone to be darkened, and can darken the portion by a touch panel operation.

An intensity of light can be gradually expressed by pressing a zone of the panel a plurality of times, and the level of brightness can be selected.

According to the embodiment, an array type light transmission means is arranged, the light transmission means has a light transmission optical system obtained by the taper 602, and transmission is performed. In this manner, a positional correspondence between the position of the light modulation device 525 and the position of the image pickup element can be achieved, and an intensity of light supplied to the object to be photographed can be controlled.

In addition, on an object to be photographed which is considerably uneven, intensities of light of arbitrary portions which are divided as zones depending on the intention of an observer or the like can be controlled by using the touch panel 604. For this reason, an endoscope image which can be easily observed can be obtained.

More specifically, the new operation panel 601 is arranged, and the intensity of the endoscope image displayed on the monitor 505 can be controlled by the operation of the observer. For this reason, the intensity of light of only an affected part and its peripheral portion is made appropriate, and an endoscope image which can be easily observed can be obtained. The same effect as that in the sixteenth embodiment can also be obtained.

The twenty-first embodiment of the present invention will be described below with reference to FIGS. 83 and 84. The same reference numerals as in the sixteenth embodiment denote the same parts in the twenty-first embodiment, and a description thereof will be omitted. The embodiment describes a device which uses microlenses corresponding to optical fibers to efficiently converge light to an array type light transmission means and which controls an illumination light at high precision.

Figure 83:
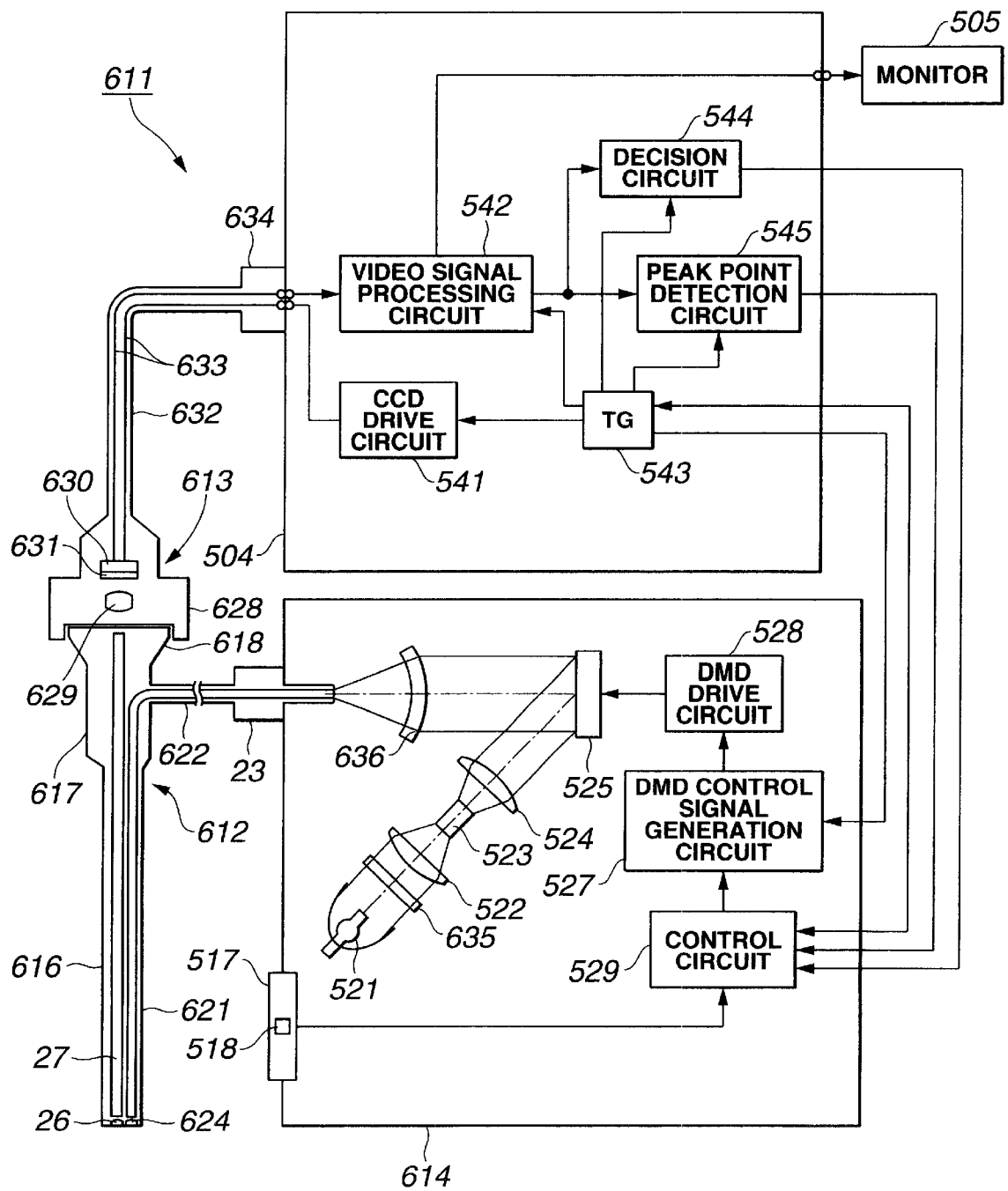
FIGS. 83 and 84 are related to the twenty-first embodiment of the present invention.

A endoscope device 611 as shown FIG. 83 is constituted by a rigid endoscope 612, a TV camera 613 connected to the rigid endoscope 612, a light source device 614, a CCU 504, and a monitor 505.

The rigid endoscope 612 has a rigid insertion portion 616, a grasping portion 617 arranged at the rear end of the eye piece portion 618, and an eyepiece portion 618 arranged at the rear end of the grasping portion 617. A light guide 621 serving as an array type optical image transmission means is inserted into the rigid endoscope 612, and the rigid endoscope 612 is inserted into a light guide table 622 extending from the grasping portion 617. A light guide connector 623 at the end of the light guide 621 is connected to the light source device 614.

An illumination light supplied from the light source device 614 is transmitted by the light guide 621, and is irradiated from the end face on the distal end side of the insertion portion 616 onto the object side through a projection lens 624.

The image of the object is formed by an objective lens 626, and the image is transmitted to the rear eyepiece portion 618 by a relay lens system 627. The image is formed on a CCD 630 by an image forming lens 629 arranged in a camera head unit 628 of the TV camera 613 connected to the eyepiece portion 618. A color separation filter 631 is attached in front of the image pickup surface of the CCD 630.

The CCD 630 is connected to a signal line 633 inserted into a cable 632 extending from the camera head unit 628, and a connector 634 at the rear end of the cable 632 is connected to the CCU 504, so that the CCD 630 is connected to a CCD drive circuit 541 and a video signal processing circuit 542 in the CCU 504. The CCU 504 has the same configuration as that of the CCU 504 described in the sixteenth embodiment.

The light source device 614 has a light source lamp 521 as described in the sixteenth embodiment. Light from the light source lamp 521 is cut by an infrared cut filter 635 with respect to infrared rays, and is incident on a convergent lens 522 to be converged. The converged light is incident on an integrator 523, and the emission light of the integrator 523 is converted into parallel fluxes of light. The parallel fluxes of light are incident on a light modulation device 525.

The light which is optically modulated by reflection of the light modulation device 525 forms an image on the end face of the light guide 621 serving as an array type light transmission means through a microlens group 636 in the embodiment, so that an illumination light is supplied.

Figure 84:
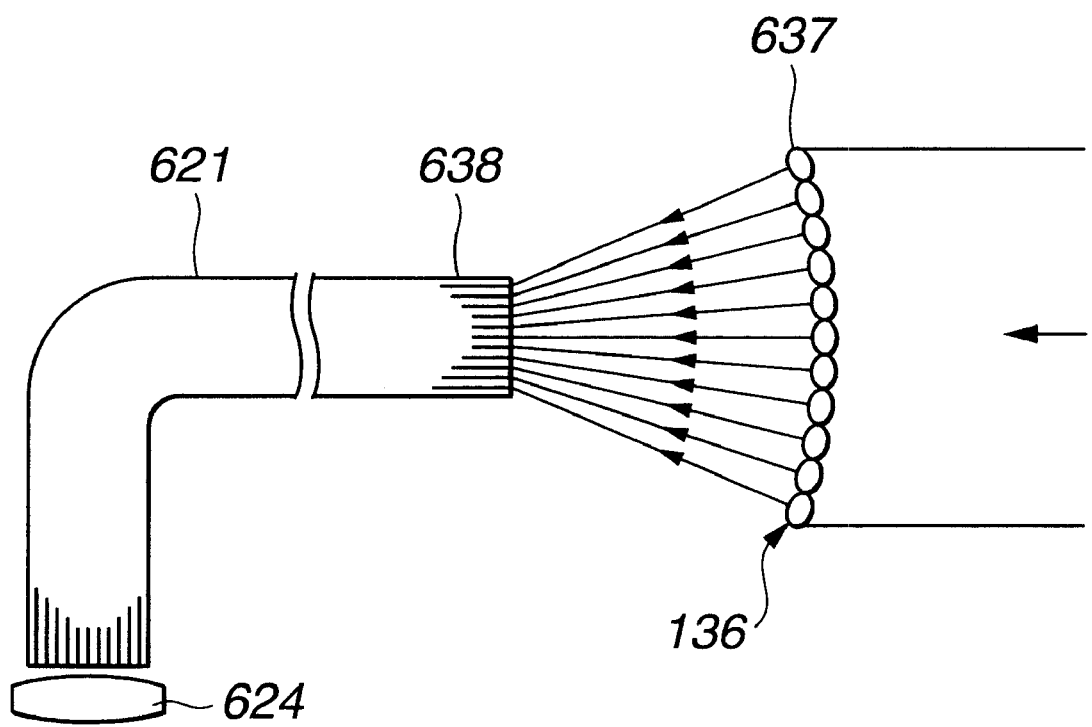

FIG. 84 shows an enlarged diagram of the microlens group 636.

An illumination light controlled by the light modulation device 525 is designed such that one microlens 637 of the microlens group 636 corresponds to one optical fiber 638 of the light guide 621 serving as a light transmission means.

As in the sixteenth embodiment, an illumination light controlled by the light modulation device 525 is incident on the corresponding optical fibers 638 in the light guide 621 of the rigid endoscope 612 by the microlens group 636, and the illumination light can be evenly transmitted, and the NA (an incident angle or the range of an incident angle at which light is transmitted) of the light guide 621 can be assured. The operation of the embodiment will be described below. When an illumination light is supplied to an object to be photographed from the light source device 614 side, the microlens 637 correspond to the optical fibers 638 in the array type light guide 621. For this reason, the NA of the optical fibers 638 can be controlled, and an optimum NA can be set. More specifically, loss when an illumination light is transmitted to the light guide 621 can be reduced, and the illumination light can evenly transmitted to the distal end of the endoscope through the microlens 637.

Since light controlled by the light modulation device 525 can be evenly irradiated on the object, light can be controlled by the element at high precision in the embodiment, loss in transmission of light can be reduced, and brightness can be kept.

More specifically, in the embodiment, an array type light transmission means is arranged, and a light transmission optical system constituted by the microlens 637 is arranged in the light transmission means. Transmission with small loss is performed to achieve a positional correspondence between the light modulation device 525 and the image pickup elements. Light transmitted to the object can be controlled.

The twenty-second embodiment of the present invention will be described below with reference to FIGS. 85 to 87C.

Figure 85:
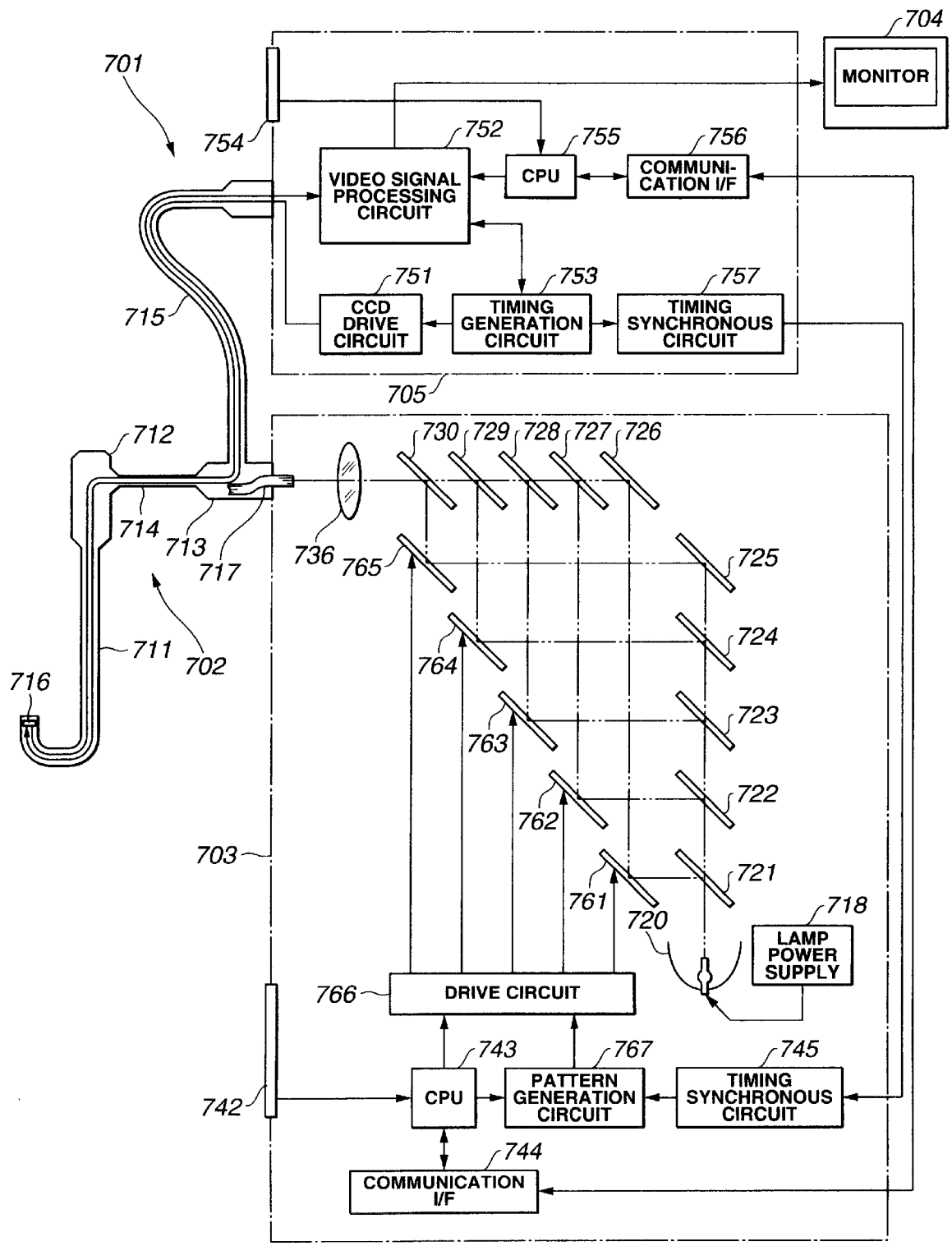
Figure 86:
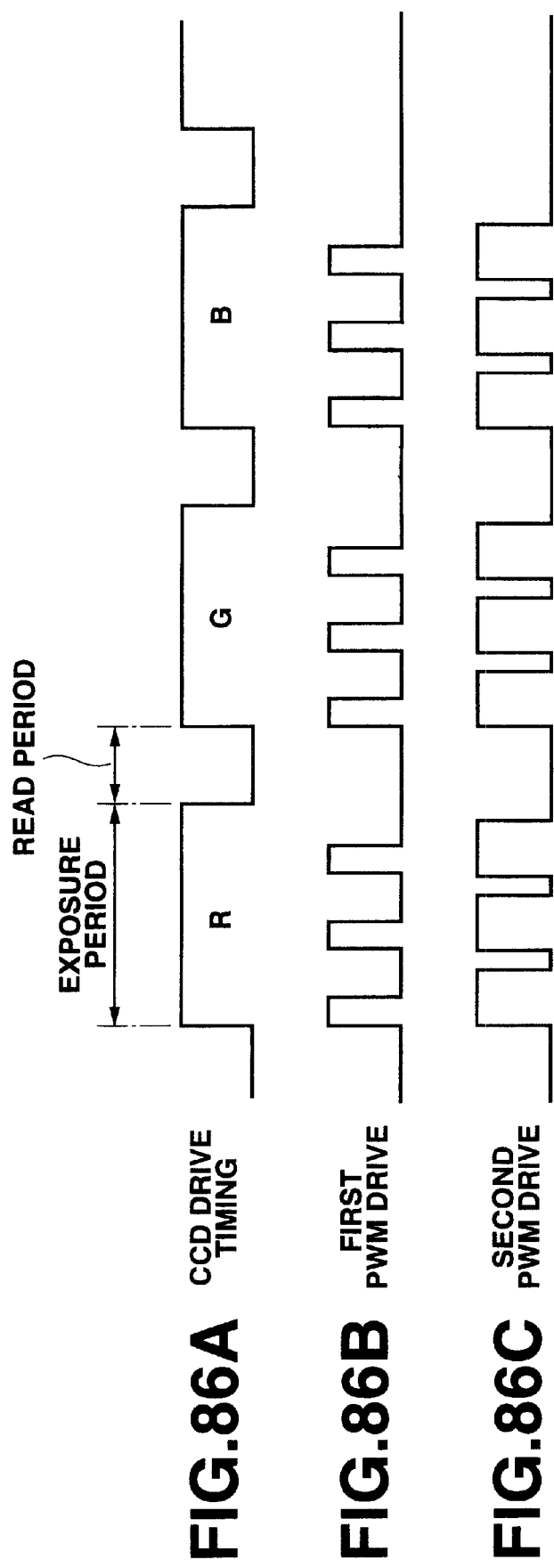
Figure 87:
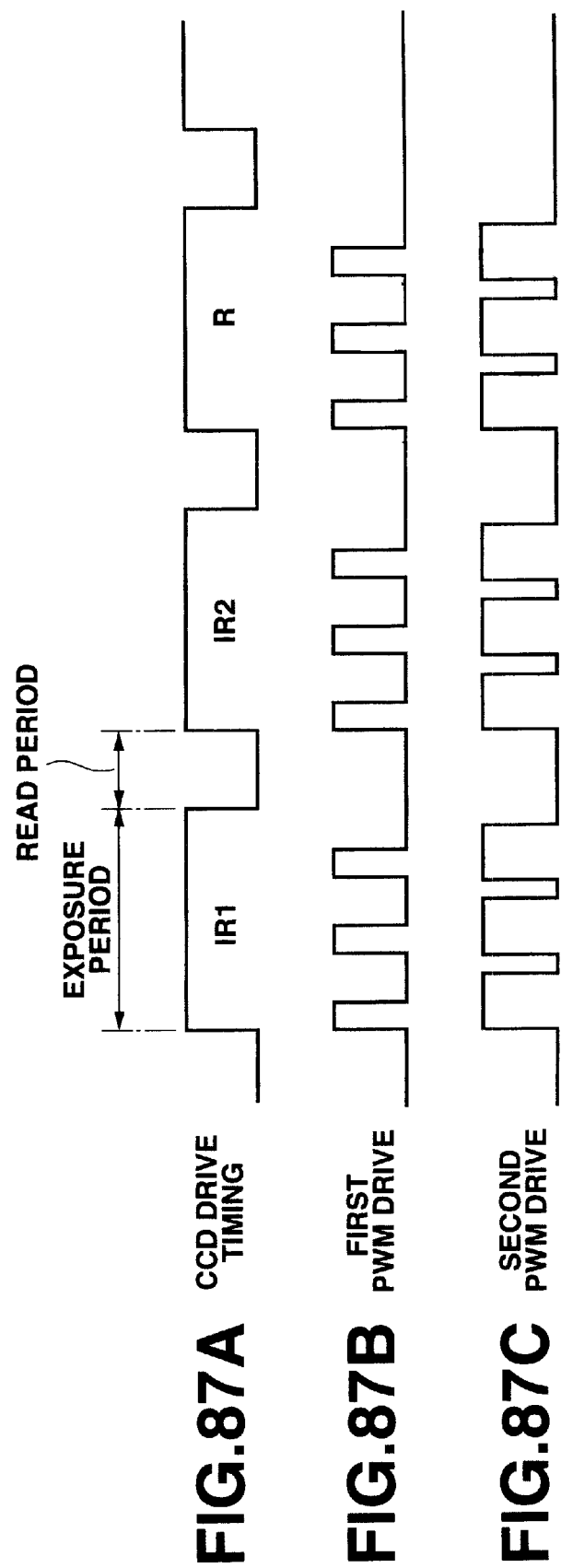

As shown in FIG. 85, an endoscope device 701 is constituted by an electronic endoscope 702 for performing image pickup of a portion to be observed in a lumen, a light source device 703 for supplying an illumination light to the electronic endoscope 702, a video signal processing device 705 for performing signal processing to an image pickup signal from the electronic endoscope 702 to display an endoscope image on a monitor 704.

The electronic endoscope 702 is constituted by: an insertion portion 711 having a long and narrow shape, flexibility, and a distal end portion which is inserted into a lumen and can be bent; an operation portion 712, connected to the proximal end of the insertion portion 711, for performing grasping and bending operations and the like; a universal cable 714 having a connector 713 extending from the operation portion 712, connected to the light source device 703, formed at the proximal end of the universal cable 714; and a signal cable 715 extending from the connector 713 and having a connector 715a connected to the video signal processing device 705 and formed at the proximal end of the signal cable 715. A CCD 716 serving as a solid state image pickup element for performing image pickup to a portion to be observed is arranged at the distal end of the insertion portion 711, and a light guide 717 for transmitting an illumination light from the light source device 70 to the distal end of the insertion portion 711 is arranged in the universal cable 714 and the operation portion 712.

The optical system of the light source device 703 is constituted by: a light source lamp 720 for causing a lamp power supply 718 to generate an illumination light; a dichroic mirror (to be referred to as a DM hereinafter) 721 for reflecting a light component IR2 having an infrared wavelength of the illumination light emitted from the light source lamp 720 and for transmitting the other light components; a DM 722 for reflecting a light component IR1 having an infrared wavelength of the illuminated through the DM 721 and for transmitting the other light components; a DM 723 for reflecting a visible light component R of the illumination light transmitted through the DM 722 and for transmitting the other light components; a DM 724 for reflecting a visible light component G of the illumination light transmitted through the DM 723; a total reflection mirror 725 for reflecting the illumination light transmitted through the DM 724; DMDs 761, 762, 763, 764, and 765 serving as light modulation devices for reflecting the light components reflected by the DM 721 to 724 and the total reflection mirror 725 by two-dimensional array elements (cells) arranged in a two-dimensional matrix to limit intensities of lights supplied to a total reflection mirror 726 and the DMs 727 to 730; the total reflection mirror 726 arranged opposite to the DMDs 761, 762, 763, 764, and 765, for reflecting the infrared wavelength light component IR2; the DM 727 for reflecting only the infrared wavelength light component IR1 reflected by the DM 762; a DM 728 for reflecting only the visible light component R reflected by the DMD 763; a DM 729 for reflecting only the visible light component G reflected by the DMD 763; a DM 730 for reflecting only a visible light component B reflected by the DM 730; and a convergent lens 736 for converging the visible light component B reflected by the DM 730, the visible light component G, the visible light component R, the infrared wavelength light component IR1, and the infrared wavelength light component IR2 which are transmitted through the DM 727 to the DM 730 to the incident end face of the light guide 717.

In this case, the DM 721 is a light-luminance xenon discharge lamp which incorporates a parabolic mirror therein and emits parallel lights.

The control system of the light source device 703 comprises: a drive circuit 766 for driving the DMDs 761 to 765;

a CPU 743 which receives a signal for switching observation states of a visible light or a special light and outputs a setting signal for setting a combination of the wavelengths of visible lights or a combination of the wavelengths of special lights; a communication I/F 744, connected to the CPU 743, for performing communication with the video signal processing device 705 and for performing a setting of a visible light mode or a special light mode and transmitting and receiving a brightness signal; a timing synchronous circuit 745 for generating a timing signal synchronized with an image pickup timing of the CCD 716 from the video signal processing device 705; and a pattern generation circuit 767, controlled by the CPU 743 on the basis of a brightness signal from the video signal processing device 705 through the communication I/F 744, for generating a two-dimensional matrix pattern for controlling the dark/bright state of the illumination light on the basis of the timing signal from the timing synchronous circuit 745.

If the illumination light is determined as a visible light on the basis of the brightness signal from the video signal processing device 705, the CPU 743 outputs a brightness signal for controlling the intensities of R, G, and B illumination light components to the pattern generation circuit 767. If the illumination light is a special light, the CPU 743 outputs a signal for controlling the intensities of illumination light components IR1, IR2, and R to the pattern generation circuit 767. The pattern generation circuit 767 performs outputting to the drive circuit 766 to change time patterns of the two-dimensional matrixes of the DMDs 761 to 765 such that the R, G, and B light components or the illumination light components IR1, IR2, and R at the image pickup timing of the CCD 716 by the brightness signal from the CPU 743.

The video signal processing device 705 comprises: a CCD drive circuit 751 for driving the CCD 716; a video signal processing circuit 752 for performing signal processing to an image pickup signal from the CCD 716 to process the signal into a video signal which can be observed with the monitor 704; a timing generation circuit 753 for generating a timing signal to obtain a drive timing signal in the CCD drive circuit 751 and a video signal in the video signal processing circuit 752; an operation panel 754 for setting and displaying a visible light mode or a special light mode; a CPU 755 for controlling the video signal processing circuit 752 on the basis of the setting of the visible light mode or the special light mode in the operation panel 754 and for outputting setting information of the visible light mode or the special light mode and brightness information from a video signal serving as a brightness signal; a communication I/F 756, connected to the CPU 755, for performing communication of the setting information of the visible light mode or the special light mode and the brightness information (brightness signal) with the communication I/F 744 of the light source device; and a timing synchronous circuit 757 for outputting a synchronous signal synchronized with a drive timing signal to the timing synchronous circuit 745 of the light source device 703.

The DMDs 761 to 765 are elements each having the following configuration. A plurality of micromirrors constituting two-dimensional array elements (cells) arrayed in a two-dimensional matrix are arranged on a silicon chip, the micromirrors are held by a holding member on a yoke rotated about the diagonals between two stable states and can be changed by ±10° in the planar direction of the silicon chip.

The light components reflected by the DMs 721 to 724 and the total reflection mirror 725 are subjected to supply reflection (reflection state of −10°)/non-supply reflection (reflection state of +10°) on the optical axes of the total reflection mirror 726 and the DMs 727 to 730 in a two-dimensional matrix.

The drive circuit 766 is a drive circuit for changing the angles of the micromirrors of the DMDs 761 to 765. The pattern generation circuit 767 is designed to generate a PWM drive pattern for performing PWM (Pulse Width Modulation) of driving of the supply reflection/non-supply reflection on the micromirrors of the DMDs 761 to 765 in the drive circuit 766.

The operation of the embodiment will be described below.

The electronic endoscope 702 is inserted into a body cavity to perform endoscope observation. In this case, observation using visible light is performed first, and general endoscope inspection is performed.

In the observation using visible light, the light source device 703 causes the operation panel 742 to select a switch for setting an observation state of the visible light, and the video signal processing device 705 causes the operation panel 754 to set the visible light mode.

In the video signal processing device 705 in observation using visible light, the CCD 716 is driven by a field sequential method and R, G, and B drive signals obtained such that a sequential charge exposure period and a charge read period are repeated in synchronism with R, G, and B illumination lights as shown in FIG. 86A.

In the embodiment, in synchronism with the R, G, and B drive signals shown in FIG. 86A, the pattern generation circuit 767 of the light source device 703 outputs a PWM control pattern for performing the first PWM drive shown in FIG. 86B to the drive circuit 766 when the CPU 743 of the light source device 703 decides that the illumination light is bright on the basis of the brightness information (brightness signal) from the video signal processing device 705. When it is determined that the illumination light is dark, a PWM control pattern a for performing the second PWM drive shown in FIG. 86C is output to the drive circuit 766, so that the brightness of visible light (R, G, and B field sequential illumination lights) is made a desired brightness.

In this manner, general endoscope inspection using visible light is performed. If a part supposed to be a lesion part is detected, a switch for setting an observation state of special light is selected by the operation panel 742 in the light source device 703, and the special light mode is set by the operation panel 754 in the video signal processing device 705. The observation using visible light is switched to the observation using special light.

In the video signal processing device 705 used in the observation using special light, the CCD 716 is driven by a field sequential method and the drive signals IR1, IR2, and R obtained such that a sequential charge integration period and a charge read period are repeated in synchronism with illumination lights IR1, IR2, and R as shown in FIG. 87A.

In this case, the pattern generation circuit 767 of the light source device 703 outputs a PWM control pattern for performing the first PWM drive shown in FIG. 87B to the drive circuit 766 when the CPU 743 of the light source device 703 decides that the illumination light is bright on the basis of the brightness information (brightness signal) from the video signal processing device 705. When it is determined that the illumination light is dark, a PWM control pattern for performing the second PWM drive shown in FIG. 87C is output to the drive circuit 766, so that the brightness of special light (field sequential illumination lights IR1, IR2, and R) is made a desired brightness.

When the special light observation state is returned to the visual light observation state, the operation panel 742 and the operation panel 754 are operated to perform control as shown in FIGS. 86A to 86C, so that observation can be performed in the visual light state.

In this manner, in the embodiment, the visible light can be instantaneously switched to the special light, and the brightness can be easily controlled to an appropriate brightness in the observation states using visible light and special light.

In addition, a DMD has a high response speed, i.e., the response speed of a micro mirror is high, i.e., ten and several $\mu$S, and the operation time of the mirror is not a problem. Even though the PWM control is performed, by the response time of the micromirror, appropriate brightness control is performed by a change in pulse width.

In this manner, in the embodiment, brightness control can be performed by only generating a simple PWM control pattern for PWM control in the pattern generation circuit 767, and the configuration of the pattern generation circuit 767 can be simplified.

In the embodiment, the PWM control is performed. However, any method such as PFM (Pulse Frequency Modulation) control which can control a pulse width can be applied.

Figure 88:
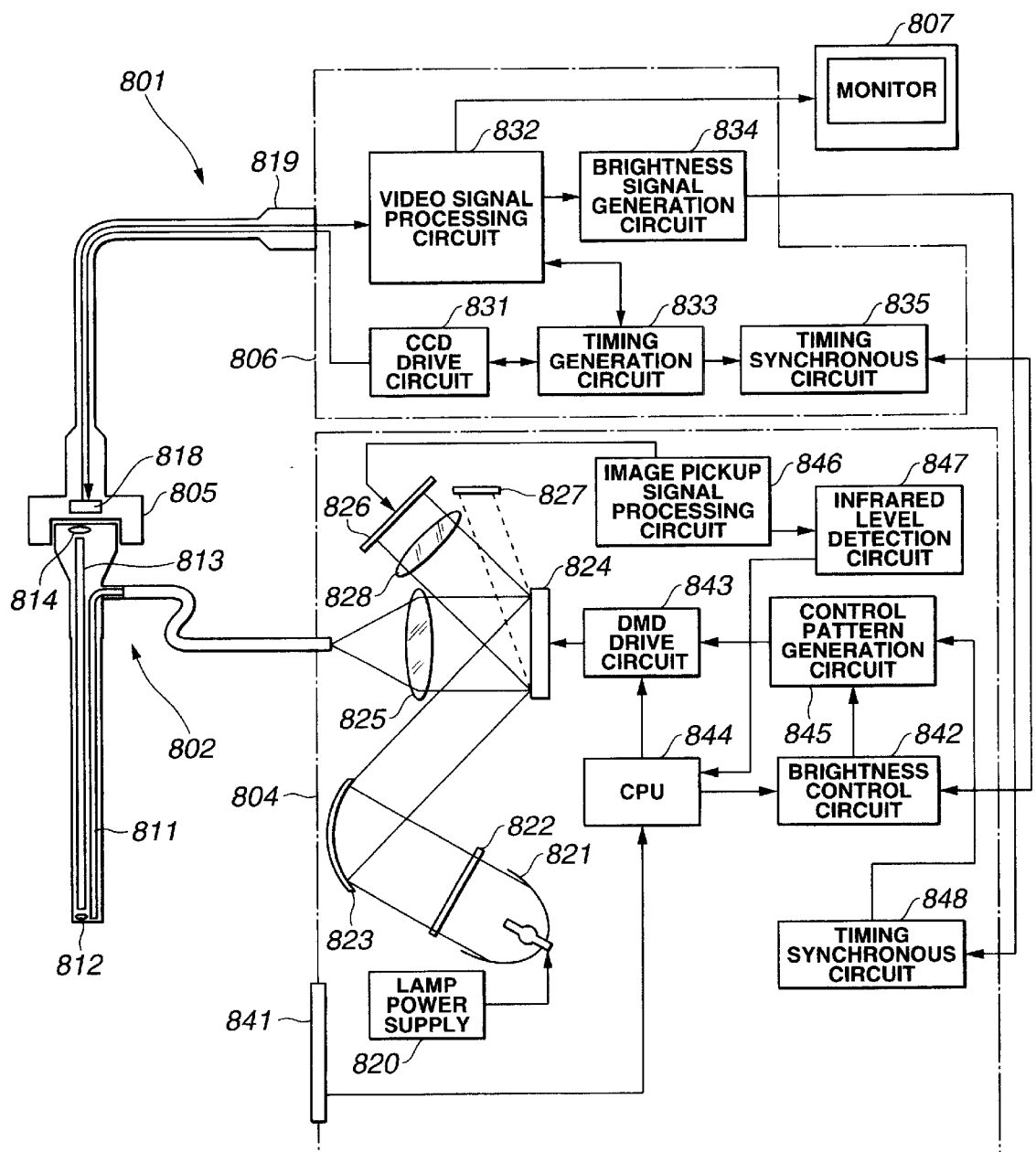
FIGS. 88 to 91 are related to the twenty-third embodiment of the present invention.
Figure 89:
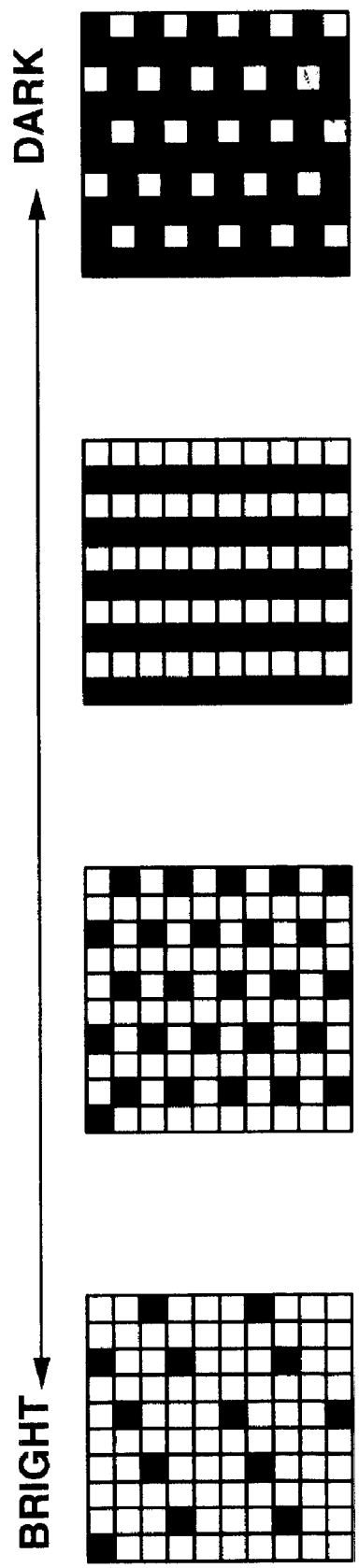
Figure 90:
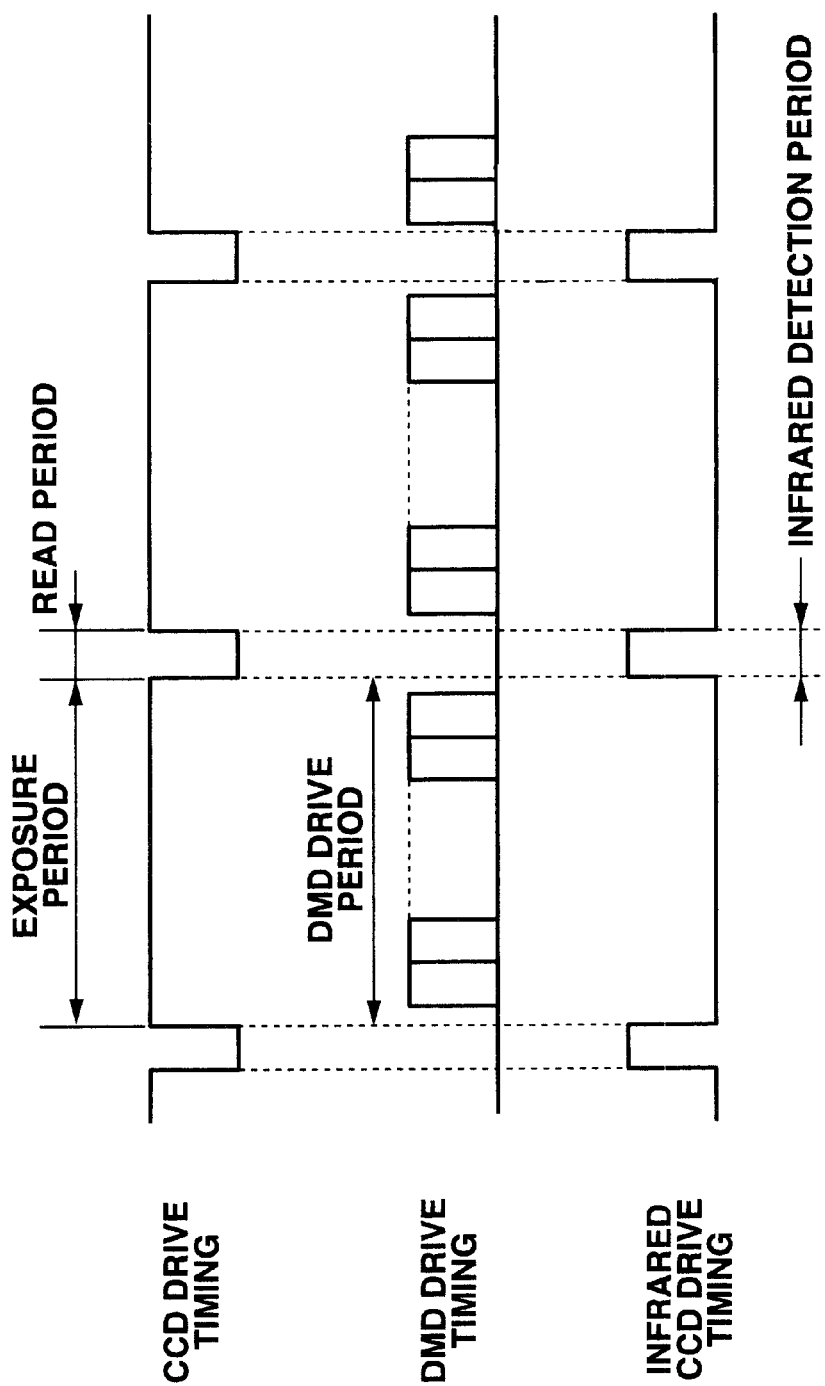

The twenty-third embodiment of the present invention will be described below with reference to FIGS. 88 to 91. As shown in FIG. 88, an endoscope device 801 according to the embodiment comprises: a rigid endoscope 802 serving as an endoscope for obtaining a tissue in vivo through, e.g., a trocar or the like; a light source device 804 for supplying an illumination light to the rigid endoscope 802 through a light guide; a TV head camera 805 for picking up an image obtained by the rigid endoscope 802 detachably connected to an eyepiece portion formed on the hand side of the rigid endoscope 802; and a video signal processing device 806 for performing signal processing of an image pickup signal picked by the TV head camera 805 to display an object to be observed on a monitor 807.

The rigid endoscope 802 is constituted by a light guide 811 for transmitting an illumination light to the distal end of the rigid endoscope 802, an objective lens 812, a relay lens system 813 for transmitting an image from the objective lens 812 to the eyepiece portion, and an eyepiece lens 814, arranged in the eyepiece portion, for observation. On the other hand, a CCD 818 is arranged in the TV head camera 805, and the TV head camera 805 is connected to the video signal processing device 806 through a connector 819.

The optical system of the light source device 804 comprises: a light source lamp 821 for generating an illumination light by a lamp power supply 820; an infrared cut filter 822 for cutting infrared rays of emission light from the light source lamp 821; a mirror 823 for reflecting the light transmitted through the infrared cut filter 822; a light modulation device 824 in which the light reflected by the mirror 823 is reflected by a plurality of micromirrors constituting two-dimensional array elements (cells) arrayed in a two-dimensional matrix; and a convergent lens 825 for converging the light reflected by the light modulation device 824 on the incident end face of the light guide 811.

The light modulation device 824 is a device having the following configuration. That is, a plurality of micromirrors constituting two-dimensional array elements (cells) arrayed in a two-dimensional matrix are arranged on a silicon chip, each micromirror is held by a holding member on a yoke rotated about diagonals between two stable states and can be angularly changed at +10°, 0°, and −10° in the planar direction of the silicon chip. The device has an intermediate position of 0°.

In the optical system of the light source device 804, light is incident on the light guide 811 when the micromirror of the light modulation device 824 is set at +10°.

The optical system comprises: an infrared detection CCD 826 for forming an image on the incident end face of the light guide 811 through an image forming lens 828 when the micromirror of the light modulation device 824 set at 0°; and an light absorber 827 for absorbing the light such that incident light obtained by the light source lamp 821 is not scattered inside the light source when the micromirror arranged near the infrared detection CCD 826 is set at −10°.

As the light absorber 827, a plate having a surface subjected to satin finish and coated with a black paint or a bubbling metal plate in which light is absorbed by microholes formed by bubbling is used. The light absorber 827 serves an important light absorber for preventing unnecessary light from being incident in the light source in, especially, the light modulation device 824.

The video signal processing device 806 comprises: a CCD drive circuit 831 for driving the CCD 818; a video signal processing circuit 832 for performing signal processing of an image pickup signal from the CCD 818 to output a video signal (for example, an NTSC television signal) to the monitor 807; a timing generation circuit 833 for generating a timing signal for synchronizing an image pickup timing of the CCD 818 with the signal processing in the video signal processing circuit 822; a signal generation circuit 834 for detecting the brightness of an image from a video signal from the video signal processing circuit 831; and a timing synchronous circuit 835 for outputting a synchronous signal synchronized with the image pickup timing of the CCD 818 from the timing generation circuit 833.

The control unit of the light source device 804 comprises: an operation panel 841 for operating a brightness setting; a brightness control circuit 842 for performing brightness control on the basis of a brightness signal from the signal generation circuit 834 of the video signal processing device 806; a DMD drive circuit 843 for driving the light modulation device 824; a CPU 844 for controlling the brightness control circuit 842 and the DMD drive circuit 843 on the basis of a setting signal input by the operation of the operation panel 841 and serving as a reference; a control pattern generation circuit 845 for generating drive and control patterns for the light modulation device 824 on the basis of the control of the timing generation circuit 833; a video signal processing circuit 846 for performing signal processing of an image pickup signal from the infrared detection CCD 826; an infrared level detection circuit 847 for detecting an infrared level of an illumination light on the basis of the video signal processed by the video signal processing circuit 846; and a timing synchronous circuit 848 for generating a synchronous signal for synchronizing an image pickup timing with an irradiation timing on the basis of a timing of the timing synchronous circuit 835 of the video signal processing device 806 and for outputting the synchronous signal to the control pattern generation circuit 845. The CPU 844 controls the DMD drive circuit 843 on the basis of the detection result obtained by the infrared level detection circuit 847.

The operation of the embodiment arranged as described above will be described below.

The TV head camera 805 is connected to the rigid endoscope 802 to perform observation in a body cavity with the monitor 807.

In this case, the light modulation device 824 drives a plurality of micromirrors constituting two-dimensional array elements arrayed in a two-dimensional matrix, and drives the micromirrors in a plurality of supply reflection/reflective absorption regularity patterns which change from brightness to darkness, so that a total intensity of supply light is controlled. Control is performed such that an illumination light is appropriate.

In this state, when the distal end of the rigid endoscope 802 is in tight contact with a tissue in a body cavity, the infrared level detection circuit 847 determines that an intensity of illumination light is too high, a warning is displayed on the operation panel 841 by the CPV 844. The CPU 846 causes the brightness control circuit 842 to generate a darkening signal to darken the illumination light.

The control pattern generation circuit 845 may be designed to generate a control pattern for performing PWM (Pulse Width Modulation) control or PFM (Pulse Frequency Modulation) for supply reflection/reflective absorption drive performed by the micromirrors.

In the video signal processing device 805, as shown in FIG. 90A, the CCD 818 is driven at a CCD drive timing at which a charge integration period and a charge read period are repeated.

On the other hand, in the light source device 804, as shown in FIG. 90B, the light modulation device 824 is driven in a supply reflection/reflective absorption regularity pattern by the DMD drive circuit 843 in the charge integration period at the CCD drive timing, and the light modulation device 824 is driven by the pattern of a received reflection state in a charge read period.

The infrared level detection circuit 847, as shown in FIG. 90C, detects infrared rays in the charge read period at the CCD drive timing, and an illumination light is not temporarily emitted. For this reason, the infrared level detection circuit 847 detects infrared rays from an image pickup signal of the infrared detection CCD 826 which forms an image on the incident end face of the light guide 811 in the charge read period. More specifically, for example, when a tissue is in tight contact with the distal end of the rigid endoscope 802, the state of the distal end obtained by the infrared rays is returned to the light guide 811 in contrast to the transmission direction of the illumination light. Since this state appears as an image on the incident end face of the light guide 811, the image is picked by the infrared detection CCD 826 to be detected by the infrared level detection circuit 847. In the infrared level detection circuit 847, the infrared state (high-temperature state) of a tissue positioned at the distal end of the rigid endoscope 802 can be decided by image processing.

Figure 91:
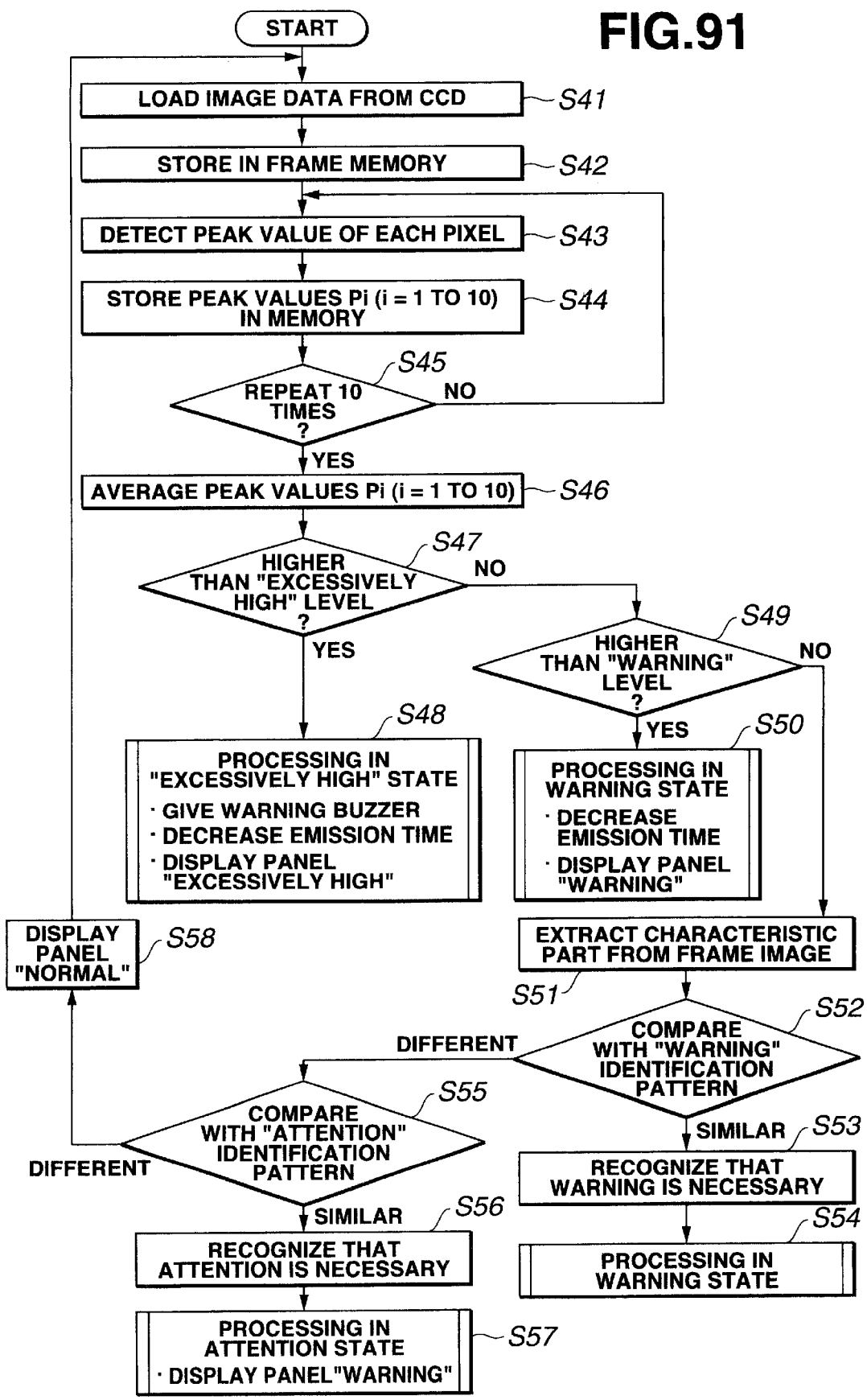

More specifically, as shown in FIG. 91, the infrared level detection circuit 847 loads image data from the infrared detection CCD 826 from the video signal processing circuit 846 in step S41. The image data loaded in step S42 is stored in the frame memory in the infrared level detection circuit 847, a peak value of each pixel is detected in step S43, and the peak value is stored in the memory in step S44. It is checked in step S45 whether the processes in steps S43 and S44 are repeated ten times, and ten peak values Pi (i=1 to 10) are averaged in step S46.

It is checked in step S47 whether the averaged peak value is equal to or larger than an "excessively high" level. If the peak value is equal to or larger than the predetermined "excessively high" level, a signal generated when the peak value is excessively high is output to the CPU 844 in step S48, so that the CPU 844 performs processes performed when the peak value is excessively high, for example, generation of warning buzzer, emission time decrease control of an illumination light, display of "excessively high" on the operation panel 841, a control process of the DMD drive circuit 43, and the like.

If it is determined in step S47 that the peak value does not reach the predetermined "excessively high" level, it is checked in step S49 whether the averaged peak value is equal to or larger than a predetermined "warning" level. If it is the averaged peak value is equal to or larger than the predetermined "warning" level, the CPU 844 outputs a warning level signal in step S50 to perform a process in warning, e.g., processes such as emission time decrease control of an illumination light, display of "warning" on the operation panel 41, a control process of the DMD drive circuit 843.

If it is determined in step S49 that the peak value does not reach the predetermined "warning" level, the infrared level detection circuit 847 extracts a characteristic portion of the frame image stored in the frame memory in step S51. The characteristic portion is compared with a predetermined warning pattern in step S52. If the characteristic portion is similar to the warning pattern, it is determined that warning is required to be made, and a warning level signal is output to the CPU 844 in step S54, so that the CPU 544 performs the same process as that performed in step S50.

If the characteristic portion is not similar to the warning pattern, the characteristic portion is compared with an attention pattern in step S56, an attention level signal is output to the CPU 844 in step S57, so that the CPU 544 performs processes in an attention state, e.g., display of "attention" on the operation panel 541, a control process of the DMD drive circuit 843, and the like.

If the characteristic pattern is not similar to the attention pattern, a normal level signal is output to the CPU 844 in step S58 to cause the CPU 844 to perform processes in a normal state, e.g., a display of "normal" on the operation panel 841 and the like, and the process of returning to step S41 is repeated.

In this manner, in the embodiment, a heating state (temperature state) of a tissue at the distal end of the rigid endoscope 802 is determined by the infrared level detection circuit 847 such that the image of the incident end face of the light guide 811 is picked up by the infrared detection CCD 826, and the CPU 844 performs display on the operation panel 841, a control process of the DMD drive circuit 843, and the like. For this reason, a temperature near a tissue to be observed is detected without making any change in the configuration of the rigid endoscope 802, and an increase in temperature near the tissue to be observed positioned at the distal end of the rigid endoscope 802 can be effectively suppressed.

The twenty-fourth embodiment of the present invention will be described below with reference to FIGS. 92 to 95.

Since the twenty-fourth embodiment is almost the same as the twenty-third embodiment, only different points will be described. The same reference numerals as in the twenty-third embodiment denote the same parts in the twenty-fourth, and a description thereof will be omitted.

Figure 92:
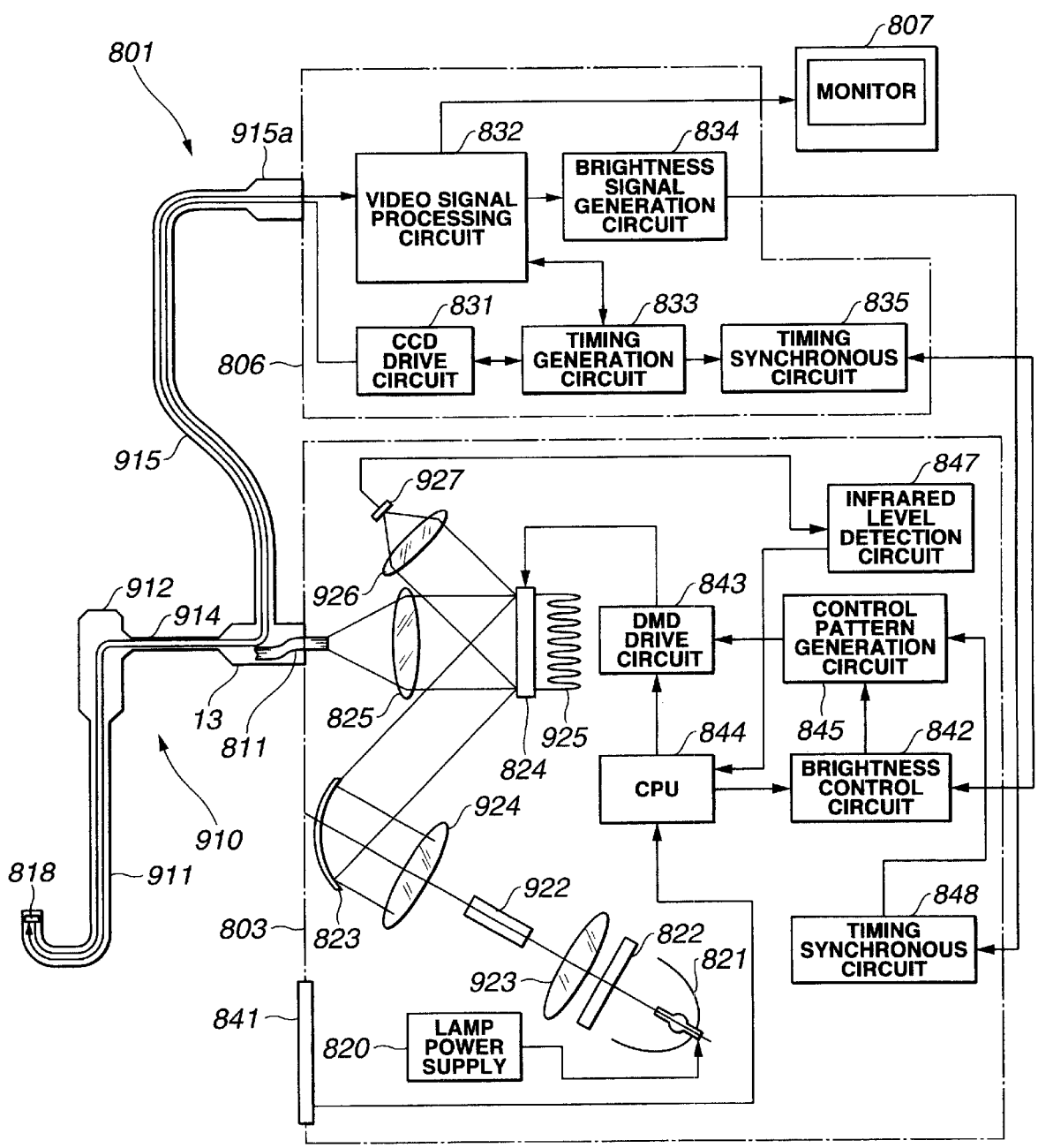
FIGS. 92 to 95 are related to the twenty-fourth embodiment of the present invention.

In the embodiment, an electronic endoscope is arranged in place of the rigid endoscope 802. More specifically, as shown in FIG. 92, an electronic endoscope 910 is constituted by an insertion portion 911 having a long and narrow shape, flexibility, and a distal end portion which is inserted into a lumen and can be bent; an operation portion 912, connected to the proximal end of the insertion portion 911, for performing grasping and bending operations and the like; a universal cable 914 having a connector 913 extending from the operation portion 912, connected to a light source device 803, formed at the distal end of the universal cable 914; and a signal cable 915 having a connector 915a formed at the signal cable 915, extending from the connector 913, and connected to the video signal processing device 805. A CCD 818 serving as a solid state image pickup element for performing image pickup to a portion to be observed is arranged at the distal end of the insertion portion 911, and a light guide 811 for transmitting an illumination light from the light source device 803 to the distal end of the insertion portion 911 is arranged in the universal cable 914 and the operation portion 912.

In the optical system of the light source device 803 according to the embodiment, light emitted from the illumination lamp 821 is transmitted through the infrared cut filter 822, and is incident on an integrator 922 by a condensation lens 923.

The light transmitted through the integrator 922 is converted into parallel lights by a lens 924, and the parallel lights are incident on the mirror 823. The mirror reflected by the mirror 823 is incident on the light modulation device 824. A heat-radiation fin 925 is arranged on the light modulation device 824 to radiate heat generated by an illumination light.

Light reflected when the micro mirror of the light modulation device 824 is set at 0° is incident on an infrared sensor 927 through a convergent lens 926. The infrared sensor 927 outputs an electric signal depending on an intensity of infrared ray being incident by a single sensor.

The output from the infrared sensor 927 is incident on the infrared level detection circuit 847, and is decided in three stages by control shown in FIG. 93 (to be described later). The decided signal is input to the CPU 844. If the decided signal is at a warning level, a buzzer makes sound. At the same time, warning is displayed on the operation panel 841. If the signal is in an excessive high state, the illumination light is darkened as in the twenty-third embodiment.

Figure 93:
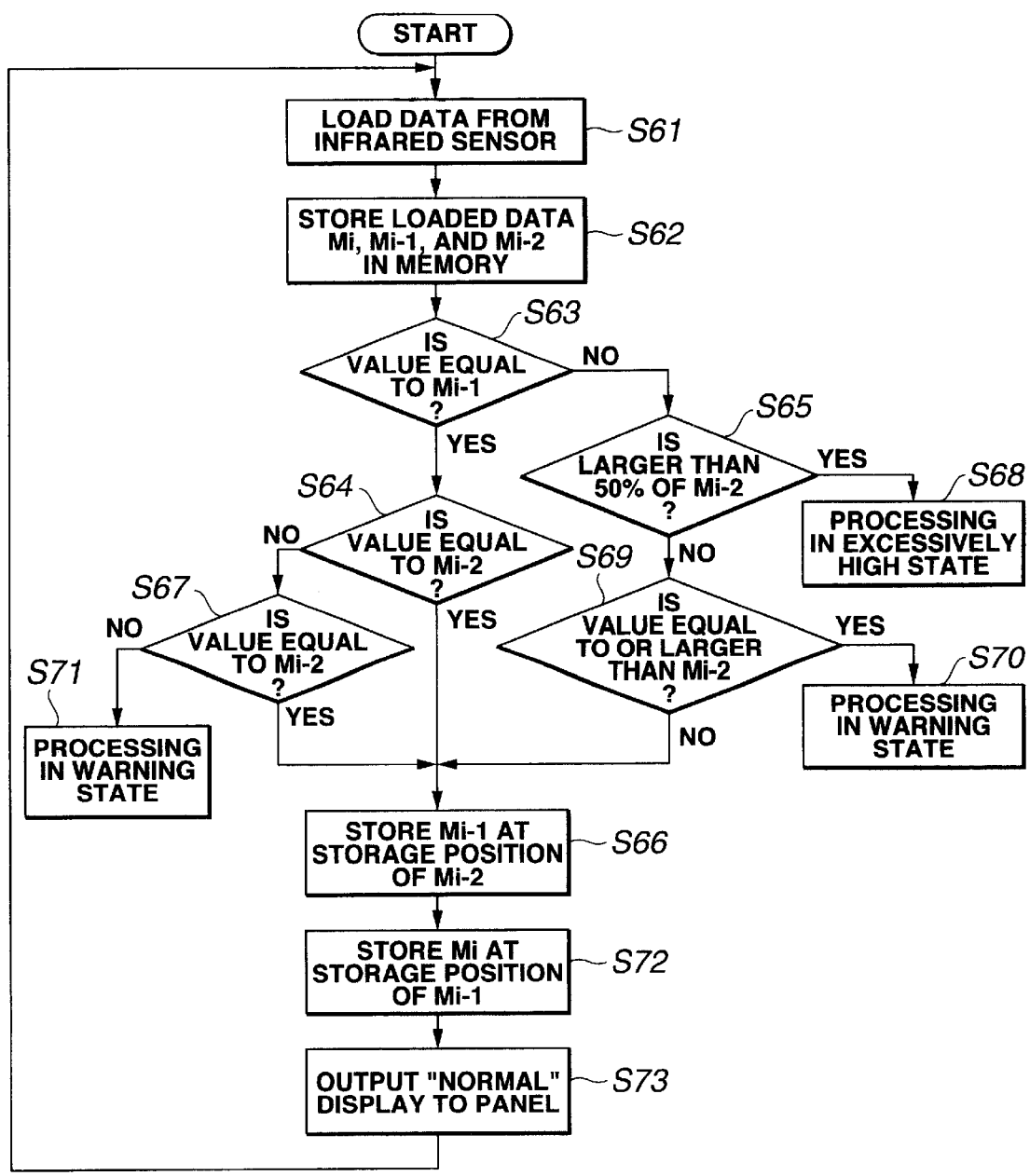

The infrared level detection circuit 847 of the embodiment, as shown in FIG. 93, loads data from the infrared sensor 927 in step S61. Three data, i.e., latest data Mi, previous data Mi-1, and further previous data Mi-2 which are loaded at a predetermined time interval in step S61 are stored in a memory in step S62. It is checked in step S63 whether the value of the data Mi is equal to the value of the data Mi-1. If these values are equal to each other, the flow shifts to step S66. If these values are not equal to each other, the flow shifts to step S67.

In step S65, it is checked that the value of the data Mi is equal to larger than 50% the value of the data Mi-1. If the value of the data Mi is equal to larger than 50% of the value of the data Mi-1, a signal having an excessively high level is output to the CPU 844 in step S68, the CPU 844 preforms processes in the excessively high state, e.g., making sound of a warning buzzer, emission time decrease control of an illumination light, display of "excessively high" on the operation panel 841, a control process of the DMD drive circuit 843, and the like.

In addition, if the value of the data Mi does not reach 50% of the value of the data Mi-1, it is checked in step S69 whether the value of the value Mi is equal to or larger than the value of the data Mi-2. If the value of the value Mi is equal to or larger than the value of the data Mi-2, a warning signal is output to the CPU 844, and the CPU 844 performs processes in a warning state, e.g., emission time decrease control of an illumination light, display of "warning" on the operation panel 841, a control process of the DMD drive circuit 843, and the like. If the value of the value Mi is not equal to or larger than the value of the data Mi-3, the flow shifts to step S66.

In step S67, it is checked whether the value of the value Mi is equal to or larger than the value of the data Mi-2. If the value of the value Mi is equal to or larger than the value of the data Mi-2, a warning level signal is output to the CPU 844 in step S71, the CPU 844 performs processes in a warning state, e.g., emission time decrease control of an illumination light, display of "warning" on the operation panel 841, a control process of the DMD drive circuit 843, and the like. If the value of the value Mi is not equal to or larger than the value of the data Mi-2, the flow shifts to step S66.

The data Mi-1 is stored at a storage position of the data Mi-2 in step S66, and in the next step S72, the data Mi is stored at a storage position of the data Mi-1. A process such as display of "normal" on the operation panel 841 is performed in step S73, and the flow returns to step S61 to repeat the processes. The other configuration and operation are the same as those of the twenty-third embodiment.

According to the embodiment, the following effect can be obtained.

In this manner, in the embodiment, in addition to the effect of the twenty-third embodiment, an infrared sensor is constituted by a single sensor, so that infrared rays can be detected by a simple structure.

Figure 94:
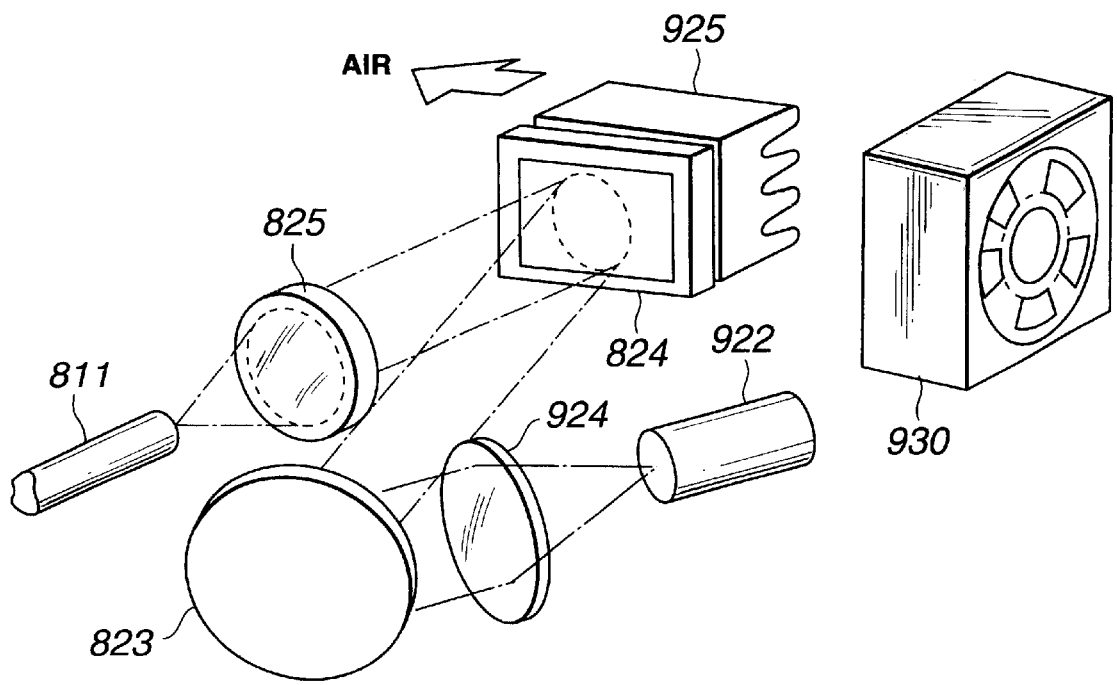
Figure 95:
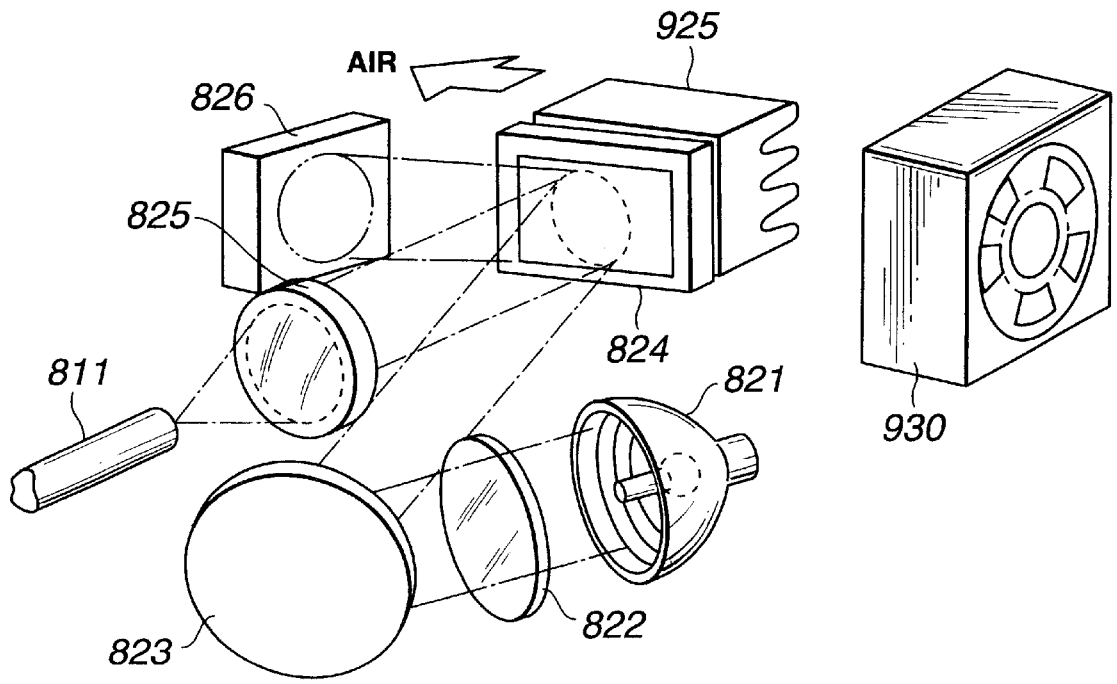

In order to improve the heat radiation effect of the heat-radiation fin 925, as shown in FIG. 94, a fan 930 for cooling the light modulation device 824 and the heat-radiation fin 925 may be arranged near the heat-radiation fin 925. In addition, in the twenty-third embodiment, as shown in FIG. 95, the heat-radiation fin 925 is arranged on the light modulation device 824, and the fan 930 may be arranged near the heat-radiation fin 925.

Figure 96:
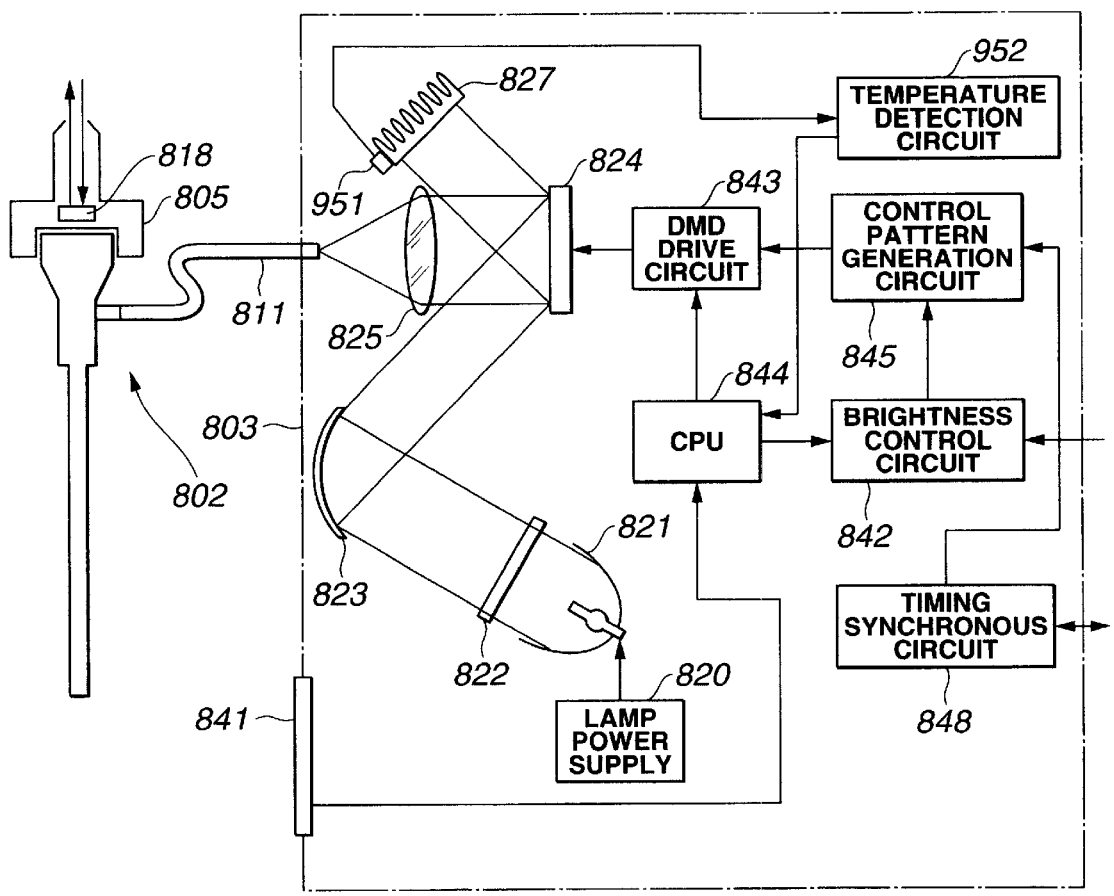
Figure 97A:
Figure 97B:

The twenty-fifth embodiment of the present invention will be described below with reference to FIGS. 96 to 97B. Since the twenty-fifth embodiment is almost the same as the twenty-third embodiment, only different points will be described. The same reference numerals as in the twenty-third embodiment denote the same parts in the twenty-fifth embodiment, and a description thereof will be omitted.

In the embodiment, heat generated from the distal end of the rigid endoscope 802 is radiated such that infrared rays are easily returned to the light source through the light guide 811.

Figure 6:
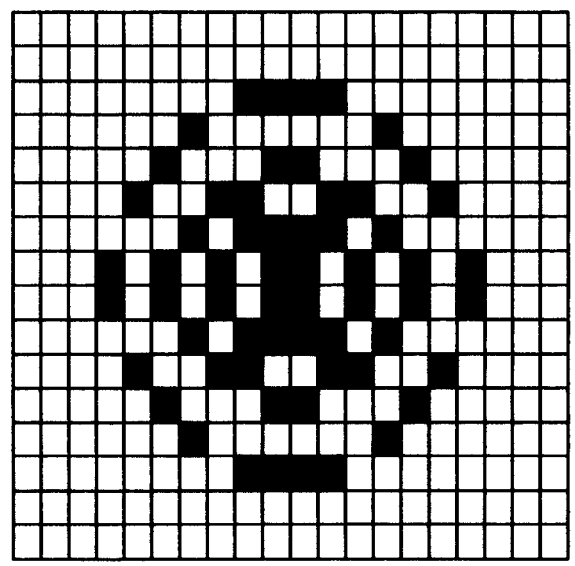
Figure 7:
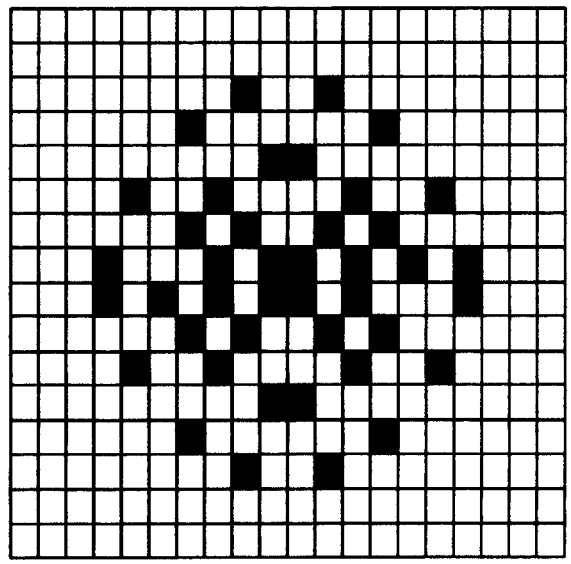
Figure 8:
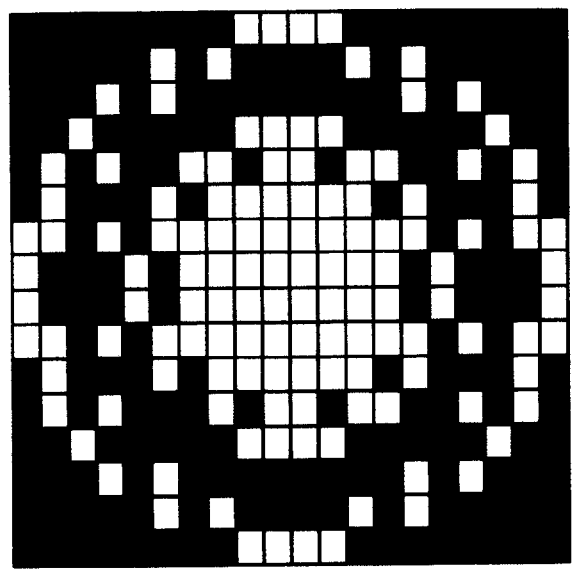
Figure 9:
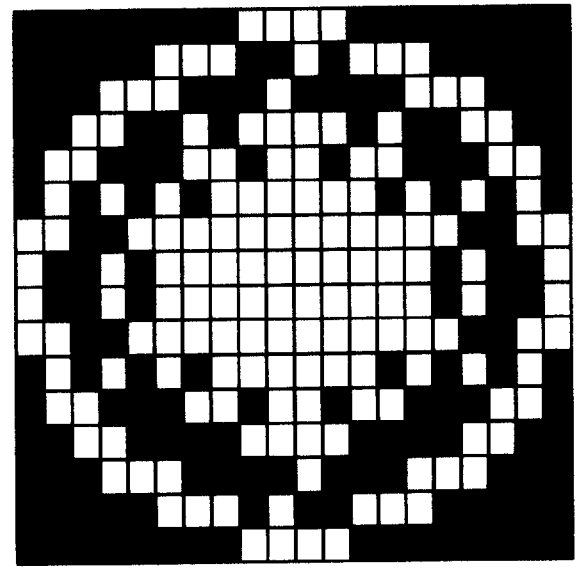
Figure 10:
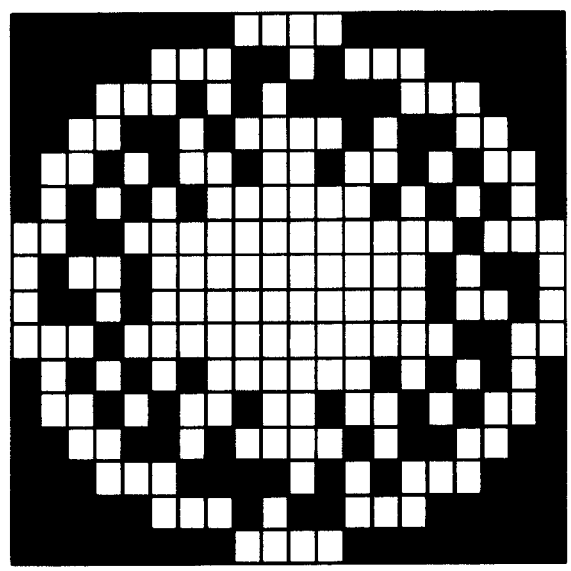
Figure 11:
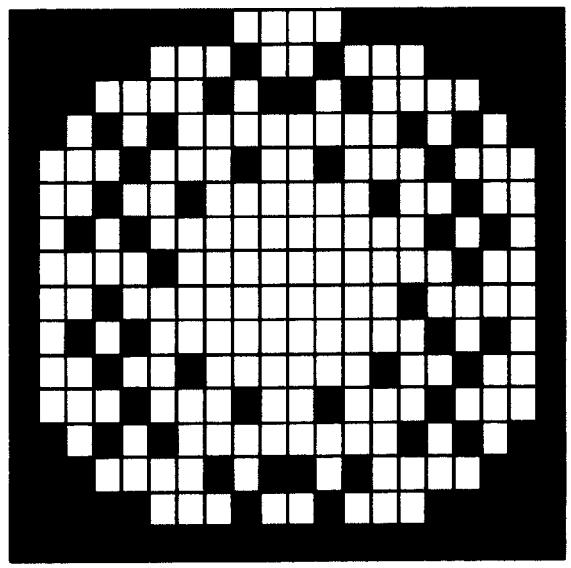

More specifically, as shown in FIG. 9 6, when the micromirror of the light modulation device 824 is set at +10°, infrared rays from the light guide 811 are designed to be incident on the light absorber 827 having a heat radiation fin.

A temperature sensor 951 is arranged on the light absorber 827 such that an increase in temperature caused by infrared absorption is detected. The detection signal is input to a temperature detection circuit 952. It is decided by the temperature detection circuit 952 that the temperature becomes a predetermined level temperature, and a decision signal is input to the CPU 844.

The CPU 844 drives the color modulation device 811 on the basis of the decision signal. In normal observation, as shown in FIG. 97A, control is performed such that an optical path switching time to infrared absorption by emission to the light absorber 827 in illumination light supply to the light guide 811 and emission to the light absorber 827 is short. When an increase in temperature is detected, as shown in FIG. 97B, control is performed such that an optical path switching time to infrared absorption by transmission to the light absorber 827 in illumination light supply to the light guide 811 and transmission to the light absorber 827 is elongated. The other configuration and operation are the same as those in the twenty-third embodiment.

In the twenty-fifth embodiment, the same effect as that in the twenty-third embodiment can be obtained.

An embodiment or the like constituted by partially combining the embodiments described above is also included in the present invention.

What is claimed is:

1. A light source device used in an endoscope device comprising:

a light source lamp, arranged at a predetermined position in the light source device, for generating light supplied to an endoscope;

a mirror device which uses a silicone chip as a base, which is arranged on an optical path of the light in the light source device, and which has reflective surfaces formed by a plurality of micromirrors for receiving the light, the micromirrors being movable in a predetermined angular range;

a receptacle to which a light guide for transmitting the light to an object to be photographed is connected, and which has a face on a proximal side of the light guide arranged at a predetermined position in the light source device;

an optical system which is arranged on an optical path of reflected light from the micromirrors from the light generated by the light source lamp when the angles of the micromirrors are at a predetermined position, and which directs the reflected light to the end on the proximal side of the light guide, the optical system forming an optical positional relationship between the micromirrors and the face on the proximal side of the light guide;

a light adjustment circuit for outputting an adjustment signal for adjusting the light incident on the optical system;

a mirror device drive circuit for outputting a drive signal for setting each of the micromirrors formed in the mirror device at a position on the basis of the adjustment signal output from the light adjustment circuit, the mirror device drive circuit operating the plurality of micromirrors at an angle at which at least some reflected light by the micromirrors from the light generated by the light source lamp is incident on the optical system and an angle at which the reflected light is not incident on the optical system.

2. A light source device according to claim 1, wherein in the mirror device, the micromirrors are two-dimensionally arranged in an arrangement state in which reflected light reflected by one of the micromirrors is incident on the light guide connected to the connector support through the optical system when the micromirror is set at an angle at which the micromirror directs reflected light in a first direction, and reflected light reflected by the micromirror is not incident on the optical system and is not incident on the light guide connected to the connector support when the micromirror is set at an angle at which the micromirror directs reflected light in a second direction different from the first direction.

3. A light source device according to claim 1, wherein a light distribution of light from the distal end of the light guide can be adjusted by the light adjustment circuit.

4. A light source device according to claim 1, wherein the optical system is a condensation optical system, and the condensation optical system condenses the light reflected by the mirror device on the face of the proximal side of the light guide arranged at an almost pupil position with respect to the micromirrors.

5. A light source device according to claim 1, wherein the optical system uniformly distributes light incident on the mirror device.

6. A light source device according to claim 1, wherein the optical system guides light reflected by the mirror device to the face of the proximal side of the light guide arranged at an almost image forming position with respect to the micromirrors.

7. A light source device according to claim 6, further comprising a video processing device for generating a video signal responsive to an image pickup element arranged in the endoscope, the video processing device having a decision circuit for deciding whether the luminance level of the video signal departs from a reference range.

8. A light source device according to claim 7, wherein the mirror device drives the mirror device such that an intensity of light irradiated on a part of the object corresponding to a video signal portion which is determined by the decision circuit when a portion which departs from the reference range.

* * * * *